(12) United States Patent
Brys et al.

(10) Patent No.: US 7,306,923 B2
(45) Date of Patent: Dec. 11, 2007

(54) METHODS FOR IDENTIFICATION, AND COMPOUNDS USEFUL FOR THE TREATMENT OF DEGENERATIVE & INFLAMMATORY DISEASES

(75) Inventors: Reginald Brys, Korbeek-Dijle (BG); Nick Vandeghinste, Duffel (BG); Peter Herwig Maria Tomme, Gent (BG)

(73) Assignee: Galapagos N.V., Mechelen (BE)

( * ) Notice: Subject to any disclaimer, the term of this patent is extended or adjusted under 35 U.S.C. 154(b) by 16 days.

(21) Appl. No.: 11/152,366

(22) Filed: Jun. 14, 2005

(65) Prior Publication Data

US 2006/0014184 A1    Jan. 19, 2006

Related U.S. Application Data

(60) Provisional application No. 60/579,307, filed on Jun. 14, 2004.

(51) Int. Cl.
  *G01N 33/53*   (2006.01)
  *C12Q 1/00*    (2006.01)
  *C07K 1/00*    (2006.01)
  *C07K 14/00*   (2006.01)
  *C07K 17/00*   (2006.01)

(52) U.S. Cl. ............................. 435/7.1; 435/4; 530/350

(58) Field of Classification Search ................ 435/7.1, 435/4; 530/350
  See application file for complete search history.

(56) References Cited

U.S. PATENT DOCUMENTS 6,538,173 B2 *  3/2003  Heber-Katz ................ 800/8
  2002/0151681 A1* 10/2002 Rosen et al. ............... 530/350
  2005/0112118 A1   5/2005 Cimbora et al.

FOREIGN PATENT DOCUMENTS

WO    02/056888 A2   7/2002
  WO    2004/037814 A1  5/2004
  WO    WO 2005/012875  * 2/2005

OTHER PUBLICATIONS

U.S. Appl. No. 11/251,465, filed Sep. 2005, Brys et al.*
Ni et al., MAPKAPK5, a novel mitogen-activated protein kinase (MAPK)-activated protein kinase, is a substrate of the extracellular-regulated kinase (ERK) and p38 kinase, 1998, Biochemical and Biophysical Research Communications, vol. 243, pp. 492-496.*
Crowe et al., 1999, Regualtion of tumor cell invasion by extracellular matrix, Histol. Histopathol., 14: 665-671.*
Ravanti et al., 2000, Matrix metalloproteinases in wound repair (Review), International Journal of Molecular Medicine, 6: 391-407.*
Widmann et al., 1999, Mitogen-activated proteins kinase: Conservation of a three-kinase module form yeast to human, Physiological Reviews, 79(1): 143-180.*
Shi et al., "Elimination of Protein Kinase MK5/PRAK Activity by Targeted Homologous Recombination," Molecular and Cellular Biology, Nov. 2003, pp. 7732-7741.
Seternes et al., "Both Binding and Activation of p38 Mitogen-Activated Protein Kinase (MAPK) Play Essential Roles in Regulation of the Nucleocytoplasmic Distribution of MAPK-Activated Protein Kinase 5 by Cellular Stress," Molecular and Cellular Biology, Oct. 2002, pp. 6931-6945.
New et al., "PRAK, a novel protein kinase regulated by the p38 MAP kinase," EMBO Journal, vol. 17, No. 12, pp. 3372-3384 (1998).
Bain et al., "The specificities of protein kinase inhibitors: an update," Biochem, J. 371, pp. 199-204.
Setemes et al., "Activation of MK5/PRAK by the atypical MAP kinase ERK3 defines a novel signal transduction pathway," EMBO Journal 23, pp. 4780-4791 (2004).

* cited by examiner

*Primary Examiner*—Mark L. Shibuya
*Assistant Examiner*—Amber D Steele
(74) *Attorney, Agent, or Firm*—Synnestvedt & Lechner LLP

(57) ABSTRACT

The present invention relates to in vivo and in vitro methods, agents and compound screening assays for inhibiting extra-cellular matrix degradation, including joint degenerative inhibiting and/or anti-inflammatory pharmaceutical compositions, and the use thereof in treating and/or preventing a disease involving extra-cellular matrix degradation in a subject.

11 Claims, 19 Drawing Sheets

Schematic view of a normal joint and its changes in rheumatoid arthritis

Figure 4A

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | P1 | P1 | N1 | N1 | P2 | P2 | N2 | N2 | P3 | P3 | N3 | N3 | P1 | P1 | N1 | N1 | P2 | P2 | N2 | N2 | P3 | P3 | N3 | N3 |
| B | P1 | Bl | N1 | Bl | P2 | Bl | N2 | Bl | P3 | Bl | N3 | Bl | P1 | Bl | N1 | Bl | P2 | Bl | N2 | Bl | P3 | Bl | N3 | Bl |
| C | N1 | N1 | P2 | P2 | N2 | N2 | P3 | P3 | N3 | N3 | P1 | P1 | N1 | N1 | P2 | P2 | N2 | N2 | P3 | P3 | N3 | N3 | P1 | P1 |
| D | N1 | Bl | P2 | Bl | N2 | Bl | P3 | Bl | N3 | Bl | P1 | Bl | N1 | Bl | P2 | Bl | N2 | Bl | P3 | Bl | N3 | Bl | P1 | Bl |
| E | P2 | P2 | N2 | N2 | P3 | P3 | N3 | N3 | P1 | P1 | N1 | N1 | P2 | P2 | N2 | N2 | P3 | P3 | N3 | N3 | P1 | P1 | N1 | N1 |
| F | P2 | Bl | N2 | Bl | P3 | Bl | N3 | Bl | P1 | Bl | N1 | Bl | P2 | Bl | N2 | Bl | P3 | Bl | N3 | Bl | P1 | Bl | N1 | Bl |
| G | N2 | N2 | P3 | P3 | N3 | N3 | P1 | P1 | N1 | N1 | P2 | P2 | N2 | N2 | P3 | P3 | N3 | N3 | P1 | P1 | N1 | N1 | P2 | P2 |
| H | N2 | Bl | P3 | Bl | N3 | Bl | P1 | Bl | N1 | Bl | P2 | Bl | N2 | Bl | P3 | Bl | N3 | Bl | P1 | Bl | N1 | Bl | P2 | Bl |
| I | P3 | P3 | N3 | N3 | P1 | P1 | N1 | N1 | P2 | P2 | N2 | N2 | P3 | P3 | N3 | N3 | P1 | P1 | N1 | N1 | P2 | P2 | N2 | N2 |
| J | P3 | Bl | N3 | Bl | P1 | Bl | N1 | Bl | P2 | Bl | N2 | Bl | P3 | Bl | N3 | Bl | P1 | Bl | N1 | Bl | P2 | Bl | N2 | Bl |
| K | N3 | N3 | P1 | P1 | N1 | N1 | P2 | P2 | N2 | N2 | P3 | P3 | N3 | N3 | P1 | P1 | N1 | N1 | P2 | P2 | N2 | N2 | P3 | P3 |
| L | N3 | Bl | P1 | Bl | N1 | Bl | P2 | Bl | N2 | Bl | P3 | Bl | N3 | Bl | P1 | Bl | N1 | Bl | P2 | Bl | N2 | Bl | P3 | Bl |
| M | P1 | P1 | N1 | N1 | P2 | P2 | N2 | N2 | P3 | P3 | N3 | N3 | P1 | P1 | N1 | N1 | P2 | P2 | N2 | N2 | P3 | P3 | N3 | N3 |
| N | P1 | Bl | N1 | Bl | P2 | Bl | N2 | Bl | P3 | Bl | N3 | Bl | P1 | Bl | N1 | Bl | P2 | Bl | N2 | Bl | P3 | Bl | N3 | Bl |
| O | N1 | N1 | P2 | P2 | N2 | N2 | P3 | P3 | N3 | N3 | P1 | P1 | N1 | N1 | P2 | P2 | N2 | N2 | P3 | P3 | N3 | N3 | P1 | P1 |
| P | N1 | Bl | P2 | Bl | N2 | Bl | P3 | Bl | N3 | Bl | P1 | Bl | N1 | Bl | P2 | Bl | N2 | Bl | P3 | Bl | N3 | Bl | P1 | Bl |

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 750.6 | 855.5 | 110.6 | 114.9 | 188.8 | 169.2 | 96.04 | 78.71 | 434.4 | 323.2 | 118.2 | 95.32 | 824.2 | 775 | 56.92 | 57.49 | 188.8 | 209.1 | 84.73 | 93.19 | 293.4 | 334.1 | 129.9 | 138.2 |
| B | 992.8 | 170.8 | 88.18 | 92.83 | 233 | 75.43 | 96.47 | 125.2 | 348.3 | 140.2 | 195.1 | 152.9 | 957.7 | 97.15 | 58.59 | 62.11 | 154.3 | 60.83 | 58.3 | 84.43 | 330.1 | 106.8 | 101.7 | 222 |
| C | 143.3 | 96.54 | 184.6 | 181.9 | 60.6 | 81.66 | 253.3 | 187.8 | 149.3 | 129.4 | 678.9 | 805.5 | 56.91 | 49.2 | 136.3 | 157 | 51.8 | 57.02 | 243.5 | 279.8 | 102.6 | 79.42 | 873.8 | 876.2 |
| D | 122.5 | 84.52 | 190 | 78.55 | 71.05 | 72.69 | 370.9 | 68.15 | 101.4 | 192.1 | 729.9 | 138.4 | 54.43 | 49.88 | 178.3 | 65.32 | 56.24 | 72.54 | 296.3 | 127.9 | 120.9 | 169.1 | 911.6 | 159.1 |
| E | 290 | 191.1 | 66.24 | 66.15 | 300.6 | 225.8 | 77 | 119.3 | 789.4 | 784.5 | 69.82 | 100.3 | 191.1 | 167.2 | 49.07 | 56.66 | 299.2 | 316.3 | 87.45 | 139.6 | 878.9 | 837 | 91.33 | 123.6 |
| F | 225.8 | 112.8 | 86.46 | 81.71 | 404.4 | 129.2 | 82.93 | 102.4 | 1016 | 78.39 | 35.99 | 64.43 | 195.4 | 42.95 | 56.57 | 103.9 | 409.9 | 160.9 | 103 | 94.56 | 880.5 | 102.9 | 54.46 | 94.26 |
| G | 75.32 | 79.75 | 397.4 | 311.8 | 109.2 | 77.27 | 885.6 | 786 | 84.34 | 45.91 | 201.6 | 197.5 | 45.24 | 56.54 | 402.6 | 411.9 | 121.8 | 108 | 807.3 | 769.6 | 57.79 | 51.29 | 147.7 | 169.2 |
| H | 89.63 | 84.49 | 384.6 | 91.71 | 77.39 | 91.73 | 1041 | 127.2 | 79.02 | 39.25 | 222.2 | 43.08 | 104.9 | 70.67 | 449.1 | 92.62 | 93.1 | 162 | 686 | 85.4 | 39.69 | 48.42 | 209.3 | 83.59 |
| I | 427.2 | 377.4 | 88.99 | 100.6 | 986.7 | 864.5 | 95 | 58.82 | 232.7 | 132.9 | 40.48 | 57.62 | 447.6 | 344 | 53.04 | 90.58 | 821.9 | 787.5 | 61.57 | 39.16 | 154.7 | 191.2 | 58.64 | 77.35 |
| J | 375 | 112.8 | 86.11 | 123.5 | 1059 | 109.9 | 60.77 | 54.79 | 214.3 | 37.14 | 42.64 | 52.62 | 350.5 | 71.41 | 115.8 | 105.3 | 861.1 | 124.2 | 55.32 | 41.83 | 152.4 | 51.95 | 64.58 | 56.2 |
| K | 110.3 | 114.8 | 793.7 | 853.7 | 88.13 | 66.26 | 194 | 188.1 | 65.01 | 46.06 | 361.7 | 217.7 | 50.76 | 85.24 | 844.8 | 844.8 | 69.67 | 36.25 | 161.3 | 156.4 | 36.62 | 41.18 | 233.5 | 196.9 |
| L | 119.3 | 115.7 | 1086 | 183.8 | 62.63 | 75.35 | 181.2 | 59.04 | 67.11 | 61.1 | 549.2 | 53.32 | 41.78 | 106.6 | 915.1 | 110 | 37.98 | 38.69 | 120.7 | 34.53 | 37.55 | 42.84 | 252.9 | 81.5 |
| M | 769.4 | 898.9 | 133 | 73.79 | 316.9 | 157.7 | 38.5 | 60.48 | 233 | 278.8 | 48.15 | 77.91 | 847.2 | 852.1 | 48.46 | 44.7 | 161.4 | 132.3 | 27.47 | 31.59 | 195.5 | 240.6 | 53.8 | 50.51 |
| N | 931.1 | 114.9 | 110.7 | 72.61 | 203 | 59.08 | 45.58 | 69.04 | 459.3 | 84.81 | 45.86 | 74.3 | 943.1 | 130.3 | 35.8 | 34.82 | 159.7 | 31.86 | 27.37 | 35.96 | 168.7 | 65.82 | 72.94 | 67.72 |
| O | 171.5 | 101 | 237.9 | 239 | 68.45 | 70.38 | 414.5 | 446.4 | 96.57 | 107.4 | 879.4 | 626.3 | 64.7 | 43.68 | 123.1 | 206.2 | 33.01 | 35.37 | 153.9 | 161.5 | 30.86 | 59.61 | 778.1 | 829.8 |
| P | 142.9 | 126 | 213.5 | 99.46 | 71.39 | 85.74 | 517.6 | 79.77 | 89.75 | 98.73 | 905.7 | 99.69 | 54.82 | 46.37 | 174.4 | 55.53 | 44.08 | 49.29 | 219.3 | 45.78 | 51.97 | 70.09 | 712.4 | 140.6 |

Figure 4B

| | | Average | Standard deviation | Cutoff | % positive | |
|---|---|---|---|---|---|---|
| Ad5-MMP-1 | P1 | 856.0 | 91.8 | | 100.0 | of 48 |
| Ad5-TRAF6 | P2 | 187.2 | 38.9 | | 16.7 | of 48 |
| Ad5-MYD88 | P3 | 325.7 | 96.8 | | 83.3 | of 48 |
| Ad5-eGFP | N1 | 75.0 | 32.9 | | 0.0 | of 48 |
| Ad5-LacZ | N2 | 60.6 | 19.7 | | 0.0 | of 48 |
| Ad5-PLAP | N3 | 93.8 | 32.1 | | 0.0 | of 48 |
| | Blanco | 89.6 | 39.5 | | 1.0 | of 96 |
| | All positives | 456.3 | 300.0 | | | |
| | All negatives | 76.4 | 31.8 | 219.4 | | |

Ad-siRNA mediated reduction in the expression of various target genes in SF's reduces the capacity of these cells to express MMP1 as a response to cytokines.

Figure 13
Recombinant adenovirus-driven expression of various target genes in primary human SFs induces MMP1 expression
Figure 13 A
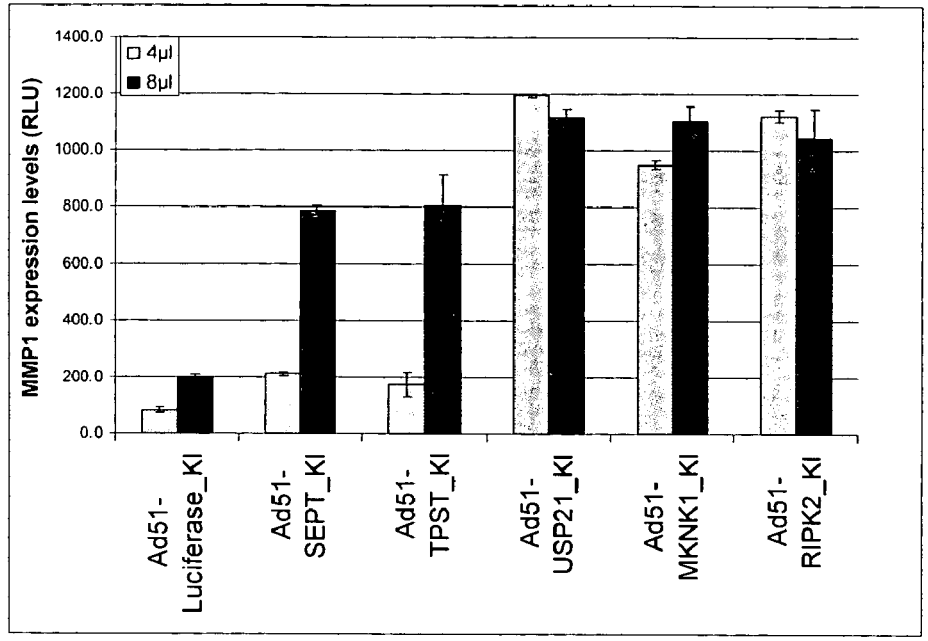
Figure 13 B
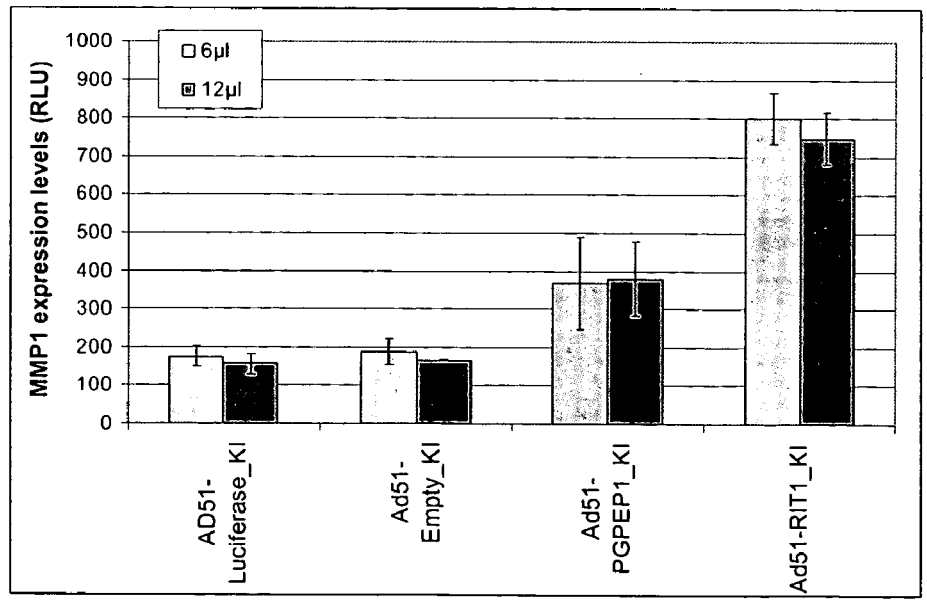

Reduction, at the protein level, of the expression of MAPKAPK5, PRKCE and CAMK4 by infection of the cells with various Ad-siRNA viruses targeting these genes.

Ad-siRNA Mediated Reduction in the Expression of MAPKAPK5 or CAMK4 in SFs Reduces the Capacity of these Cells to Degrade Native Collagen as a Response to Cytokines.

shRNA Constructed from KD Target sequence for RIPK2:

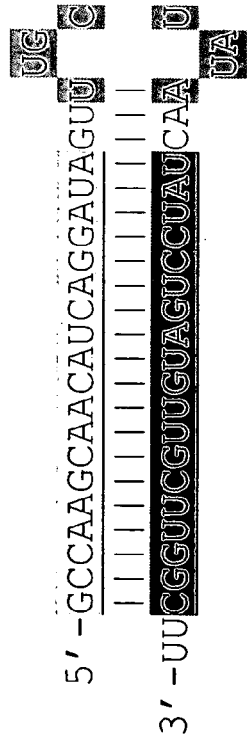

Written linearly:
5'-GCCAAGCAACAUCAGGAUAGUUUGCUAUAACUAUCCUGAUGUUGCUUGCUU-3' (SEQ ID NO: 325)

Homologous to target sequence /Loop/ Antisense to target sequence

Homologous to target sequence: GCCAAGCAACAUCAGGAUA (SEQ ID NO: 326)

Loop region: UUGCUAUA (SEQ ID NO: 26)

Antisense to target sequence: UAUCCUGAUGUUGCUUGG (SEQ ID NO: 327)

Figure 16

SEQUENCE LISTING

<160> NUMBER OF SEQ ID NOS: 295

<210> SEQ ID NO 1
<211> LENGTH: 2521
<212> TYPE: DNA
<213> ORGANISM: Homo sapiens

<400> SEQUENCE: 1

```
gaagctcttt cgcggcgcta cggcgttggc accagtctct agaaaagaag tcagctctgg      60
ttcggagaag cagcggctgg cgtgggccat ccggggaatg gcgcccctcg tgacctagtg     120
ttgcggggca aaaagggtct tgccggcctc gctcgtgcag gggcgtatct gggcgcctga     180
gcgcggcgtg ggagccttgg gagccgccgc agcaggggc acacccggaa ccggcctgag      240
cgcccgggac catgaacggg gaggccatct gcagcgccct gcccaccatt ccctaccaca     300
aactcgccga cctgcgctac ctgagccgcg gcgcctctgg cactgtgtcg tccgcccgcc     360
acgcagactg gcgcgtccag gtggccgtga agcacctgca catccacact ccgctgctcg     420
acagtgaaag aaaggatgtc ttaagagaag ctgaaatttt acacaaagct agatttagtt     480
acattcttcc aattttggga atttgcaatg agcctgaatt tttgggaata gttactgaat     540
acatgccaaa tggatcatta aatgaactcc tacataggaa aactgaatat cctgatgttg     600
cttggccatt gagatttcgc atcctgcatg aaattgccct tggtgtaaat tacctgcaca     660
atatgactcc tccttactt catcatgact gaagactca gaatatctta ttggacaatg       720
aatttcatgt taagattgca gattttggtt tatcaaagtg gcgcatgatg tccctctcac     780
agtcacgaag tagcaaatct gcaccagaag gagggacaat tatctatatg ccacctgaaa     840
actatgaacc tggacaaaaa tcaagggcca gtatcaagca cgatatatat agctatgcag     900
ttatcacatg ggaagtgtta tccagaaaac agccttttga agatgtcacc aatcctttgc     960
agataatgta tagtgtgtca caaggacatc gacctgttat taatgaagaa agtttgccat    1020
atgatatacc tcaccgagca cgtatgatct ctaataga aagtggatgg gcacaaaatc       1080
cagatgaaag accatctttc ttaaaatgtt aatagaact tgaaccagtt ttgagaacat     1140
ttgaagagat aacttttctt gaagctgtta ttcagctaaa gaaaacaaag ttacagagtg    1200
tttcaagtgc cattcaccta tgtgacaaga agaaaatgga attatctctg aacatacctg    1260
taaatcatgg tccacaagag gaatcatgtg gatcctctca gctccatgaa atagtggtt     1320
ctcctgaaac ttcaaggtcc ctgccagctc ctcaagacaa tgattttta tctagaaaag    1380
ctcaagactg ttatttatg aagctgcatc actgtcctgg aaatcacagt tgggatagca   1440
ccatttctgg atctcaaagg gctgcattct gtgatcacaa gaccactcca tgctcttcag    1500
caataataaa tccactctca actgcaggaa actcagaacg tctgcagcct ggtatagccc    1560
agcagtggat ccagagcaaa agggaagaca ttgtgaacca atgacagaa gcctgcctta    1620
accagtcgct agatgcccctt ctgtccaggg acttgatcat gaaagaggac tatgaacttg   1680
ttagtaccaa gcctacaagg acctcaaaag tcagacaatt actagacact actgacatcc    1740
aaggagaaga atttgccaaa gttatagtac aaaaattgaa agataacaaa caaatgggtc    1800
ttcagcctta cccggaaata cttgtggttt ctagatcacc atctttaaat ttacttcaaa    1860
ataaaagcat gtaagtgact gttttttcaag aagaaatgtg tttcataaaa ggatatttat    1920
atctctgttg ctttgacttt ttttatataa aatccgtgag tattaaagct ttattgaagg    1980
ttctttgggt aaatattagt ctccctccat gacactgcag tattttttt aattaataca      2040
```

```
agtaaaaagt ttgaattttg ctacatagtt caatttttat gtctcttttg ttaacagaaa      2100
ccacttttaa aggatagtaa ttattcttgt ttataacagt gccttaaggt atgatgtatt      2160
tctgatggaa gccatttca cattcatgtt cttcatggat tatttgttac ttgtctaaga      2220
tgcaatttga ttttatgaag tatataccct ttacccacca gagacagtac agaatccctg      2280
ccctaaaatc ccaggcttaa ttgccctaca aagggttatt aatttaaaac tccattatta      2340
ggattacatt ttaaagtttt atttatgaat tccctttaaa aatgatattt caaaggtaaa      2400
acaatacaat ataaagaaaa aaataaatat attaataccg gcttcctgtc cccatttta      2460 acctcagcct tccctactgt caccaacaac caagctaaat aaagtcaaca gcctgatgtg      2520
t                                                                     2521

<210> SEQ ID NO 2
<211> LENGTH: 5537
<212> TYPE: DNA
<213> ORGANISM: Homo sapiens

<400> SEQUENCE: 2
gaacccggcg aggaaataca tgcactggct gagaatcgcc cgcgccaggg cgcaacgcca        60
caaggtgtag ggagtgtgcg gggtggggcg aaaggggacc caagagtccc tgtggctcgg       120
agtgccgggc cgtcggttct tcattcctgc cctcggggca gacggagtga ccccggcccc       180
cactccccgc cccgaccatg gtagtgttca atggccttct taagatcaaa atctgcgagg       240
ccgtgagctt gaagcccaca gcctggtcgc tgcgccatgc ggtgggaccc cggccgcaga       300 cttcttct cgaccctac attgccctca atgtggacga ctcgcgcatc ggccaaacgg       360
ccaccaagca gaagaccaac agcccggcct ggcacgacga gttcgtcacc gatgtgtgca       420
acggacgcaa gatcgagctg gctgtctttc acgatgcccc cataggctac gacgacttcg       480
tggccaactg caccatccag tttgaggagc tgctgcagaa cggagccgc cacttcgagg       540 actggattga tctggagcca gaaggaagag tgtatgtgat catcgatctc tcagggtcgt       600
cgggtgaagc ccctaaagac aatgaagagc gtgtgttcag ggaacgcatg cggccgagga       660
agcggcaggg ggccgtcagg cgcagggtcc atcaggtcaa cggccacaag ttcatggcca       720
cctatcttcg gcagcccacc tactgctccc attgcagaga cttcatctgg ggtgtcatag       780
gaaagcaggg ataccagtgt caagtctgca cctgcgtggt ccacaagcgg tgccacgagc       840
tcataatcac aaagtgtgct gggttaaaga agcaggagac ccccgaccag gtgggctccc       900
agcggttcag cgtcaacatg ccccacaagt tcggtatcca caactacaag gtccctacct       960
tctgcgatca ctgtgggtcc ctgctctggg gactcttgcg gcagggtttg cagtgtaaag      1020
tctgcaaaat gaatgttcac cgtcgatgtg agaccaacgt ggctcccaac tgtggagtgg      1080
atgccagaga atcgccaaa gtactggccg acctgggcgt tacccagac aaaatcacca      1140 acagcggcca gagaaggaaa aagctcattg ctggtgccga gtccccgcag cctgcttctg      1200
gaagctcacc atctgaggaa gatcgatcca agtcagcacc cacctcccct tgtgaccagg      1260
aaataaaaga acttgagaac aacattcgga aagccttgtc atttgacaac cgaggagagg      1320
agcaccgggc agcatcgtct cctgatggca agctgatgag cccggtgag aatggcgaag      1380 tccggcaagg ccaggccaag cgcctgggcc tggatgagtt caacttcatc aaggtgttgg      1440
gcaaaggcag ctttgcaag gtcatgttgg cagaactcaa gggcaaagat gaagtatatg      1500
ctgtgaaggt cttaaagaag gacgtcatcc ttcaggatga tgacgtggac tgcacaatga      1560
```

```
cagagaagag gattttggct ctggcacgga acacccgta ccttacccaa ctctactgct    1620
gcttccagac caaggaccgc ctcttttttcg tcatggaata tgtaaatggt ggagacctca   1680
tgtttcagat tcagcgctcc cgaaaattcg acgagcctcg ttcacggttc tatgctgcag   1740
aggtcacatc ggccctcatg ttcctccacc agcatggagt catctacagg gatttgaaac   1800
tggacaacat ccttctggat gcagaaggtc actgcaagct ggctgacttc gggatgtgca   1860
aggaagggat tctgaatggt gtgacgacca ccacgttctg tgggactcct gactacatag   1920
ctcctgagat cctgcaggag ttggagtatg cccctccgt ggactggtgg ccctggggg    1980
tgctgatgta cgagatgatg gctggacagc ctcccttga ggccgacaat gaggacgacc    2040
tatttgagtc catcctccat gacgacgtgc tgtacccagt ctggctcagc aaggaggctg   2100
tcagcatctt gaaagctttc atgacgaaga atccccacaa gcgcctgggc tgtgtggcat   2160
cgcagaatgg cgaggacgcc atcaagcagc acccattctt caaagagatt gactgggtgc   2220
tcctggagca gaagaagatc aagccaccct tcaaaccacg cattaaaacc aaaagagacg   2280
tcaataattt tgaccaagac tttacccggg aagagccggt actcacccctt gtggacgaag   2340
caattgtaaa gcagatcaac caggaggaat tcaaaggttt tcctactttt ggtgaagacc    2400
tgatgccctg agagcccact gcagttggac tttgccgatg ctgcaagaag gggtgcagag    2460
aagactcctg tgttggagac actcagcagg tcttgaacta cttctcctcc tcggagcccc   2520
agtcccatgt ccactgtcta tttattgcat tcccttgccc caggccacct cctccccctc   2580
ccacctggtg accagaaggc gctctcggtt cttgtctcac cagtaatgca gactcattgg   2640
gtcagcaatt agctgtatac actgccgtgt ttggaccatt ggcaagcctg gttccactcc   2700
tcagggctc ctggcagtga agcaacttca gttcttttac tgcaaagaac agaaaaaaga    2760
aagaaagcaa acaagaagac tccggctctg ctatcggaca cagatcctga tccctcttgc   2820
ttctttttccc tcctgcaccg cagcttgcca tccctgccct tctgtcctgg agaagagact   2880
ggtgcttctc cgcacacacg agggagggcg cccttgaggc atgccctctg agggagggag   2940
accagagatg cagggattgg ccagctgggt tggtttgctc tggaatggct aactcttgcc   3000
tgctttggtt ttagcttttc agcatgccaa agtcatgtaa gtttgtgtct tgtggaagaa   3060
atcctctttg tggaaaaaga acagggttt tgaactctgt taacatttga aaatatatt    3120
ttcaaattca ctttctaatt ggccaaaaga gatgagttcc agtctgaata caggtagata   3180
ttaaagggct aataaaaaat gagaaaccgg tcgtccaagg tggatgctgt caatgcccga   3240
gtgacacatg agagctgtat gaattgagag aaaaggcaac aagtagcatt cttcatcatt   3300
caagttctac ctggacacaa aggcgaggac cctggggttc caacaaagct cagctcccag   3360
attctctttc cagtttcatc ctaagttcct agcataaaca ctatttattt tctgcagcag   3420
tgtgttattt ttgcgcactt atacaaaatg gtagtactac tgtgttgtgg ttttttaaaca   3480
ttaaacatgt aaagttatat acgaaatatc tgcttttgga ataagcagaa tgaggctaaa   3540
catgggttat acaaagggta tctggaaact gaagagcaac ttgttagaaa actgacaatg   3600
tcgcaagatg tactcagttt tgtttctgtg tgacatgcaa tggcaactca tgtggacact   3660
attgaaggga tgtgacatta cctcctgtag atatgctaac agtgttattc tttcatttcc   3720
aagggttctc tgtggctttg tgtatatgtt tcccagaggt catttgatta cctaatttac   3780
tgaactgatt tagcagggaa tggaatccat tccaactatt gcacgtggat ttcccagctg   3840
cccctaaata tatatacttg tgagtggcaa agtggcacta atgaagcttt tgcctttttgt   3900
acatttgaga ttttttgtata tagtgtttgc tgcaaggcct gtggaattaa ttcgttgcat   3960
```

-continued

```
atagaggtat caactgctgc atgttcaggc atattataaa actttagtct atgaaagaat    4020
aattataata atgtccaggt gcaatactct gtaagtctat tggttcaagt taccgagaga    4080
taggtgtgtt cctttatggg ggatgggggg gtgtgttggg gattctttgt attgtttatt    4140
tcattttggt ttattttaaa agatgtaaac atatattaag ctatattaaa tctcacatac    4200
agttcttctg tgctctatta taccctgata gagatggggg agagaaagga atgttttga    4260 tggtggtttc aaagctcgga cagtaactat cttgagccca ttagagagtc tgtgtccata    4320
tttgcatctg gctggtcata gcctttgtta ctaatgatga cattcagttc tcttttgttt    4380 ttattttta aaaactcagg tgtaattatt atctgttctt aagataattg caaatattaa    4440
atattatgat atatcaattc atgtgtttgg cataccagtg aatgatgaag aacatgagat    4500
taatttaatt tatcttcggt aacttgacat tctggagaga gactatcttc tggagttgag    4560
tacaagcaca gaaacatctt tacgtgtggca tcatctcatt ttttaggaag acatgataat    4620
actgcccatc atattcatgt gtaactactg ttctttcttc tgctttcttc accataataa    4680
actttggaca accaagcaag ctctaaccgc aatgccagat ggccttgtcc gagggcctag    4740
tgtttgcacg gcagtgggaa ctgggccttt cctacaggac aactggcaag tttgctggga    4800
agtcaaataa tacattccac ctggcagctg aaggcagcca gtcagtctgt cccagaaagg    4860 gccctttca gcacccaaag ctgggctggc tgggatgcct ctggctggtg aagttctcac    4920
ataggctgat ttaaatccag caaaggtcta tagaaaaagg cttgcgtgtt cgttgagtaa    4980
tcattgtttc attttcattt ttacgagagt ttgaaaatag acacactgtt aacacttctg    5040 ccagttttt ctgatctttc cagccccacc ccctttctct ttctctctct ctctcaaaga    5100 aaaaaaaat gggagtgcaa aaaaacaaa gccaaaaaat atatgaagga tagctgttct    5160
tctgtgttct ctcattatgg actttgtgaa gtagaaacat aatttttttt cctccaaagg    5220 tgaaaaaca atgcattctt gctttaaaaa aaaaaaagaa ggctaaaaaa ttacctcttt    5280
ttaaattatg tgcaaaataa ttctggctaa ctgtaaaatg tattcaattt taggattttt    5340
tttttttgta ttgtgatgct ttattttgtac attttttttcc tttctggatg taattttaat    5400
ctcttgccat tcattagtgt tatttcattg taaacgttat tgtgccaaat gtactgtatt    5460
caaaaggatg tgaatgtgta ttgtttcaga acctaataaa tacaatgacg ttaagtctta    5520
aaaaaaaaaa aaaaaaa    5537
```

<210> SEQ ID NO 3
<211> LENGTH: 1969
<212> TYPE: DNA
<213> ORGANISM: Homo sapiens

<400> SEQUENCE: 3

```
gcccgcgggc ctcgccgccc cgcgcggatc gtcgcggccc ggccgtcccg tcccaggaag     60
tggccgtcct gagcgccatg gctcactccc cggtgcagtc gggcctgccc ggcatgcaga    120
acctaaaggc agacccagaa gagctttttta caaaactaga gaaaattggg aagggctcct    180
ttggagaggt gttcaaaggc attgacaatc ggactcagaa agtggttgcc ataaagatca    240
ttgatctgga agaagctgaa gatgagatag aggacattca acaagaaatc acagtgctga    300
gtcagtgtga cagtccatat gtaaccaaat attatggatc ctatctgaag gatacaaaat    360
tatggataat aatggaatat cttggtggag gctccgcact agatctatta gaacctggcc    420
cattagatga aacccagatc gctactatat taagagaaat actgaaagga ctcgattatc    480
```

```
tccattcgga gaagaaaatc cacagagaca ttaaagcggc caacgtcctg ctgtctgagc    540
atggcgaggt gaagctggcg gactttggcg tggctggcca gctgacagac acccagatca    600
aaaggaacac cttcgtgggc acccccattct ggatggcacc cgaggtcatc aaacagtcgg    660
cctatgactc gaaggcagac atctggtccc tgggcataac agctattgaa cttgcaagag    720
gggaaccacc tcattccgag ctgcacccca tgaaagtttt attcctcatt ccaaagaaca    780
acccaccgac gttggaagga aactacagta aaccsctcaa ggagtttgtg gaggcctgtt    840
tgaataagga gccgagcttt agacccactg ctaaggagtt attgaagcac aagtttatac    900
tacgcaatgc aaagaaaact tcctacttga ccgagctcat cgacaggtac aagagatgga    960
aggccgagca gagccatgac gactcgagct ccgaggattc cgacgcggaa acagatggcc   1020
aagcctcggg gggcagtgat tctggggact ggatcttcac aatccgagaa aaagatccca   1080
agaatctcga gaatggagct cttcagccat cggacttgga cagaaataag atgaaagaca   1140
tcccaaagag gcctttctct cagtgtttat ctacaattat ttctcctctg tttgcagagt   1200
tgaaggagaa gagccaggcg tgcggaggga acttgggttc cattgaagag ctgcgagggg   1260
ccatctacct agcggaggag gtgtgccctg catctccga caccatggtg cccagctcg    1320 tgcagcggct ccagagatac tctctaagtg gtggaggaac ttcatcccac tgaaattcct   1380
ttggcatttg gggttttgtt tttccttttt tccttcttca tcctcctcct tttttaaaag   1440
tcaacgagag ccttcgctga ctccaccgaa gaggtgcgcc actgggagcc accccagcsc   1500
caggcgcccg tccagggaca cacacagtct tcgctgtgct gcagccagat gaagtctctc   1560
agatgggtgg ggagggtcag ctccttccag cgatcatttt attttatttt attackttg   1620 tttttaattt taaccatagc gcacatattc caggaaagtg tctttaaaaa caaaaacaaa   1680
ccctgaaatg tatatttggg attatgataa ggcaactaaa gacatgaaac ctcaggtatc   1740
ctgctttaag ttgataactc cctctgggag ctggagaatc gctctggtgg atgggtgtac   1800
agatttgtat ataatgtcat ttttacggaa acccttctgg cgtgcataag gaatcactgt   1860
gtacaaactg gccaagtgct tctgtagata acgtcagtgg agtaaatatt cgacaggcca   1920
taacttgagt ctattgcctt gcctttatta catgtacatt ttgaattcc                1969

<210> SEQ ID NO 4
<211> LENGTH: 2505
<212> TYPE: DNA
<213> ORGANISM: Homo sapiens

<400> SEQUENCE: 4 tttggggttag ggagagtgct ttcgtttgtt ttaaatggga gaaactggag catgttgcca     60
aggcagagag ccagcagaga ggggtgaatg gaagaaggag cgaaaggggg gttactgacg    120
aagccttatc ctggaggaga gaaggatgga ctccagagcc cagctttggg gactggcctt    180
gaataaaagg agggccactc tacctcatcc tggagggagc acgaacctaa aggcagaccc    240
agaagagctt tttacaaaac tagagaaaat tgggaagggc tcctttggag aggtgttcaa    300
aggcattgac aatcggactc agaaagtggt tgccataaag atcattgatc tggaagaagc    360
tgaagatgag atagaggaca ttcaacaaga atcacagtg ctgagtcagt gtgacagtcc    420
atatgtaacc aaatattatg gatcctatct gaaggataca aaattatgga taataatgga    480
atatcttggt ggaggctccg cactagatct attagaacct ggcccattag atgaacccca    540
gatcgctact atattaagag aaatactgaa aggactcgat tatctccatt cggagaagaa    600
aatccacaga gacattaaag cggccaacgt cctgctgtct gagcatggcg aggtgaagct    660
```

```
ggcggacttt ggcgtggctg gccagctgac agacacccag atcaaaagga acaccttcgt    720
gggcacccca ttctggatgg cacccgaggt catcaaacag tcggcctatg actcgaaggc    780
agacatctgg tccctgggca taacagctat tgaacttgca agaggggaac cacctcattc    840
cgagctgcac cccatgaaag ttttattcct cattccaaag aacaacccac cgacgttgga    900
aggaaactac agtaaacccc tcaaggagtt tgtggaggcc tgtttgaata aggagccgag    960
ctttagaccc actgctaagg agttattgaa gcacaagttt atactacgca atgcaaagaa   1020
aacttcctac ttgaccgagc tcatcgacag gtacaagaga tggaaggcca gcagagcca    1080 tgacgactcg agctccgagg attccgacgc ggaaacagat ggccaagcct cgggggggcag   1140 tgattctggg gactggatct tcacaatccg agaaaaagat cccaagaatc tcgagaatgg   1200
agctcttcag ccatcggact tggacagaaa taagatgaaa gacatcccaa agaggccttt   1260
ctctcagtgt ttatctacaa ttatttctcc tctgtttgca gagttgaagg agaagagcca   1320
ggcgtgcgga gggaacttgg ggtccattga agagctgcga ggggccatct acctagcgga   1380
ggaggcgtgc cctggcatct ccgacaccat ggtggcccag ctcgtgcagc ggctccagag   1440
atactctcta agtggtggag gaacttcatc ccactgaaat tcctttggca tttggggttt   1500 tgttttcct ttttccttc ttcatcctcc tccttttta aaagtcaacg agagccttcg      1560
ctgactccac cgaagaggtg cgccactggg agccaccca cgccaggcg cccgtccagg      1620 gacacacaca gtcttcactg tgctgcagcc agatgaagtc tctcagatgg gtggggaggg   1680
tcagctcctt ccagcgatca tttattttta ttttattact tttgttttta attttaacca   1740
tagtgcacat attccaggaa agtgtcttta aaaacaaaaa caaaccctga aatgtatatt   1800
tgggattatg ataaggcaac taaagacatg aaacctcagg tatcctgctt taagttgata   1860
actccctctg gagcttggag aatcgctctg gtggatgggt gtacagattt gtatataatg   1920
tcatttttac ggaaaccctt tcggcgtgca taaggaatca ctgtgtacaa actggccaag   1980
tgcttctgta gataacgtca gtggagtaaa tattcgacag gccataaact tgagtctatt   2040
gccttgcctt tattacatgt acattttgaa ttctgtgacc agtgatttgg gttttatttt   2100
gtatttgcag ggtttgtcat taataattaa tgcccctctc ttacagaaca ctcctatttg   2160
tacctcaaca aatgcaaatt ttccccgttt gccctacgcc ccttttggta cacctagagg   2220
ttgatttcct tttcatcga tggtactatt tcttagtgtt ttaaattgga acatatcttg    2280
cctcatgaag ctttaaatta taattttcag tttctcccca tgaagcgctc tcgtctgaca   2340
tttgtttgga atcgtgccac tgctggtctg cgccagatgt accgtccttt ccaatacgat   2400
tttctgttgc accttgtagt ggattctgca tatcatcttt cccacctaaa aatgtctgaa   2460
tgcttacaca aataaatttt ataacacgct taaaaaaaaa aaaaa                    2505

<210> SEQ ID NO 5
<211> LENGTH: 2060
<212> TYPE: DNA
<213> ORGANISM: Homo sapiens

<400> SEQUENCE: 5
gcggccgcgt ggggcccagc acaaagacct gtccccaggg gccgccgcct ccgccgctgc      60
tgctgccgcc agcctagagc cgcccgccga agcagagccg gcgccggggt cctcatcccc     120
accggtcccg aggggcggct gctgcccgtc gccacgaggc ccaggggccc gagtgccgag     180 cccttttgctc cctcggccgc gcggggacag ggctgctgag cagcctccgc ctctcccggc    240
```

| | |
|---|---:|
| tgtgggggcc ccactgagta tgtcggagga gagcgacatg gacaaagcca tcaaggaaac | 300 |
| ttccatttta gaagaataca gtatcaattg gactcagaag ctgggagctg gaattagtgg | 360 |
| tccagttaga gtctgtgtaa agaaatctac tcaagaacgg tttgcgctga aaattcttct | 420 |
| tgatcgtcca aaagctagaa atgaggtacg tctgcacatg atgtgtgcca cacacccaaa | 480 |
| catagttcag attattgaag tgtttgctaa cagtgtccag tttccccatg agtccagccc | 540 |
| tagggcccga ctcttaattg taatggagat gatggaaggg ggagagctat ttcacagaat | 600 |
| cagccagcac cggcacttta cagagaagca agccagccaa gtaacaaagc agatagcttt | 660 |
| ggctctgcgg cactgtcact tgttaaacat tgcgcacaga gacctcaagc ctgaaaatct | 720 |
| gcttttaag gataactctt tggatgcccc agtgaagttg tgtgactttg gatttgccaa | 780 |
| gattgaccaa ggtgacttga tgacacccca gttcaccect tattatgtag caccccaggt | 840 |
| actggaggcg caagaaggc atcagaagga gaaatctggc atcataccta cctcaccgac | 900 |
| gccctacact tacaacaaga gctgtgactt gtggtcccta ggggtgatta tctatgtgat | 960 |
| gctgtgcgga taccctcctt tttactccaa acaccacagc cggactatcc caaaggatat | 1020 |
| gcgaagaaag atcatgacag gcagttttga gttcccagag aagagtgga gtcagatctc | 1080 |
| agagatggcc aaagatgttg tgaggaagct cctgaaggtc aaaccggagg agagactcac | 1140 |
| catcgaggga gtgctggacc acccctggct caattccacc gaggccctgg ataatgtgct | 1200 |
| gccttctgct cagctgatga tggacaaggc agtggttgca ggaatccagc aggctcacgc | 1260 |
| ggaacagttg gccaacatga gaatccagga tctgaaagtc agcctcaaac ccctgcactc | 1320 |
| agtgaacaac cccattctgc ggaagaggaa gttacttggc accaagccaa aggacagtgt | 1380 |
| ctatatccac gaccatgaga atggagccga ggattccaat gttgccttgg aaaaactccg | 1440 |
| agatgtgatt gctcagtgta ttctcccccca ggctggagag aatgaagatg agaaactgaa | 1500 |
| tgaagtaatg caggaggctt ggaagtataa ccgggaatgc aaactcctaa gagatactct | 1560 |
| gcagagcttc agctggaatg gtcgtggatt cacagataaa gtagatcgac taaaactggc | 1620 |
| agaaattgtg aagcaggtga tagaagagca aaccacgtcc cacgaatccc aataatgaca | 1680 |
| gcttcagact ttgttttttt aacaatttga aaaattattc tttaatgtat aaagtaattt | 1740 |
| tatgtaaatt aataaatcat aatttcattt ccacattgat taaagctgct gtatagattt | 1800 |
| agggtgcagg acttaataat agtatagtta ttgtttgttt ttaagaaaag ctcagttcta | 1860 |
| gagacatact attactttag gactgtgtag ttgtatattt gtaagatgac agatgatgct | 1920 |
| gtcaagcaat attgttttat ttgtaataaa atatacaaaa atcacttgcc agcagtagaa | 1980 |
| aaaggaccga ctataccgac ctttctgatt agtaaacagt tgaatcaagg actctggaaa | 2040 |
| aaaaaaaaaa aaaaaaaaa | 2060 |

<210> SEQ ID NO 6
<211> LENGTH: 2066
<212> TYPE: DNA
<213> ORGANISM: Homo sapiens

<400> SEQUENCE: 6

| | |
|---|---:|
| gcggccgcgt ggggcccagc acaaagacct gtccccaggg gccgccgcct ccgccgctgc | 60 |
| tgctgccgcc agcctagagc cgcccgccga agcagagccg cgccggggt cctcatcccc | 120 |
| accggtcccg aggggcggct gctgcccgtc gccacgaggc ccaggggccc gagtgccgag | 180 |
| ccctttgctc cctcggccgc gcggggacag ggctgctgag cagcctccgc ctctcccggc | 240 |
| tgtgggggcc ccactgagta tgtcggagga gagcgacatg gacaaagcca tcaaggaaac | 300 |

-continued

```
ttccatttta gaagaataca gtatcaattg gactcagaag ctgggagctg gaattagtgg      360
tccagttaga gtctgtgtaa agaaatctac tcaagaacgg tttgcgctga aaattcttct      420
tgatcgtcca aaagctagaa atgaggtacg tctgcacatg atgtgtgcca cacacccaaa      480
catagttcag attattgaag tgtttgctaa cagtgtccag tttccccatg agtccagccc      540
tagggcccga ctcttaattg taatggagat gatggaaggg ggagagctat ttcacagaat      600
cagccagcac cggcacttta cagagaagca agccagccaa gtaacaaagc agatagcttt      660
ggctctgcgg cactgtcact tgttaaacat tgcgcacaga gacctcaagc ctgaaaatct      720 gcttttaag gataactctt tggatgcccc agtgaagttg tgtgactttg gatttgccaa       780
gattgaccaa ggtgacttga tgacacccca gttcaccccct tattatgtag caccccaggt    840
actggaggcg caaagaaggc atcagaagga gaaatctggc atcataccta cctcaccgac     900
gccctacact tacaacaaga gctgtgactt gtggtcccta ggggtgatta tctatgtgat     960
gctgtgcgga tacctccctt tttactccaa acaccacagc cggactatcc caaaggatat    1020
gcgaagaaag atcatgacag gcagttttga gttcccagag aagagtggag gtcagatctc   1080
agagatggcc aaagatgttg tgaggaagct cctgaaggtc aaaccggagg agagactcac  1140
catcgaggga gtgctggacc accctggct caattccacc gaggccctgg ataatgtgct   1200
gccttctgct cagctgatga tggacaaggc agtggttgca ggaatccagc aggctcacgc   1260
ggaacagttg gccaacatga gaatccagga tctgaaagtc agcctcaaac ccctgcactc   1320
agtgaacaac cccattctgc ggaagaggaa gttacttggc accaagccaa aggacagtgt   1380
ctatatccac gaccatgaga atggagccga ggattccaat gttgccttgg aaaaactccg   1440
agatgtgatt gctcagtgta ttctccccca ggctggtaaa ggagagaatg aagatgagaa   1500
actgaatgaa gtaatgcagg aggcttggaa gtataaccgg gaatgcaaac tcctaagaga   1560
tactctgcag agcttcagct ggaatggtcg tggattcaca gataaagtag atcgactaaa   1620
actggcagaa attgtgaagc aggtgataga agagcaaacc acgtcccacg aatcccaata   1680
atgacagctt cagactttgt ttttttaaca atttgaaaaa ttattcttta atgtataaag   1740 taatttatg taaattaata aatcataatt tcatttccac attgattaaa gctgctgtat     1800
agatttaggg tgcaggactt aataatagta tagttattgt ttgttttttaa gaaaagctca   1860 gttctagaga catactatta ctttaggact gtgtagttgt atatttgtaa gatgacagat    1920
gatgctgtca agcaatattg tttttatttgt aataaaatat acaaaaatca cttgccagca   1980
gtagaaaaag gaccgactat accgaccttt ctgattagta aacagttgaa tcaaggactc    2040
tggaaaaaaa aaaaaaaaaa aaaaaa                                        2066
```

<210> SEQ ID NO 7
<211> LENGTH: 2736
<212> TYPE: DNA
<213> ORGANISM: Homo sapiens

<400> SEQUENCE: 7

```
gcgaccgctc cccggcggga gccagcgaag gtttccatgt cagaggccga tggagaactg      60
aagattgcca cctacgcaca aaggccattg agacacttcg tgtagctgga agacaccaac      120
ttcctgacag gagctttatt tcatttggga tttcaagttt acagatggta tcttctcaaa      180
agttggaaaa acctatagag atgggcagta gcgaacccct tcccatcgca gatggtgaca     240
ggaggaggaa gaagaagcgg aggggccggg ccactgactc cttgccagga aagtttgaag    300
```

-continued

```
atatgtacaa gctgacctct gaattgcttg gagagggagc ctatgccaaa gttcaaggtg    360
ccgtgagcct acagaatggc aaagagtatg ccgtcaaaat catcgagaaa caagcagggc    420
acagtcggag tagggtgttt cgagaggtgg agacgctgta tcagtgtcag ggaaacaaga    480
acattttgga gctgattgag ttctttgaag atgacacaag gttttacttg gtctttgaga    540
aattgcaagg aggttccatc ttagcccaca tccagaagca aaagcacttc aatgagcgag    600
aagccagccg agtggtgcgg gacgttgctg ctgcccttga cttcctgcat accaaagaca    660
aagtctctct ctgtcaccta ggctggagtg ctatggcgcc atcagggctc actgcagccc    720
caacctccct gggctccagt gatcctccca cctcagcctc caagtagct gggactacag    780 gcattgctca tcgtgatctg aaaccagaaa atatattgtg tgaatctcca gaaaaggtgt    840
ctccagtgaa aatctgtgac tttgacttgg gcagtgggat gaaactgaac aactcctgta    900
cccccataac cacaccagag ctgaccaccc catgtggctc tgcagaatac atggcccctg    960
aggtagtgga ggtcttcacg gaccaggcca cattctacga caagcgctgt gacctgtgga   1020
gcctgggcgt ggtcctctac atcatgctga gtggctaccc acccttcgtg ggtcactgcg   1080
gggccgactg tggctgggac cggggcgagg tctgcagggt gtgccagaac aagctgtttg   1140
aaagcatcca ggaaggcaag tatgagtttc ctgacaagga ctgggcacac atctccagtg   1200
aagccaaaga cctcatctcc aagctcctgg tgcgagatgc aaagcagaga cttagcgccg   1260
cccaagttct gcagcaccca tgggtgcagg ggcaagctcc agaaaaggga ctccccacgc   1320
cgcaagtcct ccagaggaac agcagcacaa tggacctgac gctcttcgca gctgaggcca   1380
tcgcccttaa ccgccagcta tctcagcacg aagagaacga actagcagag gagccagagg   1440
cactagctga tggcctctgc tccatgaagc tttcccctcc ctgcaagtca cgcctggccc   1500
ggagacgggc cctggcccag gcaggccgtg gtgaagacag gagcccgccc acagcactct   1560
gaaatgctcc agtcacacct tataggcccct aggcctggcc aggcattgtc ccctggaaac   1620
ctgtgtggct aaagtctgct gagcaggcag cagcctctgc tctgtggctc cattcaggct   1680
ttttcatcta cgaaggccct gaggttccca tcaaccccca tttccctagg gtcctggagg   1740
aaaaagcttt ttccaaaggg gttgtctttg aaaaggaaag caatcacttc tcactttgca   1800
taattgcctg cagcaggaac atctcttcac tgggctccac ctgctcaccc gcctgcagat   1860
ctgggatcca gcctgctctc accgctgtag ctgtggcggc tggggctgca gcctgcaggg   1920
agaagcaaga agcatcagtt gacagaggct gccgacacgt gcctcttccc tctcttctct   1980
gtcaccctcc tctggcggtc cttccacctt cctctgtcct ccggatgtcc tctttgcccg   2040
tcttctccct tggctgagca aagccatccc ctcaattcag ggaagggcaa ggagccttcc   2100
tcattcagga aatcaaatca gtcttccggt ctgcagcacg aaaagcaca taatctttct    2160 ttgctgtgac tgaaatgtat ccctcgttta tcatcccctt tgtttgtgat tgctgctaaa   2220
gtcagtagta tcgttttttt aaaaaaaaag tttggtgttt ttaaccatgc tgttccagca   2280
aagatgatac cttaaactcc cactgcaagc ccatgaactt cccagagagt ggaacggctt   2340
gctcttcttt ctagaatgtc catgcacttg ggttttaatc agcagttccc tattattctg   2400 atttttaagct gttcctgtga tgaacttaga gacagcatcg tgtctgctg ctgtgtcccc    2460 aggtcttgtg tgggtggcac agatctgggc agttagatag tgctctgtgc ctaaggtgaa   2520
gccacactag ggtgaagcct cacttccctg tttgagcaat gcagtgcctg ctgcccgtgt   2580
gcatgaaggt acagccattc agataagtgg aactattgag ttcataaag aaaatagatt     2640 tgcatttgtc aggcagacgt ttatacaaca ccacggtgct tttatacatt gtgcttattt   2700
```
taataaaact gaaattctaa aaaaaaaaaa aaaaaa        2736

<210> SEQ ID NO 8
<211> LENGTH: 2168
<212> TYPE: DNA
<213> ORGANISM: Homo sapiens

<400> SEQUENCE: 8

| | | | | | |
|---|---|---|---|---|---|
| ctctctcgct | cctgcgttcg | caggcggcgg | ctggcggccg | gcttctcgct | cgggcagcgg | 60 |
| cggcggcggc | ggcggcggct | tccggagtcc | cgctgcgaag | atgctcaaag | tcacggtgcc | 120 |
| ctcctgctcc | gcctcgtcct | gctcttcggt | caccgccagt | gcggcccogg | ggaccgcgag | 180 |
| cctcgtcccg | gattactgga | tcgacggctc | caacagggat | gcgctgagcg | atttcttcga | 240 |
| ggtggagtcg | gagctgggac | ggggtgctac | atccattgtg | tacagatgca | aacagaaggg | 300 |
| gacccagaag | ccttatgctc | tcaaagtgtt | aaagaaaaca | gtggacaaaa | aaatcgtaag | 360 |
| aactgagata | ggagttcttc | ttcgcctctc | acatccaaac | attataaaac | ttaaagagat | 420 |
| atttgaaacc | cctacagaaa | tcagtctggt | cctagaactc | gtcacaggag | gagaactgtt | 480 |
| tgataggatt | gtggaaaagg | gatattacag | tgagcgagat | gctgcagatg | ccgttaaaca | 540 |
| aatcctggag | gcagttgctt | atctacatga | aaatgggatt | gtccatcgtg | atctcaaacc | 600 |
| agagaatctt | ctttatgcaa | ctccagcccc | agatgcacca | ctcaaaatcg | ctgattttgg | 660 |
| actctctaaa | attgtggaac | atcaagtgct | catgaagaca | gtatgtggaa | ccccagggta | 720 |
| ctgcgcacct | gaaattctta | gaggttgtgc | ctatggacct | gaggtggaca | tgtggtctgt | 780 |
| aggaataatc | acctacatct | tactttgtgg | atttgaacca | ttctatgatg | aaagaggcga | 840 |
| tcagttcatg | ttcaggagaa | ttctgaattg | tgaatattac | tttatctccc | cctggtggga | 900 |
| tgaagtatct | ctaaatgcca | aggacttggt | cagaaaatta | attgttttgg | atccaaagaa | 960 |
| acggctgact | acatttcaag | ctctccagca | tccgtgggtc | acaggtaaag | cagccaattt | 1020 |
| tgtacacatg | gataccgctc | aaaagaagct | ccaagaattc | aatgcccggc | gtaagcttaa | 1080 |
| ggcagcggtg | aaggctgtgg | tggcctcttc | gcgcctggga | agtgccagca | gcagccatgg | 1140 |
| cagcatccag | gagagccaca | aggctagccg | agacccttct | ccaatccaag | atggcaacga | 1200 |
| ggacatgaaa | gctattccag | aaggagagaa | aattcaaggc | gatgggggcc | aagccgcagt | 1260 |
| taagggggca | caggctgagc | tgatgaaggt | gcaagcctta | gagaaagtta | aggtgcaga | 1320 |
| tataaatgct | gaagaggccc | ccaaaatggt | gcccaaggca | gtggaggatg | ggataaaggt | 1380 |
| ggctgacctg | gaactagagg | agggcctagc | agaggagaag | ctgaagactg | tggaggaggc | 1440 |
| agcagctccc | agagaagggc | aaggaagctc | tgctgtgggt | tttgaagttc | cacagcaaga | 1500 |
| tgtgatcctg | ccagagtact | aaacagcttc | cttcagatct | ggaagccaaa | caccggcatt | 1560 |
| ttatgtactt | tgtccttcag | caagaaaggt | gtggaagcat | gatatgtact | atagtgattc | 1620 |
| tgttttttgag | gtgcaaaaaa | catacatata | taccagttgg | taattctaac | ttcaatgcat | 1680 |
| gtgactgctt | tatgaaaata | atagtgtctt | ctatggcatg | taatggatac | ctaataccga | 1740 |
| tgagttaaat | cttgcaagtt | aacacaacgt | aacacttaaa | agcatacatt | ttcagcaacc | 1800 |
| agtggcacat | atttgaagtg | aatagtagca | aattgttttt | gctttgaaaa | tctagccatc | 1860 |
| ctacatcctt | tggatttctt | cacaaggcag | taattccttt | gaactactgc | ttagctaata | 1920 |
| ctaggtagtg | ctaaaagaca | tgttcccata | acttttacaa | cattttactt | tttatcattg | 1980 |
| atgtgttcaa | actgtttaca | aggagatgct | tatagatgat | agttgtacat | atgtgcaaaa | 2040 |

| | |
|---|---:|
| aaaaatccac ttgcaatggt aagaaattga agtatcctta aaggccatga agccatatgt | 2100 |
| ccctaaaaaa aaaaaaaaaa aaaaaaaaaa aaaaaaaaaa aaaaaaaaaa aaaaaaaaaa | 2160 |
| aaaaaaaa | 2168 |

<210> SEQ ID NO 9
<211> LENGTH: 1634
<212> TYPE: DNA
<213> ORGANISM: Homo sapiens

<400> SEQUENCE: 9

| | |
|---|---:|
| ccctgctaac aaagggagcc acttccttcc tctctgcaca tacccccatgt ctcaccacga | 60 |
| tgatggagct acagtgggac ttggaatcca gatgtgtgaa ggatggaggg ttgaagccgc | 120 |
| actcagcttc ctgccccacc agaggaagtg gggagacg gcaggtgcag tgatggctgg | 180 |
| cggagtcatg gacaaggagt acgtgggttt tgctgccctc cccaaccagc tgcaccgcaa | 240 |
| gtctgtcaag aaggggtttg acttcacgct aatggtggca ggggagtcag gcctagggaa | 300 |
| atccacctc atcaacagcc tcttcctcac caacctctat gaggatcgcc aggtgccaga | 360 |
| ggccagtgct cgcttgacac agaccctggc cattgagcgc cggggcgtag agattgagga | 420 |
| agggggtgtg aaagtgaagc tgaccccttgt ggacacacct ggctttgggg actcagtgga | 480 |
| ctgctctgac tgctggcttc cggtggtgaa attcatcgag gagcaatttg agcagtacct | 540 |
| tagggatgag agtggcctga accggaagaa catccaggac tcccgagtcc actgctgcct | 600 |
| ctacttcatc tcacccttcg gccgggggct ccggccccta gatgtggcct tcctccgggc | 660 |
| agtacacgag aaagtcaaca tcatcccagt cattggcaaa gcggatgctc tgatgcccca | 720 |
| ggaaacccag gccctcaagc agaagatccg ggatcagttg aaggaagagg agatccacat | 780 |
| ctaccagttc cccgaatgtg actctgatga agatgaagac ttcaagaggc aggatgcaga | 840 |
| gatgaaggaa agcatccctt ttgcagtcgt gggatcatgc gaggtggtga gggatggcgg | 900 |
| gaaccggccg gtgaggggac gccgctactc ctgggggacc gtggaggtgg agaacccaca | 960 |
| tcactgcgat ttcctgaacc tgcgacggat gctggtgcag acacacctgc aggacctgaa | 1020 |
| agaggtgacg cacgatctgc tctacgaggg ctaccgggcc cgctgcctac agagcctggc | 1080 |
| ccggcctggg gctcgcgatc gagccagccg cagtaagctt tcccgccaga gcgccacaga | 1140 |
| gatcccgctg cccatgctgc ctctggcgga caccgagaag ctgatccgcg agaaagacga | 1200 |
| agagctgcgc cgcatgcaag agatgctgga gaagatgcag gcccaaatgc agcagagcca | 1260 |
| ggcccagggc gagcagtcag acgccctctg aggccacgcc ccgcccggcc ttacctcggc | 1320 |
| tccgccttca gtcggcctct tgtccaatcc ccgcgcccca cactgcccag cgccccccgg | 1380 |
| gacctccgcg ggtgccgccc tcgcgcgggc taggggagg ttctcccagc ctgagtccgt | 1440 |
| agccccgccc cggcgctggt cccgcccacc cagacaccgc ccacttcccg gcccggggcc | 1500 |
| tgcacaatct ccgaccgcat cactgtcttc cggagtcccc cttcttctcc cagactctgt | 1560 |
| cttcaataaa aactgagctt cccgcggcca aaaaaaaaa aaaaaaaaa aaaaaaaaa | 1620 |
| aaaaaaaaaa aaaa | 1634 |

<210> SEQ ID NO 10
<211> LENGTH: 747
<212> TYPE: DNA
<213> ORGANISM: Homo sapiens

<400> SEQUENCE: 10

| | |
|---|---:|
| ccgagatgtg cagcggcaca gctgtcgcgc cagtcgcaac agaagcaggt ccgaggcaca | 60 |

-continued

| | |
|---|---|
| gcccgatccc gccatggagc agccgaggaa ggcggtggta gtgacgggat ttggccctttt | 120 |
| tggggaacac accgtgaacg ccagttggat tgcagttcag gagctagaaa agctaggcct | 180 |
| tggcgacagc gtggacctgc atgtgtacga gattccggtt gagtaccaaa cagtccagag | 240 |
| actcatcccc gccctgtggg agaagcacag tccacagctg gtggtgcatg tgggggtgtc | 300 |
| aggcatggcg accacagtca cactggagaa atgtggacac aacaagggct acaaggggct | 360 |
| ggacaactgc cgcttttgcc ccggctccca gtgctgcgtg gaggacgggc ctgaaagcat | 420 |
| tgactccatc atcgacatgg atgctgtgtg caagcgagtc accacgttgg gcctggatgt | 480 |
| gtcggtgacc atctcgcagg atgccggcag gaaaaaaccc ttccctgcca aggtgactg | 540 |
| tgttttctgc cgccgaagga gggcccggtc cctccaggct cagtgtggct tctccctgac | 600 |
| ccccgcccta gaacttttgc cagtgccttt tctgaaactc ctgtgtcccg gccccccag | 660 |
| gcggagaagg atatgccgga ttctgcctgg ggctgggctc taggagaccc caaatttgac | 720 |
| accacagaac gcacatacta cacttga | 747 |

<210> SEQ ID NO 11
<211> LENGTH: 2239
<212> TYPE: DNA
<213> ORGANISM: Homo sapiens

<400> SEQUENCE: 11

| | |
|---|---|
| agtcgcaaca gaagcaggtc cgaggcacag cccgatcccg ccatggagca gccgaggaag | 60 |
| gcggtggtag tgacgggatt tggcccttt ggggaacaca ccgtgaacgc cagttggatt | 120 |
| gcagttcagg agctagaaaa gctaggcctt ggcgacagcg tggacctgca tgtgtacgag | 180 |
| attccggttg agtaccaaac agtccagaga ctcatccccg ccctgtggga agcacagt | 240 |
| ccacagctgg tggtgcatgt gggggtgtca ggcatggcga ccacagtcac actggagaaa | 300 |
| tgtggacaca acaagggcta caaggggctg acaactgcc gcttttgccc cggctcccag | 360 |
| tgctgcgtgg aggacgggcc tgaaagcatt gactccatca tcgacatgga tgctgtgtgc | 420 |
| aagcgagtca ccacgttggg cctggatgtg tcggtgacca tctcgcagga tgccggcaga | 480 |
| tatctctgcg actttaccta ctacacctct ttgtaccaga gtcacggtcg atcagccttc | 540 |
| gtccacgtgc ccccactggg gaagccgtac aacgcggacc agctgggcag ggcactgaga | 600 |
| gccatcattg aggagatgtt ggacctcctg gagcagtcag agggcaaaat caactattgc | 660 |
| cacaaacact gagggacgct caggtctcct aagacctcat cctgctgggg accccacgag | 720 |
| gggacatcca ccctctgggg tgtggccagg aaaagacaag ctcttcagct tggggatccg | 780 |
| atctggaaga gagattctga tctgcccacc tcctcttcct tcttctctac aaaagctccg | 840 |
| gttgattcga gggaagtggt gaaaattttt tttctccca ttttcctccc tgcatctggg | 900 |
| gacacagctg ccgtgaccag ggaggccagc ctgggaggtc cagatgccca gggagaatct | 960 |
| tggtctggtg aatccatgag ctgagatacc acggctgggg ccatatgttc acctgctttc | 1020 |
| ctgtccgttg gtgaaggaat tcagaattc attttatatc caagactggc ttttaccaaa | 1080 |
| tttaaaagcc tctcaatgcg tcctcgacct tgaactgtgc tcaacagcct ggcccttttct | 1140 |
| ggggccaccc tgggatatgg ctggctggct ggctggcttt cttttctttct ttctttcttt | 1200 |
| ctttctttct tctttctttt ctttctttct ttctgctttt cttcttgct ttcttcttg | 1260 |
| ctttctttct ttcttgcttt ctttctttctc tctctctctt tttttttttt ttaaatagtg | 1320 |
| ctagtttggg cacagagtaa tttatattcc ctttggttaa aatgcaggct ttttagccaa | 1380 |

-continued

```
caacaaaagt gttttcccccc caccccccact cgcccaccag ggtgatgcca ctttttgcctc      1440 ctgcccctgaa aattggactt aagatgccat gtcttggctg ggattacagg catgagccac      1500
tgcacccagc ccagttctttt cttaaaacag ctgagagttt tgttttcttc agcgttcacc      1560
ttccttgtct ccagttccga tgctggcagt ggttcctacc tctgttgggt ttctagatag      1620
tttgggaacg gggttgatgg gtttctgtga aacacatttt ccaagtcttg ggctttctct      1680
ggaggggaag gtggatgctg gcgggtgact tgcagtgggc cctggcagt gggtgtggac      1740 tgtaactgac aggtggaaat gagtaggggc actattgttc cctccatgcc agcttttttt      1800
ttgctggaaa tgccccctcc acacccctgg tagctctgtg tcctgagaaa tccagagtgt      1860
gggagacatc actgcatctg tccccccagc ttctgtgaag ggaagctgtg gcctcttttg      1920
aatgtgggga caactgaag actcaggggt cacccagagg tctggtggaa agcaacttca      1980
ggtttcatct tgctctattc ctcaaaggtc tggtctgtgg gcctctgagg agaaaacagg      2040
tctagccaag acaggggacaa aatggggaag ggggtgtgcc aggcctgaac tgagctaagc      2100
acctgccccg ggctccacac ttccatctttt cttttgtctt catttcacct ctgtgtttaa      2160
agcactgtgt gacatagctc cttagagata taacctattg tctgctcatt gtcaaaaaaa      2220
aaaaaaaaaa aaaaaaaaa                                                    2239

<210> SEQ ID NO 12
<211> LENGTH: 1531
<212> TYPE: DNA
<213> ORGANISM: Homo sapiens

<400> SEQUENCE: 12
agtcacagag ggaacacaga gcctagttgt aaacggacag agacgagagg ggcaagggag        60
gacagtggat gacagggaag acgagtgggg gcagagctgc tcaggaccat ggctgaggcc       120
atcacctatg cagatctgag gtttgtgaag gctcccctga agaagagcat ctccagccgg       180
ttaggacagg acccaggggc tgatgatgat ggggaaatca cctacgagaa tgttcaagtg       240
cccgcagtcc tagggggtgcc ctcaagcttg gcttcttctg tactagggga caaagcagcg       300
gtcaagtcgg agcagccaac tgcgtcctgg agagccgtga cgtcaccagc tgtcgggcgg       360
attctcccct gccgcacaac ctgcctgcga tacctcctgc tcggcctgct cctcacctgc       420
ctgctgttag gagtgaccgc catctgcctg ggagtgcgct atctgcaggt gtctcagcag       480
ctccagcaga cgaacagggt tctggaagtc actaacagca gcctgaggca gcagctccgc       540
ctcaagataa cgcagctggg acagagtgca gaggatctgc agggggtccag gagagagctg       600 gcgcagagtc aggaagcact acaggtggaa cagagggctc atcaggcggc cgaagggcag       660
ctacaggcct gccaggcaga cagacagaag acgaaggaga ccttgcaaag tgaggagcaa       720
cagaggaggg ccttggagca gaagctgagc aacatggaga acagactgaa gcccttcttc       780
acatgcggct cagcagacac ctgctgtccg tcgggatgga taatgcatca gaaaagctgc       840
ttttacatct cacttacttc aaaaaattgg caggagagcc aaaaacaatg tgaaactctg      900
tcttccaagc tggccacatt cagtgaaatt tatccacaat cacactctta ctacttctta      960
aattcactgt tgccaaatgg tggttcaggg aattcatatt ggactggcct cagctctaac     1020
aaggattgga agttgactga tgatacacaa cgcactagga cttatgctca aagctcaaaa     1080
tgtaacaagg tacataaaac ttggtcatgg tggacactgg agtcagagtc atgtagaagt     1140 tctcttcccct acatctgtga gatgacagct ttcaggttttc cagattagga cagtcctttg     1200
cactgagttg acactcatgc caacaagaac ctgtgccccct ccttcctaac ctgaggcctg     1260
```

```
gggttcctca gaccatctcc ttcattctgg gcagtgccag ccaccggctg acccacacct   1320
gacacttcca gccagtctgc tgcctgctcc ctcttcctga aactggactg ttcctgggaa   1380
aagggtgaag ccacctctag aagggacttt ggcctccccc caagaacttc ccatggtaga   1440
atggggtggg ggaggagggc gcacgggctg agcggatagg ggcggcccgg agccagccag   1500
gcagttttat tgaaatcttt ttaaataatt g                                  1531
```

<210> SEQ ID NO 13
<211> LENGTH: 2033
<212> TYPE: DNA
<213> ORGANISM: Homo sapiens

<400> SEQUENCE: 13

```
gactagttct agatcgcgat ctagaactag ccgcgggaga cgctgctgag gcggcttcgg    60
ttgcgggtcg gaacggcgct gctctgcggg gccggtccag gctggcagct gccggcgctt   120
ggcggtgagg gcgggctccc gagtggcccc ccaccgaagg cggtgggacc agcggctgag   180
gccaggatgc cgtccaggcg gcgcggcggc tcctcactca tcccagatgt tggttatctt   240
tctgaagtag actgtccatg gcctgaacat tttccgaaaa tcattttgag caaaatatct   300
gtttaataac aagataacca catcaagatg gttggaaagc tgaagcagaa cttactattg   360
gcatgtctgg tgattagttc tgtgactgtg ttttacctgg gccagcatgc catggaatgc   420
catcaccgga tagaggaacg tagccagcca gtcaaattgg agagcacaag gaccactgtg   480
agaactggcc tggacctcaa agccaacaaa acctttgcct atcacaaaga tatgccttta   540
atatttattg gaggtgtgcc tcggagtgga accacactca tgagggccat gctggacgca   600
catcctgaca ttcgctgtgg agaggaaacc agggtcattc cccgaatcct ggccctgaag   660
cagatgtggt cacggtcaag taaagagaag atccgcctgg atgaggctgg tgttactgat   720
gaagtgctgg attctgccat gcaagccttc ttactagaaa ttatcgttaa gcatggggag   780 ccagccccctt atttatgtaa taaagatcct tttgccctga atctttaac ttacctttct   840 aggttattcc ccaatgccaa atttctcctg atggtccgag atggccgggc atcagtacat   900
tcaatgattt ctcgaaaagt tactatagct ggatttgatc tgaacagcta tagggactgt   960
ttgacaaagt ggaatcgtgc tatagagacc atgtataacc agtgtatgga ggttggttat  1020
aaaaagtgca tgttggttca ctatgaacaa cttgtcttac atcctgaacg gtggatgaga  1080
acactcttaa agttcctcca gattccatgg aaccactcag tattgcacca tgaagagatg  1140
attgggaaag ctgggggagt gtctctgtca aaagtggaga gatctacaga ccaagtaatc  1200
aagccagtca atgtaggagc tctatcaaaa tgggttggga agataccgcc agatgtttta  1260
caagacatgg cagtgattgc tcctatgctt gccaagcttg gatatgaccc atatgccaac  1320
ccacctaact acgaaaaacc tgatcccaaa attattgaaa acactcgaag ggtctataag  1380
ggagaattcc aactacctga ctttcttaaa gaaaaaccac agactgagca agtggagtag  1440
cagaaccagg agcctcttcc atacatgagg aaagattgct gccttttcag cagaagggaa  1500
attcctagga ttggctgtcc cctgccaagc ttggtggagc gtctgcacct ggctgcgcc   1560 gcctgtgcat ttgccagttt cctcccactg agaggatgga ggtgtccgca cagctttggg  1620
cctcgtgagg gatctgcctc ctgagcaaag agctcttgat cccgatttca tgcacagccc  1680
tgcagtaagg agcccagaag gaacatgtgt tcctgttaa aactcctctt gttctctttt   1740
cttacattat gacgtttgtt ttcaaggaga gggtttaaaa atgggatcct gtaagcagac  1800
```

| ttgggcagtc tccttttgaa ataggttgtc tgtacatgtt ctaatgtttt gtagaacacg | 1860 |
| tgtgcctgtt taagtgtatt gatgtgaata atattaaata tcctaattat ttaattcatt | 1920 |
| gtattgtttc tgagaagttg ggaaattacc attatacatt tacaacctaa tgacttttgt | 1980 |
| attttatttt tcaaaataaa agctttcaat gtgaagcaaa aaaaaaaaaa aaa | 2033 |

<210> SEQ ID NO 14
<211> LENGTH: 1050
<212> TYPE: DNA
<213> ORGANISM: Homo sapiens

<400> SEQUENCE: 14

| atgaactcca ccttggatgg taatcagagc agccacccct tttgcctctt ggcatttggc | 60 |
| tatttggaaa ctgtcaattt tgccttttg gaagtattga ttattgtctt tctaactgta | 120 |
| ttgattattt ctggcaacat cattgtgatt tttgtatttc actgtgcacc tttgttgaac | 180 |
| catcacacta caagttattt tatccagact atggcatatg ctgacctttt tgttggggtg | 240 |
| agctgcgtgg tcccttcttt atcactcctc catcaccccc ttccagtaga ggagtccttg | 300 |
| acttgccaga tatttggttt tgtagtatca gttctgaaga gcgtctccat ggcttctctg | 360 |
| gcctgtatca gcattgatag atacattgcc attactaaac ctttaaccta taatactctg | 420 |
| gttacaccct ggagactacg cctgtgtatt ttcctgattt ggctatactc gaccctggtc | 480 |
| ttcctgcctt ccttttttcca ctgggcaaa cctggatatc atggagatgt gtttcagtgg | 540 |
| tgtgcggagt cctggcacac cgactcctac ttcaccctgt tcatcgtgat gatgttatat | 600 |
| gccccagcag cccttattgt ctgcttcacc tatttcaaca tcttccgcat ctgccaacag | 660 |
| cacacaaagg atatcagcga aaggcaagcc cgcttcagca gccagagtgg ggagactggg | 720 |
| gaagtgcagg cctgtcctga taagcgctat gccatggtcc tgtttcgaat cactagtgta | 780 |
| ttttacatcc tctggttgcc atatatcatc tacttcttgt tggaaagctc cactggccac | 840 |
| agcaaccgct tcgcatcctt cttgaccacc tggcttgcta ttagtaacag tttctgcaac | 900 |
| tgtgtaatt atagtctctc caacagtgta ttccaaagag gactaaagcg cctctcaggg | 960 |
| gctatgtgta cttcttgtgc aagtcagact acagccaacg acccttacac agttagaagc | 1020 |
| aaaggccctc ttaatggatg tcatatctga | 1050 |

<210> SEQ ID NO 15
<211> LENGTH: 2190
<212> TYPE: DNA
<213> ORGANISM: Homo sapiens

<400> SEQUENCE: 15

| ggtgaagccg gtggccggtg gccgggcggg accaacaaag atggcggcgg cccctgcggc | 60 |
| gggagcgatc tggcaacgg ctgcggctaa agctgcagcc gggcccacgg ggggctgca | 120 |
| cgggggtagt agggggtggc cctgaactgg ggcctggccc tggctggcct ctcccgccgc | 180 |
| ctcactgggg gacaggtcca gcctgtggtg tccacaatgc cccaggcctc tgagcaccgc | 240 |
| ctgggccgta cccgagagcc acctgttaat atccagcccc gagtgggatc caagctacca | 300 |
| tttgccccca gggcccgcag caaggagcgc agaaacccag cctctgggcc aaaccccatg | 360 |
| ttacgacctc tgcctccccg gccaggtctg cctgatgaac ggctcaagaa actggagctg | 420 |
| ggacggggac ggacctcagg ccctcgtccc agaggccccc ttcgagcaga tcatggggtt | 480 |
| ccctgcctg gctcaccacc cccaacagtg gctttgcctc tcccatctcg gaccaactta | 540 |
| gcccgttcca agtctgtgag cagtggggac ttgcgtccaa tggggattgc cttgggaggg | 600 |

```
caccgtggca ccggagagct tggggctgca ctgagccgct tggccctccg gcctgagcca    660
cccactttga gacgtagcac ttctctccgc cgcctagggg gctttcctgg acccccctacc   720
ctgttcagca tacggacaga gcccctgct tcccatggct ccttccacat gatatccgcc    780
cggtcctctg agcctttcta ctctgatgac aagatggctc atcacacact ccttctgggc    840
tctggtcatg ttggccttcg aaacctggga aacacgtgct tcctgaatgc tgtgctgcag    900
tgtctgagca gcactcgacc tcttcgggac ttctgtctga agggacttt ccggcaagag     960
gtgcctggag gaggccgagc caagagctc actgaagcct ttgcagatgt gattggtgcc    1020
ctctggcacc ctgactcctg cgaagctgtg aatcctactc gattccgagc tgtcttccag   1080
aaatatgttc cctccttctc tggatacagc cagcaggatg cccaagagtt cctgaagctc    1140
ctcatggagc ggctacacct tgaaatcaac cgccgaggcc gccgggctcc accgatactt    1200
gccaatggtc cagttccctc tccacccccgc cgaggagggg ctctgctaga agaacctgag   1260
ttaagtgatg atgaccgagc caacctaatg tggaaacgtt acctggagcg agaggacagc   1320
aagattgtgg acctgtttgt gggccagttg aaaagttgtc tcaagtgcca ggcctgtggg   1380
tatcgctcca cgaccttcga ggttttttgt gacctgtccc tgcccatccc caagaaagga   1440
tttgctgggg gcaaggtgtc tctgcgggat tgtttcaacc ttttcactaa ggaagaagag   1500
ctagagtcgg agaatgcccc agtgtgtgac cgatgtcggc agaaaactcg aagtaccaaa   1560
aagttgacag tacaaagatt ccctcgaatc ctcggcttag atctgaatcg attttctgcc   1620
tcccgaggct ccatcaaaaa aagttcagta ggtgtagact ttccactgca gcgactgagc   1680
ctagggact ttgccagtga caaagccgga agtcctgtat accagctgta tgccctttgc    1740
aaccactcag gcagcgtcca ctatggccac tacacagccc tgtgccggtg ccagactggt   1800
tggcatgtct acaatgactc tcgtgtctcc cctgtcagtg aaaaccaggt ggcatccagc   1860
gagggctacg tgctgttcta ccaactgatg caggagccac cccggtgcct gtgacacctc   1920
taagctctgg cacctgtgaa gcccttaaaa caccctttaag ccccaggctc cccgtttacc  1980
tcagagacgt ctattttgt gtcttttaa tcggggaggg gggagggggt ggttgtagct     2040
ccattatttt ttttattaaa aaataccctt ccacctggag gctcccttgt ctcccagccc   2100
catgtacaaa gctcaccaag cccctgccca tgtacagccc ccagaccctc tgcaatatca   2160
cttttttgtga ataaatttat taagaaaaaa                                    2190
```

<210> SEQ ID NO 16
<211> LENGTH: 2148
<212> TYPE: DNA
<213> ORGANISM: Homo sapiens

<400> SEQUENCE: 16

```
ggtgaagccg gtggccggtg gccgggcggg accaacaaag atggcggcgg ccctgcggc     60
gggagcgatc tgggcaacgg ctgcggctaa agctgcagcc gggcccacgg gggggctgca   120
cgggggtagt aggggggtggc cctgaactgg ggcctggccc tggctggcct ctcccgccgc  180
ctcactgggg gacaggtcca gcctgtggtg tccacaatgc cccaggcctc tgagcaccgc   240
ctgggccgta cccgagagcc acctgttaat atccagcccc gagtgggatc caagctacca   300
tttgccccca gggcccgcag caaggagcgc agaaacccag cctctgggcc aaaccccatg   360
ttacgacctc tgcctccccg gccaggtctg cctgatgaac ggctcaagaa actggagctg   420
ggacggggac ggacctcagg ccctcgtccc agaggcccc ttcgagcaga tcatggggtt    480
```

```
cccctgcctg gctcaccacc cccaacagtg gctttgcctc tcccatctcg gaccaactta     540
gcccgttcca agtctgtgag cagtggggac ttgcgtccaa tggggattgc cttgggaggg     600
caccgtggca ccggagagct tggggctgca ctgagccgct tggccctccg gcctgagcca     660
cccactttga gacgtagcac ttctctccgc cgcctagggg gctttcctgg acccctacc     720 ctgttcagca tacggacaga gcccctgct tccatggct ccttccacat gatatccgcc      780
cggtcctctg agcctttcta ctctgatgac aagatggctc atcacacact ccttctgggc   840
tctggtcatg ttggccttcg aaacctggga acacgtgct tcctgaatgc tgtgctgcag    900
tgtctgagca gcactcgacc tcttcggac ttctgtctga aagggactt ccggcaagag     960 gtgcctggag gaggccgagc ccaagagctc actgaagcct tgcagatgt gattggtgcc    1020 ctctggcacc ctgactcctg cgaagctgtg aatcctactc gattccgagc tgtcttccag   1080
aaatatgttc cctccttctc tggatacagc cagcaggatg cccaagagtt cctgaagctc   1140
ctcatggagc ggctacacct tgaaatcaac cgccgaggcc gccgggctcc accgatactt    1200
gccaatggtc cagttccctc tccaccccgc cgaggagggg ctctgctaga agaacctgag    1260
ttaagtgatg atgaccgagc caacctaatg tggaaacgtt acctggagcg agaggacagc   1320
aagattgtgg acctgtttgt gggccagttg aaaagttgtc tcaagtgcca ggcctgtggg   1380
tatcgctcca cgaccttcga ggttttttgt gacctgtccc tgcccatccc caagaaagga   1440
tttgctgggg gcaaggtgtc tctgcgggat tgtttcaacc ttttcactaa ggaagaagag   1500
ctagagtcgg agaatgcccc agtgtgtgac cgatgtcggc agaaaactcg aagtaccaaa   1560
aagttgacag tacaaagatt ccctcgaatc ctcggcttag atctgaatcg atttctgcc    1620 tcccgaggct ccatcaaaaa aagttcagta ggtgtagact ttccactgca gcgactgagc   1680
ctaggggact tgccagtga caaagccggc agcgtccact atggccacta cacagccctg   1740
tgccggtgcc agactggttg gcatgtctac aatgactctc gtgtctcccc tgtcagtgaa   1800
aaccaggtgg catccagcga gggctacgtg ctgttctacc aactgatgca ggagccaccc   1860
cggtgcctgt gacacctcta agctctggca cctgtgaagc cctttaaaca cccttaagcc   1920
ccaggctccc cgtttacctc agagacgtct attttttgtgt cttttaatc gggggagggg   1980 gagggggtgg ttgtagctcc attattttt ttattaaaaa ataccttcc acctggaggc     2040 tcccttgtct cccagcccca tgtacaaagc tcaccaagcc cctgcccatg tacagccccc   2100
agaccctctg caatatcact ttttgtgaat aaatttatta agaaaaaa                2148
```

<210> SEQ ID NO 17
<211> LENGTH: 7391
<212> TYPE: DNA
<213> ORGANISM: Homo sapiens

<400> SEQUENCE: 17

```
gctgcgcagc gctggctgct ggctggcctc gcggagacgc cgaacggacg cggccggcgc     60
cggcttgtgg gctcgccgcc tgcagccatg accctcgcag cctgtccctc ggcctcggcc    120
cgggacgtct aaaatcccac acagtcgcgc gcagctgctg gagagccggc cgctgccccc   180
tcgtcgccgc atcacactcc cgtcccggga gctgggagca gcgcgggcag ccggcgcccc    240
cgtgcaaact gggggtgtct gccagagcag ccccagccgc tgccgctgct accccgatg    300 ctggccatgg cctggcgggg cgcagggccg agcgtcccgg gggcgccgg gggcgtcggt    360 ctcagtctgg ggttgctcct gcagttgctg ctgctcctgg ggccggcgcg gggcttcggg   420
gacgaggaag agcggcgctg cgaccccatc cgcatctcca tgtgccagaa cctcggctac    480
```

```
aacgtgacca agatgcccaa cctggttggg cacgagctgc agacggacgc cgagctgcag    540
ctgacaactt tcacaccgct catccagtac ggctgctcca gccagctgca gttcttcctt    600
tgttctgttt atgtgccaat gtgcacagag aagatcaaca tccccattgg cccatgcggc    660
ggcatgtgtc tttcagtcaa gagacgctgt gaacccgtcc tgaaggaatt tggatttgcc    720
tggccagaga gtctgaactg cagcaaattc ccaccacaga acgaccacaa ccacatgtgc    780
atggaagggc caggtgatga agaggtgccc ttacctcaca aaaccccat ccagcctggg    840
gaagagtgtc actctgtggg aaccaattct gatcagtaca tctgggtgaa aaggagcctg    900
aactgtgtgc tcaagtgtgg ctatgatgct ggcttataca gccgctcagc caaggagttc    960
actgatatct ggatggctgt gtgggccagc ctgtgtttca tctccactgc cttcacagta   1020
ctgaccttcc tgatcgattc ttctaggttt tcctaccctg agcgcccat catatttctc   1080
agtatgtgct ataatattta tagcattgct tatattgtca ggctgactgt aggccgggaa   1140
aggatatcct gtgattttga agaggcagca gaacctgttc tcatccaaga aggacttaag   1200
aacacaggat gtgcaataat tttcttgctg atgtactttt ttggaatggc cagctccatt   1260
tggtgggtta ttctgacact cacttggttt ttggcagcag gactcaaatg gggtcatgaa   1320
gccattgaaa tgcacagctc ttatttccac attgcagcct gggccatccc cgcagtgaaa   1380
accattgtca tcttgattat gagactggtg gatgcagatg aactgactgg cttgtgctat   1440
gttggaaacc aaaatctcga tgccctcacc gggttcgtgg tggctcccct ctttacttat   1500
ttggtcattg aactttgtt cattgctgca ggttggtgg ccttgttcaa aattcggtca   1560
aatcttcaaa aggatgggac aaagacagac aagttagaaa gactgatggt caagattggg   1620
gtgttctcag tactgtacac agttcctgca acgtgtgtga ttgcctgtta tttttatgaa   1680
atctccaact gggcactttt tcggtattct gcagatgatt ccaacatggc tgttgaaatg   1740
ttgaaaattt ttatgtcttt gttggtgggc atcacttcag gcatgtggat ttggtctgcc   1800
aaaactcttc acacgtggca gaagtgttcc aacagattgg tgaattctgg aaaggtaaag   1860
agagagaaga gaggaaatgg ttgggtgaag cctggaaaag gcagtgagac tgtggtataa   1920
ggctagtcag cctccatgct ttcttcattt tgaagggggg aatgccagca ttttggagga   1980
aattctacta aaagttttat gcagtgaatc tcagtttgaa caaactagca acaattaagt   2040
gacccccgtc aacccactgc ctcccacccc gaccccagca tcaaaaaacc aatgattttg   2100
ctgcagactt tggaatgatc caaaatggaa aagccagtta gaggctttca aagctgtgaa   2160
aaatcaaaac gttgatcact ttagcaggtt gcagcttgga gcgtggaggt cctgcctaga   2220
ttccaggaag tccagggcga tactgttttc ccctgcaggg tgggatttga gctgtgagtt   2280
ggtaactagc agggagaaat attaactttt ttaacccttt accatttaa atactaactg   2340
ggtctttcag atagcaaagc aatctataaa cactggaaac gctgggttca gaaaagtgtt   2400
acaagagttt tatagtttgg ctgatgtaac ataaacatct tctgtggtgc gctgtctgct   2460
gtttagaact ttgtggactg cactcccaag aagtggtgtt agaatctttc agtgcctttg   2520
tcataaaaca gttatttgaa caaacaaaag tactgtactc acacacataa ggtatccagt   2580
ggattttct tctctgtctt cctctcttaa atttcaacat ctctcttctt ggctgctgct   2640
gttttcttca ttttatgtta atgactcaaa aaagtatttt ttatagaatt tttgtactgc   2700
agcatgctta aagaggggaa aaggaagggt gattcacttt ctgacaatca cttaattcag   2760
aggaaaatga gatttactaa gttgacttac ctgacggacc ccagagacct attgcattga   2820
```

-continued

```
gcagtgggga cttaatatat tttacttgtg tgattgcatc tatgcagacg ccagtctgga    2880
agagctgaaa tgttaagttt cttggcaact ttgcattcac acagattagc tgtgtaattt    2940
ttgtgtgtca attacaatta aaagcacatt gttggaccat gacatagtat actcaactga    3000
ctttaaaact atggtcaact tcaacttgca ttctcagaat gatagtgcct ttaaaaattt    3060
ttttatttt taaagcataa gaatgttatc agaatctggt ctacttagga caatggagac    3120
tttttcagtt ttataaaggg aactgaggac agctaatcca actacttggt gcgtaattgt    3180
ttcctagtaa ttggcaaagg ctccttgtaa gatttcactg gaggcagtgt ggcctggagt    3240
atttatatgg tgcttaatga atctccagaa tgccagccag aagcctgatt ggttagtagg    3300
gaataaagtg tagaccatat gaaatgaact gcaaactcta atagcccagg tcttaattgc    3360
ctttagcaga ggtatccaaa gcttttaaaa tttatgcata cgttcttcac aaggggtac     3420
ccccagcagc ctctcgaaaa ttgcacttct cttaaaactg taactggcct ttctcttacc    3480
ttgcctagg ccttctaatc atgagatctt ggggacaaat tgactatgtc acaggttgct     3540
ctccttgtaa ctcatacctg tctgcttcag caactgcttt gcaatgacat ttatttatta    3600
attcatgcct taaaaaaata ggaagggaag ctttttttt tcttttttttt ttttcaatc    3660
acactttgtg gaaaaacatt tccagggact caaaattcca aaaggtggt caaattctgg     3720
aagtaagcat ttcctctttt ttaaaaattt ggtttgagcc ttatgcccat agtttgacat    3780
ttcccttct tctttccttt ttgttttgt gtggttcttg agctctctga catcaagatg      3840
catgtaaagt cgattgtatg ttttggaagg caaagtcttg gcttttgaga ctgaagttaa    3900
gtgggcacag gtggcccctg ctgctgtgcc cagtctgagt accttggcta gactctaggt    3960
caggctccag gagcatgaga attgatcccc agaagaacca ttttaactcc atctgatact    4020
ccattgccta tgaaatgtaa aatgtgaact ccctgtgctg cttgtagaca gttcccataa    4080
ctgtccacgg ccctggagca cgcacccagg ggcagagcct gcccttactc acgctctgct    4140
ctggtgtctt gggagttgtg cagggactct ggcccaggca ggggaaggaa gaccaggcgg    4200
tagggactg tcttgctgt tagagtatag aggtttgtaa tgcagttttc ttcataatgt      4260
gtcagtgatt gtgtgaccaa ggcagcatct agcagaaagc caggcatgga gtaggtgatc    4320
gatacttgtc aatgactaaa taataacaat aaaagagcac ttgggtgaat ctgggcacct    4380
gatttctgag ttttgagttc tggagctagt gttttgacaa tgctttgggt tttgacatgc    4440
cttttccaca aatctcttgc cttttcaggg caaagtgtat ttgatcagaa gtggccattt    4500
ggattagtag ccttagcaat gctacaggt tataggcctc tcctttcaca ttccagacaa     4560
tggagagtgt ttatggtttc aggaaaagaa ctttgtggct gaggggtcag ttaccagtga    4620
ccttcaatca actccatcac ttcttaaatc ggtatttgtt aaaaaaatca gttatttat    4680
ttattgagtg ccgactgtag taaagccctg aaatagataa tctctgttct tctaactgat    4740
ctaggatggg gacgcaccca ggtctgctga actttactgt tcctctggga aaggagcagg    4800
gacctctgga attcccatct gtttcactgt ctccattcca taaatctctt cctgtgtgag    4860
ccaccacacc cagcctgggt ctctctactt ttaacacatc tctcatccct ttcccaggat    4920
tccttccaag tcagttacag gtggttttaa cagaaagcat cagctctgct tcgtgacagt    4980
ctctggagaa atcccttagg aagactatga gagtaggcca caaggacatg ggcccacaca    5040
tctgctttgg cttcgccggc aattcagggc ttggggtatt ccatgtgact tgtataggta    5100
tatttgagga cagcatcttg ctagagaaaa ggtgagggtt ggttttcttt ctctgaaacc    5160
tacagtaaat gggtatgatt gtagcttcct cagaaatccc ttggcctcca gagattaaac    5220
```

```
atggtgcaat ggcacctctg tccaacctcc tttctggtag attccttcct cctgcttcat    5280
ataggccaaa cctcagggca agggaacatg ggggtagagt ggtgctggcc agaaccatct    5340
gcttgagcta cttggttgat tcatatcctc tttcctttat ggagacccat ttcctgatct    5400
ctgagactgt tgctgaactg caacttact tgggcctgaa actggagaag gggtgacatt     5460
tttttaattt cagagatgct ttctgatttt cctctcccag gtcactgtct cacctgcact    5520
ctccaaactc aggttccggg aagcttgtgt gtctagatac tgaattgaga ttctgttcag    5580 cacctttag ctctatactc tctggctccc ctcatcctca tggtcactga attaaatgct     5640
tattgtattg agaaccaaga tgggacctga ggacacaaag atgagctcaa cagtctcagc    5700
cctagaggaa tagactcagg gatttcacca ggtcggtgca gtatttgatt tctggtgagg    5760
tgaccacagc tgcagttagg gaagggagcc attgagcaca gactttggaa ggaacctttt    5820
ttttgttgtt tgtttgtttg tttgtttgtt tgtttgtttg agacagggtc ttgctctgtc    5880
acccaggctg gggcgcaatg gcacgatctt ggctcactgc aacctctgcc tcctgggttc    5940
aagtgattct cctgccacag cctcctgagg agctgggact acaggtgcgt gctaccacgc    6000
ccagctactt ctgtattttt agtagagacg gggtttcact gtgttggcca ggctggtctc    6060
gaactcctga cctcatgatc tgcccgcctc agcctcccaa agtgctggga ttacaagtgt    6120
gagccaccac acctggcctg gaaggaacct cttaaaatca gtttacgtct tgtattttgt    6180
tctgtgatgg aggacactgg agagagttgc tattccagtc aatcatgtcg agtcactgga    6240
ctctgaaaat cctattggtt cctttatttt atttgagttt agagttccct tctgggtttg    6300
tattatgtct ggcaaatgac ctgggttatc acttttcctc cagggttaga tcatagatct    6360
tggaaactcc ttagagagca ttttgctcct accaaggatc agatactgga gccccacata    6420
atagatttca tttcactcta gcctacatag agctttctgt tgctgtctct tgccatgcac    6480
ttgtgcggtg attacacact tgacagtacc aggagacaaa tgacttacag atccccccgac    6540 atgcctcttc cccttggcaa gctcagttgc cctgatagta gcatgttttct gtttctgatg    6600 taccttttt ctcttcttct ttgcatcagc caattcccag aatttcccca ggcaatttgt     6660
agaggacctt tttggggtcc tatatgagcc atgtcctcaa agcttttaaa cctccttgct    6720
ctcctacaat attcagtaca tgaccactgt catcctagaa ggcttctgaa aagaggggca    6780
agagccactc tgcgccacaa aggttgggtc catcttctct ccgaggttgt gaaagttttc    6840
aaattgtact aataggctgg ggccctgact tggctgtggg ctttgggagg ggtaagctgc    6900
tttctagatc tctcccagtg aggcatggag gtgtttctga attttgtcta cctcacaggg    6960
atgttgtgag gctgaaaag gtcaaaaaat gatggcccct tgagctcttt gtaagaaagg     7020
tagatgaaat atcggatgta atctgaaaaa agataaaat gtgacttccc ctgctctgtg     7080
cagcagtcgg gctggatgct ctgtggcctt tcttgggtcc tcatgccacc ccacagctcc    7140
aggaaccttg aagccaatct gggggacttt cagatgtttg acaaagaggt accaggcaaa    7200
cttcctgcta cacatgccct gaatgaattg ctaaatttca aaggaaatgg accctgcttt    7260
taaggatgta caaaagtatg tctgcatcga tgtctgtact gtaaatttct aatttatcac    7320
tgtacaaaga aaaccccttg ctatttaatt ttgtattaaa ggaaaataaa gttttgtttg    7380
ttaaaaaaaa a                                                         7391
```

<210> SEQ ID NO 18
<211> LENGTH: 1302
<212> TYPE: DNA

<213> ORGANISM: Homo sapiens

<400> SEQUENCE: 18

| | | | | | |
|---|---|---|---|---|---|
| atgtgcacag | agaagatcaa | catccccatt | ggcccatgcg | gcggcatgtg | tctttcagtc | 60 |
| aagagacgct | gtgaacccgt | cctgaaggaa | tttggatttg | cctggccaga | gagtctgaac | 120 |
| tgcagcaaat | tcccaccaca | gaacgaccac | aaccacatgt | gcatggaagg | gccaggtgat | 180 |
| gaagaggtgc | ccttacctca | caaaaccccc | atccagcctg | gggaagagtg | tcactctgtg | 240 |
| ggaaccaatt | ctgatcagta | catctgggtg | aaaaggagcc | tgaactgtgt | gctcaagtgt | 300 |
| ggctatgatg | ctggcttata | cagccgctca | gccaaggagt | tcactgatat | ctggatggct | 360 |
| gtgtgggcca | gcctgtgttt | catctccact | gccttcacag | tactgacctt | cctgatcgat | 420 |
| tcttctaggt | tttcctaccc | tgagcgcccc | atcatatttc | tcagtatgtg | ctataatatt | 480 |
| tatagcattg | cttatattgt | caggctgact | gtaggccggg | aaaggatatc | ctgtgatttt | 540 |
| gaagaggcag | cagaacctgt | tctcatccaa | gaaggactta | agaacacagg | atgtgcaata | 600 |
| attttcttgc | tgatgtactt | ttttggaatg | gccagctcca | tttggtgggt | tattctgaca | 660 |
| ctcacttggt | ttttggcagc | aggactcaaa | tggggtcatg | aagccattga | aatgcacagc | 720 |
| tcttatttcc | acattgcagc | ctgggccatc | cccgcagtga | aaaccattgt | catcttgatt | 780 |
| atgagactgg | tggatgcaga | tgaactgact | ggcttgtgct | atgttggaaa | ccaaaatctc | 840 |
| gatgccctca | ccgggttcgt | ggtggctccc | ctctttactt | atttggtcat | ggaactttg | 900 |
| ttcattgctg | caggtttggt | ggccttgttc | aaaattcggt | caaatcttca | aaaggatggg | 960 |
| acaaagacag | acaagttaga | aagactgatg | gtcaagattg | gggtgttctc | agtactgtac | 1020 |
| acagttcctg | caacgtgtgt | gattgcctgt | tatttttatg | aaatctccaa | ctgggcactt | 1080 |
| tttcggtatt | ctgcagatga | ttccaacatg | gctgttgaaa | tgttgaaaat | ttttatgtct | 1140 |
| ttgttggtgg | gcatcacttc | aggcatgtgg | atttggtctg | ccaaaactct | tcacacgtgg | 1200 |
| cagaagtgtt | ccaacagatt | ggtgaattct | ggaaaggtaa | agagagagaa | gagaggaaat | 1260 |
| ggttgggtga | agcctggaaa | aggcagtgag | actgtggtat | aa | | 1302 |

<210> SEQ ID NO 19
<211> LENGTH: 1998
<212> TYPE: DNA
<213> ORGANISM: Homo sapiens

<400> SEQUENCE: 19

| | | | | | |
|---|---|---|---|---|---|
| cggcgcgatg | cgcggagacc | cccgcggggg | cggcggcggc | cgtgagcccc | gatgaggccc | 60 |
| gagcgtcccc | ggccgcgcgg | cagcgccccc | ggcccgatgg | agacccgcc | gtgggaccca | 120 |
| gcccgcaacg | actcgctgcc | gcccacgctg | accccggccc | tgcccccta | cgtgaagctt | 180 |
| ggcctcaccg | tcgtctacac | cgtgttctac | gcgctgctct | tcgtgttcat | ctacgtgcag | 240 |
| ctctggctgg | tgctgcgtta | ccgccacaag | cggctcagct | accagagcgt | cttcctcttt | 300 |
| ctctgcctct | tctgggcctc | cctgcggacc | gtcctcttct | ccttctactt | caaagacttc | 360 |
| gtggcggcca | attcgctcag | cccccttcgtc | ttctggctgc | tctactgctt | ccctgtgtgc | 420 |
| ctgcagttttt | tcaccctcac | gctgatgaac | ttgtacttca | cgcaggtgat | tttcaaagcc | 480 |
| aagtcaaaat | attctccaga | attactcaaa | taccggttgc | cctctacct | ggcctccctc | 540 |
| ttcatcagcc | ttgttttcct | gttggtgaat | ttaacctgtg | ctgtgctggt | aaagacggga | 600 |
| aattgggaga | ggaaggttat | cgtctctgtg | cgagtggcca | ttaatgacac | gctcttcgtg | 660 |
| ctgtgtgccg | tctctctctc | catctgtctc | tacaaaatct | ctaagatgtc | cttagccaac | 720 |

-continued

| | |
|---|---|
| atttacttgg agtccaaggg ctcctccgtg tgtcaagtga ctgccatcgg tgtcaccgtg | 780 |
| atactgcttt acacctctcg ggcctgctac aacctgttca tcctgtcatt ttctcagaac | 840 |
| aagagcgtcc attcctttga ttatgactgg tacaatgtat cagaccaggc agatttgaag | 900 |
| aatcagctgg gagatgctgg atacgtatta tttggagtgg tgttatttgt ttgggaactc | 960 |
| ttacctacca ccttagtcgt ttatttcttc cgagttagaa atcctacaaa ggaccttacc | 1020 |
| aaccctggaa tggtccccag ccatggattc agtcccagat cttatttctt tgacaaccct | 1080 |
| cgaagatatg acagtgatga tgaccttgcc tggaacattg cccctcaggg acttcaggga | 1140 |
| ggttttgctc cagattacta tgattgggga caacaaacta acagcttcct ggcacaagca | 1200 |
| ggaactttgc aagactcaac tttggatcct gacaaaccaa gccttgggta gcatcagtta | 1260 |
| acagttttat ggacgattcc tcagatgaaa agcttcagaa aagcatagtg acagctgaat | 1320 |
| ttttagggca cttttcctta agaaatagaa cttgatttt atttgttaca ggtttccaat | 1380 |
| ggccccatag aataagcaa taatgtagac tgataaaccc ttattttagt actaaagagg | 1440 |
| gagccttgct atttcagtgg gtataattta aacttttaa agaaaatctg tacttttata | 1500 |
| aagatgtatt ttgtataact taaataataa tgctaaagta tactagggtt ttttttttctt | 1560 |
| gagaatgtta ctgcaatcat gttgtagttt gcacagactt ttatgcataa ttcactttaa | 1620 |
| aaatatagaa tatatggtct aatagttttt taaagctttt ggactaaagt attccacaaa | 1680 |
| tcttacctct ttaggtcact gatggtcact ccgattctga gtgccacatt ggtagactcc | 1740 |
| taaaatacag ttgacaactt agccaattgc aactccagtg ttgataatta aaatgaaatg | 1800 |
| gtaaagcagc agactgtaag gtctttagag attttttttt aaggttcagg ccgtaggttc | 1860 |
| ctcaaggaat ctcttaagtt ttgcccaaag actggtactt cctttcagta gggcgctaat | 1920 |
| gtatacacat taatgataag ttgataacat taaaaatgta gctgacttat cctattaaac | 1980 |
| ctcctctgct atgttcac | 1998 |

<210> SEQ ID NO 20
<211> LENGTH: 890
<212> TYPE: DNA
<213> ORGANISM: Homo sapiens

<400> SEQUENCE: 20

| | |
|---|---|
| ctggccacac cctccgcctg gacgcagcag ccaccgccgc gtccctctct ccacgaggct | 60 |
| gccggcttag gaccccagc tccgacatgt cgccctctgg tcgcctgtgt cttctcacca | 120 |
| tcgttggcct gattctcccc accagaggac agacgttgaa agataccacg tccagttctt | 180 |
| cagcagactc aactatcatg gacattcagg tcccgacacg agcccagat gcagtctaca | 240 |
| cagaactcca gcccacctct ccaaccccaa cctggcctgc tgatgaaaca ccacaacccc | 300 |
| agacccagac ccagcaactg gaaggaacgg atgggcctct agtgacagat ccagagacac | 360 |
| acaagagcac caaagcagct catcccactg atgacaccac gacgctctct gagagaccat | 420 |
| ccccaagcac agacgtccag acagacccc agaccctcaa gccatctggt tttcatgagg | 480 |
| atgacccctt cttctatgat gaacacaccc tccggaaacg ggggctgttg gtcgcagctg | 540 |
| tgctgttcat cacaggcatc atcatcctca ccagtggcaa gtgcaggcag ctgtcccggt | 600 |
| tatgccggaa tcgttgcagg tgagtccatc agaaacagga gctgacaacc tgctgggcac | 660 |
| ccgaagacca gcccctgc cagctcaccg tgcccagcct cctgcatccc ctcgaagagc | 720 |
| ctggccagag agggaagaca cagatgatga agctggagcc agggctgccg gtccgagtct | 780 |

| | |
|---|---|
| cctacctccc ccaaccctgc ccgcccctga aggctacctg gcgccttggg ggctgtccct | 840 |
| caagttatct cctctgctaa gacaaaaagt aaagcactgt ggtctttgcc | 890 |

<210> SEQ ID NO 21
<211> LENGTH: 1104
<212> TYPE: DNA
<213> ORGANISM: Homo sapiens

<400> SEQUENCE: 21

| | |
|---|---|
| gcgcgagtga aggaagacga agtgcgtgac ccgaccggct gtggtgttcc agtccccact | 60 |
| gaccagtagg agcagcaggg cgtcggcttg tgaggtggct tttcctcggg gcaacccagg | 120 |
| aaggccccaa gaggacaatg gattctggaa ctcgcccagt tggtagctgc tgtagcagcc | 180 |
| ccgctgggct ctcacgggag tacaaactag tgatgctggg tgctggtggt gtagggaaga | 240 |
| gtgccatgac catgcagttc atcagccacc gattcccaga agatcatgat cccaccattg | 300 |
| aagatgctta taagatcagg atccgtattg atgatgagcc tgccaatctg gacattttgg | 360 |
| atacagctgg acaggcagag tttacagcca tgcgggacca gtatatgagg gcaggagaag | 420 |
| ggtttatcat ctgttactct atcacggatc gtcgaagttt ccatgaagtt cgwgagttta | 480 |
| aacagcttat ttatcgagtc cgacgtactg acgatacacc tgtggttctt gtgggaaaca | 540 |
| agtcagacct caaacagcta agacaggtca ccaaggaaga aggattggcc ttggcccgag | 600 |
| aattcagctg tcccttttttt gagacatctg ctgcataccg ctactatatt gatgatgttt | 660 |
| tccatgccct tgtacgggag atacgtagga agaaaaagga ggcagtactg gccatggaga | 720 |
| aaaaatctaa gcccaaaaac agtgtatgga agaggctaaa atcaccattc cggaagaaga | 780 |
| aagattcagt aacttgaaga gaagatgtga agtgtttatc tgtgaactgc agtgctgtat | 840 |
| caaagcagtc cagtaacctg cagtactgag tatggtgctt gctctttcac ttaactgata | 900 |
| agagggacat gcctactagg agttttttaat gatgtggtat ttaaagtatt gtctcttagt | 960 |
| taagtatgat ttattaaccc agtggagcac tgtctgcttt taaattgtca cattagaatt | 1020 |
| tgttctacca atgttttggg ttctgttgcg ctattaatta atgtaaattt gtttataccc | 1080 |
| aggagaaaaa aaaaaaaaaa aaaa | 1104 |

<210> SEQ ID NO 22
<211> LENGTH: 3651
<212> TYPE: DNA
<213> ORGANISM: Homo sapiens

<400> SEQUENCE: 22

| | |
|---|---|
| tgaagattca gttttcactt aaacaaccag caagtcttga agtctcttcc caagcaaatg | 60 |
| ggagcttctt tggaccttgg agcacacaga ggattctact ttctttaaaa ctttgttttc | 120 |
| aggcaatttc cctgagaacc gtttacttcc agaagattgg tggagcttga tctgaaggct | 180 |
| ggccatgaaa tctcaaggtc aacattggta ttccagttca gataaaaact gtaaagtgag | 240 |
| ctttcgtgag aagcttctga ttattgattc aaacctgggg gtccaagatg tggagaacct | 300 |
| caagtttctc tgcataggat tggtccccaa caagaagctg gagaagtcca gctcagcctc | 360 |
| agatgttttt gaacatctct tggcagagga tctgctgagt gaggaagacc ctttcttcct | 420 |
| ggcagaactc ctctatatca tacgcgcgaa gaagctgctg cagcacctca actgtaccaa | 480 |
| agaggaagtg gagcgactgc tgcccacccg acaaagggtt tctctgtttta gaaacctgct | 540 |
| ctacgaactg tcagaaggca ttgactcaga gaacttaaag gacatgatct tccttctgaa | 600 |
| agactcgctt cccaaaactg aaatgaccte cctaagtttc ctggcatttc tagagaaaca | 660 |

```
aggtaaaata gatgaagata atctgacatg cctggaggac tctctgcaaaa cagttgtacc    720 taaacttttg agaaacatag agaaatacaa aagagagaaa gctatccaga tagtgacacc    780
tcctgtagac aaggaagccg agtcgtatca aggagaggaa gaactagttt cccaaacaga    840
tgttaagaca ttcttggaag ccttaccgag ggcagctgtg tacaggatga atcggaacca    900
cagaggcctc tgtgtcattg tcaacaacca cagctttacc tccctgaagg acagacaagg    960
aacccataaa gatgctgaga tcctgagtca tgtgttccag tggcttgggt tcacagtgca   1020
tatacacaat aatgtgacga aagtggaaat ggagatggtc ctgcagaagc agaagtgcaa   1080
tccagcccat gccgacgggg actgcttcgt gttctgtatt ctgacccatg ggagatttgg   1140
agctgtctac tcttcggatg aggccctcat tcccattcgg gagatcatgt ctcacttcac   1200
agccctgcag tgccctagac tggctgaaaa acctaaactc ttttttcatcc aggcctgcca   1260 aggtgaagag atacagcctt ccgtatccat cgaagcagat gctctgaacc ctgagcaggc   1320
acccacttcc ctgcaggaca gtattcctgc cgaggctgac ttcctacttg gtctggccac   1380
tgtcccaggc tatgtatcct ttcggcatgt ggaggaaggc agctggtata ttcagtctct   1440
gtgtaatcat ctgaagaaat tggtcccaag acatgaagac atcttatcca tcctcactgc   1500
tgtcaacgat gatgtgagtc gaagagtgga caaacaggga acaaagaaac agatgcccca   1560
gcctgctttc acactaagga aaaaactagt attccctgtg cccctggatg cactttcatt   1620
atagcagaga gttttttgttg gttcttagac ctcaaacgaa tcattggcta taacctccag   1680
cctcctgccc agcacaggaa tcggtggtct ccacctgtca ttctagaaac aggaaacacc   1740
gtgttttctg acacagtcaa ttctgatttt cttttcttt tgcaagtcta aatgttagaa   1800
aactttcttt tttttggaga tagtctcatt ctgtcaccca gactggagtg cagggggggca   1860 atcacggctc actgtagtct cgacctccca ggctcaagct gtcctccac ctcagcctcc   1920 caagtagcta gactacagg tgtgtgtcca tgcacagcta acttttttatt ttttttgtgg   1980 agatggggtt tcactatgtt gcctaagctg gtctcaaact cctgggctca agcgatcctc   2040
ccacctcagc ttctcaaagt tctgggacta caggcatgaa atactgtgcc tggcctgggg   2100
accaggtgca ttttaaggtt ccttggtgtt caaaaaccac gttcttagcc tagattgagc   2160
ttagattgcc tctctagaca actacccctt agttataatt ctgtgtcccc tctgcatgcc   2220
cttaaacatt ggacagtgag gtcacagtcc acccaccctc tctctgatct cccccttcct   2280
aagacttctc ttttgcacat ctagtgaggt gaaaatttgg tctatgccag cccatttcc    2340 tgcttttgtg taaggaaggt gctcacatag gaagttttta tttggttaga dacaggtttc   2400
cctgtaggaa gatgatggct catttacact cagctgctct gcaagcagaa actttacaac   2460
ctgatgtcat attccatttt ggactgggtg cggtgactca tgcctgtaat cccagtactc   2520
tgggaagcca aggcaggcag atcacttgag gtcaggagtt cgagaccagc ctggccaata   2580
cggcaaaacc tcatcattac taaaaacaca aaaattagcc aggtgtggcg gcgagcacct   2640
gtaatcccag ctactcggga ggctgagaca ggagaatctc ttgaatccag gaggcagagg   2700
ctgtggtgag ccaagatgac acaactgcac tccagcttgg gcaacagggc gagaccttgt   2760
ttaaaaaaaa aattcaatat tggggttgga acatttcagt tgccattgac agaacaccca   2820
attcaaattg actgaagcaa agaagggaat ttattgcctc tttcacattg aaacccagga   2880
gtggataaca ctggcttcag gcaaagcttg aatcaggact caatctacag gccagcacct   2940
ttctcttggc cggatgtcct cagggctggc agatgcagta gactgcagtg gacagtcccc   3000
```

```
accttgttac tgctactaca ctttgctcct ctggcccaag gcatgaggag agaggctgtg    3060
tcagaaactg aagctgttct caggatcact gggctcttct tggcagaggg gatgtctggc    3120
ttgcctgaag ggagtggctc tgtaaggacg ccttgatgct ttcttcatta agattttgag    3180 cattttacg tacttgagct tttttttttt tttttttcaa tttctagagg aactttttct    3240
ctgttaattc ctggaactgt attttgaatc cttaaaggtg agccctcata gggagatcca    3300
aagtcctgtg gttaacgcct tcatttatag atgaggcagc tgaggcctgg ggatgtgaac    3360
aacctgctca cagtcctcat ttactggatt tgacttcagc caggtgaact ggaatgcctt    3420
ggggcgtgga agggcattag gagtgtttca tttgatatgt gaatgctcat aaaaaaatgt    3480
caaggaatga agaacaacaa ctctcagtgg tgcctgcatt tataattatt tatgtgaaag    3540
tcaaattcat gtacagtaaa tttgttataa gaatattcac aagaacactg ttctgatatc    3600
tctgattgtc atgtggattt gaatgtagct tgacagagaa aaaaaaaaa a             3651
```

<210> SEQ ID NO 23
<211> LENGTH: 2054
<212> TYPE: DNA
<213> ORGANISM: Homo sapiens

<400> SEQUENCE: 23

```
tgaagattca gttttcactt aaacaaccag caagtcttga agtctcttcc caagcaaatg      60
ggagcttctt tggaccttgg agcacacaga ggattctact ttcttaaaa ctttgttttc     120 aggcaatttc cctgagaacc gtttacttcc agaagattgg tggagcttga tctgaaggct     180
ggccatgaaa tctcaaggtc aacattggta ttccagttca gataaaaact gtaaagtgag     240 cttcgtgag aagcttctga ttattgattc aaacctgggg gtccaagatg tggagaacct     300
caagtttctc tgcataggat tggtccccaa caagaagctg gagaagtcca gctcagcctc     360
agatgttttt gaacatctct tggcagagga tctgctgagt gaggaagacc ctttcttcct     420
ggcagaactc ctctatatca tacggcagaa gaagctgctg cagcacctca actgtaccaa     480
agaggaagtg gagcgactgc tgcccacccg acaaagggtt tctctgttta gaaacctgct     540
ctacgaactg tcagaaggca ttgactcaga gaacttaaag gacatgatct tccttctgaa     600
agactcgctt cccaaaactg aaatgaccct cctaagtttc ctggcatttc tagaaaaca     660 aggtaaaata gatgaagata atctgacatg cctggaggac ctctgcaaaa cagttgtacc     720 taaactttg agaacatag agaaatacaa aagagagaaa gctatccaga tagtgacacc     780
tcctgtagac aaggaagccg agtcgtatca aggagaggaa gaactagttt cccaaacaga     840
tgttaagaca ttcttggaag ccttaccgca ggagtcctgg caaaataagc atgcaggtag     900
taatggtaac agagccacaa atggtgcacc aagcctggtc tccaggggga tgcaaggagc     960
atctgctaac actctaaact ctgaaaccag cacaaagagg gcagctgtgt acaggatgaa    1020
tcggaaccac agaggcctct gtgtcattgt caacaaccac agctttaccct ccctgaagga    1080 cagacaagga acccataaag atgctgagat cctgagtcat gtgttccagt ggcttgggtt    1140
cacagtgcat atacacaata atgtgacgaa agtggaaatg gagatggtcc tgcagaagca    1200
gaagtgcaat ccagcccatg ccgacgggga ctgcttcgtg ttctgtattc tgacccatgg    1260
gagatttgga gctgtctact cttcggatga ggccctcatt cccattcggg agatcatgtc    1320
tcacttcaca gccctgcagt gcctagact ggctgaaaaa cctaaactct ttttcatcca    1380
ggcctgccaa ggtgaagaga tacagccttc cgtatccatc gaagcagatg ctctgaaccc    1440
tgagcaggca cccacttccc tgcaggacag tattcctgcc gaggctgact tcctacttgg    1500
```

```
tctggccact gtcccaggct atgtatcctt tcggcatgtg gaggaaggca gctggtatat    1560
tcagtctctg tgtaatcatc tgaagaaatt ggtcccaagg atgctgaaat ttctggaaaa    1620
gacaatggaa atcaggggca ggaagagaac agtgtgggt gctaaacaga tctcagcaac     1680
ctccctgccc acggccatct ctgcgcagac acctcgaccc ccatgcgca ggtggagcag     1740 cgtttcctag ttctttccag aggcttcctt ctgcctgcct tccagccaca tcgcctgaga    1800
ttgacaacgc cctacagcaa gacggaaacc tcccttaca gcaccaccttt gcgattctgc    1860 agccacaaag ttgagacttc tgaacgtggc actcttctgt tcccttactg tttcacgtgt    1920
acctgtgtca tctttcttgt ttcatcgtaa acatacttct aaaattccca ttttctttat    1980
ttagaaatag aactacaagc ggatggttaa acaatttaaa caaatggtcc atggggaaaa    2040
gtgaatttca cact                                                      2054

<210> SEQ ID NO 24
<211> LENGTH: 3688
<212> TYPE: DNA
<213> ORGANISM: Homo sapiens

<400> SEQUENCE: 24
tgaagattca gttttcactt aaacaaccag caagtcttga agtctcttcc caagcaaatg      60
ggagcttctt tggaccttgg agcacacaga ggattctact ttctttaaaa ctttgttttc     120
aggcaatttc cctgagaacc gtttacttcc agaagattgg tggagcttga tctgaaggct     180
ggccatgaaa tctcaaggtc aacattggta ttccagttca gataaaaact gtaaagtgag     240
ctttcgtgag aagcttctga ttattgattc aaacctgggg gtccaagatg tggagaacct     300
caagtttctc tgcataggat tggtccccaa caagaagctg agaagtcca gctcagcctc      360 agatgttttt gaacatctct tggcagagga tctgctgagt gaggaagacc ctttcttcct     420
ggcagaactc ctctatatca tacggcagaa gaagctgctg cagcacctca actgtaccaa     480
agaggaagtg gagcgactgc tgcccacccg acaaagggtt tctctgttta gaaacctgct     540
ctacgaactg tcagaaggca ttgactcaga gaacttaaag gacatgatct tccttctgaa     600
agactcgctt cccaaaactg aaatgacctc ctaagtttc ctggcatttc tagagaaaca      660
aggtaaaata gatgaagata atctgacatg cctggaggac ctctgcaaaa cagttgtacc    720 taaactttttg agaaacatag agaaatacaa agagagaaa gctatccaga tagtgacacc     780
tcctgtagac aaggaagccg agtcgtatca aggagaggaa gaactagttt cccaaacaga    840
tgttaagaca ttcttggaag ccttaccgca ggagtcctgg caaaataagc atgcaggtag    900
taatgagggc agctgtgtac aggatgaatc ggaaccacag aggcctctgt gtcattgtca    960
acaaccacag ctttacctcc ctgaaggaca gacaaggaac ccataaagat gctgagatcc   1020
tgagtcatgt gttccagtgg cttgggttca cagtgcatat acacaataat gtgacgaaag   1080
tggaaatgga gatggtcctg cagaagcaga agtgcaatcc agcccatgcc gacggggact   1140
gcttcgtgtt ctgtattctg acccatggga gatttggagc tgtctactct tcggatgagg   1200
ccctcattcc cattcgggag atcatgtctc acttcacagc cctgcagtgc cctagactgg   1260
ctgaaaaacc taaactcttt ttcatccagg cctgccaagg tgaagagata cagccttccg   1320
tatccatcga agcagatgct ctgaaccctg agcaggcacc cacttccctg caggacagta   1380
ttcctgccga ggctgacttc ctacttggtc tggccactgt cccaggctat gtatcctttc   1440
ggcatgtgga ggaaggcagc tggtatattc agtctctgtg taatcatctg aagaaattgg   1500
```

```
                                -continued tcccaagaca tgaagacatc ttatccatcc tcactgctgt caacgatgat gtgagtcgaa    1560
gagtggacaa acagggaaca aagaaacaga tgccccagcc tgctttcaca ctaaggaaaa    1620
aactagtatt ccctgtgccc ctggatgcac tttcattata gcagagagtt tttgttggtt    1680
cttagacctc aaacgaatca ttggctataa cctccagcct cctgcccagc acaggaatcg    1740
gtggtctcca cctgtcattc tagaaacagg aaacaccgtg ttttctgaca cagtcaattc    1800
tgattttctt tttcttttgc aagtctaaat gttagaaaac tttctttttt ttggagatag    1860
tctcattctg tcacccagac tggagtgcag ggggcaatc acggctcact gtagtctcga     1920
cctcccaggc tcaagctgtc ctcccacctc agcctcccaa gtagctgaga ctacaggtgt    1980
gtgtccatgc acagctaact tttattttt tttgtggaga tggggtttca ctatgttgcc     2040
taagctggtc tcaaactcct gggctcaagc gatcctccca cctcagcttc tcaaagttct    2100
gggactacag gcatgaaata ctgtgcctgg cctggggacc aggtgcattt taaggttcct    2160
tggtgttcaa aaaccacgtt cttagcctag attgagctta gattgcctct ctagacaact    2220
accccttagt tataattctg tgtcccctct gcatgccctt aaacattgga cagtgaggtc    2280
acagtccacc caccctctct ctgatctccc ccttcctaag acttctcttt tgcacatcta    2340
gtgaggtgaa aatttggtct atgccaggcc catttcctgc ttttgtgtaa ggaaggtgct    2400
cacataggaa gtttttattt ggttagagac aggtttccct gtaggaagat gatggctcat    2460
ttacactcag ctgctctgca agcagaaact ttacaacctg atgtcatatt ccattttgga    2520
ctgggtgcgg tgactcatgc ctgtaatccc agtactctgg gaagccaagg caggcagatc    2580
acttgaggtc aggagttcga gaccagcctg gccaatacgg caaaacctca tcattactaa    2640
aaacacaaaa attagccagg tgtggcggcg agcacctgta atcccagcta ctcgggaggc    2700
tgagacagga gaatctcttg aatccaggag gcagaggctg tggtgagcca agatgacaca    2760
actgcactcc agcttgggca acagggcgag accttgttta aaaaaaaaat tcaatattgg    2820
ggttggaaca tttcagttgc cattgacaga acacccaatt caaattgact gaagcaaaga    2880
agggaattta ttgcctcttt cacattgaaa cccaggagtg gataacactg gcttcaggca    2940
aagcttgaat caggactcaa tctacaggcc agcacctttc tcttggccgg atgtcctcag    3000
ggctggcaga tgcagtagac tgcagtggac agtccccacc ttgttactgc tactacactt    3060
tgctcctctg gcccaaggca tgaggagaga ggctgtgtca gaaactgaag ctgttctcag    3120
gatcactggg ctcttcttgg cagaggggat gtctggcttg cctgaaggga gtggctctgt    3180
aaggacgcct tgatgctttc ttcattaaga ttttgagcat ttttacgtac ttgagctttt    3240
tttttttttt tttcaattt ctagaggaac ttttctctg ttaattcctg gaactgtatt      3300
ttgaatcctt aaaggtgagc cctcataggg agatccaaag tcctgtggtt aacgccttca    3360
tttatagatg aggcagctga ggcctgggga tgtgaacaac ctgctcacag tcctcattta    3420
ctggatttga cttcagccag gtgaactgga atgccttggg gcgtgaaggg cattaggag     3480 tgtttcattt gatatgtgaa tgctcataaa aaatgtcaa ggaatgaaga caacaactc      3540 tcagtggtgc ctgcatttat aattatttat gtgaaagtca aattcatgta cagtaaattt    3600
gttataagaa tattcacaag aacactgttc tgatatctct gattgtcatg tggatttgaa    3660
tgtagcttga cagagaaaaa aaaaaaaa                                      3688

<210> SEQ ID NO 25
<211> LENGTH: 3780
<212> TYPE: DNA
<213> ORGANISM: Homo sapiens
```

<400> SEQUENCE: 25

```
tgaagattca gttttcactt aaacaaccag caagtcttga agtctcttcc caagcaaatg      60
ggagcttctt tggaccttgg agcacacaga ggattctact ttctttaaaa ctttgttttc     120
aggcaatttc cctgagaacc gtttacttcc agaagattgg tggagcttga tctgaaggct     180
ggccatgaaa tctcaaggtc aacattggta ttccagttca gataaaaact gtaaagtgag     240
ctttcgtgag aagcttctga ttattgattc aaacctgggg gtccaagatg tggagaacct     300
caagtttctc tgcataggat tggtccccaa caagaagctg gagaagtcca gctcagcctc     360
agatgttttt gaacatctct tggcagagga tctgctgagt gaggaagacc ctttcttcct     420
ggcagaactc ctctatatca tacggcagaa gaagctgctg cagcacctca actgtaccaa     480
agaggaagtg gagcgactgc tgcccacccg acaaagggtt tctctgttta gaaacctgct     540
ctacgaactg tcagaaggca ttgactcaga gaacttaaag gacatgatct tccttctgaa     600
agactcgctt cccaaaactg aaatgacctc cctaagtttc ctggcatttc tagagaaaca     660
aggtaaaata gatgaagata atctgacatg cctggaggac ctctgcaaaa cagttgtacc     720
taaactttg agaaacatag agaaatacaa aagagagaaa gctatccaga tagtgacacc     780
tcctgtagac aaggaagccg agtcgtatca aggagaggaa gaactagttt cccaaacaga     840
tgttaagaca ttcttggaag ccttaccgca ggagtcctgg caaaataagc atgcaggtag     900
taatggtaac agagccacaa atggtgcacc aagcctggtc tccagggga tgcaaggagc     960
atctgctaac actctaaact ctgaaaccag cacaaagagg gcagctgtgt acaggatgaa    1020
tcggaaccac agaggcctct gtgtcattgt caacaaccac agctttacct ccctgaagga    1080
cagacaagga acccataaag atgctgagat cctgagtcat gtgttccagt ggcttgggtt    1140
cacagtgcat atacacaata atgtgacgaa agtggaaatg agatggtcc tgcagaagca    1200
gaagtgcaat ccagcccatg ccgacgggga ctgcttcgtg ttctgtattc tgacccatgg    1260
gagatttgga gctgtctact cttcggatga ggccctcatt cccattcggg agatcatgtc    1320
tcacttcaca gccctgcagt gccctagact ggctgaaaaa cctaaactct ttttcatcca    1380
ggcctgccaa ggtgaagaga tacagccttc cgtatccatc gaagcagatg ctctgaaccc    1440
tgagcaggca cccacttccc tgcaggacag tattcctgcc gaggctgact tcctacttgg    1500
tctggccact gtcccaggct atgtatcctt cggcatgtg gaggaaggca gctggtatat    1560
tcagtctctg tgtaatcatc tgaagaaatt ggtcccaaga catgaagaca tcttatccat    1620
cctcactgct gtcaacgatg atgtgagtcg aagagtggac aaacagggaa caaagaaaca    1680
gatgccccag cctgctttca cactaaggaa aaaactagta ttccctgtgc ccctggatgc    1740
actttcatta tagcagagag ttttttgttgg ttcttagacc tcaaacgaat cattggctat    1800
aacctccagc ctcctgccca gcacaggaat cggtggtctc cacctgtcat tctagaaaca    1860
ggaaacaccg tgttttctga cacagtcaat tctgattttc tttttctttt gcaagtctaa    1920
atgttagaaa actttctttt ttttggagat agtctcattc tgtcacccag actggagtgc    1980
agggggcaa tcacggctca ctgtagtctc gacctcccag gctcaagctg tcctcccacc    2040
tcagcctccc aagtagctga gactacaggt gtgtgtccat gcacagctaa cttttttattt    2100
tttttgtgga gatgggtttt cactatgttg cctaagctgg tctcaaactc ctgggctcaa    2160
gcgatcctcc cacctcagct tctcaaagtt ctgggactac aggcatgaaa tactgtgcct    2220
ggcctgggga ccaggtgcat tttaaggttc cttggtgttc aaaaaccacg ttcttagcct    2280
```

```
agattgagct tagattgcct ctctagacaa ctacccctta gttataattc tgtgtccect   2340 ctgcatgccc ttaaacattg gacagtgagg tcacagtcca cccaccctct ctctgatctc   2400 cccttccta agacttctct tttgcacatc tagtgaggtg aaaatttggt ctatgccagg    2460
cccatttcct gcttttgtgt aaggaaggtg ctcacatagg aagttttat ttggttagag    2520 acaggtttcc ctgtaggaag atgatggctc atttacactc agctgctctg caagcagaaa   2580
ctttacaacc tgatgtcata ttccattttg gactgggtgc ggtgactcat gcctgtaatc   2640
ccagtactct gggaagccaa ggcaggcaga tcacttgagg tcaggagttc gagaccagcc   2700
tggccaatac ggcaaaacct catcattact aaaaacacaa aaattagcca ggtgtggcgg   2760
cgagcacctg taatcccagc tactcgggag gctgagacag gagaatctct tgaatccagg   2820
aggcagaggc tgtggtgagc caagatgaca caactgcact ccagcttggg caacagggcg   2880
agaccttgtt taaaaaaaaa attcaatatt ggggttggaa catttcagtt gccattgaca   2940
gaacacccaa ttcaaattga ctgaagcaaa gaagggaatt tattgcctct ttcacattga   3000
aacccaggag tggataacac tggcttcagg caaagcttga atcaggactc aatctacagg   3060
ccagcacctt tctcttggcc ggatgtcctc agggctggca gatgcagtag actgcagtgg   3120
acagtcccca ccttgttact gctactacac tttgctcctc tggcccaagg catgaggaga   3180
gaggctgtgt cagaaactga agctgttctc aggatcactg ggctcttctt ggcagagggg   3240
atgtctggct tgcctgaagg gagtggctct gtaaggacgc cttgatgctt tcttcattaa   3300
gattttgagc atttttacgt acttgagctt tttttttttt tttttcaat ttctagagga    3360 actttttctc tgttaattcc tggaactgta ttttgaatcc ttaaaggtga gccctcatag   3420
ggagatccaa agtcctgtgg ttaacgcctt catttataga tgaggcagct gaggcctggg   3480
gatgtgaaca acctgctcac agtcctcatt tactggattt gacttcagcc aggtgaactg   3540
gaatgccttg gggcgtggaa gggcattagg agtgtttcat ttgatatgtg aatgctcata   3600
aaaaaatgtc aaggaatgaa gaacaacaac tctcagtggt gcctgcattt ataattattt   3660
atgtgaaagt caaattcatg tacagtaaat ttgttataag aatattcaca agaacactgt   3720
tctgatatct ctgattgtca tgtggatttg aatgtagctt gacagagaaa aaaaaaaaa    3780
```

<210> SEQ ID NO 26
<211> LENGTH: 8
<212> TYPE: RNA
<213> ORGANISM: Artificial Sequence
<220> FEATURE:
<223> OTHER INFORMATION: Linker sequence

<400> SEQUENCE: 26 uugcuaua                                                            8

<210> SEQ ID NO 27
<211> LENGTH: 540
<212> TYPE: PRT
<213> ORGANISM: Homo sapiens

<400> SEQUENCE: 27

Met Asn Gly Glu Ala Ile Cys Ser Ala Leu Pro Thr Ile Pro Tyr His
1               5                   10                  15

Lys Leu Ala Asp Leu Arg Tyr Leu Ser Arg Gly Ala Ser Gly Thr Val
            20                  25                  30

Ser Ser Ala Arg His Ala Asp Trp Arg Val Gln Val Ala Val Lys His
        35                  40                  45

```
Leu His Ile His Thr Pro Leu Leu Asp Ser Glu Arg Lys Asp Val Leu
    50                  55                  60

Arg Glu Ala Glu Ile Leu His Lys Ala Arg Phe Ser Tyr Ile Leu Pro
65                  70                  75                  80

Ile Leu Gly Ile Cys Asn Glu Pro Glu Phe Leu Gly Ile Val Thr Glu
                85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile Thr Phe Leu Glu
    290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
                325                 330                 335

Val Asn His Gly Pro Gln Glu Glu Ser Cys Gly Ser Ser Gln Leu His
            340                 345                 350

Glu Asn Ser Gly Ser Pro Glu Thr Ser Arg Ser Leu Pro Ala Pro Gln
        355                 360                 365

Asp Asn Asp Phe Leu Ser Arg Lys Ala Gln Asp Cys Tyr Phe Met Lys
    370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Thr Pro Cys Ser Ser
                405                 410                 415

Ala Ile Ile Asn Pro Leu Ser Thr Ala Gly Asn Ser Glu Arg Leu Gln
            420                 425                 430

Pro Gly Ile Ala Gln Gln Trp Ile Gln Ser Lys Arg Glu Asp Ile Val
        435                 440                 445

Asn Gln Met Thr Glu Ala Cys Leu Asn Gln Ser Leu Asp Ala Leu Leu
    450                 455                 460

Ser Arg Asp Leu Ile Met Lys Glu Asp Tyr Glu Leu Val Ser Thr Lys
```

```
                465                 470                 475                 480
Pro Thr Arg Thr Ser Lys Val Arg Gln Leu Leu Asp Thr Thr Asp Ile
                    485                 490                 495

Gln Gly Glu Glu Phe Ala Lys Val Ile Val Gln Lys Leu Lys Asp Asn
                500                 505                 510

Lys Gln Met Gly Leu Gln Pro Tyr Pro Glu Ile Leu Val Val Ser Arg
            515                 520                 525

Ser Pro Ser Leu Asn Leu Leu Gln Asn Lys Ser Met
        530                 535                 540

<210> SEQ ID NO 28
<211> LENGTH: 737
<212> TYPE: PRT
<213> ORGANISM: Homo sapiens

<400> SEQUENCE: 28

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
        35                  40                  45

Ser Arg Ile Gly Gln Thr Ala Thr Lys Gln Lys Thr Asn Ser Pro Ala
50                  55                  60

Trp His Asp Glu Phe Val Thr Asp Val Cys Asn Gly Arg Lys Ile Glu
65                  70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Arg Val Tyr Val Ile
        115                 120                 125

Ile Asp Leu Ser Gly Ser Ser Gly Glu Ala Pro Lys Asp Asn Glu Glu
    130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285

Ala Pro Asn Cys Gly Val Asp Ala Arg Gly Ile Ala Lys Val Leu Ala
    290                 295                 300
```

-continued

```
Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
            325                 330                 335

Ser Pro Ser Glu Glu Asp Arg Ser Lys Ser Ala Pro Thr Ser Pro Cys
            340                 345                 350

Asp Gln Glu Ile Lys Glu Leu Glu Asn Asn Ile Arg Lys Ala Leu Ser
            355                 360                 365

Phe Asp Asn Arg Gly Glu His Arg Ala Ala Ser Ser Pro Asp Gly
370                 375                 380

Gln Leu Met Ser Pro Gly Asn Gly Glu Val Arg Gln Gly Gln Ala
385                 390                 395                 400

Lys Arg Leu Gly Leu Asp Glu Phe Asn Phe Ile Lys Val Leu Gly Lys
            405                 410                 415

Gly Ser Phe Gly Lys Val Met Leu Ala Glu Leu Lys Gly Lys Asp Glu
            420                 425                 430

Val Tyr Ala Val Lys Val Leu Lys Asp Val Ile Leu Gln Asp Asp
            435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
            485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
            515                 520                 525

Ile Tyr Arg Asp Leu Lys Leu Asp Asn Ile Leu Leu Asp Ala Glu Gly
            530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
            565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
            595                 600                 605

Ala Asp Asn Glu Asp Asp Leu Phe Glu Ser Ile Leu His Asp Asp Val
610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
            645                 650                 655

Asn Gly Glu Asp Ala Ile Lys Gln His Pro Phe Phe Lys Glu Ile Asp
            660                 665                 670

Trp Val Leu Leu Glu Gln Lys Lys Ile Lys Pro Pro Phe Lys Pro Arg
            675                 680                 685

Ile Lys Thr Lys Arg Asp Val Asn Asn Phe Asp Gln Asp Phe Thr Arg
            690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
```

-continued

```
                725                 730                 735
Pro

<210> SEQ ID NO 29
<211> LENGTH: 431
<212> TYPE: PRT
<213> ORGANISM: Homo sapiens

<400> SEQUENCE: 29

Met Ala His Ser Pro Val Gln Ser Gly Leu Pro Gly Met Gln Asn Leu
1               5                   10                  15

Lys Ala Asp Pro Glu Glu Leu Phe Thr Lys Leu Glu Lys Ile Gly Lys
            20                  25                  30

Gly Ser Phe Gly Glu Val Phe Lys Gly Ile Asp Asn Arg Thr Gln Lys
        35                  40                  45

Val Val Ala Ile Lys Ile Ile Asp Leu Glu Glu Ala Glu Asp Glu Ile
    50                  55                  60

Glu Asp Ile Gln Gln Glu Ile Thr Val Leu Ser Gln Cys Asp Ser Pro
65                  70                  75                  80

Tyr Val Thr Lys Tyr Tyr Gly Ser Tyr Leu Lys Asp Thr Lys Leu Trp
                85                  90                  95

Ile Ile Met Glu Tyr Leu Gly Gly Gly Ser Ala Leu Asp Leu Leu Glu
            100                 105                 110

Pro Gly Pro Leu Asp Glu Thr Gln Ile Ala Thr Ile Leu Arg Glu Ile
        115                 120                 125

Leu Lys Gly Leu Asp Tyr Leu His Ser Glu Lys Lys Ile His Arg Asp
    130                 135                 140

Ile Lys Ala Ala Asn Val Leu Leu Ser Glu His Gly Glu Val Lys Leu
145                 150                 155                 160

Ala Asp Phe Gly Val Ala Gly Gln Leu Thr Asp Thr Gln Ile Lys Arg
                165                 170                 175

Asn Thr Phe Val Gly Thr Pro Phe Trp Met Ala Pro Glu Val Ile Lys
            180                 185                 190

Gln Ser Ala Tyr Asp Ser Lys Ala Asp Ile Trp Ser Leu Gly Ile Thr
        195                 200                 205

Ala Ile Glu Leu Ala Arg Gly Glu Pro Pro His Ser Glu Leu His Pro
    210                 215                 220

Met Lys Val Leu Phe Leu Ile Pro Lys Asn Asn Pro Pro Thr Leu Glu
225                 230                 235                 240

Gly Asn Tyr Ser Lys Pro Leu Lys Glu Phe Val Glu Ala Cys Leu Asn
                245                 250                 255

Lys Glu Pro Ser Phe Arg Pro Thr Ala Lys Glu Leu Leu Lys His Lys
            260                 265                 270

Phe Ile Leu Arg Asn Ala Lys Lys Thr Ser Tyr Leu Thr Glu Leu Ile
        275                 280                 285

Asp Arg Tyr Lys Arg Trp Lys Ala Glu Gln Ser His Asp Asp Ser Ser
    290                 295                 300

Ser Glu Asp Ser Asp Ala Glu Thr Asp Gly Gln Ala Ser Gly Gly Ser
305                 310                 315                 320

Asp Ser Gly Asp Trp Ile Phe Thr Ile Arg Glu Lys Asp Pro Lys Asn
                325                 330                 335

Leu Glu Asn Gly Ala Leu Gln Pro Ser Asp Leu Asp Arg Asn Lys Met
            340                 345                 350

Lys Asp Ile Pro Lys Arg Pro Phe Ser Gln Cys Leu Ser Thr Ile Ile
```

```
                355                 360                 365
Ser Pro Leu Phe Ala Glu Leu Lys Glu Lys Ser Gln Ala Cys Gly Gly
    370                 375                 380

Asn Leu Gly Ser Ile Glu Glu Leu Arg Gly Ala Ile Tyr Leu Ala Glu
385                 390                 395                 400

Glu Val Cys Pro Gly Ile Ser Asp Thr Met Val Ala Gln Leu Val Gln
                405                 410                 415

Arg Leu Gln Arg Tyr Ser Leu Ser Gly Gly Thr Ser Ser His
                420                 425                 430

<210> SEQ ID NO 30
<211> LENGTH: 443
<212> TYPE: PRT
<213> ORGANISM: Homo sapiens

<400> SEQUENCE: 30

Met Asp Ser Arg Ala Gln Leu Trp Gly Leu Ala Leu Asn Lys Arg Arg
1               5                   10                  15

Ala Thr Leu Pro His Pro Gly Gly Ser Thr Asn Leu Lys Ala Asp Pro
            20                  25                  30

Glu Glu Leu Phe Thr Lys Leu Glu Lys Ile Gly Lys Gly Ser Phe Gly
        35                  40                  45

Glu Val Phe Lys Gly Ile Asp Asn Arg Thr Gln Lys Val Val Ala Ile
    50                  55                  60

Lys Ile Ile Asp Leu Glu Glu Ala Glu Asp Glu Ile Glu Asp Ile Gln
65                  70                  75                  80

Gln Glu Ile Thr Val Leu Ser Gln Cys Asp Ser Pro Tyr Val Thr Lys
                85                  90                  95

Tyr Tyr Gly Ser Tyr Leu Lys Asp Thr Lys Leu Trp Ile Ile Met Glu
            100                 105                 110

Tyr Leu Gly Gly Gly Ser Ala Leu Asp Leu Leu Glu Pro Gly Pro Leu
        115                 120                 125

Asp Glu Thr Gln Ile Ala Thr Ile Leu Arg Glu Ile Leu Lys Gly Leu
    130                 135                 140

Asp Tyr Leu His Ser Glu Lys Lys Ile His Arg Asp Ile Lys Ala Ala
145                 150                 155                 160

Asn Val Leu Leu Ser Glu His Gly Glu Val Lys Leu Ala Asp Phe Gly
                165                 170                 175

Val Ala Gly Gln Leu Thr Asp Thr Gln Ile Lys Arg Asn Thr Phe Val
            180                 185                 190

Gly Thr Pro Phe Trp Met Ala Pro Glu Val Ile Lys Gln Ser Ala Tyr
        195                 200                 205

Asp Ser Lys Ala Asp Ile Trp Ser Leu Gly Ile Thr Ala Ile Glu Leu
    210                 215                 220

Ala Arg Gly Glu Pro Pro His Ser Glu Leu His Pro Met Lys Val Leu
225                 230                 235                 240

Phe Leu Ile Pro Lys Asn Asn Pro Pro Thr Leu Glu Gly Asn Tyr Ser
                245                 250                 255

Lys Pro Leu Lys Glu Phe Val Glu Ala Cys Leu Asn Lys Glu Pro Ser
            260                 265                 270

Phe Arg Pro Thr Ala Lys Glu Leu Leu Lys His Lys Phe Ile Leu Arg
        275                 280                 285

Asn Ala Lys Lys Thr Ser Tyr Leu Thr Glu Leu Ile Asp Arg Tyr Lys
    290                 295                 300
```

```
Arg Trp Lys Ala Glu Gln Ser His Asp Asp Ser Ser Glu Asp Ser
305                 310                 315                 320

Asp Ala Glu Thr Asp Gly Gln Ala Ser Gly Gly Ser Asp Ser Gly Asp
            325                 330                 335

Trp Ile Phe Thr Ile Arg Glu Lys Asp Pro Lys Asn Leu Glu Asn Gly
            340                 345                 350

Ala Leu Gln Pro Ser Asp Leu Asp Arg Asn Lys Met Lys Asp Ile Pro
        355                 360                 365

Lys Arg Pro Phe Ser Gln Cys Leu Ser Thr Ile Ile Ser Pro Leu Phe
    370                 375                 380

Ala Glu Leu Lys Glu Lys Ser Gln Ala Cys Gly Asn Leu Gly Ser
385                 390                 395                 400

Ile Glu Glu Leu Arg Gly Ala Ile Tyr Leu Ala Glu Ala Cys Pro
                405                 410                 415

Gly Ile Ser Asp Thr Met Val Ala Gln Leu Val Gln Arg Leu Gln Arg
            420                 425                 430

Tyr Ser Leu Ser Gly Gly Gly Thr Ser Ser His
        435                 440

<210> SEQ ID NO 31
<211> LENGTH: 471
<212> TYPE: PRT
<213> ORGANISM: Homo sapiens

<400> SEQUENCE: 31

Met Ser Glu Glu Ser Asp Met Asp Lys Ala Ile Lys Glu Thr Ser Ile
1               5                   10                  15

Leu Glu Glu Tyr Ser Ile Asn Trp Thr Gln Lys Leu Gly Ala Gly Ile
            20                  25                  30

Ser Gly Pro Val Arg Val Cys Val Lys Lys Ser Thr Gln Glu Arg Phe
        35                  40                  45

Ala Leu Lys Ile Leu Leu Asp Arg Pro Lys Ala Arg Asn Glu Val Arg
    50                  55                  60

Leu His Met Met Cys Ala Thr His Pro Asn Ile Val Gln Ile Ile Glu
65                  70                  75                  80

Val Phe Ala Asn Ser Val Gln Phe Pro His Glu Ser Ser Pro Arg Ala
                85                  90                  95

Arg Leu Leu Ile Val Met Glu Met Met Glu Gly Gly Glu Leu Phe His
            100                 105                 110

Arg Ile Ser Gln His Arg His Phe Thr Glu Lys Gln Ala Ser Gln Val
        115                 120                 125

Thr Lys Gln Ile Ala Leu Ala Leu Arg His Cys His Leu Leu Asn Ile
    130                 135                 140

Ala His Arg Asp Leu Lys Pro Glu Asn Leu Leu Phe Lys Asp Asn Ser
145                 150                 155                 160

Leu Asp Ala Pro Val Lys Leu Cys Asp Phe Gly Phe Ala Lys Ile Asp
                165                 170                 175

Gln Gly Asp Leu Met Thr Pro Gln Phe Thr Pro Tyr Tyr Val Ala Pro
            180                 185                 190

Gln Val Leu Glu Ala Gln Arg Arg His Gln Lys Glu Lys Ser Gly Ile
        195                 200                 205

Ile Pro Thr Ser Pro Thr Pro Tyr Thr Tyr Asn Lys Ser Cys Asp Leu
    210                 215                 220

Trp Ser Leu Gly Val Ile Ile Tyr Val Met Leu Cys Gly Tyr Pro Pro
225                 230                 235                 240
```

```
Phe Tyr Ser Lys His His Ser Arg Thr Ile Pro Lys Asp Met Arg Arg
                245                 250                 255

Lys Ile Met Thr Gly Ser Phe Glu Phe Pro Glu Glu Glu Trp Ser Gln
            260                 265                 270

Ile Ser Glu Met Ala Lys Asp Val Arg Lys Leu Leu Lys Val Lys
        275                 280                 285

Pro Glu Glu Arg Leu Thr Ile Glu Gly Val Leu Asp His Pro Trp Leu
    290                 295                 300

Asn Ser Thr Glu Ala Leu Asp Asn Val Leu Pro Ser Ala Gln Leu Met
305                 310                 315                 320

Met Asp Lys Ala Val Val Ala Gly Ile Gln Gln Ala His Ala Glu Gln
                325                 330                 335

Leu Ala Asn Met Arg Ile Gln Asp Leu Lys Val Ser Leu Lys Pro Leu
                340                 345                 350

His Ser Val Asn Asn Pro Ile Leu Arg Lys Arg Lys Leu Leu Gly Thr
            355                 360                 365

Lys Pro Lys Asp Ser Val Tyr Ile His Asp His Glu Asn Gly Ala Glu
    370                 375                 380

Asp Ser Asn Val Ala Leu Glu Lys Leu Arg Asp Val Ile Ala Gln Cys
385                 390                 395                 400

Ile Leu Pro Gln Ala Gly Glu Asn Glu Asp Glu Lys Leu Asn Glu Val
                405                 410                 415

Met Gln Glu Ala Trp Lys Tyr Asn Arg Glu Cys Lys Leu Leu Arg Asp
                420                 425                 430

Thr Leu Gln Ser Phe Ser Trp Asn Gly Arg Gly Phe Thr Asp Lys Val
            435                 440                 445

Asp Arg Leu Lys Leu Ala Glu Ile Val Lys Gln Val Ile Glu Glu Gln
    450                 455                 460

Thr Thr Ser His Glu Ser Gln
465                 470

<210> SEQ ID NO 32
<211> LENGTH: 473
<212> TYPE: PRT
<213> ORGANISM: Homo sapiens

<400> SEQUENCE: 32

Met Ser Glu Glu Ser Asp Met Asp Lys Ala Ile Lys Glu Thr Ser Ile
1               5                   10                  15

Leu Glu Glu Tyr Ser Ile Asn Trp Thr Gln Lys Leu Gly Ala Gly Ile
            20                  25                  30

Ser Gly Pro Val Arg Val Cys Val Lys Lys Ser Thr Gln Glu Arg Phe
        35                  40                  45

Ala Leu Lys Ile Leu Leu Asp Arg Pro Lys Ala Arg Asn Glu Val Arg
    50                  55                  60

Leu His Met Met Cys Ala Thr His Pro Asn Ile Val Gln Ile Ile Glu
65                  70                  75                  80

Val Phe Ala Asn Ser Val Gln Phe Pro His Glu Ser Ser Pro Arg Ala
                85                  90                  95

Arg Leu Leu Ile Val Met Glu Met Met Glu Gly Gly Glu Leu Phe His
                100                 105                 110

Arg Ile Ser Gln His Arg His Phe Thr Glu Lys Gln Ala Ser Gln Val
            115                 120                 125

Thr Lys Gln Ile Ala Leu Ala Leu Arg His Cys His Leu Leu Asn Ile
```

```
                130                 135                 140
Ala His Arg Asp Leu Lys Pro Glu Asn Leu Leu Phe Lys Asp Asn Ser
145                 150                 155                 160

Leu Asp Ala Pro Val Lys Leu Cys Asp Phe Gly Phe Ala Lys Ile Asp
                165                 170                 175

Gln Gly Asp Leu Met Thr Pro Gln Phe Thr Pro Tyr Tyr Val Ala Pro
                180                 185                 190

Gln Val Leu Glu Ala Gln Arg His Gln Lys Glu Lys Ser Gly Ile
                195                 200                 205

Ile Pro Thr Ser Pro Thr Pro Tyr Thr Tyr Asn Lys Ser Cys Asp Leu
    210                 215                 220

Trp Ser Leu Gly Val Ile Ile Tyr Val Met Leu Cys Gly Tyr Pro Pro
225                 230                 235                 240

Phe Tyr Ser Lys His His Ser Arg Thr Ile Pro Lys Asp Met Arg Arg
                245                 250                 255

Lys Ile Met Thr Gly Ser Phe Glu Phe Pro Glu Glu Glu Trp Ser Gln
                260                 265                 270

Ile Ser Glu Met Ala Lys Asp Val Val Arg Lys Leu Leu Lys Val Lys
    275                 280                 285

Pro Glu Glu Arg Leu Thr Ile Glu Gly Val Leu Asp His Pro Trp Leu
    290                 295                 300

Asn Ser Thr Glu Ala Leu Asp Asn Val Leu Pro Ser Ala Gln Leu Met
305                 310                 315                 320

Met Asp Lys Ala Val Val Ala Gly Ile Gln Gln Ala His Ala Glu Gln
                325                 330                 335

Leu Ala Asn Met Arg Ile Gln Asp Leu Lys Val Ser Leu Lys Pro Leu
                340                 345                 350

His Ser Val Asn Asn Pro Ile Leu Arg Lys Arg Lys Leu Leu Gly Thr
                355                 360                 365

Lys Pro Lys Asp Ser Val Tyr Ile His Asp His Glu Asn Gly Ala Glu
    370                 375                 380

Asp Ser Asn Val Ala Leu Glu Lys Leu Arg Asp Val Ile Ala Gln Cys
385                 390                 395                 400

Ile Leu Pro Gln Ala Gly Lys Gly Glu Asn Glu Asp Glu Lys Leu Asn
                405                 410                 415

Glu Val Met Gln Glu Ala Trp Lys Tyr Asn Arg Glu Cys Lys Leu Leu
                420                 425                 430

Arg Asp Thr Leu Gln Ser Phe Ser Trp Asn Gly Arg Gly Phe Thr Asp
                435                 440                 445

Lys Val Asp Arg Leu Lys Leu Ala Glu Ile Val Lys Gln Val Ile Glu
    450                 455                 460

Glu Gln Thr Thr Ser His Glu Ser Gln
465                 470

<210> SEQ ID NO 33
<211> LENGTH: 465
<212> TYPE: PRT
<213> ORGANISM: Homo sapiens

<400> SEQUENCE: 33

Met Val Ser Ser Gln Lys Leu Glu Lys Pro Ile Glu Met Gly Ser Ser
1               5                   10                  15

Glu Pro Leu Pro Ile Ala Asp Gly Asp Arg Arg Arg Lys Lys Lys Arg
                20                  25                  30
```

-continued

```
Arg Gly Arg Ala Thr Asp Ser Leu Pro Gly Lys Phe Glu Asp Met Tyr
        35                  40                  45
Lys Leu Thr Ser Glu Leu Leu Gly Glu Gly Ala Tyr Ala Lys Val Gln
 50                  55                  60
Gly Ala Val Ser Leu Gln Asn Gly Lys Glu Tyr Ala Val Lys Ile Ile
 65                  70                  75                  80
Glu Lys Gln Ala Gly His Ser Arg Ser Arg Val Phe Arg Glu Val Glu
                 85                  90                  95
Thr Leu Tyr Gln Cys Gln Gly Asn Lys Asn Ile Leu Glu Leu Ile Glu
            100                 105                 110
Phe Phe Glu Asp Asp Thr Arg Phe Tyr Leu Val Phe Glu Lys Leu Gln
        115                 120                 125
Gly Gly Ser Ile Leu Ala His Ile Gln Lys Gln Lys His Phe Asn Glu
    130                 135                 140
Arg Glu Ala Ser Arg Val Val Arg Asp Val Ala Ala Ala Leu Asp Phe
145                 150                 155                 160
Leu His Thr Lys Asp Lys Val Ser Leu Cys His Leu Gly Trp Ser Ala
                165                 170                 175
Met Ala Pro Ser Gly Leu Thr Ala Ala Pro Thr Ser Leu Gly Ser Ser
            180                 185                 190
Asp Pro Pro Thr Ser Ala Ser Gln Val Ala Gly Thr Thr Gly Ile Ala
        195                 200                 205
His Arg Asp Leu Lys Pro Glu Asn Ile Leu Cys Glu Ser Pro Glu Lys
    210                 215                 220
Val Ser Pro Val Lys Ile Cys Asp Phe Asp Leu Gly Ser Gly Met Lys
225                 230                 235                 240
Leu Asn Asn Ser Cys Thr Pro Ile Thr Thr Pro Glu Leu Thr Thr Pro
                245                 250                 255
Cys Gly Ser Ala Glu Tyr Met Ala Pro Glu Val Val Glu Val Phe Thr
            260                 265                 270
Asp Gln Ala Thr Phe Tyr Asp Lys Arg Cys Asp Leu Trp Ser Leu Gly
        275                 280                 285
Val Val Leu Tyr Ile Met Leu Ser Gly Tyr Pro Pro Phe Val Gly His
    290                 295                 300
Cys Gly Ala Asp Cys Gly Trp Asp Arg Gly Glu Val Cys Arg Val Cys
305                 310                 315                 320
Gln Asn Lys Leu Phe Glu Ser Ile Gln Glu Gly Lys Tyr Glu Phe Pro
                325                 330                 335
Asp Lys Asp Trp Ala His Ile Ser Ser Glu Ala Lys Asp Leu Ile Ser
            340                 345                 350
Lys Leu Leu Val Arg Asp Ala Lys Gln Arg Leu Ser Ala Ala Gln Val
        355                 360                 365
Leu Gln His Pro Trp Val Gln Gly Gln Ala Pro Glu Lys Gly Leu Pro
    370                 375                 380
Thr Pro Gln Val Leu Gln Arg Asn Ser Ser Thr Met Asp Leu Thr Leu
385                 390                 395                 400
Phe Ala Ala Glu Ala Ile Ala Leu Asn Arg Gln Leu Ser Gln His Glu
                405                 410                 415
Glu Asn Glu Leu Ala Glu Glu Pro Glu Ala Leu Ala Asp Gly Leu Cys
            420                 425                 430
Ser Met Lys Leu Ser Pro Pro Cys Lys Ser Arg Leu Ala Arg Arg Arg
        435                 440                 445
Ala Leu Ala Gln Ala Gly Arg Gly Glu Asp Arg Ser Pro Pro Thr Ala
```

-continued

```
                450                 455                 460
Leu
465

<210> SEQ ID NO 34
<211> LENGTH: 473
<212> TYPE: PRT
<213> ORGANISM: Homo sapiens

<400> SEQUENCE: 34

Met Leu Lys Val Thr Val Pro Ser Cys Ser Ala Ser Ser Cys Ser Ser
1               5                   10                  15

Val Thr Ala Ser Ala Ala Pro Gly Thr Ala Ser Leu Val Pro Asp Tyr
            20                  25                  30

Trp Ile Asp Gly Ser Asn Arg Asp Ala Leu Ser Asp Phe Phe Glu Val
        35                  40                  45

Glu Ser Glu Leu Gly Arg Gly Ala Thr Ser Ile Val Tyr Arg Cys Lys
    50                  55                  60

Gln Lys Gly Thr Gln Lys Pro Tyr Ala Leu Lys Val Leu Lys Lys Thr
65                  70                  75                  80

Val Asp Lys Lys Ile Val Arg Thr Glu Ile Gly Val Leu Leu Arg Leu
                85                  90                  95

Ser His Pro Asn Ile Ile Lys Leu Lys Glu Ile Phe Glu Thr Pro Thr
            100                 105                 110

Glu Ile Ser Leu Val Leu Glu Leu Val Thr Gly Gly Glu Leu Phe Asp
        115                 120                 125

Arg Ile Val Glu Lys Gly Tyr Tyr Ser Glu Arg Asp Ala Ala Asp Ala
    130                 135                 140

Val Lys Gln Ile Leu Glu Ala Val Ala Tyr Leu His Glu Asn Gly Ile
145                 150                 155                 160

Val His Arg Asp Leu Lys Pro Glu Asn Leu Leu Tyr Ala Thr Pro Ala
                165                 170                 175

Pro Asp Ala Pro Leu Lys Ile Ala Asp Phe Gly Leu Ser Lys Ile Val
            180                 185                 190

Glu His Gln Val Leu Met Lys Thr Val Cys Gly Thr Pro Gly Tyr Cys
        195                 200                 205

Ala Pro Glu Ile Leu Arg Gly Cys Ala Tyr Gly Pro Glu Val Asp Met
    210                 215                 220

Trp Ser Val Gly Ile Ile Thr Tyr Ile Leu Leu Cys Gly Phe Glu Pro
225                 230                 235                 240

Phe Tyr Asp Glu Arg Gly Asp Gln Phe Met Phe Arg Arg Ile Leu Asn
                245                 250                 255

Cys Glu Tyr Tyr Phe Ile Ser Pro Trp Trp Asp Glu Val Ser Leu Asn
            260                 265                 270

Ala Lys Asp Leu Val Arg Lys Leu Ile Val Leu Asp Pro Lys Lys Arg
        275                 280                 285

Leu Thr Thr Phe Gln Ala Leu Gln His Pro Trp Val Thr Gly Lys Ala
    290                 295                 300

Ala Asn Phe Val His Met Asp Thr Ala Gln Lys Lys Leu Gln Glu Phe
305                 310                 315                 320

Asn Ala Arg Arg Lys Leu Lys Ala Ala Val Lys Ala Val Val Ala Ser
                325                 330                 335

Ser Arg Leu Gly Ser Ala Ser Ser Ser His Gly Ser Ile Gln Glu Ser
            340                 345                 350
```

-continued

His Lys Ala Ser Arg Asp Pro Ser Pro Ile Gln Asp Gly Asn Glu Asp
          355                 360                 365

Met Lys Ala Ile Pro Glu Gly Glu Lys Ile Gln Gly Asp Gly Ala Gln
    370                 375                 380

Ala Ala Val Lys Gly Ala Gln Ala Glu Leu Met Lys Val Gln Ala Leu
385                 390                 395                 400

Glu Lys Val Lys Gly Ala Asp Ile Asn Ala Glu Glu Ala Pro Lys Met
                405                 410                 415

Val Pro Lys Ala Val Glu Asp Gly Ile Lys Val Ala Asp Leu Glu Leu
            420                 425                 430

Glu Glu Gly Leu Ala Glu Glu Lys Leu Lys Thr Val Glu Glu Ala Ala
        435                 440                 445

Ala Pro Arg Glu Gly Gln Gly Ser Ser Ala Val Gly Phe Glu Val Pro
    450                 455                 460

Gln Gln Asp Val Ile Leu Pro Glu Tyr
465                 470

<210> SEQ ID NO 35
<211> LENGTH: 367
<212> TYPE: PRT
<213> ORGANISM: Homo sapiens

<400> SEQUENCE: 35

Met Asp Lys Glu Tyr Val Gly Phe Ala Ala Leu Pro Asn Gln Leu His
1               5                   10                  15

Arg Lys Ser Val Lys Lys Gly Phe Asp Phe Thr Leu Met Val Ala Gly
                20                  25                  30

Glu Ser Gly Leu Gly Lys Ser Thr Leu Ile Asn Ser Leu Phe Leu Thr
            35                  40                  45

Asn Leu Tyr Glu Asp Arg Gln Val Pro Glu Ala Ser Ala Arg Leu Thr
        50                  55                  60

Gln Thr Leu Ala Ile Glu Arg Arg Gly Val Glu Ile Glu Glu Gly Gly
65                  70                  75                  80

Val Lys Val Lys Leu Thr Leu Val Asp Thr Pro Gly Phe Gly Asp Ser
                85                  90                  95

Val Asp Cys Ser Asp Cys Trp Leu Pro Val Val Lys Phe Ile Glu Glu
            100                 105                 110

Gln Phe Glu Gln Tyr Leu Arg Asp Glu Ser Gly Leu Asn Arg Lys Asn
        115                 120                 125

Ile Gln Asp Ser Arg Val His Cys Cys Leu Tyr Phe Ile Ser Pro Phe
    130                 135                 140

Gly Arg Gly Leu Arg Pro Leu Asp Val Ala Phe Leu Arg Ala Val His
145                 150                 155                 160

Glu Lys Val Asn Ile Ile Pro Val Ile Gly Lys Ala Asp Ala Leu Met
                165                 170                 175

Pro Gln Glu Thr Gln Ala Leu Lys Gln Lys Ile Arg Asp Gln Leu Lys
            180                 185                 190

Glu Glu Glu Ile His Ile Tyr Gln Phe Pro Glu Cys Asp Ser Asp Glu
        195                 200                 205

Asp Glu Asp Phe Lys Arg Gln Asp Ala Glu Met Lys Glu Ser Ile Pro
    210                 215                 220

Phe Ala Val Val Gly Ser Cys Glu Val Arg Asp Gly Gly Asn Arg
225                 230                 235                 240

Pro Val Arg Gly Arg Arg Tyr Ser Trp Gly Thr Val Glu Val Glu Asn
                245                 250                 255

```
Pro His His Cys Asp Phe Leu Asn Leu Arg Arg Met Leu Val Gln Thr
        260                 265                 270

His Leu Gln Asp Leu Lys Glu Val Thr His Asp Leu Leu Tyr Glu Gly
        275                 280                 285

Tyr Arg Ala Arg Cys Leu Gln Ser Leu Ala Arg Pro Gly Ala Arg Asp
        290                 295                 300

Arg Ala Ser Arg Ser Lys Leu Ser Arg Gln Ser Ala Thr Glu Ile Pro
305                 310                 315                 320

Leu Pro Met Leu Pro Leu Ala Asp Thr Glu Lys Leu Ile Arg Glu Lys
                325                 330                 335

Asp Glu Glu Leu Arg Arg Met Gln Glu Met Leu Glu Lys Met Gln Ala
                340                 345                 350

Gln Met Gln Gln Ser Gln Ala Gln Gly Glu Gln Ser Asp Ala Leu
                355                 360                 365
```

<210> SEQ ID NO 36
<211> LENGTH: 209
<212> TYPE: PRT
<213> ORGANISM: Homo sapiens

<400> SEQUENCE: 36

```
Met Glu Gln Pro Arg Lys Ala Val Val Thr Gly Phe Gly Pro Phe
1               5                   10                  15

Gly Glu His Thr Val Asn Ala Ser Trp Ile Ala Val Gln Glu Leu Glu
                20                  25                  30

Lys Leu Gly Leu Gly Asp Ser Val Asp Leu His Val Tyr Glu Ile Pro
                35                  40                  45

Val Glu Tyr Gln Thr Val Gln Arg Leu Ile Pro Ala Leu Trp Glu Lys
        50                  55                  60

His Ser Pro Gln Leu Val Val His Val Gly Val Ser Gly Met Ala Thr
65                  70                  75                  80

Thr Val Thr Leu Glu Lys Cys Gly His Asn Lys Gly Tyr Lys Gly Leu
                85                  90                  95

Asp Asn Cys Arg Phe Cys Pro Gly Ser Gln Cys Cys Val Glu Asp Gly
                100                 105                 110

Pro Glu Ser Ile Asp Ser Ile Ile Asp Met Asp Ala Val Cys Lys Arg
                115                 120                 125

Val Thr Thr Leu Gly Leu Asp Val Ser Val Thr Ile Ser Gln Asp Ala
130                 135                 140

Gly Arg Lys Lys Pro Phe Pro Ala Lys Gly Asp Cys Val Phe Cys Arg
145                 150                 155                 160

Arg Arg Arg Ala Arg Ser Leu Gln Ala Gln Cys Gly Phe Ser Leu Thr
                165                 170                 175

Pro Ala Leu Glu Leu Leu Pro Val Pro Phe Leu Lys Leu Leu Cys Pro
                180                 185                 190

Gly Pro Pro Arg Arg Arg Arg Ile Cys Arg Ile Leu Pro Gly Ala Gly
                195                 200                 205

Leu
```

<210> SEQ ID NO 37
<211> LENGTH: 209
<212> TYPE: PRT
<213> ORGANISM: Homo sapiens

<400> SEQUENCE: 37

```
Met Gln Pro Arg Lys Ala Val Val Thr Gly Phe Gly Pro Phe
1               5                   10                  15

Gly Glu His Thr Val Asn Ala Ser Trp Ile Ala Val Gln Glu Leu Glu
            20                  25                  30

Lys Leu Gly Leu Gly Asp Ser Val Asp Leu His Val Tyr Glu Ile Pro
                35                  40                  45

Val Glu Tyr Gln Thr Val Gln Arg Leu Ile Pro Ala Leu Trp Glu Lys
    50                  55                  60

His Ser Pro Gln Leu Val Val His Val Gly Val Ser Gly Met Ala Thr
65                  70                  75                  80

Thr Val Thr Leu Glu Lys Cys Gly His Asn Lys Gly Tyr Lys Gly Leu
                85                  90                  95

Asp Asn Cys Arg Phe Cys Pro Gly Ser Gln Cys Cys Val Glu Asp Gly
                100                 105                 110

Pro Glu Ser Ile Asp Ser Ile Ile Asp Met Asp Ala Val Cys Lys Arg
                115                 120                 125

Val Thr Thr Leu Gly Leu Asp Val Ser Val Thr Ile Ser Gln Asp Ala
    130                 135                 140

Gly Arg Tyr Leu Cys Asp Phe Thr Tyr Tyr Thr Ser Leu Tyr Gln Ser
145                 150                 155                 160

His Gly Arg Ser Ala Phe Val His Val Pro Pro Leu Gly Lys Pro Tyr
                165                 170                 175

Asn Ala Asp Gln Leu Gly Arg Ala Leu Arg Ala Ile Glu Glu Met
                180                 185                 190

Leu Asp Leu Leu Glu Gln Ser Glu Gly Lys Ile Asn Tyr Cys His Lys
        195                 200                 205

His

<210> SEQ ID NO 38
<211> LENGTH: 359
<212> TYPE: PRT
<213> ORGANISM: Homo sapiens

<400> SEQUENCE: 38

Met Ala Glu Ala Ile Thr Tyr Ala Asp Leu Arg Phe Val Lys Ala Pro
1               5                   10                  15

Leu Lys Lys Ser Ile Ser Ser Arg Leu Gly Gln Asp Pro Gly Ala Asp
                20                  25                  30

Asp Asp Gly Glu Ile Thr Tyr Glu Asn Val Gln Val Pro Ala Val Leu
            35                  40                  45

Gly Val Pro Ser Ser Leu Ala Ser Ser Val Leu Gly Asp Lys Ala Ala
    50                  55                  60

Val Lys Ser Glu Gln Pro Thr Ala Ser Trp Arg Ala Val Thr Ser Pro
65                  70                  75                  80

Ala Val Gly Arg Ile Leu Pro Cys Arg Thr Thr Cys Leu Arg Tyr Leu
                85                  90                  95

Leu Leu Gly Leu Leu Leu Thr Cys Leu Leu Gly Val Thr Ala Ile
                100                 105                 110

Cys Leu Gly Val Arg Tyr Leu Gln Val Ser Gln Gln Leu Gln Gln Thr
        115                 120                 125

Asn Arg Val Leu Glu Val Thr Asn Ser Ser Leu Arg Gln Gln Leu Arg
    130                 135                 140

Leu Lys Ile Thr Gln Leu Gly Gln Ser Ala Glu Asp Leu Gln Gly Ser
145                 150                 155                 160
```

```
Arg Arg Glu Leu Ala Gln Ser Gln Glu Ala Leu Gln Val Glu Gln Arg
                165                 170                 175

Ala His Gln Ala Ala Glu Gly Gln Leu Gln Ala Cys Gln Ala Asp Arg
            180                 185                 190

Gln Lys Thr Lys Glu Thr Leu Gln Ser Glu Glu Gln Gln Arg Arg Ala
        195                 200                 205

Leu Glu Gln Lys Leu Ser Asn Met Glu Asn Arg Leu Lys Pro Phe Phe
    210                 215                 220

Thr Cys Gly Ser Ala Asp Thr Cys Cys Pro Ser Gly Trp Ile Met His
225                 230                 235                 240

Gln Lys Ser Cys Phe Tyr Ile Ser Leu Thr Ser Lys Asn Trp Gln Glu
                245                 250                 255

Ser Gln Lys Gln Cys Glu Thr Leu Ser Ser Lys Leu Ala Thr Phe Ser
            260                 265                 270

Glu Ile Tyr Pro Gln Ser His Ser Tyr Tyr Phe Leu Asn Ser Leu Leu
        275                 280                 285

Pro Asn Gly Gly Ser Gly Asn Ser Tyr Trp Thr Gly Leu Ser Ser Asn
    290                 295                 300

Lys Asp Trp Lys Leu Thr Asp Asp Thr Gln Arg Thr Arg Thr Tyr Ala
305                 310                 315                 320

Gln Ser Ser Lys Cys Asn Lys Val His Lys Thr Trp Ser Trp Trp Thr
                325                 330                 335

Leu Glu Ser Glu Ser Cys Arg Ser Ser Leu Pro Tyr Ile Cys Glu Met
            340                 345                 350

Thr Ala Phe Arg Phe Pro Asp
        355

<210> SEQ ID NO 39
<211> LENGTH: 370
<212> TYPE: PRT
<213> ORGANISM: Homo sapiens

<400> SEQUENCE: 39

Met Val Gly Lys Leu Lys Gln Asn Leu Leu Leu Ala Cys Leu Val Ile
1               5                   10                  15

Ser Ser Val Thr Val Phe Tyr Leu Gly Gln His Ala Met Glu Cys His
            20                  25                  30

His Arg Ile Glu Glu Arg Ser Gln Pro Val Lys Leu Glu Ser Thr Arg
        35                  40                  45

Thr Thr Val Arg Thr Gly Leu Asp Leu Lys Ala Asn Lys Thr Phe Ala
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110

Met Trp Ser Arg Ser Ser Lys Glu Lys Ile Arg Leu Asp Glu Ala Gly
        115                 120                 125

Val Thr Asp Glu Val Leu Asp Ser Ala Met Gln Ala Phe Leu Leu Glu
    130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175
```

```
Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
            195                 200                 205

Arg Asp Cys Leu Thr Lys Trp Asn Arg Ala Ile Glu Thr Met Tyr Asn
    210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His Glu Glu Met Ile
            260                 265                 270

Gly Lys Ala Gly Gly Val Ser Leu Ser Lys Val Glu Arg Ser Thr Asp
            275                 280                 285

Gln Val Ile Lys Pro Val Asn Val Gly Ala Leu Ser Lys Trp Val Gly
        290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Asn Tyr Gly
                325                 330                 335

Lys Pro Asp Pro Lys Ile Ile Glu Asn Thr Arg Arg Val Tyr Lys Gly
                340                 345                 350

Glu Phe Gln Leu Pro Asp Phe Leu Lys Glu Lys Pro Gln Thr Glu Gln
                355                 360                 365

Val Glu
    370

<210> SEQ ID NO 40
<211> LENGTH: 349
<212> TYPE: PRT
<213> ORGANISM: Homo sapiens

<400> SEQUENCE: 40

Met Asn Ser Thr Leu Asp Gly Asn Gln Ser His Pro Phe Cys Leu
1               5                   10                  15

Leu Ala Phe Gly Tyr Leu Glu Thr Val Asn Phe Cys Leu Leu Glu Val
            20                  25                  30

Leu Ile Ile Val Phe Leu Thr Val Leu Ile Ile Ser Gly Asn Ile Ile
        35                  40                  45

Val Ile Phe Val Phe His Cys Ala Pro Leu Leu Asn His His Thr Thr
    50                  55                  60

Ser Tyr Phe Ile Gln Thr Met Ala Tyr Ala Asp Leu Phe Val Gly Val
65                  70                  75                  80

Ser Cys Val Val Pro Ser Leu Ser Leu Leu His His Pro Leu Pro Val
                85                  90                  95

Glu Glu Ser Leu Thr Cys Gln Ile Phe Gly Phe Val Val Ser Val Leu
            100                 105                 110

Lys Ser Val Ser Met Ala Ser Leu Ala Cys Ile Ser Ile Asp Arg Tyr
        115                 120                 125

Ile Ala Ile Thr Lys Pro Leu Thr Tyr Asn Thr Leu Val Thr Pro Trp
    130                 135                 140

Arg Leu Arg Leu Cys Ile Phe Leu Ile Trp Leu Tyr Ser Thr Leu Val
145                 150                 155                 160

Phe Leu Pro Ser Phe Phe His Trp Gly Lys Pro Gly Tyr His Gly Asp
```

```
                165                 170                 175
Val Phe Gln Trp Cys Ala Glu Ser Trp His Thr Asp Ser Tyr Phe Thr
            180                 185                 190

Leu Phe Ile Val Met Met Leu Tyr Ala Pro Ala Leu Ile Val Cys
            195                 200             205

Phe Thr Tyr Phe Asn Ile Phe Arg Ile Cys Gln Gln His Thr Lys Asp
        210                 215             220

Ile Ser Glu Arg Gln Ala Arg Phe Ser Ser Gln Ser Gly Glu Thr Gly
225                 230                 235                 240

Glu Val Gln Ala Cys Pro Asp Lys Arg Tyr Ala Met Val Leu Phe Arg
                245                 250                 255

Ile Thr Ser Val Phe Tyr Ile Leu Trp Leu Pro Tyr Ile Ile Tyr Phe
            260                 265                 270

Leu Leu Glu Ser Ser Thr Gly His Ser Asn Arg Phe Ala Ser Phe Leu
            275                 280             285

Thr Thr Trp Leu Ala Ile Ser Asn Ser Phe Cys Asn Cys Val Ile Tyr
            290                 295             300

Ser Leu Ser Asn Ser Val Phe Gln Arg Gly Leu Lys Arg Leu Ser Gly
305                 310                 315                 320

Ala Met Cys Thr Ser Cys Ala Ser Gln Thr Thr Ala Asn Asp Pro Tyr
                325                 330                 335

Thr Val Arg Ser Lys Gly Pro Leu Asn Gly Cys His Ile
            340                 345

<210> SEQ ID NO 41
<211> LENGTH: 565
<212> TYPE: PRT
<213> ORGANISM: Homo sapiens

<400> SEQUENCE: 41

Met Pro Gln Ala Ser Glu His Arg Leu Gly Arg Thr Arg Glu Pro Pro
1               5                   10                  15

Val Asn Ile Gln Pro Arg Val Gly Ser Lys Leu Pro Phe Ala Pro Arg
            20                  25                  30

Ala Arg Ser Lys Glu Arg Arg Asn Pro Ala Ser Gly Pro Asn Pro Met
        35                  40                  45

Leu Arg Pro Leu Pro Pro Arg Pro Gly Leu Pro Asp Glu Arg Leu Lys
    50                  55                  60

Lys Leu Glu Leu Gly Arg Gly Arg Thr Ser Gly Pro Arg Pro Arg Gly
65                  70                  75                  80

Pro Leu Arg Ala Asp His Gly Val Pro Leu Pro Gly Ser Pro Pro Pro
                85                  90                  95

Thr Val Ala Leu Pro Leu Pro Ser Arg Thr Asn Leu Ala Arg Ser Lys
            100                 105                 110

Ser Val Ser Ser Gly Asp Leu Arg Pro Met Gly Ile Ala Leu Gly Gly
        115                 120                 125

His Arg Gly Thr Gly Glu Leu Gly Ala Ala Leu Ser Arg Leu Ala Leu
    130                 135                 140

Arg Pro Glu Pro Pro Thr Leu Arg Arg Ser Thr Ser Leu Arg Arg Leu
145                 150                 155                 160

Gly Gly Phe Pro Gly Pro Pro Thr Leu Phe Ser Ile Arg Thr Glu Pro
                165                 170                 175

Pro Ala Ser His Gly Ser Phe His Met Ile Ser Ala Arg Ser Ser Glu
            180                 185                 190
```

```
Pro Phe Tyr Ser Asp Asp Lys Met Ala His His Thr Leu Leu Leu Gly
        195                 200                 205

Ser Gly His Val Gly Leu Arg Asn Leu Gly Asn Thr Cys Phe Leu Asn
        210                 215                 220

Ala Val Leu Gln Cys Leu Ser Ser Thr Arg Pro Leu Arg Asp Phe Cys
225                 230                 235                 240

Leu Arg Arg Asp Phe Arg Gln Glu Val Pro Gly Gly Arg Ala Gln
                245                 250                 255

Glu Leu Thr Glu Ala Phe Ala Asp Val Ile Gly Ala Leu Trp His Pro
            260                 265                 270

Asp Ser Cys Glu Ala Val Asn Pro Thr Arg Phe Arg Ala Val Phe Gln
        275                 280                 285

Lys Tyr Val Pro Ser Phe Ser Gly Tyr Ser Gln Gln Asp Ala Gln Glu
        290                 295                 300

Phe Leu Lys Leu Leu Met Glu Arg Leu His Leu Glu Ile Asn Arg Arg
305                 310                 315                 320

Gly Arg Arg Ala Pro Pro Ile Leu Ala Asn Gly Pro Val Pro Ser Pro
                325                 330                 335

Pro Arg Arg Gly Gly Ala Leu Leu Glu Glu Pro Glu Leu Ser Asp Asp
            340                 345                 350

Asp Arg Ala Asn Leu Met Trp Lys Arg Tyr Leu Glu Arg Glu Asp Ser
        355                 360                 365

Lys Ile Val Asp Leu Phe Val Gly Gln Leu Lys Ser Cys Leu Lys Cys
        370                 375                 380

Gln Ala Cys Gly Tyr Arg Ser Thr Thr Phe Glu Val Phe Cys Asp Leu
385                 390                 395                 400

Ser Leu Pro Ile Pro Lys Lys Gly Phe Ala Gly Gly Lys Val Ser Leu
                405                 410                 415

Arg Asp Cys Phe Asn Leu Phe Thr Lys Glu Glu Glu Leu Glu Ser Glu
            420                 425                 430

Asn Ala Pro Val Cys Asp Arg Cys Arg Gln Lys Thr Arg Ser Thr Lys
        435                 440                 445

Lys Leu Thr Val Gln Arg Phe Pro Arg Ile Leu Gly Leu Asp Leu Asn
        450                 455                 460

Arg Phe Ser Ala Ser Arg Gly Ser Ile Lys Lys Ser Ser Val Gly Val
465                 470                 475                 480

Asp Phe Pro Leu Gln Arg Leu Ser Leu Gly Asp Phe Ala Ser Asp Lys
                485                 490                 495

Ala Gly Ser Pro Val Tyr Gln Leu Tyr Ala Leu Cys Asn His Ser Gly
            500                 505                 510

Ser Val His Tyr Gly His Tyr Thr Ala Leu Cys Arg Cys Gln Thr Gly
        515                 520                 525

Trp His Val Tyr Asn Asp Ser Arg Val Ser Pro Val Ser Glu Asn Gln
        530                 535                 540

Val Ala Ser Ser Glu Gly Tyr Val Leu Phe Tyr Gln Leu Met Gln Glu
545                 550                 555                 560

Pro Pro Arg Cys Leu
                565

<210> SEQ ID NO 42
<211> LENGTH: 551
<212> TYPE: PRT
<213> ORGANISM: Homo sapiens

<400> SEQUENCE: 42
```

```
Met Pro Gln Ala Ser Glu His Arg Leu Gly Arg Thr Arg Glu Pro Pro
1               5                   10                  15

Val Asn Ile Gln Pro Arg Val Gly Ser Lys Leu Pro Phe Ala Pro Arg
            20                  25                  30

Ala Arg Ser Lys Glu Arg Arg Asn Pro Ala Ser Gly Pro Asn Pro Met
        35                  40                  45

Leu Arg Pro Leu Pro Pro Arg Pro Gly Leu Pro Asp Glu Arg Leu Lys
    50                  55                  60

Lys Leu Glu Leu Gly Arg Gly Arg Thr Ser Gly Pro Arg Pro Arg Gly
65              70                  75                  80

Pro Leu Arg Ala Asp His Gly Val Pro Leu Pro Gly Ser Pro Pro Pro
                85                  90                  95

Thr Val Ala Leu Pro Leu Pro Ser Arg Thr Asn Leu Ala Arg Ser Lys
            100                 105                 110

Ser Val Ser Ser Gly Asp Leu Arg Pro Met Gly Ile Ala Leu Gly Gly
        115                 120                 125

His Arg Gly Thr Gly Glu Leu Gly Ala Ala Leu Ser Arg Leu Ala Leu
    130                 135                 140

Arg Pro Glu Pro Pro Thr Leu Arg Arg Ser Thr Ser Leu Arg Arg Leu
145                 150                 155                 160

Gly Gly Phe Pro Gly Pro Pro Thr Leu Phe Ser Ile Arg Thr Glu Pro
                165                 170                 175

Pro Ala Ser His Gly Ser Phe His Met Ile Ser Ala Arg Ser Ser Glu
            180                 185                 190

Pro Phe Tyr Ser Asp Asp Lys Met Ala His His Thr Leu Leu Leu Gly
        195                 200                 205

Ser Gly His Val Gly Leu Arg Asn Leu Gly Asn Thr Cys Phe Leu Asn
    210                 215                 220

Ala Val Leu Gln Cys Leu Ser Ser Thr Arg Pro Leu Arg Asp Phe Cys
225                 230                 235                 240

Leu Arg Arg Asp Phe Arg Gln Glu Val Pro Gly Gly Gly Arg Ala Gln
                245                 250                 255

Glu Leu Thr Glu Ala Phe Ala Asp Val Ile Gly Ala Leu Trp His Pro
            260                 265                 270

Asp Ser Cys Glu Ala Val Asn Pro Thr Arg Phe Arg Ala Val Phe Gln
        275                 280                 285

Lys Tyr Val Pro Ser Phe Ser Gly Tyr Ser Gln Gln Asp Ala Gln Glu
    290                 295                 300

Phe Leu Lys Leu Leu Met Glu Arg Leu His Leu Glu Ile Asn Arg Arg
305                 310                 315                 320

Gly Arg Arg Ala Pro Pro Ile Leu Ala Asn Gly Pro Val Pro Ser Pro
                325                 330                 335

Pro Arg Arg Gly Gly Ala Leu Leu Glu Glu Pro Glu Leu Ser Asp Asp
            340                 345                 350

Asp Arg Ala Asn Leu Met Trp Lys Arg Tyr Leu Glu Arg Glu Asp Ser
        355                 360                 365

Lys Ile Val Asp Leu Phe Val Gly Gln Leu Lys Ser Cys Leu Lys Cys
    370                 375                 380

Gln Ala Cys Gly Tyr Arg Ser Thr Thr Phe Glu Val Phe Cys Asp Leu
385                 390                 395                 400

Ser Leu Pro Ile Pro Lys Lys Gly Phe Ala Gly Gly Lys Val Ser Leu
                405                 410                 415
```

-continued

```
Arg Asp Cys Phe Asn Leu Phe Thr Lys Glu Glu Leu Glu Ser Glu
            420                 425                 430

Asn Ala Pro Val Cys Asp Arg Cys Arg Gln Lys Thr Arg Ser Thr Lys
        435                 440                 445

Lys Leu Thr Val Gln Arg Phe Pro Arg Ile Leu Gly Leu Asp Leu Asn
450                 455                 460

Arg Phe Ser Ala Ser Arg Gly Ser Ile Lys Lys Ser Val Gly Val
465                 470                 475                 480

Asp Phe Pro Leu Gln Arg Leu Ser Leu Gly Asp Phe Ala Ser Asp Lys
                485                 490                 495

Ala Gly Ser Val His Tyr Gly His Tyr Thr Ala Leu Cys Arg Cys Gln
            500                 505                 510

Thr Gly Trp His Val Tyr Asn Asp Ser Arg Val Ser Pro Val Ser Glu
            515                 520                 525

Asn Gln Val Ala Ser Ser Glu Gly Tyr Val Leu Phe Tyr Gln Leu Met
530                 535                 540

Gln Glu Pro Pro Arg Cys Leu
545                 550
```

<210> SEQ ID NO 43
<211> LENGTH: 537
<212> TYPE: PRT
<213> ORGANISM: Homo sapiens

<400> SEQUENCE: 43

```
Met Ala Trp Arg Gly Ala Gly Pro Ser Val Pro Gly Ala Pro Gly Gly
1               5                   10                  15

Val Gly Leu Ser Leu Gly Leu Leu Gln Leu Leu Leu Leu Leu Gly
            20                  25                  30

Pro Ala Arg Gly Phe Gly Asp Glu Glu Glu Arg Arg Cys Asp Pro Ile
        35                  40                  45

Arg Ile Ser Met Cys Gln Asn Leu Gly Tyr Asn Val Thr Lys Met Pro
    50                  55                  60

Asn Leu Val Gly His Glu Leu Gln Thr Asp Ala Glu Leu Gln Leu Thr
65                  70                  75                  80

Thr Phe Thr Pro Leu Ile Gln Tyr Gly Cys Ser Ser Gln Leu Gln Phe
                85                  90                  95

Phe Leu Cys Ser Val Tyr Val Pro Met Cys Thr Glu Lys Ile Asn Ile
            100                 105                 110

Pro Ile Gly Pro Cys Gly Gly Met Cys Leu Ser Val Lys Arg Arg Cys
        115                 120                 125

Glu Pro Val Leu Lys Glu Phe Gly Phe Ala Trp Pro Glu Ser Leu Asn
    130                 135                 140

Cys Ser Lys Phe Pro Pro Gln Asn Asp His Asn His Met Cys Met Glu
145                 150                 155                 160

Gly Pro Gly Asp Glu Glu Val Pro Leu Pro His Lys Thr Pro Ile Gln
                165                 170                 175

Pro Gly Glu Glu Cys His Ser Val Gly Thr Asn Ser Asp Gln Tyr Ile
            180                 185                 190

Trp Val Lys Arg Ser Leu Asn Cys Val Leu Lys Cys Gly Tyr Asp Ala
        195                 200                 205

Gly Leu Tyr Ser Arg Ser Ala Lys Glu Phe Thr Asp Ile Trp Met Ala
    210                 215                 220

Val Trp Ala Ser Leu Cys Phe Ile Ser Thr Ala Phe Thr Val Leu Thr
225                 230                 235                 240
```

```
Phe Leu Ile Asp Ser Ser Arg Phe Ser Tyr Pro Glu Arg Pro Ile Ile
                245                 250                 255
Phe Leu Ser Met Cys Tyr Asn Ile Tyr Ser Ile Ala Tyr Ile Val Arg
            260                 265                 270
Leu Thr Val Gly Arg Glu Arg Ile Ser Cys Asp Phe Glu Glu Ala Ala
        275                 280                 285
Glu Pro Val Leu Ile Gln Glu Gly Leu Lys Asn Thr Gly Cys Ala Ile
    290                 295                 300
Ile Phe Leu Leu Met Tyr Phe Gly Met Ala Ser Ser Ile Trp Trp
305                 310                 315                 320
Val Ile Leu Thr Leu Thr Trp Phe Leu Ala Ala Gly Leu Lys Trp Gly
                325                 330                 335
His Glu Ala Ile Glu Met His Ser Ser Tyr Phe His Ile Ala Ala Trp
            340                 345                 350
Ala Ile Pro Ala Val Lys Thr Ile Val Ile Leu Ile Met Arg Leu Val
        355                 360                 365
Asp Ala Asp Glu Leu Thr Gly Leu Cys Tyr Val Gly Asn Gln Asn Leu
    370                 375                 380
Asp Ala Leu Thr Gly Phe Val Val Ala Pro Leu Phe Thr Tyr Leu Val
385                 390                 395                 400
Ile Gly Thr Leu Phe Ile Ala Ala Gly Leu Val Ala Leu Phe Lys Ile
                405                 410                 415
Arg Ser Asn Leu Gln Lys Asp Gly Thr Lys Thr Asp Lys Leu Glu Arg
            420                 425                 430
Leu Met Val Lys Ile Gly Val Phe Ser Val Leu Tyr Thr Val Pro Ala
        435                 440                 445
Thr Cys Val Ile Ala Cys Tyr Phe Tyr Glu Ile Ser Asn Trp Ala Leu
    450                 455                 460
Phe Arg Tyr Ser Ala Asp Asp Ser Asn Met Ala Val Glu Met Leu Lys
465                 470                 475                 480
Ile Phe Met Ser Leu Leu Val Gly Ile Thr Ser Gly Met Trp Ile Trp
                485                 490                 495
Ser Ala Lys Thr Leu His Thr Trp Gln Lys Cys Ser Asn Arg Leu Val
            500                 505                 510
Asn Ser Gly Lys Val Lys Arg Glu Lys Arg Gly Asn Gly Trp Val Lys
        515                 520                 525
Pro Gly Lys Gly Ser Glu Thr Val Val
    530                 535

<210> SEQ ID NO 44
<211> LENGTH: 433
<212> TYPE: PRT
<213> ORGANISM: Homo sapiens

<400> SEQUENCE: 44

Met Cys Thr Glu Lys Ile Asn Ile Pro Ile Gly Pro Cys Gly Gly Met
1               5                   10                  15
Cys Leu Ser Val Lys Arg Arg Cys Glu Pro Val Leu Lys Glu Phe Gly
            20                  25                  30
Phe Ala Trp Pro Glu Ser Leu Asn Cys Ser Lys Phe Pro Pro Gln Asn
        35                  40                  45
Asp His Asn His Met Cys Met Glu Gly Pro Gly Asp Glu Glu Val Pro
    50                  55                  60
Leu Pro His Lys Thr Pro Ile Gln Pro Gly Glu Glu Cys His Ser Val
```

-continued

```
                65                  70                  75                  80
Gly Thr Asn Ser Asp Gln Tyr Ile Trp Val Lys Arg Ser Leu Asn Cys
                    85                  90                  95

Val Leu Lys Cys Gly Tyr Asp Ala Gly Leu Tyr Ser Arg Ser Ala Lys
                100                 105                 110

Glu Phe Thr Asp Ile Trp Met Ala Val Trp Ala Ser Leu Cys Phe Ile
                115                 120                 125

Ser Thr Ala Phe Thr Val Leu Thr Phe Leu Ile Asp Ser Ser Arg Phe
            130                 135                 140

Ser Tyr Pro Glu Arg Pro Ile Ile Phe Leu Ser Met Cys Tyr Asn Ile
145                 150                 155                 160

Tyr Ser Ile Ala Tyr Ile Val Arg Leu Thr Val Gly Arg Glu Arg Ile
                165                 170                 175

Ser Cys Asp Phe Glu Ala Ala Glu Pro Val Leu Ile Gln Glu Gly
                180                 185                 190

Leu Lys Asn Thr Gly Cys Ala Ile Phe Leu Leu Met Tyr Phe Phe
            195                 200                 205

Gly Met Ala Ser Ser Ile Trp Trp Val Ile Leu Thr Leu Thr Trp Phe
210                 215                 220

Leu Ala Ala Gly Leu Lys Trp Gly His Glu Ala Ile Glu Met His Ser
225                 230                 235                 240

Ser Tyr Phe His Ile Ala Ala Trp Ala Ile Pro Ala Val Lys Thr Ile
                245                 250                 255

Val Ile Leu Ile Met Arg Leu Val Asp Ala Asp Glu Leu Thr Gly Leu
            260                 265                 270

Cys Tyr Val Gly Asn Gln Asn Leu Asp Ala Leu Thr Gly Phe Val Val
            275                 280                 285

Ala Pro Leu Phe Thr Tyr Leu Val Ile Gly Thr Leu Phe Ile Ala Ala
        290                 295                 300

Gly Leu Val Ala Leu Phe Lys Ile Arg Ser Asn Leu Gln Lys Asp Gly
305                 310                 315                 320

Thr Lys Thr Asp Lys Leu Glu Arg Leu Met Val Lys Ile Gly Val Phe
                325                 330                 335

Ser Val Leu Tyr Thr Val Pro Ala Thr Cys Val Ile Ala Cys Tyr Phe
            340                 345                 350

Tyr Glu Ile Ser Asn Trp Ala Leu Phe Arg Tyr Ser Ala Asp Asp Ser
        355                 360                 365

Asn Met Ala Val Glu Met Leu Lys Ile Phe Met Ser Leu Leu Val Gly
        370                 375                 380

Ile Thr Ser Gly Met Trp Ile Trp Ser Ala Lys Thr Leu His Thr Trp
385                 390                 395                 400

Gln Lys Cys Ser Asn Arg Leu Val Asn Ser Gly Lys Val Lys Arg Glu
                405                 410                 415

Lys Arg Gly Asn Gly Trp Val Lys Pro Gly Lys Gly Ser Glu Thr Val
                420                 425                 430

Val
```

<210> SEQ ID NO 45
<211> LENGTH: 399
<212> TYPE: PRT
<213> ORGANISM: Homo sapiens

<400> SEQUENCE: 45

Met Arg Pro Glu Arg Pro Arg Pro Arg Gly Ser Ala Pro Gly Pro Met

```
                1               5                   10                  15
            Glu Thr Pro Pro Trp Asp Pro Ala Arg Asn Asp Ser Leu Pro Pro Thr
                            20                  25                  30

Leu Thr Pro Ala Val Pro Pro Tyr Val Lys Leu Gly Leu Thr Val Val
                        35                  40                  45

Tyr Thr Val Phe Tyr Ala Leu Leu Phe Val Phe Ile Tyr Val Gln Leu
                    50                  55                  60

Trp Leu Val Leu Arg Tyr Arg His Lys Arg Leu Ser Tyr Gln Ser Val
             65                 70                  75                  80

Phe Leu Phe Leu Cys Leu Phe Trp Ala Ser Leu Arg Thr Val Leu Phe
                            85                  90                  95

Ser Phe Tyr Phe Lys Asp Phe Val Ala Ala Asn Ser Leu Ser Pro Phe
                            100                 105                 110

Val Phe Trp Leu Leu Tyr Cys Phe Pro Val Cys Leu Gln Phe Phe Thr
                        115                 120                 125

Leu Thr Leu Met Asn Leu Tyr Phe Thr Gln Val Ile Phe Lys Ala Lys
                        130                 135                 140

Ser Lys Tyr Ser Pro Glu Leu Leu Lys Tyr Arg Leu Pro Leu Tyr Leu
            145                 150                 155                 160

Ala Ser Leu Phe Ile Ser Leu Val Phe Leu Leu Val Asn Leu Thr Cys
                            165                 170                 175

Ala Val Leu Val Lys Thr Gly Asn Trp Glu Arg Lys Val Ile Val Ser
                        180                 185                 190

Val Arg Val Ala Ile Asn Asp Thr Leu Phe Val Leu Cys Ala Val Ser
                        195                 200                 205

Leu Ser Ile Cys Leu Tyr Lys Ile Ser Lys Met Ser Leu Ala Asn Ile
                        210                 215                 220

Tyr Leu Glu Ser Lys Gly Ser Ser Val Cys Gln Val Thr Ala Ile Gly
            225                 230                 235                 240

Val Thr Val Ile Leu Leu Tyr Thr Ser Arg Ala Cys Tyr Asn Leu Phe
                            245                 250                 255

Ile Leu Ser Phe Ser Gln Asn Lys Ser Val His Ser Phe Asp Tyr Asp
                        260                 265                 270

Trp Tyr Asn Val Ser Asp Gln Ala Asp Leu Lys Asn Gln Leu Gly Asp
                        275                 280                 285

Ala Gly Tyr Val Leu Phe Gly Val Leu Phe Val Trp Glu Leu Leu
                        290                 295                 300

Pro Thr Thr Leu Val Val Tyr Phe Phe Arg Val Arg Asn Pro Thr Lys
            305                 310                 315                 320

Asp Leu Thr Asn Pro Gly Met Val Pro Ser His Gly Phe Ser Pro Arg
                        325                 330                 335

Ser Tyr Phe Phe Asp Asn Pro Arg Arg Tyr Asp Ser Asp Asp Asp Leu
                        340                 345                 350

Ala Trp Asn Ile Ala Pro Gln Gly Leu Gln Gly Gly Phe Ala Pro Asp
                        355                 360                 365

Tyr Tyr Asp Trp Gly Gln Gln Thr Asn Ser Phe Leu Ala Gln Ala Gly
                        370                 375                 380

Thr Leu Gln Asp Ser Thr Leu Asp Pro Asp Lys Pro Ser Leu Gly
            385                 390                 395

<210> SEQ ID NO 46
<211> LENGTH: 178
<212> TYPE: PRT
<213> ORGANISM: Homo sapiens
```

<400> SEQUENCE: 46

| Met | Ser | Pro | Ser | Gly | Arg | Leu | Cys | Leu | Leu | Thr | Ile | Val | Gly | Leu | Ile |
|-----|-----|-----|-----|-----|-----|-----|-----|-----|-----|-----|-----|-----|-----|-----|-----|
| 1 | | | | 5 | | | | | 10 | | | | | 15 | |

| Leu | Pro | Thr | Arg | Gly | Gln | Thr | Leu | Lys | Asp | Thr | Thr | Ser | Ser | Ser |
|-----|-----|-----|-----|-----|-----|-----|-----|-----|-----|-----|-----|-----|-----|-----|
| | | | 20 | | | | | 25 | | | | | 30 | |

Ala Asp Ser Thr Ile Met Asp Ile Gln Val Pro Thr Arg Ala Pro Asp
            35                  40                  45

Ala Val Tyr Thr Glu Leu Gln Pro Thr Ser Pro Thr Pro Thr Trp Pro
 50                      55                  60

Ala Asp Glu Thr Pro Gln Pro Gln Thr Gln Thr Gln Gln Leu Glu Gly
 65                      70                  75                  80

Thr Asp Gly Pro Leu Val Thr Asp Pro Glu Thr His Lys Ser Thr Lys
                    85                  90                  95

Ala Ala His Pro Thr Asp Asp Thr Thr Thr Leu Ser Glu Arg Pro Ser
                100                 105                 110

Pro Ser Thr Asp Val Gln Thr Asp Pro Gln Thr Leu Lys Pro Ser Gly
                115                 120                 125

Phe His Glu Asp Asp Pro Phe Phe Tyr Asp Glu His Thr Leu Arg Lys
            130                 135                 140

Arg Gly Leu Leu Val Ala Ala Val Leu Phe Ile Thr Gly Ile Ile Ile
145                 150                 155                 160

Leu Thr Ser Gly Lys Cys Arg Gln Leu Ser Arg Leu Cys Arg Asn Arg
                165                 170                 175

Cys Arg

<210> SEQ ID NO 47
<211> LENGTH: 219
<212> TYPE: PRT
<213> ORGANISM: Homo sapiens

<400> SEQUENCE: 47

Met Asp Ser Gly Thr Arg Pro Val Gly Ser Cys Cys Ser Ser Pro Ala
 1               5                  10                  15

Gly Leu Ser Arg Glu Tyr Lys Leu Val Met Leu Gly Ala Gly Gly Val
                20                  25                  30

Gly Lys Ser Ala Met Thr Met Gln Phe Ile Ser His Arg Phe Pro Glu
            35                  40                  45

Asp His Asp Pro Thr Ile Glu Asp Ala Tyr Lys Ile Arg Ile Arg Ile
     50                  55                  60

Asp Asp Glu Pro Ala Asn Leu Asp Ile Leu Asp Thr Ala Gly Gln Ala
 65                      70                  75                  80

Glu Phe Thr Ala Met Arg Asp Gln Tyr Met Arg Ala Gly Glu Gly Phe
                85                  90                  95

Ile Ile Cys Tyr Ser Ile Thr Asp Arg Arg Ser Phe His Glu Val Arg
                100                 105                 110

Glu Phe Lys Gln Leu Ile Tyr Arg Val Arg Arg Thr Asp Asp Thr Pro
            115                 120                 125

Val Val Leu Val Gly Asn Lys Ser Asp Leu Lys Gln Leu Arg Gln Val
        130                 135                 140

Thr Lys Glu Glu Gly Leu Ala Leu Ala Arg Glu Phe Ser Cys Pro Phe
145                 150                 155                 160

Phe Glu Thr Ser Ala Ala Tyr Arg Tyr Tyr Ile Asp Asp Val Phe His
                165                 170                 175

```
Ala Leu Val Arg Glu Ile Arg Arg Lys Glu Lys Glu Ala Val Leu Ala
            180                 185                 190

Met Glu Lys Lys Ser Lys Pro Lys Asn Ser Val Trp Lys Arg Leu Lys
        195                 200                 205

Ser Pro Phe Arg Lys Lys Lys Asp Ser Val Thr
    210                 215

<210> SEQ ID NO 48
<211> LENGTH: 479
<212> TYPE: PRT
<213> ORGANISM: Homo sapiens

<400> SEQUENCE: 48

Met Lys Ser Gln Gly Gln His Trp Tyr Ser Ser Asp Lys Asn Cys
 1               5                  10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
            35                  40                  45

Asn Lys Lys Leu Glu Lys Ser Ser Ala Ser Asp Val Phe Glu His
 50                  55                  60

Leu Leu Ala Glu Asp Leu Leu Ser Glu Glu Asp Pro Phe Phe Leu Ala
 65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Arg Ala Ala Val Tyr Arg Met Asn Arg Asn His Arg
225                 230                 235                 240

Gly Leu Cys Val Ile Val Asn Asn His Ser Phe Thr Ser Leu Lys Asp
                245                 250                 255

Arg Gln Gly Thr His Lys Asp Ala Glu Ile Leu Ser His Val Phe Gln
            260                 265                 270

Trp Leu Gly Phe Thr Val His Ile His Asn Asn Val Thr Lys Val Glu
        275                 280                 285

Met Glu Met Val Leu Gln Lys Gln Lys Cys Asn Pro Ala His Ala Asp
    290                 295                 300

Gly Asp Cys Phe Val Phe Cys Ile Leu Thr His Gly Arg Phe Gly Ala
305                 310                 315                 320

Val Tyr Ser Ser Asp Glu Ala Leu Ile Pro Ile Arg Glu Ile Met Ser
                325                 330                 335
```

```
His Phe Thr Ala Leu Gln Cys Pro Arg Leu Ala Glu Lys Pro Lys Leu
                340                 345                 350

Phe Phe Ile Gln Ala Cys Gln Gly Glu Glu Ile Gln Pro Ser Val Ser
            355                 360                 365

Ile Glu Ala Asp Ala Leu Asn Pro Glu Gln Ala Pro Thr Ser Leu Gln
        370                 375                 380

Asp Ser Ile Pro Ala Glu Ala Asp Phe Leu Leu Gly Leu Ala Thr Val
385                 390                 395                 400

Pro Gly Tyr Val Ser Phe Arg His Val Glu Glu Gly Ser Trp Tyr Ile
                405                 410                 415

Gln Ser Leu Cys Asn His Leu Lys Lys Leu Val Pro Arg His Glu Asp
            420                 425                 430

Ile Leu Ser Ile Leu Thr Ala Val Asn Asp Asp Val Ser Arg Arg Val
        435                 440                 445

Asp Lys Gln Gly Thr Lys Lys Gln Met Pro Gln Pro Ala Phe Thr Leu
450                 455                 460

Arg Lys Lys Leu Val Phe Pro Val Pro Leu Asp Ala Leu Ser Leu
465                 470                 475

<210> SEQ ID NO 49
<211> LENGTH: 521
<212> TYPE: PRT
<213> ORGANISM: Homo sapiens

<400> SEQUENCE: 49

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
    50                  55                  60

Leu Leu Ala Glu Asp Leu Ser Glu Glu Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
```

-continued

```
                225                 230                 235                 240
Gly Asn Arg Ala Thr Asn Gly Ala Pro Ser Leu Val Ser Arg Gly Met
                245                 250                 255
Gln Gly Ala Ser Ala Asn Thr Leu Asn Ser Glu Thr Ser Thr Lys Arg
                260                 265                 270
Ala Ala Val Tyr Arg Met Asn Arg Asn His Arg Gly Leu Cys Val Ile
                275                 280                 285
Val Asn Asn His Ser Phe Thr Ser Leu Lys Asp Arg Gln Gly Thr His
                290                 295                 300
Lys Asp Ala Glu Ile Leu Ser His Val Phe Gln Trp Leu Gly Phe Thr
305                 310                 315                 320
Val His Ile His Asn Asn Val Thr Lys Val Glu Met Glu Met Val Leu
                325                 330                 335
Gln Lys Gln Lys Cys Asn Pro Ala His Ala Asp Gly Asp Cys Phe Val
                340                 345                 350
Phe Cys Ile Leu Thr His Gly Arg Phe Gly Ala Val Tyr Ser Ser Asp
                355                 360                 365
Glu Ala Leu Ile Pro Ile Arg Glu Ile Met Ser His Phe Thr Ala Leu
                370                 375                 380
Gln Cys Pro Arg Leu Ala Glu Lys Pro Lys Leu Phe Phe Ile Gln Ala
385                 390                 395                 400
Cys Gln Gly Glu Glu Ile Gln Pro Ser Val Ser Ile Glu Ala Asp Ala
                405                 410                 415
Leu Asn Pro Glu Gln Ala Pro Thr Ser Leu Gln Asp Ser Ile Pro Ala
                420                 425                 430
Glu Ala Asp Phe Leu Leu Gly Leu Ala Thr Val Pro Gly Tyr Val Ser
                435                 440                 445
Phe Arg His Val Glu Glu Gly Ser Trp Tyr Ile Gln Ser Leu Cys Asn
                450                 455                 460
His Leu Lys Lys Leu Val Pro Arg Met Leu Lys Phe Leu Glu Lys Thr
465                 470                 475                 480
Met Glu Ile Arg Gly Arg Lys Arg Thr Val Trp Gly Ala Lys Gln Ile
                485                 490                 495
Ser Ala Thr Ser Leu Pro Thr Ala Ile Ser Ala Gln Thr Pro Arg Pro
                500                 505                 510
Pro Met Arg Arg Trp Ser Ser Val Ser
                515                 520

<210> SEQ ID NO 50
<211> LENGTH: 273
<212> TYPE: PRT
<213> ORGANISM: Homo sapiens

<400> SEQUENCE: 50

Met Lys Ser Gln Gly Gln His Trp Tyr Ser Ser Asp Lys Asn Cys
1               5                   10                  15
Lys Val Ser Phe Arg Glu Lys Leu Leu Ile Ile Asp Ser Asn Leu Gly
                20                  25                  30
Val Gln Asp Val Glu Asn Leu Lys Phe Leu Cys Ile Gly Leu Val Pro
                35                  40                  45
Asn Lys Lys Leu Glu Lys Ser Ser Ala Ser Asp Val Phe Glu His
    50                  55                  60
Leu Leu Ala Glu Asp Leu Leu Ser Glu Glu Asp Pro Phe Phe Leu Ala
65                  70                  75                  80
```

```
Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225                 230                 235                 240

Glu Gly Ser Cys Val Gln Asp Glu Ser Glu Pro Gln Arg Pro Leu Cys
                245                 250                 255

His Cys Gln Gln Pro Gln Leu Tyr Leu Pro Glu Gly Gln Thr Arg Asn
            260                 265                 270

Pro

<210> SEQ ID NO 51
<211> LENGTH: 522
<212> TYPE: PRT
<213> ORGANISM: Homo sapiens

<400> SEQUENCE: 51

Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
                20                  25                  30

Val Gln Asp Val Glu Asn Leu Lys Phe Leu Cys Ile Gly Leu Val Pro
            35                  40                  45

Asn Lys Lys Leu Glu Lys Ser Ser Ala Ser Asp Val Phe Glu His
        50                  55                  60

Leu Leu Ala Glu Asp Leu Leu Ser Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175
```

```
Val Val Pro Lys Leu Leu Arg Asn Ile Glu Lys Tyr Lys Arg Glu Lys
            180                 185                 190

Ala Ile Gln Ile Val Thr Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225                 230                 235                 240

Gly Asn Arg Ala Thr Asn Gly Ala Pro Ser Leu Val Ser Arg Gly Met
                245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
        275                 280                 285

Val Asn Asn His Ser Phe Thr Ser Leu Lys Asp Arg Gln Gly Thr His
    290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
                325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
        355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
                405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
        435                 440                 445

Phe Arg His Val Glu Glu Gly Ser Trp Tyr Ile Gln Ser Leu Cys Asn
    450                 455                 460

His Leu Lys Lys Leu Val Pro Arg His Glu Asp Ile Leu Ser Ile Leu
465                 470                 475                 480

Thr Ala Val Asn Asp Asp Val Ser Arg Arg Val Asp Lys Gln Gly Thr
                485                 490                 495

Lys Lys Gln Met Pro Gln Pro Ala Phe Thr Leu Arg Lys Lys Leu Val
            500                 505                 510

Phe Pro Val Pro Leu Asp Ala Leu Ser Leu
        515                 520

<210> SEQ ID NO 52
<211> LENGTH: 19
<212> TYPE: DNA
<213> ORGANISM: Artificial Sequence
<220> FEATURE:
<223> OTHER INFORMATION: Target sequence

<400> SEQUENCE: 52
tatcctgatg ttgcttggc                                               19
```

```
<210> SEQ ID NO 53
<211> LENGTH: 19
<212> TYPE: DNA
<213> ORGANISM: Artificial Sequence
<220> FEATURE:
<223> OTHER INFORMATION: Target sequence

<400> SEQUENCE: 53
gtggcgcatg atgtccctc                                                   19

<210> SEQ ID NO 54
<211> LENGTH: 19
<212> TYPE: DNA
<213> ORGANISM: Artificial Sequence
<220> FEATURE:
<223> OTHER INFORMATION: Target sequence

<400> SEQUENCE: 54
tcaagggcca gtatcaagc                                                   19

<210> SEQ ID NO 55
<211> LENGTH: 19
<212> TYPE: DNA
<213> ORGANISM: Artificial Sequence
<220> FEATURE:
<223> OTHER INFORMATION: Target sequence

<400> SEQUENCE: 55
gatgtcacca atcctttgc                                                   19

<210> SEQ ID NO 56
<211> LENGTH: 19
<212> TYPE: DNA
<213> ORGANISM: Artificial Sequence
<220> FEATURE:
<223> OTHER INFORMATION: Target sequence

<400> SEQUENCE: 56
tcatgtggat cctctcagc                                                   19

<210> SEQ ID NO 57
<211> LENGTH: 19
<212> TYPE: DNA
<213> ORGANISM: Artificial Sequence
<220> FEATURE:
<223> OTHER INFORMATION: Target sequence

<400> SEQUENCE: 57
cttcatcaag gtgttgggc                                                   19

<210> SEQ ID NO 58
<211> LENGTH: 19
<212> TYPE: DNA
<213> ORGANISM: Artificial Sequence
<220> FEATURE:
<223> OTHER INFORMATION: Target sequence

<400> SEQUENCE: 58
gccttgtcat ttgacaacc                                                   19

<210> SEQ ID NO 59
<211> LENGTH: 19
<212> TYPE: DNA
<213> ORGANISM: Artificial Sequence
<220> FEATURE:
<223> OTHER INFORMATION: Target sequence
```

```
<400> SEQUENCE: 59
ctacaaggtc cctaccttc                                            19

<210> SEQ ID NO 60
<211> LENGTH: 19
<212> TYPE: DNA
<213> ORGANISM: Artificial Sequence
<220> FEATURE:
<223> OTHER INFORMATION: Target sequence

<400> SEQUENCE: 60
ggtcatgttg gcagaactc                                            19

<210> SEQ ID NO 61
<211> LENGTH: 19
<212> TYPE: DNA
<213> ORGANISM: Artificial Sequence
<220> FEATURE:
<223> OTHER INFORMATION: Target sequence

<400> SEQUENCE: 61
gaagatcaag ccaccttc                                             19

<210> SEQ ID NO 62
<211> LENGTH: 19
<212> TYPE: DNA
<213> ORGANISM: Artificial Sequence
<220> FEATURE:
<223> OTHER INFORMATION: Target sequence

<400> SEQUENCE: 62
ggcattgaca atcggactc                                            19

<210> SEQ ID NO 63
<211> LENGTH: 19
<212> TYPE: DNA
<213> ORGANISM: Artificial Sequence
<220> FEATURE:
<223> OTHER INFORMATION: Target sequence

<400> SEQUENCE: 63
ttcctacttg accgagctc                                            19

<210> SEQ ID NO 64
<211> LENGTH: 19
<212> TYPE: DNA
<213> ORGANISM: Artificial Sequence
<220> FEATURE:
<223> OTHER INFORMATION: Target sequence

<400> SEQUENCE: 64
acttcctact tgaccgagc                                            19

<210> SEQ ID NO 65
<211> LENGTH: 19
<212> TYPE: DNA
<213> ORGANISM: Artificial Sequence
<220> FEATURE:
<223> OTHER INFORMATION: Target sequence

<400> SEQUENCE: 65
attaaagcgg ccaacgtcc                                            19

<210> SEQ ID NO 66
<211> LENGTH: 19
```

```
<212> TYPE: DNA
<213> ORGANISM: Artificial Sequence
<220> FEATURE:
<223> OTHER INFORMATION: Target sequence

<400> SEQUENCE: 66
ctggcccatt agatgaaac                                                19

<210> SEQ ID NO 67
<211> LENGTH: 19
<212> TYPE: DNA
<213> ORGANISM: Artificial Sequence
<220> FEATURE:
<223> OTHER INFORMATION: Target sequence

<400> SEQUENCE: 67
agccatcaag gaaacttcc                                                19

<210> SEQ ID NO 68
<211> LENGTH: 19
<212> TYPE: DNA
<213> ORGANISM: Artificial Sequence
<220> FEATURE:
<223> OTHER INFORMATION: Target sequence

<400> SEQUENCE: 68
gctagaaatg aggtacgtc                                                19

<210> SEQ ID NO 69
<211> LENGTH: 19
<212> TYPE: DNA
<213> ORGANISM: Artificial Sequence
<220> FEATURE:
<223> OTHER INFORMATION: Target sequence

<400> SEQUENCE: 69
gtgtttgcta acagtgtcc                                                19

<210> SEQ ID NO 70
<211> LENGTH: 19
<212> TYPE: DNA
<213> ORGANISM: Artificial Sequence
<220> FEATURE:
<223> OTHER INFORMATION: Target sequence

<400> SEQUENCE: 70
gccagccaag taacaaagc                                                19

<210> SEQ ID NO 71
<211> LENGTH: 19
<212> TYPE: DNA
<213> ORGANISM: Artificial Sequence
<220> FEATURE:
<223> OTHER INFORMATION: Target sequence

<400> SEQUENCE: 71
caaagcagat agctttggc                                                19

<210> SEQ ID NO 72
<211> LENGTH: 19
<212> TYPE: DNA
<213> ORGANISM: Artificial Sequence
<220> FEATURE:
<223> OTHER INFORMATION: Target sequence

<400> SEQUENCE: 72
```

```
ctggcagaaa ttgtgaagc                                                    19

<210> SEQ ID NO 73
<211> LENGTH: 19
<212> TYPE: DNA
<213> ORGANISM: Artificial Sequence
<220> FEATURE:
<223> OTHER INFORMATION: Target sequence

<400> SEQUENCE: 73
accacgtccc acgaatccc                                                    19

<210> SEQ ID NO 74
<211> LENGTH: 19
<212> TYPE: DNA
<213> ORGANISM: Artificial Sequence
<220> FEATURE:
<223> OTHER INFORMATION: Target sequence

<400> SEQUENCE: 74
ggacagtgtc tatatccac                                                    19

<210> SEQ ID NO 75
<211> LENGTH: 19
<212> TYPE: DNA
<213> ORGANISM: Artificial Sequence
<220> FEATURE:
<223> OTHER INFORMATION: Target sequence

<400> SEQUENCE: 75
acaccacagc cggactatc                                                    19

<210> SEQ ID NO 76
<211> LENGTH: 19
<212> TYPE: DNA
<213> ORGANISM: Artificial Sequence
<220> FEATURE:
<223> OTHER INFORMATION: Target sequence

<400> SEQUENCE: 76
ctcctaagag atactctgc                                                    19

<210> SEQ ID NO 77
<211> LENGTH: 19
<212> TYPE: DNA
<213> ORGANISM: Artificial Sequence
<220> FEATURE:
<223> OTHER INFORMATION: Target sequence

<400> SEQUENCE: 77
agttcaaggt gccgtgagc                                                    19

<210> SEQ ID NO 78
<211> LENGTH: 19
<212> TYPE: DNA
<213> ORGANISM: Artificial Sequence
<220> FEATURE:
<223> OTHER INFORMATION: Target sequence

<400> SEQUENCE: 78
gttcaaggtg ccgtgagcc                                                    19

<210> SEQ ID NO 79
<211> LENGTH: 19
<212> TYPE: DNA
<213> ORGANISM: Artificial Sequence
```

```
<220> FEATURE:
<223> OTHER INFORMATION: Target sequence

<400> SEQUENCE: 79
tggcaaagag tatgccgtc                                                19

<210> SEQ ID NO 80
<211> LENGTH: 19
<212> TYPE: DNA
<213> ORGANISM: Artificial Sequence
<220> FEATURE:
<223> OTHER INFORMATION: Target sequence

<400> SEQUENCE: 80
attgcaagga ggttccatc                                                19

<210> SEQ ID NO 81
<211> LENGTH: 19
<212> TYPE: DNA
<213> ORGANISM: Artificial Sequence
<220> FEATURE:
<223> OTHER INFORMATION: Target sequence

<400> SEQUENCE: 81
ggaggttcca tcttagccc                                                19

<210> SEQ ID NO 82
<211> LENGTH: 19
<212> TYPE: DNA
<213> ORGANISM: Artificial Sequence
<220> FEATURE:
<223> OTHER INFORMATION: Target sequence

<400> SEQUENCE: 82
atcagtctgg tcctagaac                                                19

<210> SEQ ID NO 83
<211> LENGTH: 19
<212> TYPE: DNA
<213> ORGANISM: Artificial Sequence
<220> FEATURE:
<223> OTHER INFORMATION: Target sequence

<400> SEQUENCE: 83
ctcgtcacag gaggagaac                                                19

<210> SEQ ID NO 84
<211> LENGTH: 19
<212> TYPE: DNA
<213> ORGANISM: Artificial Sequence
<220> FEATURE:
<223> OTHER INFORMATION: Target sequence

<400> SEQUENCE: 84
atcaagtgct catgaagac                                                19

<210> SEQ ID NO 85
<211> LENGTH: 19
<212> TYPE: DNA
<213> ORGANISM: Artificial Sequence
<220> FEATURE:
<223> OTHER INFORMATION: Target sequence

<400> SEQUENCE: 85
gaggacatga aagctattc                                                19
```

-continued

```
<210> SEQ ID NO 86
<211> LENGTH: 19
<212> TYPE: DNA
<213> ORGANISM: Artificial Sequence
<220> FEATURE:
<223> OTHER INFORMATION: Target sequence

<400> SEQUENCE: 86
atccattgtg tacagatgc                                                19

<210> SEQ ID NO 87
<211> LENGTH: 19
<212> TYPE: DNA
<213> ORGANISM: Artificial Sequence
<220> FEATURE:
<223> OTHER INFORMATION: Target sequence

<400> SEQUENCE: 87
ccacatcact gcgatttcc                                                19

<210> SEQ ID NO 88
<211> LENGTH: 19
<212> TYPE: DNA
<213> ORGANISM: Artificial Sequence
<220> FEATURE:
<223> OTHER INFORMATION: Target sequence

<400> SEQUENCE: 88
catcatccca gtcattggc                                                19

<210> SEQ ID NO 89
<211> LENGTH: 19
<212> TYPE: DNA
<213> ORGANISM: Artificial Sequence
<220> FEATURE:
<223> OTHER INFORMATION: Target sequence

<400> SEQUENCE: 89
caacctctat gaggatcgc                                                19

<210> SEQ ID NO 90
<211> LENGTH: 19
<212> TYPE: DNA
<213> ORGANISM: Artificial Sequence
<220> FEATURE:
<223> OTHER INFORMATION: Target sequence

<400> SEQUENCE: 90
tgctctgact gctggcttc                                                19

<210> SEQ ID NO 91
<211> LENGTH: 19
<212> TYPE: DNA
<213> ORGANISM: Artificial Sequence
<220> FEATURE:
<223> OTHER INFORMATION: Target sequence

<400> SEQUENCE: 91
gagatgctgg agaagatgc                                                19

<210> SEQ ID NO 92
<211> LENGTH: 19
<212> TYPE: DNA
<213> ORGANISM: Artificial Sequence
<220> FEATURE:
<223> OTHER INFORMATION: Target sequence
```

```
<400> SEQUENCE: 92
atggatgctg tgtgcaagc                                               19

<210> SEQ ID NO 93
<211> LENGTH: 19
<212> TYPE: DNA
<213> ORGANISM: Artificial Sequence
<220> FEATURE:
<223> OTHER INFORMATION: Target sequence

<400> SEQUENCE: 93
ctgcatgtgt acgagattc                                               19

<210> SEQ ID NO 94
<211> LENGTH: 19
<212> TYPE: DNA
<213> ORGANISM: Artificial Sequence
<220> FEATURE:
<223> OTHER INFORMATION: Target sequence

<400> SEQUENCE: 94
gagattccgg ttgagtacc                                               19

<210> SEQ ID NO 95
<211> LENGTH: 19
<212> TYPE: DNA
<213> ORGANISM: Artificial Sequence
<220> FEATURE:
<223> OTHER INFORMATION: Target sequence

<400> SEQUENCE: 95
cagtccagag actcatccc                                               19

<210> SEQ ID NO 96
<211> LENGTH: 19
<212> TYPE: DNA
<213> ORGANISM: Artificial Sequence
<220> FEATURE:
<223> OTHER INFORMATION: Target sequence

<400> SEQUENCE: 96
actggagaaa tgtggacac                                               19

<210> SEQ ID NO 97
<211> LENGTH: 19
<212> TYPE: DNA
<213> ORGANISM: Artificial Sequence
<220> FEATURE:
<223> OTHER INFORMATION: Target sequence

<400> SEQUENCE: 97
gctgagcaac atggagaac                                               19

<210> SEQ ID NO 98
<211> LENGTH: 19
<212> TYPE: DNA
<213> ORGANISM: Artificial Sequence
<220> FEATURE:
<223> OTHER INFORMATION: Target sequence

<400> SEQUENCE: 98
cgcactagga cttatgctc                                               19

<210> SEQ ID NO 99
```

```
<211> LENGTH: 19
<212> TYPE: DNA
<213> ORGANISM: Artificial Sequence
<220> FEATURE:
<223> OTHER INFORMATION: Target sequence

<400> SEQUENCE: 99
ttccaagctg gccacattc                                                19

<210> SEQ ID NO 100
<211> LENGTH: 19
<212> TYPE: DNA
<213> ORGANISM: Artificial Sequence
<220> FEATURE:
<223> OTHER INFORMATION: Target sequence

<400> SEQUENCE: 100
aacctgcctg cgatacctc                                                19

<210> SEQ ID NO 101
<211> LENGTH: 19
<212> TYPE: DNA
<213> ORGANISM: Artificial Sequence
<220> FEATURE:
<223> OTHER INFORMATION: Target sequence

<400> SEQUENCE: 101
taggacttat gctcaaagc                                                19

<210> SEQ ID NO 102
<211> LENGTH: 19
<212> TYPE: DNA
<213> ORGANISM: Artificial Sequence
<220> FEATURE:
<223> OTHER INFORMATION: Target sequence

<400> SEQUENCE: 102
cggatagagg aacgtagcc                                                19

<210> SEQ ID NO 103
<211> LENGTH: 19
<212> TYPE: DNA
<213> ORGANISM: Artificial Sequence
<220> FEATURE:
<223> OTHER INFORMATION: Target sequence

<400> SEQUENCE: 103
tgggttggga agataccgc                                                19

<210> SEQ ID NO 104
<211> LENGTH: 19
<212> TYPE: DNA
<213> ORGANISM: Artificial Sequence
<220> FEATURE:
<223> OTHER INFORMATION: Target sequence

<400> SEQUENCE: 104
gacatggcag tgattgctc                                                19

<210> SEQ ID NO 105
<211> LENGTH: 19
<212> TYPE: DNA
<213> ORGANISM: Artificial Sequence
<220> FEATURE:
<223> OTHER INFORMATION: Target sequence

<400> SEQUENCE: 105
```
aagacatggc agtgattgc    19

<210> SEQ ID NO 106
<211> LENGTH: 19
<212> TYPE: DNA
<213> ORGANISM: Artificial Sequence
<220> FEATURE:
<223> OTHER INFORMATION: Target sequence

<400> SEQUENCE: 106
gtgctggatt ctgccatgc    19

<210> SEQ ID NO 107
<211> LENGTH: 19
<212> TYPE: DNA
<213> ORGANISM: Artificial Sequence
<220> FEATURE:
<223> OTHER INFORMATION: Target sequence

<400> SEQUENCE: 107
ctggcttgct attagtaac    19

<210> SEQ ID NO 108
<211> LENGTH: 19
<212> TYPE: DNA
<213> ORGANISM: Artificial Sequence
<220> FEATURE:
<223> OTHER INFORMATION: Target sequence

<400> SEQUENCE: 108
atcttccgca tctgccaac    19

<210> SEQ ID NO 109
<211> LENGTH: 19
<212> TYPE: DNA
<213> ORGANISM: Artificial Sequence
<220> FEATURE:
<223> OTHER INFORMATION: Target sequence

<400> SEQUENCE: 109
gaggactaaa gcgcctctc    19

<210> SEQ ID NO 110
<211> LENGTH: 19
<212> TYPE: DNA
<213> ORGANISM: Artificial Sequence
<220> FEATURE:
<223> OTHER INFORMATION: Target sequence

<400> SEQUENCE: 110
tgtgcacctt tgttgaacc    19

<210> SEQ ID NO 111
<211> LENGTH: 19
<212> TYPE: DNA
<213> ORGANISM: Artificial Sequence
<220> FEATURE:
<223> OTHER INFORMATION: Target sequence

<400> SEQUENCE: 111
tacagccaac gacccttac    19

<210> SEQ ID NO 112
<211> LENGTH: 19
<212> TYPE: DNA

```
<213> ORGANISM: Artificial Sequence
<220> FEATURE:
<223> OTHER INFORMATION: Target sequence

<400> SEQUENCE: 112
gccggaagtc ctgtatacc                                              19

<210> SEQ ID NO 113
<211> LENGTH: 19
<212> TYPE: DNA
<213> ORGANISM: Artificial Sequence
<220> FEATURE:
<223> OTHER INFORMATION: Target sequence

<400> SEQUENCE: 113
agccggaagt cctgtatac                                              19

<210> SEQ ID NO 114
<211> LENGTH: 19
<212> TYPE: DNA
<213> ORGANISM: Artificial Sequence
<220> FEATURE:
<223> OTHER INFORMATION: Target sequence

<400> SEQUENCE: 114
gatggctcat cacacactc                                              19

<210> SEQ ID NO 115
<211> LENGTH: 19
<212> TYPE: DNA
<213> ORGANISM: Artificial Sequence
<220> FEATURE:
<223> OTHER INFORMATION: Target sequence

<400> SEQUENCE: 115
cggctcaaga aactggagc                                              19

<210> SEQ ID NO 116
<211> LENGTH: 19
<212> TYPE: DNA
<213> ORGANISM: Artificial Sequence
<220> FEATURE:
<223> OTHER INFORMATION: Target sequence

<400> SEQUENCE: 116
gttgtctcaa gtgccaggc                                              19

<210> SEQ ID NO 117
<211> LENGTH: 19
<212> TYPE: DNA
<213> ORGANISM: Artificial Sequence
<220> FEATURE:
<223> OTHER INFORMATION: Target sequence

<400> SEQUENCE: 117
acacgtgctt cctgaatgc                                              19

<210> SEQ ID NO 118
<211> LENGTH: 19
<212> TYPE: DNA
<213> ORGANISM: Artificial Sequence
<220> FEATURE:
<223> OTHER INFORMATION: Target sequence

<400> SEQUENCE: 118
cctgggaaac acgtgcttc                                              19
```

<210> SEQ ID NO 119
<211> LENGTH: 19
<212> TYPE: DNA
<213> ORGANISM: Artificial Sequence
<220> FEATURE:
<223> OTHER INFORMATION: Target sequence

<400> SEQUENCE: 119
cgaccacaac cacatgtgc                                               19

<210> SEQ ID NO 120
<211> LENGTH: 19
<212> TYPE: DNA
<213> ORGANISM: Artificial Sequence
<220> FEATURE:
<223> OTHER INFORMATION: Target sequence

<400> SEQUENCE: 120
cgtgaccaag atgcccaac                                               19

<210> SEQ ID NO 121
<211> LENGTH: 19
<212> TYPE: DNA
<213> ORGANISM: Artificial Sequence
<220> FEATURE:
<223> OTHER INFORMATION: Target sequence

<400> SEQUENCE: 121
tgcagctgac aactttcac                                               19

<210> SEQ ID NO 122
<211> LENGTH: 19
<212> TYPE: DNA
<213> ORGANISM: Artificial Sequence
<220> FEATURE:
<223> OTHER INFORMATION: Target sequence

<400> SEQUENCE: 122
actctgtggg aaccaattc                                               19

<210> SEQ ID NO 123
<211> LENGTH: 19
<212> TYPE: DNA
<213> ORGANISM: Artificial Sequence
<220> FEATURE:
<223> OTHER INFORMATION: Target sequence

<400> SEQUENCE: 123
attcccacca cagaacgac                                               19

<210> SEQ ID NO 124
<211> LENGTH: 19
<212> TYPE: DNA
<213> ORGANISM: Artificial Sequence
<220> FEATURE:
<223> OTHER INFORMATION: Target sequence

<400> SEQUENCE: 124
agctaccaga gcgtcttcc                                               19

<210> SEQ ID NO 125
<211> LENGTH: 19
<212> TYPE: DNA
<213> ORGANISM: Artificial Sequence
<220> FEATURE:

```
<223> OTHER INFORMATION: Target sequence

<400> SEQUENCE: 125
tctctccatc tgtctctac                                                 19

<210> SEQ ID NO 126
<211> LENGTH: 19
<212> TYPE: DNA
<213> ORGANISM: Artificial Sequence
<220> FEATURE:
<223> OTHER INFORMATION: Target sequence

<400> SEQUENCE: 126
tgatgaactt gtacttcac                                                 19

<210> SEQ ID NO 127
<211> LENGTH: 19
<212> TYPE: DNA
<213> ORGANISM: Artificial Sequence
<220> FEATURE:
<223> OTHER INFORMATION: Target sequence

<400> SEQUENCE: 127
cgtgatactg ctttacacc                                                 19

<210> SEQ ID NO 128
<211> LENGTH: 19
<212> TYPE: DNA
<213> ORGANISM: Artificial Sequence
<220> FEATURE:
<223> OTHER INFORMATION: Target sequence

<400> SEQUENCE: 128
cattaatgac acgctcttc                                                 19

<210> SEQ ID NO 129
<211> LENGTH: 19
<212> TYPE: DNA
<213> ORGANISM: Artificial Sequence
<220> FEATURE:
<223> OTHER INFORMATION: Target sequence

<400> SEQUENCE: 129
atcccactga tgacaccac                                                 19

<210> SEQ ID NO 130
<211> LENGTH: 19
<212> TYPE: DNA
<213> ORGANISM: Artificial Sequence
<220> FEATURE:
<223> OTHER INFORMATION: Target sequence

<400> SEQUENCE: 130
atcacaggca tcatcatcc                                                 19

<210> SEQ ID NO 131
<211> LENGTH: 19
<212> TYPE: DNA
<213> ORGANISM: Artificial Sequence
<220> FEATURE:
<223> OTHER INFORMATION: Target sequence

<400> SEQUENCE: 131
aagagcacca aagcagctc                                                 19
```

```
<210> SEQ ID NO 132
<211> LENGTH: 19
<212> TYPE: DNA
<213> ORGANISM: Artificial Sequence
<220> FEATURE:
<223> OTHER INFORMATION: Target sequence

<400> SEQUENCE: 132
gtccagttct tcagcagac                                             19

<210> SEQ ID NO 133
<211> LENGTH: 19
<212> TYPE: DNA
<213> ORGANISM: Artificial Sequence
<220> FEATURE:
<223> OTHER INFORMATION: Target sequence

<400> SEQUENCE: 133
cttcttctat gatgaacac                                             19

<210> SEQ ID NO 134
<211> LENGTH: 19
<212> TYPE: DNA
<213> ORGANISM: Artificial Sequence
<220> FEATURE:
<223> OTHER INFORMATION: Target sequence

<400> SEQUENCE: 134
aagtcagacc tcaaacagc                                             19

<210> SEQ ID NO 135
<211> LENGTH: 19
<212> TYPE: DNA
<213> ORGANISM: Artificial Sequence
<220> FEATURE:
<223> OTHER INFORMATION: Target sequence

<400> SEQUENCE: 135
caccgattcc cagaagatc                                             19

<210> SEQ ID NO 136
<211> LENGTH: 19
<212> TYPE: DNA
<213> ORGANISM: Artificial Sequence
<220> FEATURE:
<223> OTHER INFORMATION: Target sequence

<400> SEQUENCE: 136
atctgctgca taccgctac                                             19

<210> SEQ ID NO 137
<211> LENGTH: 19
<212> TYPE: DNA
<213> ORGANISM: Artificial Sequence
<220> FEATURE:
<223> OTHER INFORMATION: Target sequence

<400> SEQUENCE: 137
catgcagttc atcagccac                                             19

<210> SEQ ID NO 138
<211> LENGTH: 19
<212> TYPE: DNA
<213> ORGANISM: Artificial Sequence
<220> FEATURE:
<223> OTHER INFORMATION: Target sequence
```

```
<400> SEQUENCE: 138
tgcagtgctg tatcaaagc                                          19

<210> SEQ ID NO 139
<211> LENGTH: 19
<212> TYPE: DNA
<213> ORGANISM: Artificial Sequence
<220> FEATURE:
<223> OTHER INFORMATION: Target sequence

<400> SEQUENCE: 139
ctcctgacct caagtgatc                                          19

<210> SEQ ID NO 140
<211> LENGTH: 19
<212> TYPE: DNA
<213> ORGANISM: Artificial Sequence
<220> FEATURE:
<223> OTHER INFORMATION: Target sequence

<400> SEQUENCE: 140
tctgcatagg attggtccc                                          19

<210> SEQ ID NO 141
<211> LENGTH: 19
<212> TYPE: DNA
<213> ORGANISM: Artificial Sequence
<220> FEATURE:
<223> OTHER INFORMATION: Target sequence

<400> SEQUENCE: 141
catctcttgg cagaggatc                                          19

<210> SEQ ID NO 142
<211> LENGTH: 19
<212> TYPE: DNA
<213> ORGANISM: Artificial Sequence
<220> FEATURE:
<223> OTHER INFORMATION: Target sequence

<400> SEQUENCE: 142
gagtggacaa acagggaac                                          19

<210> SEQ ID NO 143
<211> LENGTH: 19
<212> TYPE: DNA
<213> ORGANISM: Artificial Sequence
<220> FEATURE:
<223> OTHER INFORMATION: Target sequence

<400> SEQUENCE: 143
tgcttcgtgt tctgtattc                                          19

<210> SEQ ID NO 144
<211> LENGTH: 19
<212> TYPE: DNA
<213> ORGANISM: Artificial Sequence
<220> FEATURE:
<223> OTHER INFORMATION: Target sequence

<400> SEQUENCE: 144
acagatctca gcaacctcc                                          19

<210> SEQ ID NO 145
<211> LENGTH: 19
```

```
<212> TYPE: DNA
<213> ORGANISM: Artificial Sequence
<220> FEATURE:
<223> OTHER INFORMATION: Target sequence

<400> SEQUENCE: 145
gacggaaacc tccctttac                                                    19

<210> SEQ ID NO 146
<211> LENGTH: 19
<212> TYPE: DNA
<213> ORGANISM: Artificial Sequence
<220> FEATURE:
<223> OTHER INFORMATION: Target sequence

<400> SEQUENCE: 146
aaccacagct ttacctccc                                                    19

<210> SEQ ID NO 147
<211> LENGTH: 12
<212> TYPE: DNA
<213> ORGANISM: Artificial Sequence
<220> FEATURE:
<223> OTHER INFORMATION: Target sequence

<400> SEQUENCE: 147
gtttgctata ac                                                           12

<210> SEQ ID NO 148
<211> LENGTH: 19
<212> TYPE: DNA
<213> ORGANISM: Artificial Sequence
<220> FEATURE:
<223> OTHER INFORMATION: Target sequence

<400> SEQUENCE: 148
ttcaatgccc ggcgtaagc                                                    19

<210> SEQ ID NO 149
<211> LENGTH: 19
<212> TYPE: DNA
<213> ORGANISM: Artificial Sequence
<220> FEATURE:
<223> OTHER INFORMATION: Target sequence

<400> SEQUENCE: 149
tctaaactct gaaaccagc                                                    19

<210> SEQ ID NO 150
<211> LENGTH: 19
<212> TYPE: DNA
<213> ORGANISM: Artificial Sequence
<220> FEATURE:
<223> OTHER INFORMATION: Target sequence

<400> SEQUENCE: 150
atggtggttc agggaattc                                                    19

<210> SEQ ID NO 151
<211> LENGTH: 19
<212> TYPE: DNA
<213> ORGANISM: Artificial Sequence
<220> FEATURE:
<223> OTHER INFORMATION: Target sequence

<400> SEQUENCE: 151
```
aggtgagtcc atcagaaac                                              19

<210> SEQ ID NO 152
<211> LENGTH: 19
<212> TYPE: DNA
<213> ORGANISM: Artificial Sequence
<220> FEATURE:
<223> OTHER INFORMATION: Target sequence

<400> SEQUENCE: 152
agggtcttgc tctgtcacc                                              19

<210> SEQ ID NO 153
<211> LENGTH: 19
<212> TYPE: DNA
<213> ORGANISM: Artificial Sequence
<220> FEATURE:
<223> OTHER INFORMATION: Target sequence

<400> SEQUENCE: 153
ggatgggaca aagacagac                                              19

<210> SEQ ID NO 154
<211> LENGTH: 19
<212> TYPE: DNA
<213> ORGANISM: Artificial Sequence
<220> FEATURE:
<223> OTHER INFORMATION: Target sequence

<400> SEQUENCE: 154
gaggcagcag aacctgttc                                              19

<210> SEQ ID NO 155
<211> LENGTH: 19
<212> TYPE: DNA
<213> ORGANISM: Artificial Sequence
<220> FEATURE:
<223> OTHER INFORMATION: Target sequence

<400> SEQUENCE: 155
ctttgttgaa ccatcacac                                              19

<210> SEQ ID NO 156
<211> LENGTH: 19
<212> TYPE: DNA
<213> ORGANISM: Artificial Sequence
<220> FEATURE:
<223> OTHER INFORMATION: Target sequence

<400> SEQUENCE: 156
ggcatcagaa ggagaaatc                                              19

<210> SEQ ID NO 157
<211> LENGTH: 19
<212> TYPE: DNA
<213> ORGANISM: Artificial Sequence
<220> FEATURE:
<223> OTHER INFORMATION: Target sequence

<400> SEQUENCE: 157
atgatgtgtg ccacacacc                                              19

<210> SEQ ID NO 158
<211> LENGTH: 19
<212> TYPE: DNA
<213> ORGANISM: Artificial Sequence

```
<220> FEATURE:
<223> OTHER INFORMATION: Target sequence

<400> SEQUENCE: 158
cggcacttta cagagaagc                                                19

<210> SEQ ID NO 159
<211> LENGTH: 19
<212> TYPE: DNA
<213> ORGANISM: Artificial Sequence
<220> FEATURE:
<223> OTHER INFORMATION: Target sequence

<400> SEQUENCE: 159
gagctgtgac ttgtggtcc                                                19

<210> SEQ ID NO 160
<211> LENGTH: 19
<212> TYPE: DNA
<213> ORGANISM: Artificial Sequence
<220> FEATURE:
<223> OTHER INFORMATION: Target sequence

<400> SEQUENCE: 160
ctccgagatg tgattgctc                                                19

<210> SEQ ID NO 161
<211> LENGTH: 19
<212> TYPE: DNA
<213> ORGANISM: Artificial Sequence
<220> FEATURE:
<223> OTHER INFORMATION: Target sequence

<400> SEQUENCE: 161
cattgcgcac agagacctc                                                19

<210> SEQ ID NO 162
<211> LENGTH: 19
<212> TYPE: DNA
<213> ORGANISM: Artificial Sequence
<220> FEATURE:
<223> OTHER INFORMATION: Target sequence

<400> SEQUENCE: 162
ctgaacaact cctgtaccc                                                19

<210> SEQ ID NO 163
<211> LENGTH: 19
<212> TYPE: DNA
<213> ORGANISM: Artificial Sequence
<220> FEATURE:
<223> OTHER INFORMATION: Target sequence

<400> SEQUENCE: 163
gacctcatct ccaagctcc                                                19

<210> SEQ ID NO 164
<211> LENGTH: 19
<212> TYPE: DNA
<213> ORGANISM: Artificial Sequence
<220> FEATURE:
<223> OTHER INFORMATION: Target sequence

<400> SEQUENCE: 164
ggagccgagc tttagaccc                                                19
```

<210> SEQ ID NO 165
<211> LENGTH: 19
<212> TYPE: DNA
<213> ORGANISM: Artificial Sequence
<220> FEATURE:
<223> OTHER INFORMATION: Target sequence

<400> SEQUENCE: 165
ctactacacc tctttgtac                                                19

<210> SEQ ID NO 166
<211> LENGTH: 19
<212> TYPE: DNA
<213> ORGANISM: Artificial Sequence
<220> FEATURE:
<223> OTHER INFORMATION: Target sequence

<400> SEQUENCE: 166
atgtggacac aacaagggc                                                19

<210> SEQ ID NO 167
<211> LENGTH: 19
<212> TYPE: DNA
<213> ORGANISM: Artificial Sequence
<220> FEATURE:
<223> OTHER INFORMATION: Target sequence

<400> SEQUENCE: 167
tgtggacgac tcgcgcatc                                                19

<210> SEQ ID NO 168
<211> LENGTH: 19
<212> TYPE: DNA
<213> ORGANISM: Artificial Sequence
<220> FEATURE:
<223> OTHER INFORMATION: Target sequence

<400> SEQUENCE: 168
cgagcacgta tgatctctc                                                19

<210> SEQ ID NO 169
<211> LENGTH: 19
<212> TYPE: DNA
<213> ORGANISM: Artificial Sequence
<220> FEATURE:
<223> OTHER INFORMATION: Target sequence

<400> SEQUENCE: 169
agggctgcat tctgtgatc                                                19

<210> SEQ ID NO 170
<211> LENGTH: 19
<212> TYPE: DNA
<213> ORGANISM: Artificial Sequence
<220> FEATURE:
<223> OTHER INFORMATION: Target sequence

<400> SEQUENCE: 170
ctgcacaata tgactcctc                                                19

<210> SEQ ID NO 171
<211> LENGTH: 19
<212> TYPE: DNA
<213> ORGANISM: Artificial Sequence
<220> FEATURE:
<223> OTHER INFORMATION: Target sequence

```
<400> SEQUENCE: 171
cctcatcaac agcctcttc                                                19

<210> SEQ ID NO 172
<211> LENGTH: 19
<212> TYPE: DNA
<213> ORGANISM: Artificial Sequence
<220> FEATURE:
<223> OTHER INFORMATION: Target sequence

<400> SEQUENCE: 172
atcggtgtca ccgtgatac                                                19

<210> SEQ ID NO 173
<211> LENGTH: 19
<212> TYPE: DNA
<213> ORGANISM: Artificial Sequence
<220> FEATURE:
<223> OTHER INFORMATION: Target sequence

<400> SEQUENCE: 173
ccaggagcct cttccatac                                                19

<210> SEQ ID NO 174
<211> LENGTH: 19
<212> TYPE: DNA
<213> ORGANISM: Artificial Sequence
<220> FEATURE:
<223> OTHER INFORMATION: Target sequence

<400> SEQUENCE: 174
tcgattccga gctgtcttc                                                19

<210> SEQ ID NO 175
<211> LENGTH: 19
<212> TYPE: DNA
<213> ORGANISM: Artificial Sequence
<220> FEATURE:
<223> OTHER INFORMATION: Target sequence

<400> SEQUENCE: 175
gacagcaaga ttgtggacc                                                19

<210> SEQ ID NO 176
<211> LENGTH: 50
<212> TYPE: RNA
<213> ORGANISM: Artificial Sequence
<220> FEATURE:
<223> OTHER INFORMATION: siRNA

<400> SEQUENCE: 176
gccaagcaac aucaggauag uuugcuauaa cuauccugau guugcuuggc              50

<210> SEQ ID NO 177
<211> LENGTH: 19
<212> TYPE: RNA
<213> ORGANISM: Artificial Sequence
<220> FEATURE:
<223> OTHER INFORMATION: siRNA

<400> SEQUENCE: 177
gccaagcaac aucaggaua                                                19

<210> SEQ ID NO 178
```

```
<211> LENGTH: 19
<212> TYPE: RNA
<213> ORGANISM: Artificial Sequence
<220> FEATURE:
<223> OTHER INFORMATION: siRNA

<400> SEQUENCE: 178
uauccugaug uugcuuggc                                                   19

<210> SEQ ID NO 179
<211> LENGTH: 19
<212> TYPE: DNA
<213> ORGANISM: Artificial Sequence
<220> FEATURE:
<223> OTHER INFORMATION: Target sequence

<400> SEQUENCE: 179
gctgaccctg aagttcatc                                                   19

<210> SEQ ID NO 180
<211> LENGTH: 19
<212> TYPE: DNA
<213> ORGANISM: Artificial Sequence
<220> FEATURE:
<223> OTHER INFORMATION: Target sequence

<400> SEQUENCE: 180
gctgaccctg aagttcatc                                                   19

<210> SEQ ID NO 181
<211> LENGTH: 27
<212> TYPE: DNA
<213> ORGANISM: Artificial Sequence
<220> FEATURE:
<223> OTHER INFORMATION: PCR primers

<400> SEQUENCE: 181
gcgaagcttg cggcatggac gaactgt                                          27

<210> SEQ ID NO 182
<211> LENGTH: 27
<212> TYPE: DNA
<213> ORGANISM: Artificial Sequence
<220> FEATURE:
<223> OTHER INFORMATION: PCR primers

<400> SEQUENCE: 182
gcgggatccc aggcgtcacc cccttag                                          27

<210> SEQ ID NO 183
<211> LENGTH: 25
<212> TYPE: DNA
<213> ORGANISM: Artificial Sequence
<220> FEATURE:
<223> OTHER INFORMATION: PCR primers

<400> SEQUENCE: 183
gttctggggt gtggtgtctc acagc                                            25

<210> SEQ ID NO 184
<211> LENGTH: 25
<212> TYPE: DNA
<213> ORGANISM: Artificial Sequence
<220> FEATURE:
<223> OTHER INFORMATION: PCR primers

<400> SEQUENCE: 184
```
caaactgagc cacatcaggc actcc                                             25

<210> SEQ ID NO 185
<211> LENGTH: 26
<212> TYPE: DNA
<213> ORGANISM: Artificial Sequence
<220> FEATURE:
<223> OTHER INFORMATION: PCR primers

<400> SEQUENCE: 185
ccagtctgaa agtgactgct gtgtgg                                            26

<210> SEQ ID NO 186
<211> LENGTH: 26
<212> TYPE: DNA
<213> ORGANISM: Artificial Sequence
<220> FEATURE:
<223> OTHER INFORMATION: PCR primers

<400> SEQUENCE: 186
caactggaca tttgtgacct gcatcc                                            26

<210> SEQ ID NO 187
<211> LENGTH: 19
<212> TYPE: DNA
<213> ORGANISM: Artificial Sequence
<220> FEATURE:
<223> OTHER INFORMATION: Target sequence

<400> SEQUENCE: 187
gctgaccctg aagttcatc                                                    19

<210> SEQ ID NO 188
<211> LENGTH: 20
<212> TYPE: DNA
<213> ORGANISM: Artificial Sequence
<220> FEATURE:
<223> OTHER INFORMATION: PCR primers

<400> SEQUENCE: 188
ggtgggaggt ctatataagc                                                   20

<210> SEQ ID NO 189
<211> LENGTH: 22
<212> TYPE: DNA
<213> ORGANISM: Artificial Sequence
<220> FEATURE:
<223> OTHER INFORMATION: PCR primers

<400> SEQUENCE: 189
ggacaaacca caactagaat gc                                                22

<210> SEQ ID NO 190
<211> LENGTH: 18
<212> TYPE: DNA
<213> ORGANISM: Artificial Sequence
<220> FEATURE:
<223> OTHER INFORMATION: PCR primers

<400> SEQUENCE: 190
ccccaggcac tggtgttg                                                     18

<210> SEQ ID NO 191
<211> LENGTH: 19
<212> TYPE: DNA

```
<213> ORGANISM: Artificial Sequence
<220> FEATURE:
<223> OTHER INFORMATION: PCR primers

<400> SEQUENCE: 191
acggaccact tggccttct                                                    19

<210> SEQ ID NO 192
<211> LENGTH: 25
<212> TYPE: DNA
<213> ORGANISM: Artificial Sequence
<220> FEATURE:
<223> OTHER INFORMATION: PCR primers

<400> SEQUENCE: 192
ccggtttttc aaagggaata agtac                                             25

<210> SEQ ID NO 193
<211> LENGTH: 24
<212> TYPE: DNA
<213> ORGANISM: Artificial Sequence
<220> FEATURE:
<223> OTHER INFORMATION: PCR primers

<400> SEQUENCE: 193
ttcacagttc tagggaagcc aaag                                              24

<210> SEQ ID NO 194
<211> LENGTH: 18
<212> TYPE: DNA
<213> ORGANISM: Artificial Sequence
<220> FEATURE:
<223> OTHER INFORMATION: PCR primers

<400> SEQUENCE: 194
cagcatccgt gggtcaca                                                     18

<210> SEQ ID NO 195
<211> LENGTH: 20
<212> TYPE: DNA
<213> ORGANISM: Artificial Sequence
<220> FEATURE:
<223> OTHER INFORMATION: PCR primers

<400> SEQUENCE: 195
ttcaccgctg ccttaagctt                                                   20

<210> SEQ ID NO 196
<211> LENGTH: 24
<212> TYPE: DNA
<213> ORGANISM: Artificial Sequence
<220> FEATURE:
<223> OTHER INFORMATION: PCR primers

<400> SEQUENCE: 196
tgaggacgac ctatttgagt ccat                                              24

<210> SEQ ID NO 197
<211> LENGTH: 22
<212> TYPE: DNA
<213> ORGANISM: Artificial Sequence
<220> FEATURE:
<223> OTHER INFORMATION: PCR primers

<400> SEQUENCE: 197
gggattcttc gtcatgaaag ct                                                22
```

<210> SEQ ID NO 198
<211> LENGTH: 23
<212> TYPE: DNA
<213> ORGANISM: Artificial Sequence
<220> FEATURE:
<223> OTHER INFORMATION: PCR primers

<400> SEQUENCE: 198
ctgcgaagct gtgaatccta ctc                                           23

<210> SEQ ID NO 199
<211> LENGTH: 20
<212> TYPE: DNA
<213> ORGANISM: Artificial Sequence
<220> FEATURE:
<223> OTHER INFORMATION: PCR primers

<400> SEQUENCE: 199
ggcatcctgc tggctgtatc                                               20

<210> SEQ ID NO 200
<211> LENGTH: 27
<212> TYPE: DNA
<213> ORGANISM: Artificial Sequence
<220> FEATURE:
<223> OTHER INFORMATION: PCR primers

<400> SEQUENCE: 200
tcctggcaga actcctctat atcatac                                       27

<210> SEQ ID NO 201
<211> LENGTH: 25
<212> TYPE: DNA
<213> ORGANISM: Artificial Sequence
<220> FEATURE:
<223> OTHER INFORMATION: PCR primers

<400> SEQUENCE: 201
tgacagttcg tagagcaggt ttcta                                         25

<210> SEQ ID NO 202
<211> LENGTH: 22
<212> TYPE: DNA
<213> ORGANISM: Artificial Sequence
<220> FEATURE:
<223> OTHER INFORMATION: PCR primers

<400> SEQUENCE: 202
gaacttgtac ttcacgcagg tg                                            22

<210> SEQ ID NO 203
<211> LENGTH: 22
<212> TYPE: DNA
<213> ORGANISM: Artificial Sequence
<220> FEATURE:
<223> OTHER INFORMATION: PCR primers

<400> SEQUENCE: 203
caacaggaaa acaaggctga tg                                            22

<210> SEQ ID NO 204
<211> LENGTH: 22
<212> TYPE: DNA
<213> ORGANISM: Artificial Sequence
<220> FEATURE:

<223> OTHER INFORMATION: PCR primers

<400> SEQUENCE: 204
tgcgtggtcc cttctttatc ac                                             22

<210> SEQ ID NO 205
<211> LENGTH: 20
<212> TYPE: DNA
<213> ORGANISM: Artificial Sequence
<220> FEATURE:
<223> OTHER INFORMATION: PCR primers

<400> SEQUENCE: 205
gccatggaga cgctcttcag                                                20

<210> SEQ ID NO 206
<211> LENGTH: 28
<212> TYPE: DNA
<213> ORGANISM: Artificial Sequence
<220> FEATURE:
<223> OTHER INFORMATION: PCR primers

<400> SEQUENCE: 206
cattaaatga actcctacat aggaaaac                                       28

<210> SEQ ID NO 207
<211> LENGTH: 20
<212> TYPE: DNA
<213> ORGANISM: Artificial Sequence
<220> FEATURE:
<223> OTHER INFORMATION: PCR primers

<400> SEQUENCE: 207
agggcaattt catgcaggat                                                20

<210> SEQ ID NO 208
<211> LENGTH: 23
<212> TYPE: DNA
<213> ORGANISM: Artificial Sequence
<220> FEATURE:
<223> OTHER INFORMATION: PCR primers

<400> SEQUENCE: 208
ggagtgtctc tgtcaaaagt gga                                            23

<210> SEQ ID NO 209
<211> LENGTH: 26
<212> TYPE: DNA
<213> ORGANISM: Artificial Sequence
<220> FEATURE:
<223> OTHER INFORMATION: PCR primers

<400> SEQUENCE: 209
acccattttg atagagctcc tacatt                                         26

<210> SEQ ID NO 210
<211> LENGTH: 20
<212> TYPE: DNA
<213> ORGANISM: Artificial Sequence
<220> FEATURE:
<223> OTHER INFORMATION: PCR primers

<400> SEQUENCE: 210
gacattaaag cggccaacgt                                                20

```
<210> SEQ ID NO 211
<211> LENGTH: 18
<212> TYPE: DNA
<213> ORGANISM: Artificial Sequence
<220> FEATURE:
<223> OTHER INFORMATION: PCR primers

<400> SEQUENCE: 211
ctcgggtgcc atccagaa                                                 18

<210> SEQ ID NO 212
<211> LENGTH: 21
<212> TYPE: DNA
<213> ORGANISM: Artificial Sequence
<220> FEATURE:
<223> OTHER INFORMATION: PCR primers

<400> SEQUENCE: 212
gcgagaaaga cgaagagctg c                                             21

<210> SEQ ID NO 213
<211> LENGTH: 18
<212> TYPE: DNA
<213> ORGANISM: Artificial Sequence
<220> FEATURE:
<223> OTHER INFORMATION: PCR primers

<400> SEQUENCE: 213
gcctggctct gctgcatt                                                 18

<210> SEQ ID NO 214
<211> LENGTH: 25
<212> TYPE: DNA
<213> ORGANISM: Artificial Sequence
<220> FEATURE:
<223> OTHER INFORMATION: PCR primers

<400> SEQUENCE: 214
cagtgaaatt tatccacaat cacac                                         25

<210> SEQ ID NO 215
<211> LENGTH: 22
<212> TYPE: DNA
<213> ORGANISM: Artificial Sequence
<220> FEATURE:
<223> OTHER INFORMATION: PCR primers

<400> SEQUENCE: 215
agagctgagg ccagtccaat at                                            22

<210> SEQ ID NO 216
<211> LENGTH: 22
<212> TYPE: DNA
<213> ORGANISM: Artificial Sequence
<220> FEATURE:
<223> OTHER INFORMATION: PCR primers

<400> SEQUENCE: 216
ggtgtaggga agagtgccat ga                                            22

<210> SEQ ID NO 217
<211> LENGTH: 21
<212> TYPE: DNA
<213> ORGANISM: Artificial Sequence
<220> FEATURE:
<223> OTHER INFORMATION: PCR primers
```

-continued

```
<400> SEQUENCE: 217
gcatcttcaa tggtgggatc a                                              21

<210> SEQ ID NO 218
<211> LENGTH: 20
<212> TYPE: DNA
<213> ORGANISM: Artificial Sequence
<220> FEATURE:
<223> OTHER INFORMATION: PCR primers

<400> SEQUENCE: 218
tggtcgcctg tgtcttctca                                                20

<210> SEQ ID NO 219
<211> LENGTH: 25
<212> TYPE: DNA
<213> ORGANISM: Artificial Sequence
<220> FEATURE:
<223> OTHER INFORMATION: PCR primers

<400> SEQUENCE: 219
gtggtatctt tcaacgtctg tcctc                                          25

<210> SEQ ID NO 220
<211> LENGTH: 20
<212> TYPE: DNA
<213> ORGANISM: Artificial Sequence
<220> FEATURE:
<223> OTHER INFORMATION: PCR primers

<400> SEQUENCE: 220
gaggaaggcg gtggtagtga                                                20

<210> SEQ ID NO 221
<211> LENGTH: 22
<212> TYPE: DNA
<213> ORGANISM: Artificial Sequence
<220> FEATURE:
<223> OTHER INFORMATION: PCR primers

<400> SEQUENCE: 221
ctcaaccgga atctcgtaca ca                                             22

<210> SEQ ID NO 222
<211> LENGTH: 24
<212> TYPE: DNA
<213> ORGANISM: Artificial Sequence
<220> FEATURE:
<223> OTHER INFORMATION: PCR primers

<400> SEQUENCE: 222
tgggagataa cttgggtctc tgat                                           24

<210> SEQ ID NO 223
<211> LENGTH: 21
<212> TYPE: DNA
<213> ORGANISM: Artificial Sequence
<220> FEATURE:
<223> OTHER INFORMATION: PCR primers

<400> SEQUENCE: 223
aagccaattc tggtcgagct t                                              21

<210> SEQ ID NO 224
<211> LENGTH: 21
```

<212> TYPE: DNA
<213> ORGANISM: Artificial Sequence
<220> FEATURE:
<223> OTHER INFORMATION: PCR primers

<400> SEQUENCE: 224
agggagccta tgccaaagtt c                                              21

<210> SEQ ID NO 225
<211> LENGTH: 22
<212> TYPE: DNA
<213> ORGANISM: Artificial Sequence
<220> FEATURE:
<223> OTHER INFORMATION: PCR primers

<400> SEQUENCE: 225
ctcgatgatt ttgacggcat ac                                             22

<210> SEQ ID NO 226
<211> LENGTH: 23
<212> TYPE: DNA
<213> ORGANISM: Artificial Sequence
<220> FEATURE:
<223> OTHER INFORMATION: PCR primers

<400> SEQUENCE: 226
gaggaagctc ctgaaggtca aac                                            23

<210> SEQ ID NO 227
<211> LENGTH: 20
<212> TYPE: DNA
<213> ORGANISM: Artificial Sequence
<220> FEATURE:
<223> OTHER INFORMATION: PCR primers

<400> SEQUENCE: 227
caaccactgc cttgtccatc                                                20

<210> SEQ ID NO 228
<211> LENGTH: 21
<212> TYPE: DNA
<213> ORGANISM: Artificial Sequence
<220> FEATURE:
<223> OTHER INFORMATION: PCR primers

<400> SEQUENCE: 228
agccagctgc agttcttcct t                                              21

<210> SEQ ID NO 229
<211> LENGTH: 23
<212> TYPE: DNA
<213> ORGANISM: Artificial Sequence
<220> FEATURE:
<223> OTHER INFORMATION: PCR primers

<400> SEQUENCE: 229
tcacagcgtc tcttgactga aag                                            23

<210> SEQ ID NO 230
<211> LENGTH: 20
<212> TYPE: DNA
<213> ORGANISM: Artificial Sequence
<220> FEATURE:
<223> OTHER INFORMATION: PCR primers

<400> SEQUENCE: 230
ggtgggaggt ctatataagc                                                    20

<210> SEQ ID NO 231
<211> LENGTH: 22
<212> TYPE: DNA
<213> ORGANISM: Artificial Sequence
<220> FEATURE:
<223> OTHER INFORMATION: PCR primers

<400> SEQUENCE: 231
ggacaaacca caactagaat gc                                                 22

<210> SEQ ID NO 232
<211> LENGTH: 31
<212> TYPE: PRT
<213> ORGANISM: Artificial Sequence
<220> FEATURE:
<223> OTHER INFORMATION: GPCR Domain

<400> SEQUENCE: 232

Met Asn Ser Thr Leu Asp Gly Asn Gln Ser Ser His Pro Phe Cys Leu
1               5                   10                  15
Leu Ala Phe Gly Tyr Leu Glu Thr Val Asn Phe Cys Leu Leu Glu
            20                  25                  30

<210> SEQ ID NO 233
<211> LENGTH: 23
<212> TYPE: PRT
<213> ORGANISM: Artificial Sequence
<220> FEATURE:
<223> OTHER INFORMATION: GPCR Domain

<400> SEQUENCE: 233

Val Leu Ile Ile Val Phe Leu Thr Val Leu Ile Ile Ser Gly Asn Ile
1               5                   10                  15
Ile Val Ile Phe Val Phe His
            20

<210> SEQ ID NO 234
<211> LENGTH: 11
<212> TYPE: PRT
<213> ORGANISM: Artificial Sequence
<220> FEATURE:
<223> OTHER INFORMATION: GPCR Domain

<400> SEQUENCE: 234

Cys Ala Pro Leu Leu Asn His His Thr Thr Ser
1               5                   10

<210> SEQ ID NO 235
<211> LENGTH: 23
<212> TYPE: PRT
<213> ORGANISM: Artificial Sequence
<220> FEATURE:
<223> OTHER INFORMATION: GPCR Domain

<400> SEQUENCE: 235

Tyr Phe Ile Gln Thr Met Ala Tyr Ala Asp Leu Phe Val Gly Val Ser
1               5                   10                  15
Cys Val Val Pro Ser Leu Ser
            20

<210> SEQ ID NO 236
<211> LENGTH: 14
<212> TYPE: PRT

```
<213> ORGANISM: Artificial Sequence
<220> FEATURE:
<223> OTHER INFORMATION: GPCR Domain

<400> SEQUENCE: 236

Leu Leu His His Pro Leu Pro Val Glu Glu Ser Leu Thr Cys
1               5                   10

<210> SEQ ID NO 237
<211> LENGTH: 23
<212> TYPE: PRT
<213> ORGANISM: Artificial Sequence
<220> FEATURE:
<223> OTHER INFORMATION: GPCR Domain

<400> SEQUENCE: 237

Gln Ile Phe Gly Phe Val Val Ser Val Leu Lys Ser Val Ser Met Ala
1               5                   10                  15

Ser Leu Ala Cys Ile Ser Ile
            20

<210> SEQ ID NO 238
<211> LENGTH: 20
<212> TYPE: PRT
<213> ORGANISM: Artificial Sequence
<220> FEATURE:
<223> OTHER INFORMATION: GPCR Domain

<400> SEQUENCE: 238

Asp Arg Tyr Ile Ala Ile Thr Lys Pro Leu Thr Tyr Asn Thr Leu Val
1               5                   10                  15

Thr Pro Trp Arg
            20

<210> SEQ ID NO 239
<211> LENGTH: 23
<212> TYPE: PRT
<213> ORGANISM: Artificial Sequence
<220> FEATURE:
<223> OTHER INFORMATION: GPCR Domain

<400> SEQUENCE: 239

Leu Arg Leu Cys Ile Phe Leu Ile Trp Leu Tyr Ser Thr Leu Val Phe
1               5                   10                  15

Leu Pro Ser Phe Phe His Trp
            20

<210> SEQ ID NO 240
<211> LENGTH: 24
<212> TYPE: PRT
<213> ORGANISM: Artificial Sequence
<220> FEATURE:
<223> OTHER INFORMATION: GPCR Domain

<400> SEQUENCE: 240

Gly Lys Pro Gly Tyr His Gly Asp Val Phe Gln Trp Cys Ala Glu Ser
1               5                   10                  15

Trp His Thr Asp Ser Tyr Phe Thr
            20

<210> SEQ ID NO 241
<211> LENGTH: 23
<212> TYPE: PRT
<213> ORGANISM: Artificial Sequence
<220> FEATURE:
```

<223> OTHER INFORMATION: GPCR Domain

<400> SEQUENCE: 241

Leu Phe Ile Val Met Met Leu Tyr Ala Pro Ala Ala Leu Ile Val Cys
1               5                   10                  15

Phe Thr Tyr Phe Asn Ile Phe
            20

<210> SEQ ID NO 242
<211> LENGTH: 36
<212> TYPE: PRT
<213> ORGANISM: Artificial Sequence
<220> FEATURE:
<223> OTHER INFORMATION: GPCR Domain

<400> SEQUENCE: 242

Arg Ile Cys Gln Gln His Thr Lys Asp Ile Ser Glu Arg Gln Ala Arg
1               5                   10                  15

Phe Ser Ser Gln Ser Gly Glu Thr Gly Glu Val Gln Ala Cys Pro Asp
            20                  25                  30

Lys Arg Tyr Ala
        35

<210> SEQ ID NO 243
<211> LENGTH: 23
<212> TYPE: PRT
<213> ORGANISM: Artificial Sequence
<220> FEATURE:
<223> OTHER INFORMATION: GPCR Domain

<400> SEQUENCE: 243

Met Val Leu Phe Arg Ile Thr Ser Val Phe Tyr Ile Leu Trp Leu Pro
1               5                   10                  15

Tyr Ile Ile Tyr Phe Leu Leu
            20

<210> SEQ ID NO 244
<211> LENGTH: 9
<212> TYPE: PRT
<213> ORGANISM: Artificial Sequence
<220> FEATURE:
<223> OTHER INFORMATION: GPCR Domain

<400> SEQUENCE: 244

Glu Ser Ser Thr Gly His Ser Asn Arg
1               5

<210> SEQ ID NO 245
<211> LENGTH: 23
<212> TYPE: PRT
<213> ORGANISM: Artificial Sequence
<220> FEATURE:
<223> OTHER INFORMATION: GPCR Domain

<400> SEQUENCE: 245

Phe Ala Ser Phe Leu Thr Thr Trp Leu Ala Ile Ser Asn Ser Phe Cys
1               5                   10                  15

Asn Cys Val Ile Tyr Ser Leu
            20

<210> SEQ ID NO 246
<211> LENGTH: 43
<212> TYPE: PRT
<213> ORGANISM: Artificial Sequence

```
<220> FEATURE:
<223> OTHER INFORMATION: GPCR Domain

<400> SEQUENCE: 246

Ser Asn Ser Val Phe Gln Arg Gly Leu Lys Arg Leu Ser Gly Ala Met
1               5                   10                  15

Cys Thr Ser Cys Ala Ser Gln Thr Thr Ala Asn Asp Pro Tyr Thr Val
            20                  25                  30

Arg Ser Lys Gly Pro Leu Asn Gly Cys His Ile
        35                  40

<210> SEQ ID NO 247
<211> LENGTH: 9
<212> TYPE: PRT
<213> ORGANISM: Artificial Sequence
<220> FEATURE:
<223> OTHER INFORMATION: GPCR Domain

<400> SEQUENCE: 247

Met Ala Trp Arg Gly Ala Gly Pro Ser
1               5

<210> SEQ ID NO 248
<211> LENGTH: 23
<212> TYPE: PRT
<213> ORGANISM: Artificial Sequence
<220> FEATURE:
<223> OTHER INFORMATION: GPCR Domain

<400> SEQUENCE: 248

Val Pro Gly Ala Pro Gly Gly Val Gly Leu Ser Leu Gly Leu Leu Leu
1               5                   10                  15

Gln Leu Leu Leu Leu Leu Gly
            20

<210> SEQ ID NO 249
<211> LENGTH: 188
<212> TYPE: PRT
<213> ORGANISM: Artificial Sequence
<220> FEATURE:
<223> OTHER INFORMATION: GPCR Domain

<400> SEQUENCE: 249

Pro Ala Arg Gly Phe Gly Asp Glu Glu Arg Arg Cys Asp Pro Ile
1               5                   10                  15

Arg Ile Ser Met Cys Gln Asn Leu Gly Tyr Asn Val Thr Lys Met Pro
            20                  25                  30

Asn Leu Val Gly His Glu Leu Gln Thr Asp Ala Glu Leu Gln Leu Thr
        35                  40                  45

Thr Phe Thr Pro Leu Ile Gln Tyr Gly Cys Ser Ser Gln Leu Gln Phe
    50                  55                  60

Phe Leu Cys Ser Val Tyr Val Pro Met Cys Thr Glu Lys Ile Asn Ile
65                  70                  75                  80

Pro Ile Gly Pro Cys Gly Gly Met Cys Leu Ser Val Lys Arg Arg Cys
                85                  90                  95

Glu Pro Val Leu Lys Glu Phe Gly Phe Ala Trp Pro Glu Ser Leu Asn
            100                 105                 110

Cys Ser Lys Phe Pro Pro Gln Asn Asp His Asn His Met Cys Met Glu
        115                 120                 125

Gly Pro Gly Asp Glu Glu Val Pro Leu Pro His Lys Thr Pro Ile Gln
    130                 135                 140
```

-continued

```
Pro Gly Glu Glu Cys His Ser Val Gly Thr Asn Ser Asp Gln Tyr Ile
145                 150                 155                 160

Trp Val Lys Arg Ser Leu Asn Cys Val Leu Lys Cys Gly Tyr Asp Ala
                165                 170                 175

Gly Leu Tyr Ser Arg Ser Ala Lys Glu Phe Thr Asp
            180                 185

<210> SEQ ID NO 250
<211> LENGTH: 23
<212> TYPE: PRT
<213> ORGANISM: Artificial Sequence
<220> FEATURE:
<223> OTHER INFORMATION: GPCR Domain

<400> SEQUENCE: 250

Ile Trp Met Ala Val Trp Ala Ser Leu Cys Phe Ile Ser Thr Ala Phe
1               5                   10                  15

Thr Val Leu Thr Phe Leu Ile
            20

<210> SEQ ID NO 251
<211> LENGTH: 9
<212> TYPE: PRT
<213> ORGANISM: Artificial Sequence
<220> FEATURE:
<223> OTHER INFORMATION: GPCR Domain

<400> SEQUENCE: 251

Asp Ser Ser Arg Phe Ser Tyr Pro Glu
1               5

<210> SEQ ID NO 252
<211> LENGTH: 23
<212> TYPE: PRT
<213> ORGANISM: Artificial Sequence
<220> FEATURE:
<223> OTHER INFORMATION: GPCR Domain

<400> SEQUENCE: 252

Arg Pro Ile Ile Phe Leu Ser Met Cys Tyr Asn Ile Tyr Ser Ile Ala
1               5                   10                  15

Tyr Ile Val Arg Leu Thr Val
            20

<210> SEQ ID NO 253
<211> LENGTH: 25
<212> TYPE: PRT
<213> ORGANISM: Artificial Sequence
<220> FEATURE:
<223> OTHER INFORMATION: GPCR Domain

<400> SEQUENCE: 253

Gly Arg Glu Arg Ile Ser Cys Asp Phe Glu Glu Ala Ala Glu Pro Val
1               5                   10                  15

Leu Ile Gln Glu Gly Leu Lys Asn Thr
            20                  25

<210> SEQ ID NO 254
<211> LENGTH: 23
<212> TYPE: PRT
<213> ORGANISM: Artificial Sequence
<220> FEATURE:
<223> OTHER INFORMATION: GPCR Domain
```

-continued

```
<400> SEQUENCE: 254

Gly Cys Ala Ile Ile Phe Leu Leu Met Tyr Phe Phe Gly Met Ala Ser
1               5                   10                  15

Ser Ile Trp Trp Val Ile Leu
            20

<210> SEQ ID NO 255
<211> LENGTH: 70
<212> TYPE: PRT
<213> ORGANISM: Artificial Sequence
<220> FEATURE:
<223> OTHER INFORMATION: GPCR Domain

<400> SEQUENCE: 255

Thr Leu Thr Trp Phe Leu Ala Ala Gly Leu Lys Trp Gly His Glu Ala
1               5                   10                  15

Ile Glu Met His Ser Ser Tyr Phe His Ile Ala Ala Trp Ala Ile Pro
            20                  25                  30

Ala Val Lys Thr Ile Val Ile Leu Ile Met Arg Leu Val Asp Ala Asp
        35                  40                  45

Glu Leu Thr Gly Leu Cys Tyr Val Gly Asn Gln Asn Leu Asp Ala Leu
    50                  55                  60

Thr Gly Phe Val Val Ala
65                  70

<210> SEQ ID NO 256
<211> LENGTH: 23
<212> TYPE: PRT
<213> ORGANISM: Artificial Sequence
<220> FEATURE:
<223> OTHER INFORMATION: GPCR Domain

<400> SEQUENCE: 256

Pro Leu Phe Thr Tyr Leu Val Ile Gly Thr Leu Phe Ile Ala Ala Gly
1               5                   10                  15

Leu Val Ala Leu Phe Lys Ile
            20

<210> SEQ ID NO 257
<211> LENGTH: 20
<212> TYPE: PRT
<213> ORGANISM: Artificial Sequence
<220> FEATURE:
<223> OTHER INFORMATION: GPCR Domain

<400> SEQUENCE: 257

Arg Ser Asn Leu Gln Lys Asp Gly Thr Lys Thr Asp Lys Leu Glu Arg
1               5                   10                  15

Leu Met Val Lys
            20

<210> SEQ ID NO 258
<211> LENGTH: 23
<212> TYPE: PRT
<213> ORGANISM: Artificial Sequence
<220> FEATURE:
<223> OTHER INFORMATION: GPCR Domain

<400> SEQUENCE: 258

Ile Gly Val Phe Ser Val Leu Tyr Thr Val Pro Ala Thr Cys Val Ile
1               5                   10                  15

Ala Cys Tyr Phe Tyr Glu Ile
```

20

<210> SEQ ID NO 259
<211> LENGTH: 14
<212> TYPE: PRT
<213> ORGANISM: Artificial Sequence
<220> FEATURE:
<223> OTHER INFORMATION: GPCR Domain

<400> SEQUENCE: 259

Ser Asn Trp Ala Leu Phe Arg Tyr Ser Ala Asp Asp Ser Asn
1               5                   10

<210> SEQ ID NO 260
<211> LENGTH: 23
<212> TYPE: PRT
<213> ORGANISM: Artificial Sequence
<220> FEATURE:
<223> OTHER INFORMATION: GPCR Domain

<400> SEQUENCE: 260

Met Ala Val Glu Met Leu Lys Ile Phe Met Ser Leu Leu Val Gly Ile
1               5                   10                  15

Thr Ser Gly Met Trp Ile Trp
            20

<210> SEQ ID NO 261
<211> LENGTH: 41
<212> TYPE: PRT
<213> ORGANISM: Artificial Sequence
<220> FEATURE:
<223> OTHER INFORMATION: GPCR Domain

<400> SEQUENCE: 261

Ser Ala Lys Thr Leu His Thr Trp Gln Lys Cys Ser Asn Arg Leu Val
1               5                   10                  15

Asn Ser Gly Lys Val Lys Arg Glu Lys Arg Gly Asn Gly Trp Val Lys
            20                  25                  30

Pro Gly Lys Gly Ser Glu Thr Val Val
        35                  40

<210> SEQ ID NO 262
<211> LENGTH: 45
<212> TYPE: PRT
<213> ORGANISM: Artificial Sequence
<220> FEATURE:
<223> OTHER INFORMATION: GPCR Domain

<400> SEQUENCE: 262

Met Arg Pro Glu Arg Pro Arg Pro Arg Gly Ser Ala Pro Gly Pro Met
1               5                   10                  15

Glu Thr Pro Pro Trp Asp Pro Ala Arg Asn Asp Ser Leu Pro Pro Thr
            20                  25                  30

Leu Thr Pro Ala Val Pro Pro Tyr Val Lys Leu Gly Leu
        35                  40                  45

<210> SEQ ID NO 263
<211> LENGTH: 23
<212> TYPE: PRT
<213> ORGANISM: Artificial Sequence
<220> FEATURE:
<223> OTHER INFORMATION: GPCR Domain

<400> SEQUENCE: 263

```
Thr Val Val Tyr Thr Val Phe Tyr Ala Leu Leu Phe Val Phe Ile Tyr
1               5                   10                  15

Val Gln Leu Trp Leu Val Leu
            20

<210> SEQ ID NO 264
<211> LENGTH: 12
<212> TYPE: PRT
<213> ORGANISM: Artificial Sequence
<220> FEATURE:
<223> OTHER INFORMATION: GPCR Domain

<400> SEQUENCE: 264

Arg Tyr Arg His Lys Arg Leu Ser Tyr Gln Ser Val
1               5                   10

<210> SEQ ID NO 265
<211> LENGTH: 20
<212> TYPE: PRT
<213> ORGANISM: Artificial Sequence
<220> FEATURE:
<223> OTHER INFORMATION: GPCR Domain

<400> SEQUENCE: 265

Phe Leu Phe Leu Cys Leu Phe Trp Ala Ser Leu Arg Thr Val Leu Phe
1               5                   10                  15

Ser Phe Tyr Phe
            20

<210> SEQ ID NO 266
<211> LENGTH: 14
<212> TYPE: PRT
<213> ORGANISM: Artificial Sequence
<220> FEATURE:
<223> OTHER INFORMATION: GPCR Domain

<400> SEQUENCE: 266

Lys Asp Phe Val Ala Ala Asn Ser Leu Ser Pro Phe Val Phe
1               5                   10

<210> SEQ ID NO 267
<211> LENGTH: 23
<212> TYPE: PRT
<213> ORGANISM: Artificial Sequence
<220> FEATURE:
<223> OTHER INFORMATION: GPCR Domain

<400> SEQUENCE: 267

Trp Leu Leu Tyr Cys Phe Pro Val Cys Leu Gln Phe Phe Thr Leu Thr
1               5                   10                  15

Leu Met Asn Leu Tyr Phe Thr
            20

<210> SEQ ID NO 268
<211> LENGTH: 20
<212> TYPE: PRT
<213> ORGANISM: Artificial Sequence
<220> FEATURE:
<223> OTHER INFORMATION: GPCR Domain

<400> SEQUENCE: 268

Gln Val Ile Phe Lys Ala Lys Ser Lys Tyr Ser Pro Glu Leu Leu Lys
1               5                   10                  15

Tyr Arg Leu Pro
            20
```

```
<210> SEQ ID NO 269
<211> LENGTH: 23
<212> TYPE: PRT
<213> ORGANISM: Artificial Sequence
<220> FEATURE:
<223> OTHER INFORMATION: GPCR Domain

<400> SEQUENCE: 269

Leu Tyr Leu Ala Ser Leu Phe Ile Ser Leu Val Phe Leu Leu Val Asn
1               5                   10                  15

Leu Thr Cys Ala Val Leu Val
            20

<210> SEQ ID NO 270
<211> LENGTH: 14
<212> TYPE: PRT
<213> ORGANISM: Artificial Sequence
<220> FEATURE:
<223> OTHER INFORMATION: GPCR Domain

<400> SEQUENCE: 270

Lys Thr Gly Asn Trp Glu Arg Lys Val Ile Val Ser Val Arg
1               5                   10

<210> SEQ ID NO 271
<211> LENGTH: 23
<212> TYPE: PRT
<213> ORGANISM: Artificial Sequence
<220> FEATURE:
<223> OTHER INFORMATION: GPCR Domain

<400> SEQUENCE: 271

Val Ala Ile Asn Asp Thr Leu Phe Val Leu Cys Ala Val Ser Leu Ser
1               5                   10                  15

Ile Cys Leu Tyr Lys Ile Ser
            20

<210> SEQ ID NO 272
<211> LENGTH: 20
<212> TYPE: PRT
<213> ORGANISM: Artificial Sequence
<220> FEATURE:
<223> OTHER INFORMATION: GPCR Domain

<400> SEQUENCE: 272

Lys Met Ser Leu Ala Asn Ile Tyr Leu Glu Ser Lys Gly Ser Ser Val
1               5                   10                  15

Cys Gln Val Thr
            20

<210> SEQ ID NO 273
<211> LENGTH: 23
<212> TYPE: PRT
<213> ORGANISM: Artificial Sequence
<220> FEATURE:
<223> OTHER INFORMATION: GPCR Domain

<400> SEQUENCE: 273

Ala Ile Gly Val Thr Val Ile Leu Leu Tyr Thr Ser Arg Ala Cys Tyr
1               5                   10                  15

Asn Leu Phe Ile Leu Ser Phe
            20
```

```
<210> SEQ ID NO 274
<211> LENGTH: 30
<212> TYPE: PRT
<213> ORGANISM: Artificial Sequence
<220> FEATURE:
<223> OTHER INFORMATION: GPCR Domain

<400> SEQUENCE: 274

Ser Gln Asn Lys Ser Val His Ser Phe Asp Tyr Asp Trp Tyr Asn Val
1               5                   10                  15

Ser Asp Gln Ala Asp Leu Lys Asn Gln Leu Gly Asp Ala Gly
            20                  25                  30

<210> SEQ ID NO 275
<211> LENGTH: 23
<212> TYPE: PRT
<213> ORGANISM: Artificial Sequence
<220> FEATURE:
<223> OTHER INFORMATION: GPCR Domain

<400> SEQUENCE: 275

Tyr Val Leu Phe Gly Val Val Leu Phe Val Trp Glu Leu Leu Pro Thr
1               5                   10                  15

Thr Leu Val Val Tyr Phe Phe
            20

<210> SEQ ID NO 276
<211> LENGTH: 86
<212> TYPE: PRT
<213> ORGANISM: Artificial Sequence
<220> FEATURE:
<223> OTHER INFORMATION: GPCR Domain

<400> SEQUENCE: 276

Arg Val Arg Asn Pro Thr Lys Asp Leu Thr Asn Pro Gly Met Val Pro
1               5                   10                  15

Ser His Gly Phe Ser Pro Arg Ser Tyr Phe Phe Asp Asn Pro Arg Arg
            20                  25                  30

Tyr Asp Ser Asp Asp Leu Ala Trp Asn Ile Ala Pro Gln Gly Leu
        35                  40                  45

Gln Gly Gly Phe Ala Pro Asp Tyr Tyr Asp Trp Gly Gln Gln Thr Asn
    50                  55                  60

Ser Phe Leu Ala Gln Ala Gly Thr Leu Gln Asp Ser Thr Leu Asp Pro
65                  70                  75                  80

Asp Lys Pro Ser Leu Gly
            85

<210> SEQ ID NO 277
<211> LENGTH: 95
<212> TYPE: PRT
<213> ORGANISM: Artificial Sequence
<220> FEATURE:
<223> OTHER INFORMATION: GPCR Domain

<400> SEQUENCE: 277

Met Ala Glu Ala Ile Thr Tyr Ala Asp Leu Arg Phe Val Lys Ala Pro
1               5                   10                  15

Leu Lys Lys Ser Ile Ser Ser Arg Leu Gly Gln Asp Pro Gly Ala Asp
            20                  25                  30

Asp Asp Gly Glu Ile Thr Tyr Glu Asn Val Gln Val Pro Ala Val Leu
        35                  40                  45

Gly Val Pro Ser Ser Leu Ala Ser Ser Val Leu Gly Asp Lys Ala Ala
```

```
                50                  55                  60
Val Lys Ser Glu Gln Pro Thr Ala Ser Trp Arg Ala Val Thr Ser Pro
 65                  70                  75                  80

Ala Val Gly Arg Ile Leu Pro Cys Arg Thr Thr Cys Leu Arg Tyr
                 85                  90                  95

<210> SEQ ID NO 278
<211> LENGTH: 23
<212> TYPE: PRT
<213> ORGANISM: Artificial Sequence
<220> FEATURE:
<223> OTHER INFORMATION: GPCR Domain

<400> SEQUENCE: 278

Leu Leu Leu Gly Leu Leu Leu Thr Cys Leu Leu Gly Val Thr Ala
 1               5                  10                  15

Ile Cys Leu Gly Val Arg Tyr
                 20

<210> SEQ ID NO 279
<211> LENGTH: 241
<212> TYPE: PRT
<213> ORGANISM: Artificial Sequence
<220> FEATURE:
<223> OTHER INFORMATION: GPCR Domain

<400> SEQUENCE: 279

Leu Gln Val Ser Gln Gln Leu Gln Gln Thr Asn Arg Val Leu Glu Val
 1               5                  10                  15

Thr Asn Ser Ser Leu Arg Gln Gln Leu Arg Leu Lys Ile Thr Gln Leu
                20                  25                  30

Gly Gln Ser Ala Glu Asp Leu Gln Gly Ser Arg Arg Glu Leu Ala Gln
                35                  40                  45

Ser Gln Glu Ala Leu Gln Val Glu Gln Arg Ala His Gln Ala Ala Glu
    50                  55                  60

Gly Gln Leu Gln Ala Cys Gln Ala Asp Arg Gln Lys Thr Lys Glu Thr
 65                  70                  75                  80

Leu Gln Ser Glu Glu Gln Gln Arg Arg Ala Leu Glu Gln Lys Leu Ser
                85                  90                  95

Asn Met Glu Asn Arg Leu Lys Pro Phe Phe Thr Cys Gly Ser Ala Asp
                100                 105                 110

Thr Cys Cys Pro Ser Gly Trp Ile Met His Gln Lys Ser Cys Phe Tyr
                115                 120                 125

Ile Ser Leu Thr Ser Lys Asn Trp Gln Glu Ser Gln Lys Gln Cys Glu
                130                 135                 140

Thr Leu Ser Ser Lys Leu Ala Thr Phe Ser Glu Ile Tyr Pro Gln Ser
145                 150                 155                 160

His Ser Tyr Tyr Phe Leu Asn Ser Leu Leu Pro Asn Gly Gly Ser Gly
                165                 170                 175

Asn Ser Tyr Trp Thr Gly Leu Ser Ser Asn Lys Asp Trp Lys Leu Thr
                180                 185                 190

Asp Asp Thr Gln Arg Thr Arg Thr Tyr Ala Gln Ser Ser Lys Cys Asn
                195                 200                 205

Lys Val His Lys Thr Trp Ser Trp Trp Thr Leu Glu Ser Glu Ser Cys
                210                 215                 220

Arg Ser Ser Leu Pro Tyr Ile Cys Glu Met Thr Ala Phe Arg Phe Pro
225                 230                 235                 240
```

-continued

Asp

<210> SEQ ID NO 280
<211> LENGTH: 145
<212> TYPE: PRT
<213> ORGANISM: Artificial Sequence
<220> FEATURE:
<223> OTHER INFORMATION: GPCR Domain

<400> SEQUENCE: 280

```
Met Ser Pro Ser Gly Arg Leu Cys Leu Thr Ile Val Gly Leu Ile
1               5                   10                  15

Leu Pro Thr Arg Gly Gln Thr Leu Lys Asp Thr Thr Ser Ser Ser
                20                  25                  30

Ala Asp Ser Thr Ile Met Asp Ile Gln Val Pro Thr Arg Ala Pro Asp
            35                  40                  45

Ala Val Tyr Thr Glu Leu Gln Pro Thr Ser Pro Thr Pro Thr Trp Pro
        50                  55                  60

Ala Asp Glu Thr Pro Gln Pro Gln Thr Gln Thr Gln Gln Leu Glu Gly
65                  70                  75                  80

Thr Asp Gly Pro Leu Val Thr Asp Pro Glu Thr His Lys Ser Thr Lys
                85                  90                  95

Ala Ala His Pro Thr Asp Asp Thr Thr Thr Leu Ser Glu Arg Pro Ser
                100                 105                 110

Pro Ser Thr Asp Val Gln Thr Asp Pro Gln Thr Leu Lys Pro Ser Gly
            115                 120                 125

Phe His Glu Asp Asp Pro Phe Phe Tyr Asp Glu His Thr Leu Arg Lys
        130                 135                 140

Arg
145
```

<210> SEQ ID NO 281
<211> LENGTH: 19
<212> TYPE: PRT
<213> ORGANISM: Artificial Sequence
<220> FEATURE:
<223> OTHER INFORMATION: GPCR Domain

<400> SEQUENCE: 281

```
Gly Leu Leu Val Ala Ala Val Leu Phe Ile Thr Gly Ile Ile Ile Leu
1               5                   10                  15

Thr Ser Gly
```

<210> SEQ ID NO 282
<211> LENGTH: 14
<212> TYPE: PRT
<213> ORGANISM: Artificial Sequence
<220> FEATURE:
<223> OTHER INFORMATION: GPCR Domain

<400> SEQUENCE: 282

```
Lys Cys Arg Gln Leu Ser Arg Leu Cys Arg Asn Arg Cys Arg
1               5                   10
```

<210> SEQ ID NO 283
<211> LENGTH: 116
<212> TYPE: PRT
<213> ORGANISM: Artificial Sequence
<220> FEATURE:
<223> OTHER INFORMATION: GPCR Domain

<400> SEQUENCE: 283

Met Cys Thr Glu Lys Ile Asn Ile Pro Ile Gly Pro Cys Gly Met
1               5                   10                  15

Cys Leu Ser Val Lys Arg Arg Cys Glu Pro Val Leu Lys Glu Phe Gly
            20                  25                  30

Phe Ala Trp Pro Glu Ser Leu Asn Cys Ser Lys Phe Pro Pro Gln Asn
        35                  40                  45

Asp His Asn His Met Cys Met Glu Gly Pro Gly Asp Glu Glu Val Pro
    50                  55                  60

Leu Pro His Lys Thr Pro Ile Gln Pro Gly Glu Glu Cys His Ser Val
65                  70                  75                  80

Gly Thr Asn Ser Asp Gln Tyr Ile Trp Val Lys Arg Ser Leu Asn Cys
                85                  90                  95

Val Leu Lys Cys Gly Tyr Asp Ala Gly Leu Tyr Ser Arg Ser Ala Lys
            100                 105                 110

Glu Phe Thr Asp
        115

<210> SEQ ID NO 284
<211> LENGTH: 23
<212> TYPE: PRT
<213> ORGANISM: Artificial Sequence
<220> FEATURE:
<223> OTHER INFORMATION: GPCR Domain

<400> SEQUENCE: 284

Ile Trp Met Ala Val Trp Ala Ser Leu Cys Phe Ile Ser Thr Ala Phe
1               5                   10                  15

Thr Val Leu Thr Phe Leu Ile
            20

<210> SEQ ID NO 285
<211> LENGTH: 9
<212> TYPE: PRT
<213> ORGANISM: Artificial Sequence
<220> FEATURE:
<223> OTHER INFORMATION: GPCR Domain

<400> SEQUENCE: 285

Asp Ser Ser Arg Phe Ser Tyr Pro Glu
1               5

<210> SEQ ID NO 286
<211> LENGTH: 23
<212> TYPE: PRT
<213> ORGANISM: Artificial Sequence
<220> FEATURE:
<223> OTHER INFORMATION: GPCR Domain

<400> SEQUENCE: 286

Arg Pro Ile Ile Phe Leu Ser Met Cys Tyr Asn Ile Tyr Ser Ile Ala
1               5                   10                  15

Tyr Ile Val Arg Leu Thr Val
            20

<210> SEQ ID NO 287
<211> LENGTH: 25
<212> TYPE: PRT
<213> ORGANISM: Artificial Sequence
<220> FEATURE:
<223> OTHER INFORMATION: GPCR Domain

<400> SEQUENCE: 287

Gly Arg Glu Arg Ile Ser Cys Asp Phe Glu Glu Ala Ala Pro Val
1               5                   10                  15

Leu Ile Gln Glu Gly Leu Lys Asn Thr
            20                  25

<210> SEQ ID NO 288
<211> LENGTH: 23
<212> TYPE: PRT
<213> ORGANISM: Artificial Sequence
<220> FEATURE:
<223> OTHER INFORMATION: GPCR Domain

<400> SEQUENCE: 288

Gly Cys Ala Ile Ile Phe Leu Leu Met Tyr Phe Phe Gly Met Ala Ser
1               5                   10                  15

Ser Ile Trp Trp Val Ile Leu
            20

<210> SEQ ID NO 289
<211> LENGTH: 70
<212> TYPE: PRT
<213> ORGANISM: Artificial Sequence
<220> FEATURE:
<223> OTHER INFORMATION: GPCR Domain

<400> SEQUENCE: 289

Thr Leu Thr Trp Phe Leu Ala Ala Gly Leu Lys Trp Gly His Glu Ala
1               5                   10                  15

Ile Glu Met His Ser Ser Tyr Phe His Ile Ala Ala Trp Ala Ile Pro
            20                  25                  30

Ala Val Lys Thr Ile Val Ile Leu Ile Met Arg Leu Val Asp Ala Asp
        35                  40                  45

Glu Leu Thr Gly Leu Cys Tyr Val Gly Asn Gln Asn Leu Asp Ala Leu
    50                  55                  60

Thr Gly Phe Val Val Ala
65                  70

<210> SEQ ID NO 290
<211> LENGTH: 23
<212> TYPE: PRT
<213> ORGANISM: Artificial Sequence
<220> FEATURE:
<223> OTHER INFORMATION: GPCR Domain

<400> SEQUENCE: 290

Pro Leu Phe Thr Tyr Leu Val Ile Gly Thr Leu Phe Ile Ala Ala Gly
1               5                   10                  15

Leu Val Ala Leu Phe Lys Ile
            20

<210> SEQ ID NO 291
<211> LENGTH: 20
<212> TYPE: PRT
<213> ORGANISM: Artificial Sequence
<220> FEATURE:
<223> OTHER INFORMATION: GPCR Domain

<400> SEQUENCE: 291

Arg Ser Asn Leu Gln Lys Asp Gly Thr Lys Thr Asp Lys Leu Glu Arg
1               5                   10                  15

Leu Met Val Lys
            20

<210> SEQ ID NO 292
<211> LENGTH: 23
<212> TYPE: PRT
<213> ORGANISM: Artificial Sequence
<220> FEATURE:
<223> OTHER INFORMATION: GPCR Domain

<400> SEQUENCE: 292

Ile Gly Val Phe Ser Val Leu Tyr Thr Val Pro Ala Thr Cys Val Ile
1               5                   10                  15

Ala Cys Tyr Phe Tyr Glu Ile
            20

<210> SEQ ID NO 293
<211> LENGTH: 14
<212> TYPE: PRT
<213> ORGANISM: Artificial Sequence
<220> FEATURE:
<223> OTHER INFORMATION: GPCR Domain

<400> SEQUENCE: 293

Ser Asn Trp Ala Leu Phe Arg Tyr Ser Ala Asp Asp Ser Asn
1               5                   10

<210> SEQ ID NO 294
<211> LENGTH: 23
<212> TYPE: PRT
<213> ORGANISM: Artificial Sequence
<220> FEATURE:
<223> OTHER INFORMATION: GPCR Domain

<400> SEQUENCE: 294

Met Ala Val Glu Met Leu Lys Ile Phe Met Ser Leu Leu Val Gly Ile
1               5                   10                  15

Thr Ser Gly Met Trp Ile Trp
            20

<210> SEQ ID NO 295
<211> LENGTH: 41
<212> TYPE: PRT
<213> ORGANISM: Artificial Sequence
<220> FEATURE:
<223> OTHER INFORMATION: GPCR Domain

<400> SEQUENCE: 295

Ser Ala Lys Thr Leu His Thr Trp Gln Lys Cys Ser Asn Arg Leu Val
1               5                   10                  15

Asn Ser Gly Lys Val Lys Arg Glu Lys Arg Gly Asn Gly Trp Val Lys
                20                  25                  30

Pro Gly Lys Gly Ser Glu Thr Val Val
            35                  40

METHODS FOR IDENTIFICATION, AND COMPOUNDS USEFUL FOR THE TREATMENT OF DEGENERATIVE & INFLAMMATORY DISEASES

CROSS-REFERENCE TO RELATED APPLICATIONS

This application claims priority to U.S. Provisional Application No. 60/579,307, filed Jun. 14, 2004, the disclosure of which is incorporated herein by reference.

FIELD OF INVENTION

The present invention relates to a methods for identifying compounds, and expression-inhibition agents, capable of inhibiting the expression of proteins involved in the pathway resulting in the degradation of extra-cellular matrix (ECM), which inhibition is useful in the prevention and treatment of joint degeneration and diseases involving such degradation and/or inflammation.

Diseases involving the degradation of extra-cellular matrix include, but are not limited to, psoriatic arthritis, juvenile arthritis, early arthritis, reactive arthritis, osteoarthritis, ankylosing spondylitis. osteoporosis, muskulo skeletal diseases like tendinitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Although it is widely accepted that RA is an auto-immune disease, there is no consensus concerning the precise mechanisms driving the 'initiation stage' of the disease. What is known is that the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). When the disease progresses, the cellular activation and cytokine production cascade becomes self-perpetuating. At this early stage, the destruction of joint structures is already very clear at this early stage. Thirty percent of the patients have radiographic evidence of bony erosions at the time of diagnosis and this proportion increases to 60 percent after two years.

Histologic analysis of the joints of RA patients clearly evidences the mechanisms involved in the RA-associated degradative processes. The synovium is a cell layer, composed of a sublining and a lining region that separates the joint capsule from the synovial cavity. The inflamed synovium is central to the pathophysiology of RA. Histological differences in the synovium between normal and RA patients are indicated in FIG. 1: A. The synovial joint is composed of two adjacent bony ends each covered with a layer of cartilage, separated by a joint space and surrounded by the synovial membrane and joint capsule. The synovial membrane is composed of the synovial lining (facing the cartilage and bone) which consists of a thin (1-3 cells) layer of synoviocytes and the sublining connective tissue layer that is highly vascularised. The synovial membrane covers almost all intra-articular structures except for cartilage. B. Like many other forms of arthritis, rheumatoid arthritis (RA) is initially characterized by an inflammatory response of the synovial membrane ('synovitis') that is characterised by an important influx of various types of mononuclear cells as well as by the activation of the local or infiltrated mononuclear cells. The lining layer becomes hyperplastic (it can have a thickness of >20 cells) and the synovial membrane expands. However, in addition, the hallmark of RA is joint destruction: the joint spaces narrow or disappear as a sign of cartilage degradation and destructions of the adjacent bone, also termed 'erosions', have occurred. The destructive portion of the synovial membrane is termed 'pannus'. Enzymes secreted by synoviocytes lead to cartilage degradation.

This analysis shows that the main effector responsible for RA-associated joint degradation is the pannus, where the synovial fibroblast, by producing diverse proteolytic enzymes, is the prime driver of cartilage and bone erosion. In the advanced RA patient, the pannus mediates the degradation of the adjacent cartilage, leading to the narrowing of the joint space, and has the potential to invade adjacent bone and cartilage. As bone and cartilage tissues are composed mainly of collagen type I or II, respectively, the pannus destructive and invasive properties are mediated by the secretion of collagenolytic proteases, principally the matrix metallo proteinases (MMPs). The erosion of the bone under and adjacent to the cartilage is also part of the RA process, and results principally from the presence of osteoclasts at the interface of bone and pannus. Osteoclasts adhere to the bone tissue and form a closed compartment, within which the osteoclasts secrete proteases (Cathepsin K, MMP9) that degrade the bone tissue. The osteoclast population in the joint is abnormally increased by osteoblast formation from precursor cells induced by the secretion of the receptor activator of NFkB ligand (RANKL) by activated SFs and T-cells.

Various collagen types have a key role in defining the stability of the extra-cellular matrix (ECM). Collagens type I and collagen type II, for example, are the main components of bone and cartilage, respectively. Collagen proteins typically organise into multimeric structures referred to as collagen fibrils. Native collagen fibrils are very resistant to proteolytic cleavage. Only a few types of ECM-degrading proteins have been reported to have the capacity to degrade native collagen: matrix-metallo proteases (MMPs) and Cathepsins. Among the Cathepsins, cathepsin K, which is active mainly in osteoclasts, is the best characterised. Among the MMPs, MMP1, MMP2, MMP8 MMP13 and MMP14 are known to have collagenolytic properties. The correlation between an increased expression of MMP1 by synovial fibroblasts (SFs) and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation. Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteo-arthritis, and ankylosing spondylitis. Other diseases that may be treatable with compounds identified according to the present invention and using the targets involved in the expression of MMPs as described herein are osteoporosis, muskulo skeletal diseases like tendinitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reiff et al., 2005), cardiovascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

REPORTED DEVELOPMENTS

NSAIDS (Non-steroidal anti-inflammatory drugs) are used to reduce the pain associated with RA and improve life quality of the patients. These drugs will not, however, put a brake on the RA-associated joint destruction.

Corticosteroids are found to decrease the progression of RA as detected radiographically and are used at low doses to treat part of the RA patients (30 to 60%). Serious side effects, however, are associated with long corticosteroid use (Skin thinning, osteoporosis, cataracts, hypertension, hyperlipidemia).

Synthetic DMARDs (Disease-Modifying Anti-Rheumatic Drugs) (e.g. methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve a ACR50 score after 24 months treatment with methotrexate. This means that, according to the American College of Rheumatology, only 30% of the patients do achieve a 50% improvement of their symptoms (O'Dell et al., 1996). In addition, the precise mechanism of action of DMARDs is often unclear.

Biological DMARDs (Infliximab, Etanercept, Adalimumab, Rituximab, CTLA4-Ig) are therapeutic proteins that do inactivate cytokines (e.g. TNF-α) or cells (e.g. T-cells or B-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR50) in disease symptoms in 50-60% of patients after 12 months therapy (St Clair et al., 2004). Some adverse events warnings for anti-TNF-α drugs exist, shedding a light on the side effects associated to this type of drugs. Increased risk for infections (tuberculosis) hematologic events and demyelinating disorders have been described for the TNF-α blockers. (see also Gomez-Reino et al., 2003). Besides the serious side effects, the TNF-α blockers do also share the general disadvantages of the biologicals class of therapeutics, which are the unpleasant way of administration (frequent injections accompanied by infusion site reactions) and the high production cost. Newer agents in late development phase target T-cell co-stimulatory molecules and B-cells. The efficacy of these agents is expected to be similar to that of the TNF-α blockers. The fact that a variety of targeted therapies have similar but limited efficacies, suggests that there is a multiplicity of pathogenic factors for RA. This is also indicative for the deficiencies in our understanding of pathogenic events relevant to RA.

The current therapies for RA are not satisfactory due to a limited efficacy (no adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

The histological analysis of RA patient joints clearly identifies the pannus, as an aggressive, invasive tissue that represents the main culprit in joint degradation. Within the pannus, the synovial fibroblasts represent a link between the initiation of the abnormally triggered immune system that lies at the basis of RA pathogenesis, and the ultimate joint erosion. As no current RA therapy efficiently abolishes the erosive activity of the pannus in the long term, the discovery of novel drugs and/or drug targets that inhibit the generation, and/or the activity, of the pannus would represent an important milestone for the development of novel RA treatments.

The present invention is based on the discovery of that certain proteins function in the pathway that results in the expression of extra-cellular matrix (ECM) degradation proteases, such as MMP1, and that inhibitors of the activity of these proteins, are useful for the treatment of diseases involving the abnormally high expression of such proteases.

SUMMARY OF THE INVENTION

The present invention relates to a method for identifying compounds that inhibit extra-cellular matrix (ECM) degradation, comprising contacting a compound with a polypeptide comprising an amino acid sequence selected from the group consisting of SEQ ID NO: 27-51 (hereinafter "TARGETS") and fragments thereof under conditions that allow said polypeptide to bind to the compound, and measuring a compound-polypeptide property related to extra-cellular matrix (ECM) degradation.

Aspects of the present method include the in vitro assay of compounds using polypeptide of a TARGET and fragments thereof including selected from the group consisting of SEQ ID NO. 232-295, and cellular assays wherein TARGET inhibition is followed by observing indicators of efficacy including, for example, TARGET expression levels and/or Matrix Metallo Proteinase -1 levels.

The present invention also relates to expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a polypeptide comprising an amino acid sequence selected from the group consisting of SEQ ID NO: 27-51 and 232-295, pharmaceutical compositions comprising said agent, useful in the treatment, or prevention, of chronic joint degenerative diseases such as rheumatoid arthritis.

Another aspect of the invention is a method of treatment, or prevention, of a condition involving extra-cellular matrix (ECM) degradation, in a subject suffering or susceptible thereto, by administering a pharmaceutical composition comprising an effective TARGET-expression inhibiting amount of a expression-inhibitory agent.

A further aspect of the present invention is a method for diagnosis relating to disease conditions characterized by extra-cellular matrix (ECM) degradation comprising measurement of indicators of levels of TARGET expression in a subject.

Another aspect of this invention relates to the use of the present compound in a therapeutic method, a pharmaceutical composition, and the manufacture of such composition, useful for the treatment of a disease involving inflammation, and in particular, a disease characteristic of abnormal matrix metallo proteases activity.

BRIEF DESCRIPTION OF THE DRAWINGS

FIG. 4A. Layout of the 384 control plate produced for the MMP1 ELISA assay.

FIG. 4B. A representative example of the performance of the control plate tested with the protocol described in Example 2.

FIG. 16. Structure of short-hairpin RNA (shRNA) targeted against *Homo sapiens* receptor-interacting serine-threonine kinase 2 (RIPK2) mRNA.

DETAILED DESCRIPTION

Figure 1:
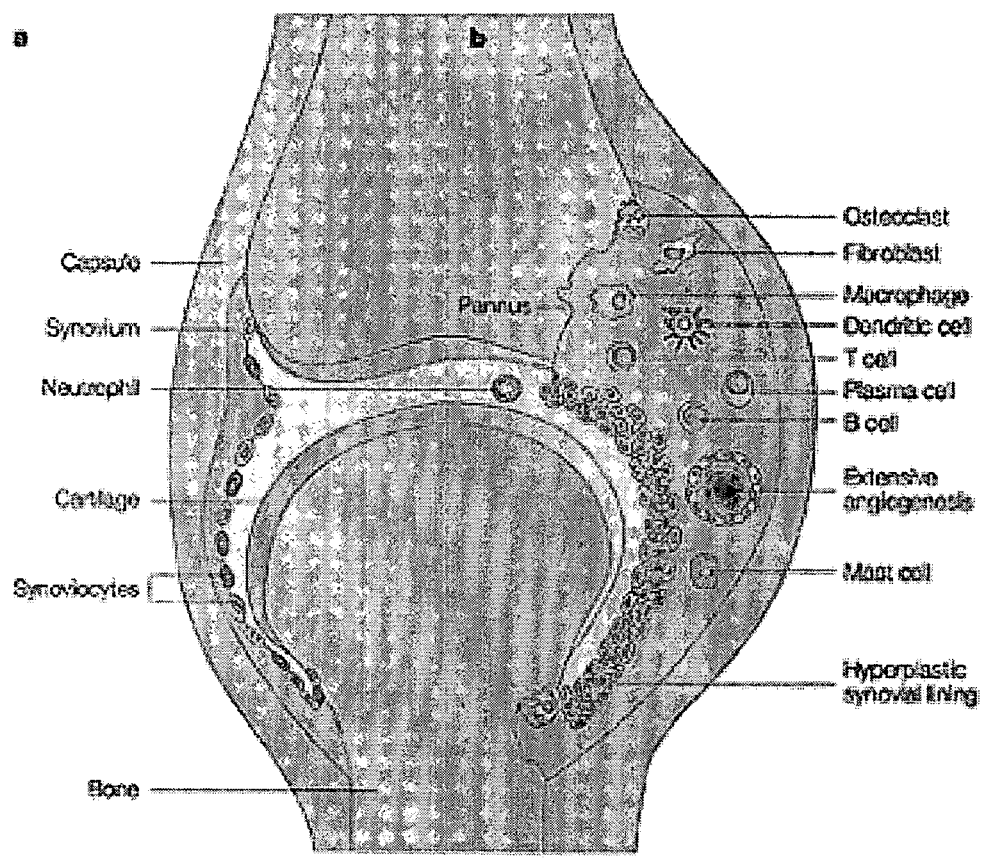
FIG. 1. Schematic view of a normal joint and its changes in rheumatoid arthritis (From Smolen and Steiner, 2003).

The following terms are intended to have the meanings presented therewith below and are useful in understanding the description and intended scope of the present invention.

The term "agent" means any molecule, including polypeptides, polynucleotides and small molecules.

The term "agonist" refers to a ligand that stimulates the receptor the ligand binds to in the broadest sense.

The term "assay" means any process used to measure a specific property of a compound. A "screening assay" means a process used to characterize or select compounds based upon their activity from a collection of compounds.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_D$).

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "complex" means the entity created when two or more compounds bind to each other.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

The term "condition" or "disease" means the overt presentation of symptoms (i.e., illness) or the manifestation of abnormal clinical indicators (e.g., biochemical indicators). Alternatively, the term "disease" refers to a genetic or environmental risk of or propensity for developing such symptoms or abnormal clinical indicators.

The term "contact" or "contacting" means bringing at least two moieties together, whether in an in vitro system or an in vivo system.

The term "derivatives of a polypeptide" relates to those peptides, oligopeptides, polypeptides, proteins and enzymes that comprise a stretch of contiguous amino acid residues of the polypeptide and that retain the biological activity of the protein, e.g. polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents compared to the amino acid sequence of a naturally occurring form of the polypeptide, for example a reporter molecule or other ligand, covalently or non-covalently bound to the amino acid sequence.

The term "derivatives of a polynucleotide" relates to DNA-molecules, RNA-molecules, and oligonucleotides that comprise a stretch or nucleic acid residues of the polynucleotide, e.g. polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy)ethyl-phosphorothioate, non-naturally occurring nucleic acid residues, or one or more nuclei acid substituents, such as methyl-, thio-, sulphate, benzoyl-, phenyl-, amino-, propyl-, chloro-, and methanocarbanucleosides, or a reporter molecule to facilitate its detection.

The terms "ECM-degrading protein" and "ECM-degrading activity" refer to a protein and activity, respectively, that is capable of degrading extra-cellular matrixes found in bone and cartilage.

The term "effective amount" or "therapeutically effective amount" means that amount of a compound or agent that will elicit the biological or medical response of a subject that is being sought by a medical doctor or other clinician.

The term "endogenous" shall mean a material that a mammal naturally produces. Endogenous in reference to the term "protease", "kinase", or G-Protein Coupled Receptor ("GPCR") shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both "in vivo" and "in vitro" systems. For example, and not a limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term "expressible nucleic acid" means a nucleic acid coding for a proteinaceous molecule, an RNA molecule, or a DNA molecule.

The term "expression" comprises both endogenous expression and overexpression by transduction.

The term "expression inhibitory agent" means a polynucleotide designed to interfere selectively with the transcription, translation and/or expression of a specific polypeptide or protein normally expressed within a cell. More particularly, "expression inhibitory agent" comprises a DNA or RNA molecule that contains a nucleotide sequence identical to or complementary to at least about 17 sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

The term "expressible nucleic acid" means a nucleic acid coding for a proteinaceous molecule, an RNA molecule, or a DNA molecule.

The term "fragment of a polynucleotide" relates to oligonucleotides that comprise a stretch of contiguous nucleic acid residues that exhibit substantially a similar, but not necessarily identical, activity as the complete sequence.

The term "fragment of a polypeptide" relates to peptides, oligopeptides, polypeptides, proteins and enzymes that comprise a stretch of contiguous amino acid residues, and exhibit substantially a similar, but not necessarily identical, functional activity as the complete sequence.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution (e.g., $C_{0t}$ or $R_{0t}$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, e.g., formamide, temperature, and other conditions well known in the art. In particular, reducing the concentration of salt, increasing the concentration of formamide, or raising the hybridization temperature can increase stringency.

The term "inhibit" or "inhibiting", in relationship to the term "response" means that a response is decreased or prevented in the presence of a compound as opposed to in the absence of the compound.

The term "inhibition" refers to the reduction, down regulation of a process or the elimination of a stimulus for a process that results in the absence or minimization of the expression of a protein or polypeptide.

The term "induction" refers to the inducing, up-regulation, or stimulation of a process that results in the expression of a protein or polypeptide.

The term "ligand" means an endogenous, naturally occurring molecule specific for an endogenous, naturally occurring receptor.

The term "pharmaceutically acceptable salts" refers to the non-toxic, inorganic and organic acid addition salts, and base addition salts, of compounds of the present invention. These salts can be prepared in situ during the final isolation and purification of compounds useful in the present invention.

The term "polypeptide" relates to proteins, proteinaceous molecules, fractions of proteins, peptides, oligopeptides, enzymes (such as kinases, proteases, GCPR's etc.).

The term "polynucleotide" means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy)ethylphosphorothioate. The polynucleotides are described by sequences that vary in length, that range from about 10 to about 5000 bases, preferably about 100 to about 4000 bases, more preferably about 250 to about 2500 bases. One polynucleotide embodiment comprises from about 10 to about 30 bases in length. A special embodiment of polynucleotide is the polyribonucleotide of from about 10 to about 22 nucleotides, more commonly described as small interfering RNAs (siRNAs). Another special embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term "polypeptide" relates to proteins (such as TARGETS), proteinaceous molecules, fractions of proteins peptides and oligopeptides.

The term "solvate" means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

The term "subject" includes humans and other mammals.

The term "TARGET" or "TARGETS" means the protein(s) identified in accordance with the present assay to be involved in the induction of MMP1 levels. The preferred TARGETS are identified as SEQ ID NOS. 27-51 in Table 1. The more preferred TARGETS are the kinases, proteases and G-Protein Coupled Receptors (GPCRs) identified in Table 1.

"Therapeutically effective amount" means that amount of a drug or pharmaceutical agent that will elicit the biological or medical response of a subject that is being sought by a medical doctor or other clinician. In particular, with regard to treating an disease condition characterized by the degradation of extracellular matrix, the term "effective matrix metallo-protease inhibiting amount" is intended to mean that effective amount of a compound of the present invention that will bring about a biologically meaningful decrease in the production of MMP-1 in the subject's disease affected tissues such that extracellular matrix degradation is meaningfully reduced. A compound having matrix metallo-protease inhibiting properties or a "matrix metallo-protease inhibiting compound" means a compound that provided to a cell in effective amounts is able to cause a biologically meaningful decrease in the production of MMP-1 in such cells.

The term "treating" means an intervention performed with the intention of preventing the development or altering the pathology of, and thereby alleviating a disorder, disease or condition, including one or more symptoms of such disorder or condition. Accordingly, "treating" refers to both therapeutic treatment and prophylactic or preventative measures. Those in need of treating include those already with the disorder as well as those in which the disorder is to be prevented. The related term "treatment," as used herein, refers to the act of treating a disorder, symptom, disease or condition, as the term "treating" is defined above.

Applicants' Invention Based on TARGET Relationship to Extra-cellular Matrix Degradation As noted above, the present invention is based on the present inventors' discovery that the TARGET polypeptides are factors in the up-regulation and/or induction of extra-cellular matrix degradation. The activity of the ECM-degrading protein is believed to be causative and to correlate with the progression of various diseases associated with an increased degradation of the extra-cellular matrix, including diseases that involve the degradation of the joint.

The present invention relates to a method for assaying for drug candidate compounds that inhibit extra-cellular matrix degradation, comprising contacting the compound with a polypeptide comprising an amino acid sequence of SEQ ID NO: 27-51 and 232-295 under conditions that allow said polypeptide to bind to the compound, and detecting the formation of a complex between the polypeptide and the compound. One preferred means of measuring the complex formation is to determine the binding affinity of said compound to said polypeptide.

More particularly, the invention relates to a method for identifying an agent that inhibits extra-cellular matrix degradation, the method comprising further:

(a) contacting a population of mammalian cells with one or more compound that exhibits binding affinity for a TARGET polypeptide, and (b) measuring a compound-polypeptide property related to extra-cellular matrix degradation.

The compound-polypeptide property referred to above is related to the expression of the TARGET, and is a measurable phenomenon chosen by the person of ordinary skill in the art. The measurable property may be, e.g., the binding affinity for a peptide domain of the polypeptide TARGET such as for SEQ ID NO: 232-295, or the level of any one of a number of biochemical marker levels of extra-cellular matrix degradation. Extra-cellular matrix degradation can e.g. be measured by measuring the level of enzymes that are induced during the process, such as expression of a MMP and/or a Cathepsin polypeptide.

In a preferred embodiment of the invention, the TARGET polypeptide comprises an amino acid knockdown (KD) sequence selected from the group consisting of SEQ ID No: 27-51 as listed in Table 1.

TABLE 1

| Hit No. | Gene Name | Description | Ref/SEQ accession (DNA) | SEQ ID NO DNA | Ref/SEQ accession (Protein) | SEQ ID NO Protein | Protein Class | SEQ ID KD Target |
|---|---|---|---|---|---|---|---|---|
| H31-290 | RIPK2 | *Homo sapiens* receptor-interacting serine-threonine kinase 2 (RIPK2), mRNA. | NM_003821 | 1 | NP_003812 | 27 | Kinase | 52-56 168-170 |
| H31-035 | PRKCE | *Homo sapiens* protein kinase C, epsilon (PRKCE), mRNA. | NM_005400 | 2 | NP_005391 | 28 | Kinase | 57-61 167 |
| H31-319 | MST3 | *Homo sapiens* kinase SK246 from Manning et al., Science. | SK246 | 3 | | 29 | Kinase | 62-66 164 |
| | | | NM_003576 | 4 | | 30 | Kinase | 62-66 164 |
| H34-088 | MAPKAPK5 | *Homo sapiens* mitogen-activated protein kinase-activated protein kinase 5 (MAPKAPK5), transcript variant 1, mRNA. | NM_003668 | 5 | NP_003659 | 31 | Kinase | 67-71 156-161 |
| | | | NM_139078 | 6 | | 32 | Kinase | 72-76 156-161 |
| H34-087 | MKNK1 | *Homo sapiens* MAP kinase-interacting serine/threonine kinase 1 (MKNK1), mRNA. | NM_003684 | 7 | NP_003675 | 33 | Kinase | 77-81 162-163 |
| H31-031 | CAMK4 | *Homo sapiens* calcium/calmodulin-dependent protein kinase IV (CAMK4), mRNA. | NM_001744 | 8 | NP_001735 | 34 | Kinase | 82-86 148 |
| | CAMK4 | | SK061 | 9 | | 35 | Kinase | 87-91 171 |
| H31-347 | SEPT1 | *Homo sapiens* septin 1 (SEPT1), mRNA. | NM_052838 | 10 | NP_443070 | 36 | Secreted | 92-96 |
| H31-450 | PGPEP1 | *Homo sapiens* pyroglutamyl-peptidase I | NM_017712 | 11 | | 37 | Protease | 92-96 165-166 |
| H31-351 | CD72 | *Homo sapiens* CD72 antigen (CD72), mRNA. | NM_001782 | 12 | NP_001773 | 38 | Secreted | 97-101 |
| H31-301 | TPST1 | *Homo sapiens* tyrosylprotein sulfotransferase 1 (TPST1), mRNA. | NM_003596 | 13 | NP_003587 | 39 | Enzyme | 102-106 150, 173 |
| H31-242 | GPR21 | *Homo sapiens* G protein-coupled receptor 21 (GPR21), mRNA. | NM_005294 | 14 | NP_005285 | 40 | GPCR | 107-111 155 |
| H31-047 | USP21 | *Homo sapiens* ubiquitin specific protease 21 (USP21), transcript variant 1, mRNA. | NM_012475 | 15 | NP_036607 | 41 | Protease | 112-116 174-175 |
| | USP21 | *Homo sapiens* ubiquitin specific protease 21 (USP21), transcript variant 2, mRNA. | NM_016572 | 16 | NP_057656 | 42 | Protease | 114-118 174-175 |
| H34-092 | FZD4 | *Homo sapiens* frizzled homolog 4 (*Drosophila*) (FZD4), mRNA. | NM_012193 | 17 | NP_036325; | 43 | GPCR | 119-123 152-154 |
| | | | GAL_GPCR_0379 | 18 | GAL_GPCR_0379 | 44 | GPCR | 119-123 |
| H31-180 | TM7SF1 | *Homo sapiens* transmembrane 7 superfamily member 1 (upregulated in kidney) (TM7SF1), mRNA. | NM_003272 | 19 | NP_003263 | 45 | GPCR | 124-128 172 |
| H31-384 | FXYD5 | *Homo sapiens* FXYD domain containing ion transport regulator 5 (FXYD5), mRNA. | NM_014164 | 20 | NP_054883 | 46 | Secreted | 129-133 151 |
| H31-360 | RIT1 | *Homo sapiens* Ras-like without CAAX 1 (RIT1), mRNA | NM_006912 | 21 | NP_008843 | 47 | Enzyme | 134-138 |
| H31-049 | CASP10 | *Homo sapiens* caspase 10, apoptosis-related cysteine protease (CASP10), transcript variant A, mRNA. | NM_001230 | 22 | NP_001221 | 48 | Protease | 139-143 146 |
| | CASP10 | *Homo sapiens* caspase 10, apoptosis-related cysteine protease (CASP10), transcript variant B, mRNA. | NM_032974 | 23 | NP_116756 | 49 | Protease | 140-141 143-146 149 |
| | CASP10 | *Homo sapiens* caspase 10, apoptosis-related cysteine protease (CASP10), transcript variant C, mRNA. | NM_032976 | 24 | NP_116758 | 50 | Enzyme | 139-143 146 |
| | CASP10 | *Homo sapiens* caspase 10, apoptosis-related cysteine protease (CASP10), transcript variant D, mRNA. loop | NM_032977 | 25 | NP_116759 | 51 | Protease | 140-143 146, 149 26 |

Depending on the choice of the skilled artisan, the present assay method may be designed to function as a series of measurements, each of which is designed to determine whether the drug candidate compound is indeed acting on the polypeptide to thereby inhibit extra-cellular matrix degradation. For example, an assay designed to determine the binding affinity of a compound to the polypeptide, or fragment thereof, may be necessary, but not sufficient, to ascertain whether the test compound would be useful for inhibiting extra-cellular matrix degradation when administered to a subject.

Such binding information would be useful in identifying a set of test compounds for use in an assay that would measure a different property, further down the biochemical pathway, such as for example MMP-1 expression. Such second assay may be designed to confirm that the test compound, having binding affinity for the polypeptide, actually inhibits extra-cellular matrix degradation. Suitable controls should always be in place to insure against false positive readings.

The order of taking these measurements is not believed to be critical to the practice of the present invention, which may be practiced in any order. For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide. However, for the present assay to be meaningful to the ultimate use of the drug candidate compounds, a measurement of extra-cellular matrix degradation activity is necessary. Validation studies including controls, and measurements of binding affinity to the polypeptides of the invention are nonetheless useful in identifying a compound useful in any therapeutic or diagnostic application.

The present assay method may be practiced in vitro, using one or more of the TARGET proteins, or fragments thereof. The amino acid sequences of exemplary protein domain fragments of selected TARGETS are SEQ ID NO: 232-295, listed in Table 1A below.

TABLE 1A

| Accession | Name | Protein Segment | SEQ ID NO Protein segment |
|---|---|---|---|
| NM_005294 | GPR21 | Extracellular domain | 232 |
| NM_005294 | GPR21 | Transmembrane domain | 233 |
| NM_005294 | GPR21 | Intracellular domain | 234 |
| NM_005294 | GPR21 | Transmembrane domain | 235 |
| NM_005294 | GPR21 | Extracellular domain | 236 |
| NM_005294 | GPR21 | Transmembrane domain | 237 |
| NM_005294 | GPR21 | Intracellular domain | 238 |
| NM_005294 | GPR21 | Transmembrane domain | 239 |
| NM_005294 | GPR21 | Extracellular domain | 240 |
| NM_005294 | GPR21 | Transmembrane domain | 241 |
| NM_005294 | GPR21 | Intracellular domain | 242 |
| NM_005294 | GPR21 | Transmembrane domain | 243 |
| NM_005294 | GPR21 | Extracellular domain | 244 |
| NM_005294 | GPR21 | Transmembrane domain | 245 |
| NM_005294 | GPR21 | Intracellular domain | 246 |
| NM_012193 | FZD4 | Extracellular domain | 247 |
| NM_012193 | FZD4 | Transmembrane domain | 248 |
| NM_012193 | FZD4 | Intracellular domain | 249 |
| NM_012193 | FZD4 | Transmembrane domain | 250 |
| NM_012193 | FZD4 | Extracellular domain | 251 |
| NM_012193 | FZD4 | Transmembrane domain | 252 |
| NM_012193 | FZD4 | Intracellular domain | 253 |
| NM_012193 | FZD4 | Transmembrane domain | 254 |

TABLE 1A-continued

| Accession | Name | Protein Segment | SEQ ID NO Protein segment |
|---|---|---|---|
| NM_012193 | FZD4 | Extracellular domain | 255 |
| NM_012193 | FZD4 | Transmembrane domain | 256 |
| NM_012193 | FZD4 | Intracellular domain | 257 |
| NM_012193 | FZD4 | Transmembrane domain | 258 |
| NM_012193 | FZD4 | Extracellular domain | 259 |
| NM_012193 | FZD4 | Transmembrane domain | 260 |
| NM_012193 | FZD4 | Intracellular domain | 261 |
| NM_003272 | TM7SF1 | Extracellular domain | 262 |
| NM_003272 | TM7SF1 | Transmembrane domain | 263 |
| NM_003272 | TM7SF1 | Intracellular domain | 264 |
| NM_003272 | TM7SF1 | Transmembrane domain | 265 |
| NM_003272 | TM7SF1 | Extracellular domain | 266 |
| NM_003272 | TM7SF1 | Transmembrane domain | 267 |
| NM_003272 | TM7SF1 | Intracellular domain | 268 |
| NM_003272 | TM7SF1 | Transmembrane domain | 269 |
| NM_003272 | TM7SF1 | Extracellular domain | 270 |
| NM_003272 | TM7SF1 | Transmembrane domain | 271 |
| NM_003272 | TM7SF1 | Intracellular domain | 272 |
| NM_003272 | TM7SF1 | Transmembrane domain | 273 |
| NM_003272 | TM7SF1 | Extracellular domain | 274 |
| NM_003272 | TM7SF1 | Transmembrane domain | 275 |
| NM_003272 | TM7SF1 | Intracellular domain | 276 |
| NM_001782 | CD72 | Intracellular domain | 277 |
| NM_001782 | CD72 | Transmembrane domain | 278 |
| NM_001782 | CD72 | Extracellular domain | 279 |
| NM_014164 | FXYD5 | Extracellular domain | 280 |
| NM_014164 | FXYD5 | Transmembrane domain | 281 |
| NM_014164 | FXYD5 | Intracellular domain | 282 |
| GAL_GPCR0379 | FZD4 | Intracellular domain | 283 |
| GAL_GPCR0379 | FZD4 | Transmembrane domain | 284 |
| GAL_GPCR0379 | FZD4 | Extracellular domain | 285 |
| GAL_GPCR0379 | FZD4 | Transmembrane domain | 286 |
| GAL_GPCR0379 | FZD4 | Intracellular domain | 287 |
| GAL_GPCR0379 | FZD4 | Transmembrane domain | 288 |
| GAL_GPCR0379 | FZD4 | Extracellular domain | 289 |
| GAL_GPCR0379 | FZD4 | Transmembrane domain | 290 |
| GAL_GPCR0379 | FZD4 | Intracellular domain | 291 |
| GAL_GPCR0379 | FZD4 | Transmembrane domain | 292 |
| GAL_GPCR0379 | FZD4 | Extracellular domain | 293 |
| GAL_GPCR0379 | FZD4 | Transmembrane domain | 294 |
| GAL_GPCR0379 | FZD4 | Intracellular domain | 295 |

The binding affinity of a compound with the polypeptide TARGET can be measured by methods known in the art, such as using surface plasmon resonance biosensors (Biacore), by saturation binding analysis with a labeled compound (e.g. Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as IC50 or EC50. The IC50 represents the concentration of a compound that is required for 50% inhibition of binding of another ligand to the polypeptide. The EC50 represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, IC50 and EC50 values, i.e. in the range of 100 nM to 1 pM; a moderate to low affinity binding relates to a high Kd, IC50 and EC50 values, i.e. in the micromolar range.

The present assay method may also be practiced in a cellular assay, A host cell expressing the TARGET can be a cell with endogenous expression or a cell over-expressing the TARGET e.g. by transduction. When the endogenous expression of the polypeptide is not sufficient to determine a baseline that can easily be measured, one may use using host cells that over-express TARGET. Over-expression has the advantage that the level of the TARGET substrate end products is higher than the activity level by endogenous expression. Accordingly, measuring such levels using presently available techniques is easier.

One embodiment of the present method for identifying a compound that decreases extra-cellular matrix (ECM) degradation comprises culturing a population of mammalian cells expressing a TARGET polypeptide, or a functional fragment or derivative thereof; determining a first level of ECM degradation in said population of cells; exposing said population of cells to a compound, or a mixture of compounds; determining a second level of ECM degradation in said population of cells during or after exposure of said population of cells to said compound, or the mixture of said compounds; and identifying the compound(s) that decreases ECM degradation. As noted above, ECM degradation may be determined by measuring the expression and/or activity of the TARGET polypeptide and/or a known ECM-degrading protein. In a preferred embodiment, said ECM-degrading protein is able to degrade collagen, and more preferably, is able to degrade collagen type I and/or collagen type II. In another preferred embodiment of the present invention, said ECM-degrading protein is a Matrix Metallo Proteinase (MMP), and more preferably is selected from the group consisting of: MMP1, MMP2, MMP3, MMP8, MMP9, MMP13 and MMP14. In this context, the most preferred ECM-degrading protein is Matrix Metalloprotease 1 (MMP1). In yet another preferred embodiment, said ECM-degrading protein is Cathepsin K.

The expression of an ECM-degrading protein can be determined by methods known in the art such as Western blotting using specific antibodies, or an ELISA using antibodies specifically recognizing a particular ECM-degrading protein.

The activity of an ECM-degrading protein can be determined by using fluorogenic small peptide substrates. The specificity of these substrates, however, is often limited. In general, the use of these substrates is limited to the testing of purified proteases in biochemical assays, to avoid interference of other proteases.

The present inventors have developed a protocol allowing the detection, in a high throughput mode, of the activity of collagen degrading enzymes in complex media such as the supernatant of cultured cells. This protocol makes use of native collagen, being labelled with a fluorescent label, as a substrate.

The present inventors identified target genes involved in ECM-degradation by using a 'knock-in' library. This type of library is a screen in which cDNA molecules are transduced into cells by recombinant adenoviruses that induce the expression and activity of a specific gene and corresponding gene product in a cell. Each cDNA in a viral vector corresponds to a specific natural gene. By identifying a cDNA that stimulates ECM-degradation, a direct correlation between can be drawn between the specific gene expression and ECM degradation. The TARGET genes identified using the knock-in library (the protein expression products thereof herein referred to as "TARGET" polypeptides) are then used in the present inventive method for identifying compounds that can be used to prevent ECM-degradation. Indeed, shRNA compounds comprising the sequences listed in Table 3 (SEQ ID NO: 52-175) and the antisense sequences corresponding thereto inhibit the expression and/or activity of these TARGET genes and decrease the ECM-degrading activity of cells, confirming the role of these TARGET genes in ECM-degradation.

TABLE 3

List of target sequences selected within the coding sequences of the genes identified as modulators of the collagenolytic activity of SFs for use in RNAi-based down-regulation of the expression of these genes.

| DISPLAY_ID | ACCESSION | NAME | SIRNA_NAME | SEQ ID NO |
|---|---|---|---|---|
| CAMK4 | NM_001744 | A150100-CAMK4_v1 | NM_001744_idx445 | 83 |
| CAMK4 | NM_001744 | A150100-CAMK4_v10 | NM_001744_idx1045 | 148 |
| CAMK4 | NM_001744 | A150100-CAMK4_v11 | NM_001744_idx1186 | 85 |
| CAMK4 | NM_001744 | A150100-CAMK4_v2 | NM_001744_idx258 | 86 |
| CAMK4 | NM_001744 | A150100-CAMK4_v3 | NM_001744_idx668 | 84 |
| CAMK4 | NM_001744 | A150100-CAMK4_v9 | NM_001744_idx427 | 82 |
| CASP10 | NM_001230 | A150100-CASP10_v1 | NM_001230_idx934 | 146 |
| CASP10 | NM_001230 | A150100-CASP10_v10 | NM_001230_idx1532 | 142 |
| CASP10 | NM_001230 | A150100-CASP10_v13 | NM_001230_idx1111 | 143 |
| CASP10 | NM_001230 | A150100-CASP10_v2 | NM_001230_idx382 | 141 |
| CASP10 | NM_001230 | A150100-CASP10_v8 | NM_032974_idx317 | 140 |
| CASP10 | NM_032974 | A150100-CASP10_v1 | NM_001230_idx934 | 146 |
| CASP10 | NM_032974 | A150100-CASP10_v11 | NM_032974_idx1674 | 144 |
| CASP10 | NM_032974 | A150100-CASP10_v12 | NM_032974_idx1829 | 145 |
| CASP10 | NM_032974 | A150100-CASP10_v13 | NM_001230_idx1111 | 143 |
| CASP10 | NM_032974 | A150100-CASP10_v2 | NM_001230_idx382 | 141 |
| CASP10 | NM_032974 | A150100-CASP10_v7 | NM_032974_idx981 | 149 |
| CASP10 | NM_032974 | A150100-CASP10_v8 | NM_032974_idx317 | 140 |
| CASP10 | NM_032976 | A150100-CASP10_v1 | NM_001230_idx934 | 146 |
| CASP10 | NM_032976 | A150100-CASP10_v10 | NM_001230_idx532 | 142 |
| CASP10 | NM_032976 | A150100-CASP10_v13 | NM_001230_idx1111 | 143 |
| CASP10 | NM_032976 | A150100-CASP10_v2 | NM_001230_idx382 | 141 |
| CASP10 | NM_032976 | A150100-CASP10_v8 | NM_032974_idx317 | 140 |
| CASP10 | NM_032977 | A150100-CASP10_v1 | NM_001230_idx934 | 146 |
| CASP10 | NM_032977 | A150100-CASP10_v10 | NM_001230_idx1532 | 142 |
| CASP10 | NM_032977 | A150100-CASP10_v13 | NM_001230_idx1111 | 143 |
| CASP10 | NM_032977 | A150100-CASP10_v2 | NM_001230_idx382 | 141 |
| CASP10 | NM_032977 | A150100-CASP10_v7 | NM_032974_idx981 | 149 |

TABLE 3-continued

List of target sequences selected within the coding sequences of the genes identified as modulators of the collagenolytic activity of SFs for use in RNAi-based down-regulation of the expression of these genes.

| DISPLAY_ID | ACCESSION | NAME | SIRNA_NAME | SEQ ID NO |
|---|---|---|---|---|
| CASP10 | NM_032977 | A150100-CASP10_v8 | NM_032974_idx317 | 140 |
| CD72 | NM_001782 | A150100-CD72_v2 | NM_001782_idx376 | 100 |
| CD72 | NM_001782 | A150100-CD72_v3 | NM_001782_idx742 | 97 |
| CD72 | NM_001782 | A150100-CD72_v4 | NM_001782_idx975 | 150 |
| CD72 | NM_001782 | A150100-CD72_v5 | NM_001782_idx1049 | 98 |
| CD72 | NM_001782 | A150100-CD72_v6 | NM_001782_idx1054 | 101 |
| CD72 | NM_001782 | A150100-CD72_v7 | NM_001782_idx901 | 99 |
| FXYD5 | NM_014164 | A150100-FXYD5_v2 | NM_014164_idx224 | 132 |
| FXYD5 | NM_014164 | A150100-FXYD5_v3 | NM_014164_idx417 | 131 |
| FXYD5 | NM_014164 | A150100-FXYD5_v4 | NM_014164_idx436 | 129 |
| FXYD5 | NM_014164 | A150100-FXYD5_v5 | NM_014164_idx542 | 133 |
| FXYD5 | NM_014164 | A150100-FXYD5_v6 | NM_014164_idx603 | 130 |
| FXYD5 | NM_014164 | A150100-FXYD5_v7 | NM_014164_idx672 | 151 |
| FZD4 | NM_012193 | A150100-C(27)-3BETA-HSD_v3 | NM_025193_idx1374 | 152 |
| FZD4 | NM_012193 | A150100-FZD4_v10 | NM_012193_idx849 | 122 |
| FZD4 | NM_012193 | A150100-FZD4_v5 | NM_012193_idx481 | 120 |
| FZD4 | NM_012193 | A150100-FZD4_v6 | NM_012193_idx1570 | 153 |
| FZD4 | NM_012193 | A150100-FZD4_v7 | NM_012193_idx745 | 123 |
| FZD4 | NM_012193 | A150100-FZD4_v8 | NM_012193_idx1160 | 154 |
| FZD4 | NM_012193 | A150100-FZD4_v9 | NM_012193_idx534 | 121 |
| GPR21 | NM_005294 | A150100-GPR21_v10 | NM_005294_idx638 | 108 |
| GPR21 | NM_005294 | A150100-GPR21_v11 | NM_005294_idx936 | 109 |
| GPR21 | NM_005294 | A150100-GPR21_v12 | NM_005294_idx168 | 155 |
| GPR21 | NM_005294 | A150100-GPR21_v13 | NM_005294_idx868 | 107 |
| GPR21 | NM_005294 | A150100-GPR21_v14 | NM_005294_idx988 | 111 |
| GPR21 | NM_005294 | A150100-GPR21_v9 | NM_005294_idx161 | 110 |
| MAPKAPK5 | NM_003668 | A150100-MAPKAPK5_v1 | oKD102 | 79 |
| MAPKAPK5 | NM_003668 | A150100-MAPKAPK5_v10 | NM_003668_idx856 | 156 |
| MAPKAPK5 | NM_003668 | A150100-MAPKAPK5_v11 | NM_003668_idx1542 | 76 |
| MAPKAPK5 | NM_003668 | A150100-MAPKAPK5_v12 | NM_003668_idx456 | 157 |
| MAPKAPK5 | NM_003668 | A150100-MAPKAPK5_v13 | NM_003668_idx609 | 158 |
| MAPKAPK5 | NM_003668 | A150100-MAPKAPK5_v2 | oKD103 | 159 |
| MAPKAPK5 | NM_003668 | A150100-MAPKAPK5_v8 | oKD104 | 160 |
| MAPKAPK5 | NM_003668 | A150100-MAPKAPK5_v9 | NM_003668_idx686 | 161 |
| MAPKAPK5 | NM_139078 | A150100-MAPKAPK5_v1 | oKD102 | 70 |
| MAPKAPK5 | NM_139078 | A150100-MAPKAPK5_v10 | NM_003668_idx856 | 156 |
| MAPKAPK5 | NM_139078 | A150100-MAPKAPK5_v11 | NM_003668_idx1542 | 76 |
| MAPKAPK5 | NM_139078 | A150100-MAPKAPK5_v12 | NM_003668_idx456 | 157 |
| MAPKAPK5 | NM_139078 | A150100-MAPKAPK5_v13 | NM_003668_idx609 | 158 |
| MAPKAPK5 | NM_139078 | A150100-MAPKAPK5_v2 | oKD103 | 159 |
| MAPKAPK5 | NM_139078 | A150100-MAPKAPK5_v8 | oKD104 | 160 |
| MAPKAPK5 | NM_139078 | A150100-MAPKAPK5_v9 | NM_003668_idx686 | 161 |
| MKNK1 | NM_003684 | A150100-MKNK1_v1 | oKD110 | 162 |
| MKNK1 | NM_003684 | A150100-MKNK1_v14 | oKD109 | 81 |
| MKNK1 | NM_003684 | A150100-MKNK1_v15 | oKD108 | 77 |
| MKNK1 | NM_003684 | A150100-MKNK1_v16 | NM_003684_idx384 | 79 |
| MKNK1 | NM_003684 | A150100-MKNK1_v17 | NM_003684_idx549 | 80 |
| MKNK1 | NM_003684 | A150100-MKNK1_v18 | NM_003684_idx1216 | 163 |
| MST3 | SK246 | A150100-MST3_v2 | SK246_idx413 | 66 |
| MST3 | SK246 | A150100-MST3_v3 | SK246_idx508 | 65 |
| MST3 | SK246 | A150100-MST3_v4 | SK246_idx918 | 63 |
| MST3 | SK246 | A150100-STK24_v1 | NM_003576_idx300 | 62 |
| MST3 | SK246 | A150100-STK24_v2 | NM_003576_idx950 | 164 |
| MST3 | SK246 | A150100-STK24_v3 | NM_003576_idx1020 | 64 |
| PGPEP1 | NM_017712 | A150100-FLJ20208_v10 | NM_017712_idx176 | 94 |

TABLE 3-continued

List of target sequences selected within the coding sequences of the genes identified as modulators of the collagenolytic activity of SFs for use in RNAi-based down-regulation of the expression of these genes.

| DISPLAY_ID | ACCESSION | NAME | SIRNA_NAME | SEQ ID NO |
|---|---|---|---|---|
| PGPEP1 | NM_017712 | A150100-FLJ20208_v11 | NM_017712_idx404 | 92 |
| PGPEP1 | NM_017712 | A150100-FLJ20208_v5 | NM_017712_idx289 | 96 |
| PGPEP1 | NM_017712 | A150100-FLJ20208_v6 | NM_017712_idx164 | 93 |
| PGPEP1 | NM_017712 | A150100-FLJ20208_v7 | NM_017712_idx496 | 165 |
| PGPEP1 | NM_017712 | A150100-FLJ20208_v8 | NM_017712_idx198 | 95 |
| PGPEP1 | NM_017712 | A150100-FLJ20208_v9 | NM_017712_idx298 | 166 |
| PRKCE | NM_005400 | A150100-PRKCE_v10 | NM_005400_idx760 | 59 |
| PRKCE | NM_005400 | A150100-PRKCE_v11 | NM_005400_idx1276 | 60 |
| PRKCE | NM_005400 | A150100-PRKCE_v2 | NM_005400_idx1240 | 57 |
| PRKCE | NM_005400 | A150100-PRKCE_v7 | NM_005400_idx1109 | 58 |
| PRKCE | NM_005400 | A150100-PRKCE_v8 | NM_005400_idx2050 | 61 |
| PRKCE | NM_005400 | A150100-PRKCE_v9 | NM_005400_idx148 | 167 |
| RIPK2 | NM_003821 | A150100-RIPK2_v1 | oKD111 | 52 |
| RIPK2 | NM_003821 | A150100-RIPK2_v10 | NM_003821_idx993 | 168 |
| RIPK2 | NM_003821 | A150100-RIPK2_v11 | NM_003821_idx1416 | 169 |
| RIPK2 | NM_003821 | A150100-RIPK2_v2 | oKD112 | 54 |
| RIPK2 | NM_003821 | A150100-RIPK2_v3 | oKD113 | 55 |
| RIPK2 | NM_003821 | A150100-RIPK2_v9 | NM_003821_idx612 | 170 |
| RIT1 | NM_006912 | A150100-RIT_v2 | NM_006912_idx247 | 137 |
| RIT1 | NM_006912 | A150100-RIT_v3 | NM_006912_idx536 | 134 |
| RIT1 | NM_006912 | A150100-RIT_v4 | NM_006912_idx622 | 136 |
| RIT1 | NM_006912 | A150100-RIT_v5 | NM_006912_idx824 | 138 |
| RIT1 | NM_006912 | A150100-RIT_v6 | NM_006912_idx263 | 135 |
| SEPT1 | NM_052838 | A150100-SEPT1_v2 | NM_052838_idx305 | 171 |
| SEPT1 | NM_052838 | A150100-SEPT1_v3 | NM_052838_idx329 | 89 |
| SEPT1 | NM_052838 | A150100-SEPT1_v4 | NM_052838_idx480 | 90 |
| SEPT1 | NM_052838 | A150100-SEPT1_v5 | NM_052838_idx677 | 88 |
| SEPT1 | NM_052838 | A150100-SEPT1_v6 | NM_052838_idx954 | 87 |
| SEPT1 | NM_052838 | A150100-SEPT1_v7 | NM_052838_idx1218 | 91 |
| MST3 | NM_003576 | A150100-MST3_v2 | SK246_idx413 | 66 |
| MST3 | NM_003576 | A150100-MST3_v3 | SK246_idx508 | 65 |
| MST3 | NM_003576 | A150100-MST3_v4 | SK246_idx918 | 63 |
| MST3 | NM_003576 | A150100-STK24_v1 | NM_003576_idx300 | 62 |
| MST3 | NM_003576 | A150100-STK24_v2 | NM_003576_idx950 | 164 |
| MST3 | NM_003576 | A150100-STK24_v3 | NM_003576_idx1020 | 64 |
| TM7SF1 | NM_003272 | A150100-TM7SF1_v11 | NM_003272_idx637 | 128 |
| TM7SF1 | NM_003272 | A150100-TM7SF1_v12 | NM_003272_idx673 | 125 |
| TM7SF1 | NM_003272 | A150100-TM7SF1_v13 | NM_003272_idx764 | 172 |
| TM7SF1 | NM_003272 | A150100-TM7SF1_v14 | NM_003272_idx775 | 127 |
| TM7SF1 | NM_003272 | A150100-TM7SF1_v9 | NM_003272_idx275 | 124 |
| TPST1 | NM_003596 | A150100-TPST1_v1 | NM_003596_idx722 | 106 |
| TPST1 | NM_003596 | A150100-TPST1_v2 | NM_003596_idx1262 | 104 |
| TPST1 | NM_003596 | A150100-TPST1_v3 | NM_003596_idx425 | 102 |
| TPST1 | NM_003596 | A150100-TPST1_v5 | NM_003596_idx1229 | 103 |
| TPST1 | NM_003596 | A150100-TPST1_v6 | NM_003596_idx1260 | 105 |
| TPST1 | NM_003596 | A150100-TPST1_v7 | NM_003596_idx1444 | 173 |
| USP21 | NM_012475 | A150100-USP21_v1 | NM_012475_idx1574 | 112 |
| USP21 | NM_012475 | A150100-USP21_v13 | NM_012475_idx741 | 117 |
| USP21 | NM_012475 | A150100-USP21_v14 | NM_012475_idx928 | 174 |
| USP21 | NM_012475 | A150100-USP21_v15 | NM_012475_idx682 | 114 |
| USP21 | NM_012475 | A150100-USP21_v16 | NM_012475_idx733 | 118 |
| USP21 | NM_012475 | A150100-USP21_v17 | NM_012475_idx1573 | 113 |
| USP21 | NM_012475 | A150100-USP21_v2 | NM_012475_idx1224 | 116 |
| USP21 | NM_012475 | A150100-USP21_v3 | NM_012475_idx269 | 115 |
| USP21 | NM_012475 | A150100-mmUsp21_v5 | NM_013919_idx1120 | 175 |
| USP21 | NM_016572 | A150100-USP21_v13 | NM_012475_idx741 | 117 |
| USP21 | NM_016572 | A150100-USP21_v14 | NM_012475_idx928 | 174 |
| USP21 | NM_016572 | A150100-USP21_v15 | NM_012475_idx682 | 114 |
| USP21 | NM_016572 | A150100-USP21_v16 | NM_012475_idx733 | 118 |
| USP21 | NM_016572 | A150100-USP21_v2 | NM_012475_idx1224 | 116 |
| USP21 | NM_016572 | A150100-USP21_v3 | NM_012475_idx269 | 115 |
| USP21 | NM_016572 | A150100-mmUsp21_v5 | NM_013919_idx1120 | 175 |

It should be understood that the TARGET genes represented in Table 1 encode different kinds of polypeptides. For example, the TARGETS represented by SEQ ID NO: 40, 43-45 as disclosed herein (Table 1) are GPCRs. Each of these GPCRs is capable of activating an effector protein, resulting in changes in second messenger levels in the cell. The activity of a GPCR can be measured by measuring the activity level of such second messengers. Two important and useful second messengers in the cell are cyclic AMP (cAMP) and $Ca^{2+}$. The activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis.

The activity level of the one or more secondary messengers may typically be determined with a reporter gene controlled by a promoter, wherein the promoter is responsive to the second messenger. Promotors known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

Many of the TARGETS as disclosed herein are kinases and phospatases, such as the targets represented by SEQ ID NO: 27-34. Specific methods to determine the activity of a kinase or phosphatase by measuring the phosphorylation of a substrate by the kinase or phosphastase, which measurements are performed in the presence or absence of a compound, are well known in the art, whereas some are described in the examples.

The TARGETS representedby SEQ ID NO: 37, 41, 42, 48, 49, and 51 are proteases. Specific methods to determine the inhibition by the compound by measuring the cleavage of the substrate by the polypeptide, which is a protease, are well known in the art.

It should be understood that the cells expressing the polypeptides, may be cells naturally expressing the polypeptides, or the cells may be may be transfected to express the polypeptides, as described above.

In one embodiment it is preferred that the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of ECM degradation. In a preferred embodiment, the cells used in the present method are mammalian synovial fibroblasts and the triggers that may be used to induce the ECM-degrading activity are cytokines relevant in the field of arthritis: for instance TNFalpha, IL1beta, IL6, OSM, IL17, and MIF1alpha. In another preferred embodiment, the trigger is a mixture of factors generated by contacting cytokine-producing cells relevant in the field of arthritis, such as monocytes, macrophages, T-cells, and B-cells. The cytokine-producing cells will respond to the contact by producing a complex and unbiased mixture of factors. If the cytokine-producing cell used is also found in a pannus, and the cytokine applied to this trigger is found in the synovial fluid of rheumatoid arthritis patients, the mixture of factors ultimately produced will contain part of the factors that are present in the joints of arthritis patients.

The present invention further relates to a method for identifying a compound that inhibits extra-cellular matrix degradation, comprising:

(a) contacting a compound with a polypeptide comprising an amino acid sequence selected from the group consisting of SEQ ID NO: 27-51 and 232-295;

(b) determining the binding affinity of the compound to the polypeptide;

(c) contacting a population of mammalian cells expressing said polypeptide with the compound that exhibits a binding affinity of at least 10 micromolar; and (d) identifying the compound that inhibits extra-cellular matrix degradation.

The population of cells may be exposed to the compound or the mixture of compounds through different means, for instance by direct incubation in the medium, or by nucleic acid transfer into the cells. Such transfer may be achieved by a wide variety of means, for instance by direct transfection of naked isolated DNA, or RNA, or by means of delivery systems, such as recombinant vectors. Other delivery means such as liposomes, or other lipid-based vectors may also be used. Preferably, the nucleic acid compound is delivered by means of a (recombinant) vector such as a recombinant virus.

For high-throughput purposes, libraries of compounds may be used such as antibody fragment libraries, peptide phage display libraries, peptide libraries (e.g. LOPAP™, Sigma Aldrich), lipid libraries (BioMol), synthetic compound libraries (e.g. LOPAC™, Sigma Aldrich) or natural compound libraries (Specs, TimTec).

Preferred drug candidate compounds are low molecular weight compounds. Low molecular weight compounds, i.e. with a molecular weight of 500 Dalton or less, are likely to have good absorption and permeation in biological systems and are consequently more likely to be successful drug candidates than compounds with a molecular weight above 500 Dalton (Lipinski et al. (1997)). Peptides comprise another preferred class of drug candidate compounds. Many GPCRs have a peptide as an agonist or antagonist. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound. Many GPCRs have lipids as a ligand.

Another preferred class of drug candidate compounds is an antibody. The present invention also provides antibodies directed against a TARGET. These antibodies may be endogenously produced to bind to the TARGET within the cell, or added to the tissue to bind to TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library. In another embodiment, the compound may be a nanobody, the smallest functional fragment of naturally occurring single-domain antibodies (Cortez-Retamozo et al. 2004).

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRs) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, e.g. Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boemer, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGET polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively; the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET; the other one is for another domain of the same or different TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method uses a drug candidate compound identified as having a binding affinity for a TARGET, and/or has already been identified as having down-regulating activity such as antagonist activity vis-à-vis one or more TARGET.

The present invention further relates to a method for inhibiting extra-cellular matrix degradation comprising contacting mammalian cells with an expression inhibitory agent comprising a polyribonucleotide sequence that complements at least about 17 to about 30 contiguous nucleotides of the nucleotide sequence selected from the group consisting of SEQ ID NO: 1-25.

Another aspect of the present invention relates to a method for inhibiting extra-cellular matrix degradation, comprising by contacting mammalian cells with an expression-inhibiting agent that inhibits the translation in the cell of a polyribonucleotide encoding a TARGET polypeptide. A particular embodiment relates to a composition comprising a polynucleotide including at least one antisense strand that functions to pair the agent with the TARGET mRNA, and thereby down-regulate or block the expression of TARGET polypeptide. The inhibitory agent preferably comprises antisense polynucleotide, a ribozyme, and a small interfering RNA (siRNA), wherein said agent comprises a nucleic acid sequence complementary to, or engineered from, a naturally-occurring polynucleotide sequence selected from the group consisting of SEQ ID NO: 1-25.

A special embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 1-25, a small interfering RNA (siRNA, preferably shRNA,) that is sufficiently homologous to a portion of the polyribonucleotide corresponding to SEQ ID NO: 1-25, such that the siRNA, preferably shRNA, interferes with the translation of the TARGET polyribonucleotide to the TARGET polypeptide.

Another embodiment of the present invention relates to a method wherein the expression-inhibiting agent is a nucleic acid expressing the antisense RNA, antisense oligodeoxynucleotide (ODN), a ribozyme that cleaves the polyribonucleotide encoded by SEQ ID NO: 1-25, a small interfering RNA (siRNA, preferably shRNA,) that is sufficiently complementary to a portion of the polyribonucleotide corresponding to SEQ ID NO: 1-25, such that the siRNA, preferably shRNA, interferes with the translation of the TARGET polyribonucleotide to the TARGET polypeptide. Preferably the expression-inhibiting agent is an antisense RNA, ribozyme, antisense oligodeoxynucleotide, or siRNA, preferably shRNA, comprising a polyribonucleotide sequence that complements at least about 17 to about 30 contiguous nucleotides of a nucleotide sequence selected from the group consisting of SEQ ID NO: 1-25. More preferably, the expression-inhibiting agent is an antisense RNA, ribozyme, antisense oligodeoxynucleotide, or siRNA, preferably shRNA, comprising a polyribonucleotide sequence that complements at least about 17 to about 25 contiguous nucleotides of a nucleotide sequence selected from the group consisting of SEQ ID NO: 1-25. A special embodiment comprises a polyribonucleotide sequence that complements a polynucleotide sequence selected from the group consisting of SEQ ID NO: 52-175.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-25. For example, an antisense nucleic acid (e.g. DNA) may be introduced into cells in vitro, or administered to a subject in vivo, as gene therapy to inhibit cellular expression of nucleic acids comprising SEQ ID NO: 1-25. Antisense oligonucleotides preferably comprise a sequence containing from about 17 to about 100 nucleotides and more preferably the antisense oligonucleotides comprise from about 18 to about 30 nucleotides. Antisense nucleic acids may be prepared from about 17 to about 30 contiguous nucleotides selected from the sequences of SEQ ID NO: 1-25, expressed in the opposite orientation.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RNA-DNA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

A particularly preferred inhibitory agent is a small interfering RNA (siRNA, preferably small hairpin RNA, "shRNA"). siRNA, preferably shRNA, mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences described in SEQ ID NO: 1-25, preferably from the group of sequences described in SEQ ID No: 52-175, and an antisense strand of 17-25 nucleotides complementary to the sense strand. The most preferred siRNA comprises sense and anti-sense strands that are 100 percent complementary to each other and the TARGET polynucleotide sequence. Preferably the siRNA further comprises a ioop region linking the sense and the antisense strand.

A self-complementing single stranded shRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. In a most preferred embodiment the linker sequence is UUGCUAUA (SEQ ID NO: 26; see FIG. 16). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO2004094636, published Nov. 4, 2004, and UA20030198627, are hereby incorporated by reference).

The present invention also relates to compositions, and methods using said compositions, comprising a DNA expression vector capable of expressing a polynucleotide capable of inhibiting extra-cellular matrix degradation and described hereinabove as an expression inhibition agent.

A special aspect of these compositions and methods relates to the down-regulation or blocking of the expression of a TARGET polypeptide by the induced expression of a polynucleotide encoding an intracellular binding protein that is capable of selectively interacting with the TARGET polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the TARGET polypeptide of SEQ ID NO: 27-51, preferably to a domain of SEQ ID NO: 232-295. More preferably, the intracellular binding protein is a single chain antibody.

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 27-51, and a small interfering RNA (siRNA) that is sufficiently homologous to a portion of the polyribonucleotide corresponding to SEQ ID NO: 1-25, such that the siRNA interferes with the translation of the TARGET polyribonucleotide to the TARGET polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in TARGET cells.

Preferably, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the TARGET cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US Published Patent Applications 20030180258 and 20040071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to TARGET the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention. Retroviral systems and herpes virus system may be preferred vehicles for transfection of neuronal cells.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda P.sub.r, P.sub.1, and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315:338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient. For example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Felgner, et. al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Felgner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of TARGETing. Targeted peptides, e.g., hormones or neurotransmitters, and proteins for example, antibodies, or non-peptide molecules could be coupled to liposomes chemically. Other molecules are also useful for facilitating transfection of a nucleic acid in vivo, for example, a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce a DNA vector in vivo as a naked DNA plasmid (see U.S. Pat. Nos. 5,693,622, 5,589, 466 and 5,580,859). Naked DNA vectors for therapeutic purposes can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, extra-cellular matrix degradation inhibiting compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, e.g., in a form able to effect a biological activity. For example, a compound of the invention would have inverse agonist or antagonist activity on the TARGET; a nucleic acid would be able to replicate, translate a message, or hybridize to a complementary mRNA of a TARGET; a vector would be able to transfect a TARGET cell and expression the antisense, antibody, ribozyme or siRNA as described hereinabove; an antibody would bind a TARGET polypeptide domain.

A preferred biologically compatible composition is an aqueous solution that is buffered using, e.g., Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particularly preferred embodiment of the present composition invention is a extra-cellular matrix degradation inhibiting pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a condition involving ECM degradation, or a susceptibility to the condition, comprising an effective extra-cellular matrix degradation inhibiting amount of a TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (e.g. monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to targeted tissues, complexed with cationic lipids, packaged within liposomes, or delivered to targeted cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the prior art.

The present invention also provides methods of inhibiting extra-cellular matrix degradation, comprising administering, to a subject suffering from a disease condition involving extra-cellular matrix degradation, an extra-cellular matrix degradation inhibiting pharmaceutical composition as described herein, preferably a therapeutically effective amount of an expression-inhibiting agent of the present invention. The diseases involving extra-cellular marix degradation, include psoriatic arthritis, juvenile arthritis, early arthritis, reactive arthritis, osteoarthritis, ankylosing spondylitis. osteoporosis, muskulo skeletal diseases such as tendinitis and periodontal disease, cancer metastasis, airway diseases (COPD, asthma), renal and liver fibrosis, cardiovascular diseases such as atherosclerosis and heart failure, and neurological diseases such as neuroinflammation and multiple sclerosis. More preferred diseases for treatment in accordance with the present invention are the degenerative joint diseases such as psoriatic arthritis, juvenile arthritis, early arthritis, reactive arthritis, osteoarthritis, ankylosing spondylitis. The most preferred degenerative joint disease for treatment in accordance with the present method is rheumatoid arthritis, Administering of the expression-inhibiting agent of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The expression-inhibiting agent of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammatory, with an effective inhibiting amount of an expression-inhibiting agent of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a expression-inhibiting agent of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

The invention also relates to the use of an agent as described above for the preparation of a medicament for treating or preventing a disease involving extra-cellular matrix degradation.

Preferably the pathological condition is arthritis. More preferably, the pathological condition is rheumatoid arthritis.

The polypeptides and polynucleotides useful in the practice of the present invention described herein may be free in solution, affixed to a solid support, borne on a cell surface, or located intracellularly. To perform the methods it is feasible to immobilize either the TARGET polypeptide or the compound to facilitate separation of complexes from uncomplexed forms of the polypeptide, as well as to accommodate automation of the assay. Interaction (e.g., binding of) of the TARGET polypeptide with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the TARGET polypeptide can be "His" tagged, and subsequently adsorbed onto Ni-NTA microtitre plates, or ProtA fusions with the TARGET polypeptides can be adsorbed to IgG, which are then combined with the cell lysates (e.g., $(35)^S$-labelled) and the candidate compound, and the mixture incubated under conditions favorable for complex formation (e.g., at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the TARGET protein quantified from the gel using standard electrophoretic techniques.

Other techniques for immobilizing protein on matrices can also be used in the method of identifying compounds. For example, either the TARGET or the compound can be immobilized utilizing conjugation of biotin and streptavidin. Biotinylated TARGET protein molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the TARGETS but which do not interfere with binding of the TARGET to the compound can be derivatized to the wells of the plate, and the TARGET can be trapped in the wells by antibody conjugation. As described above, preparations of a labeled candidate compound are incubated in the wells of the plate presenting the TARGETS, and the amount of complex trapped in the well can be quantitated.

The polynucleotides encoding the TARGET polypeptides are identified as SEQ ID NO: 1-25. Applicants have shown that transfection of mammalian cells with these polynucleotides in an expressible form increase the release of factors that promote extra-cellular matrix degradation.

The present invention also relates to a method for diagnosis of a pathological condition involving ECM degradation, comprising determining the nucleic acid sequence of at least one of the genes of SEQ ID NO: 1-25 within the genomic DNA of a subject; comparing the sequence with the nucleic acid sequence obtained from a database and/or a healthy subject; and identifying any difference(s) related to the onset of the pathological condition.

Still another aspect of the invention relates to a method for diagnosing a pathological condition involving extra-cellular matrix degradation or a susceptibility to the condition in a subject, comprising determining the amount of polypeptide comprising an amino acid sequence selected from the group consisting of SEQ ID NO: 27-51 in a biological sample, and comparing the amount with the amount of the polypeptide in a healthy subject, wherein an increase of the amount of polypeptide compared to the healthy subject is indicative of the presence of the pathological condition.

The invention is further illustrated in the following figures and examples.

EXAMPLES

The following assays, when used in combination with arrayed adenoviral libraries (the production and use of which are described in WO99/64582), are useful for the discovery of factors that modulate the capacity of synovial fibroblasts (SFs) to degrade collagen, the main component of cartilage. Candidate factors are filtered first through a primary followed by a secondary assay. Example 1 describes the development and setup of the primary assay screen of an adenoviral cDNA library using an ELISA for detection of protein levels of Matrix Metalloprotease 1 (MMP1), and is referred to herein as the "MMP1 assay". Example 2 describes the screening and its results. Examples 3 and 4 describe the secondary assay, which is more functionally oriented, detects collagen degradation in the supernatant of SFs, and is referred to herein as the "collagen degradation assay". Example 5 describes the testing for the endogenous expression of factors in SFs. This method in referred to as "expression profiling" of hits in various RA-derived SFs (RASFs). Example 6 describes the effect of the reduction in activity of various genes on the cytokine-induced SF MMP1 expression thereby determining the collagenolytic activity of RASF's.

Control Viruses Used:

The control viruses used in these studies are listed below. dE1/dE2A adenoviruses are generated from these adapter plasmids by co-transfection of the helper plasmid pWEAd5AflII-rITR.dE2A in PER.E2A packaging cells, as described in WO99/64582.

(A) Negative Control Viruses:

Ad5-LacZ: Described as pIPspAdApt6-lacZ in WO02/070744.

Ad5-ALPP: The 1.9 kb insert is isolated from pGT65-PLAP (Invitrogen) by digestion with pentoxy, pentoxy, NsiI; blunted; followed by digestion with EcoR1 and cloned into EcoRI and HpaI-digested pIPspAdApt6.

Ad5-eGFP: Described as pIPspAdApt6-EGFP in WO02/070744.

Ad5-eGFP_KD: Target sequence: GCTGACCCTGAAGTTCATC (SEQ ID NO: 179). Cloned using Sap1-sites into vector and virus generated as described in WO03/020931.

Ad5-Luciferase_KD_v13: Target sequence: GCTGACCCTGAAGTTCATC (SEQ ID NO: 180). Cloned using Sap1-sites into vector and virus generated as described in WO03/020931.

Ad5-M6PR_KD_v1: Target sequence: GCTGACCCTGAAGTTCATC (SEQ ID NO: 296). Cloned using Sap1-sites into vector and virus generated as described in WO03/020931.

(B) Positive Control Viruses:

Ad5-RELA: The cDNA encoding RELA is obtained by PCR on a human placenta cDNA library with the following primers:

```
upstream:
GCGAAGCTTGCGGCATGGACGAACTGT      (SEQ ID NO: 181)
and
```

-continued

```
downstream:
GCGGGATCCCAGGCGTCACCCCCTTAG.        (SEQ ID NO: 182)
```

A 1681 bp DNA insert is generated of which the 5' sequence corresponds to NM_021975. Primers are designed such that the PCR products can be inserted into the pIPspAdapt6 vector by HindIII-BamHI cloning.

Ad5-MMP1: The cDNA encoding MMP1, cloned into the pIPspAdapt6 plasmid, is isolated from a human placenta cDNA library (see WO02/070744) by classical filter colony hybridisation strategy. A human placental cDNA library is transformed into bacteria and plated out on agar plates. Thousands of individual colonies are picked (using a Q-pix device (Genetix)) and re-arrayed on agar plates. After growing bacteria up, these plates are overlayed on hybridisation filters. These filters are subjected to a classical hybridisation procedure with a MMP1 specific probe. This probe is obtained by PCR on a placenta cDNA library using the following primers:

```
upstream:
GTTCTGGGGTGTGGTGTCTCACAGC;          (SEQ ID NO: 183)
and downstream:
CAAACTGAGCCACATCAGGCACTCC.          (SEQ ID NO: 184)
```

A bacterial colony, at a position corresponding to that of a positive signal spot on the filter after hybridisation, is picked and used for plasmid preparation. 5' sequence verification confirms that the 5' sequence of the insert corresponds to NM_002421.

Ad5-TRAF6: The cDNA encoding TRAF6 is isolated according to the same colony hybridisation technique as the one described for MMP1. The TRAF6 specific probe is obtained by PCR on a placenta cDNA library using the following primers:

```
upstream:
CCAGTCTGAAAGTGACTGCTGTGTGG;         (SEQ ID NO: 185)
and downstream:
CAACTGGACATTTGTGACCTGCATCC.         (SEQ ID NO: 186)
```

A bacterial colony, at a position corresponding to that of a positive signal spot on the filter after hybridisation, is picked and used for plasmid preparation. 5' sequence verification confirms that the 5' sequence of the insert corresponds to NM_004620.2.

Ad5-MMP13: The cDNA of MMP13 is isolated from a cDNA preparation from human synovial fibroblasts by PCR. The 1498 bp PCR product is cloned into pIPspAdapt6 using a HindIII/EcoRI cloning strategy. Sequence verification confirms that the insert corresponds to bp 18 to 1497 of NM_002427.

Ad5-MYD88: This cDNA is isolated from a human placenta cDNA library constructed in pIPspAdapt6. The virus mediating the expression of MYD88 is identified as a hit in one of the genomic screen run at Galapagos Genomics. Sequence verification of the insert confirms that the insert corresponds to bp 40 to 930 of NM_002468.

Ad5TNFRIA: This virus is isolated from a human placenta cDNA library constructed in pIPspAdapt6. The virus mediating the expression of MYD88 is identified as a hit in one of the genomic screen run at Galapagos Genomics. 5' sequence verification of the 1.4 Kb insert reveals that the insert starts at bp 958 of NM_001065. Virus is generated as described in WO03/020931.

Ad5-MMP1_KD_v10: Target sequence: GCTGACCCTGAAGTTCATC (SEQ ID NO: 187). Cloned using Sap1-sites into vector and virus generated as described in WO03/020931.

Example 1

Development of the MMP Assay

Matrix Metallo Proteases (MMPs) possess various physiological roles, for example, they are involved in the maturation of other proteases, growth factors, and the degradation of extra-cellular matrix components. MMP1 is a member of the MMP family and is able to degrade native collagen, the main component of bone and cartilage. Increased expression of MMP1 by synovial fibroblasts (SFs) is diagnostic for the progression of the arthritic disease and is predictive for erosive processes in the joint (Cunnane et al., 2001). SF expression of MMP1 can be increased by the activation of SFs with triggers relevant for rheumatoid arthritis, such as the cytokines TNF-α and IL1β (Andreakos et al., 2003). The measurement of the MMP1 levels produced by activated SFs is highly relevant in the context of RA as this event reflects the level of activation of SFs towards an erosive phenotype as it is seen in the pannus. If reduced expression of a candidate target protein in activated SFs leads to the reduction of MMP1 expression in these cells, then the target is shown to be involved in the regulation of MMP1 expression and thus considered relevant for the development of therapeutic strategies for the treatment of RA. The identification of such target proteins involves the screening of a collection of recombinant adenoviruses mediating the expression of a library of cDNAs, further referred to as "Ad-cDNAs". The collection used herein is further referred to as "adenoviral cDNA library" or the "FlexSelect collection" (see WO99/64582).

The MMP1 assay is developed by first testing the capacity of Synovial fibroblasts (SFs) to produce MMP1.

A. To evaluate the capacity of SFs to produce MMP1, a set of adenoviruses mediating the expression of TRAF6 and MYD88, adaptor molecules in the IL1β pathway, and p65/RelA, a subunit of the NFκB transcription factor that is known to increase expression of factors involved in the immune and inflammatory responses, both of which are expected to increase MMP1 expression (see Vincenti and Brinckerhoff, 2002) are used to infect SFs.

40,000 SFs are seeded per well of a 6-well plate in DMEM+10% FBS and infected with a multiplicity of infection (MOI) of 7500 viral particles per cell (vp/cell). The expression of MMP1 by SFs is first determined at the mRNA level, by means of real-time, quantitative PCR. RNA of the cells infected with the control viruses is prepared 48 h post infection using the SV RNA isolation kit (Promega), according to the instructions of the manufacturer. cDNA is prepared from this RNA using Multiscribe reverse transcriptase (50 U/μl, Applied Biosystems) and random hexamers. cDNA synthesis is performed in 25 μl total volume consisting of 1× TaqMan buffer A (PE Applied Biosystems), 5 mM MgCl2, 500 mM total dNTPs, 2,5 mM random hexamers, 0.4 U/μl RNase Inhibitor, and 1.25 U/μl MultiScribe Reverse Transcriptase. The mixture is incubated for 10 min at 25° C., 30 min at 48° C., and 5 min at 95° C. Specific DNA products are amplified from the resulting cDNA with AmpliTaq Gold DNA polymerase (Applied BioSystems) during 40 PCR cycles using suited primer pairs. Amplification of the specific DNA products is monitored on an ABI PRISM® 7000 Sequence Detection System. The subsequent real time PCR reaction contained 5 μl of the RT reaction product in a total volume of 25 μl consisting of 1× SYBR Green mix (Applied Biosystems), 300 nM forward primer, and 300 nM reverse primer. Each sample is analyzed in duplicate. The PCR reaction is performed using the following program: 10 min at 95° C. followed by 40 cycles of (15 sec 95° C., 1 min 60° C.). After each PCR reaction the products are analysed by measuring the dissociation curve by incubating for 15 sec 95° C., and 15 sec at 60° C., followed by increasing the temperature to 95° C. over a 20 min time period, ending with 15 sec at 95° C. The sequences of the primer pairs used for the detection of MMP1, 18S and β-actin expression are listed in Table 2.

TABLE 2

List of primers and their sequences used herein.

| Hit number | Primer name | Primer Sequence | SEQ ID NO |
|---|---|---|---|
| NA | pAdapt_FW | GGTGGGAGGTCTATATAAGC | 188 |
|  | pAdapt_REV | GGACAAACCACAACTAGAATGC | 189 |
| NA | MMP2_For | CCCCAGGCACTGGTGTTG | 190 |
|  | MMP2_Rev | ACGGACCACTTGGCCTTCT | 191 |
| NA | MMP1_For | CCGGTTTTTCAAAGGGAATAAGTAC | 192 |
|  | MMP1_Rev | TTCACAGTTCTAGGGAAGCCAAAG | 193 |
| H31-031 | CAMK4_For | CAGCATCCGTGGGTCACA | 194 |
|  | CAMK4_Rev | TTCACCGCTGCCTTAAGCTT | 195 |
| H31-035 | PRKCE_For | TGAGGACGACCTATTTGAGTCCAT | 196 |
|  | PRKCE_Rev | GGGATTCTTCGTCATGAAAGCT | 197 |
| H31-047 | USP21_For | CTGCGAAGCTGTGAATCCTACTC | 198 |
|  | USP21_Rev | GGCATCCTGCTGGCTGTATC | 199 |
| H31-049 | CASP10_For | TCCTGGCAGAACTCCTCTATATCATAC | 200 |
|  | CASP10_Rev | TGACAGTTCGTAGAGCAGGTTTCTA | 201 |
| H31-180 | TM7SF1_For | GAACTTGTACTTCACGCAGGTG | 202 |
|  | TM7SF1_Rev | CAACAGGAAAACAAGGCTGATG | 203 |
| H31-242 | GPR21_For | TGCGTGGTCCCTTCTTTATCAC | 204 |
|  | GPR21_Rev | GCCATGGAGACGCTCTTCAG | 205 |
| H31-290 | RIPK2_For | CATTAAATGAACTCCTACATAGGAAAAC | 206 |
|  | RIPK2_Rev | AGGGCAATTTCATGCAGGAT | 207 |
| H31-301 | TPST1_For | GGAGTGTCTCTGTCAAAAGTGGA | 208 |
|  | TPST1_Rev | ACCCATTTTGATAGAGCTCCTACATT | 209 |
| H31-319 | MST3_For | GACATTAAAGCGGCCAACGT | 210 |
|  | MST3_Rev | CTCGGGTGCCATCCAGAA | 211 |
| H31-347 | SEPT1_For | GCGAGAAAGACGAAGAGCTGC | 212 |
|  | SEPT1_Rev | GCCTGGCTCTGCTGCATT | 213 |
| H31-351 | CD72_For | CAGTGAAATTTTATCCACAATCACAC | 214 |
|  | CD72_Rev | AGAGCTGAGGCCAGTCCAATAT | 215 |
| H31-360 | RIT_For | GGTGTAGGGAAGAGTGCCATGA | 216 |
|  | RIT_Rev | GCATCTTCAATGGTGGGATCA | 217 |
| H31-384 | FXYD5_For | TGGTCGCCTGTGTCTTCTCA | 218 |
|  | FXYD5_Rev | GTGGTATCTTTCAACGTCTGTCCTC | 219 |
| H31-450 | Q9ESW8_For | GAGGAAGGCGGTGGTAGTGA | 220 |
|  | Q9ESW8_Rev | CTCAACCGGAATCTCGTACACA | 221 |
| H34-067 | FZD6_For | TGGGAGATAACTTGGGTCTCTGAT | 222 |
|  | FZD6_Rev | AAGCCAATTCTGGTCGAGCTT | 223 |
| H34-087 | MKNK1_For | AGGGAGCCTATGCCAAAGTTC | 224 |
|  | MKNK1_Rev | CTCGATGATTTTGACGGCATAC | 225 |
| H34-088 | MAPKAPK5_For | GAGGAAGCTCCTGAAGGTCAAAC | 226 |
|  | MAPKAPK5_Rev | CAACCACTGCCTTGTCCATC | 227 |

TABLE 2-continued

List of primers and their sequences used herein.

| Hit number | Primer name | Primer Sequence | SEQ ID NO |
|---|---|---|---|
| H34-092 | FZD4_For | AGCCAGCTGCAGTTCTTCCTT | 228 |
|  | FZD4_Rev | TCACAGCGTCTCTTGACTGAAAG | 229 |

MMP1 is detected using the SYBR Green method, whereas the levels of 18S rRNA, used as internal calibrator for the PCR reaction, is measured using a Taqman probe (TaqMan® Ribosomal RNA Control Reagents, Applied Biosystems). The amplification plot and the resulting threshold Ct value are indicators for the amount of specific mRNAs present in the samples. Delta-delta Ct values are presented, meaning the normalized (relative to the 18S calibrator) levels of MMP1 mRNA in the samples infected with the positive control viruses relative to the expression levels in a Ad5-eGFP infected control sample. Results indicate a strong up-regulation of the MMP1 mRNA levels upon expression of p65/RelA, TRAF6 or MYD88 in SFs as compared to the non-infected or Ad5-eGFP-infected SFs.

Figure 2:
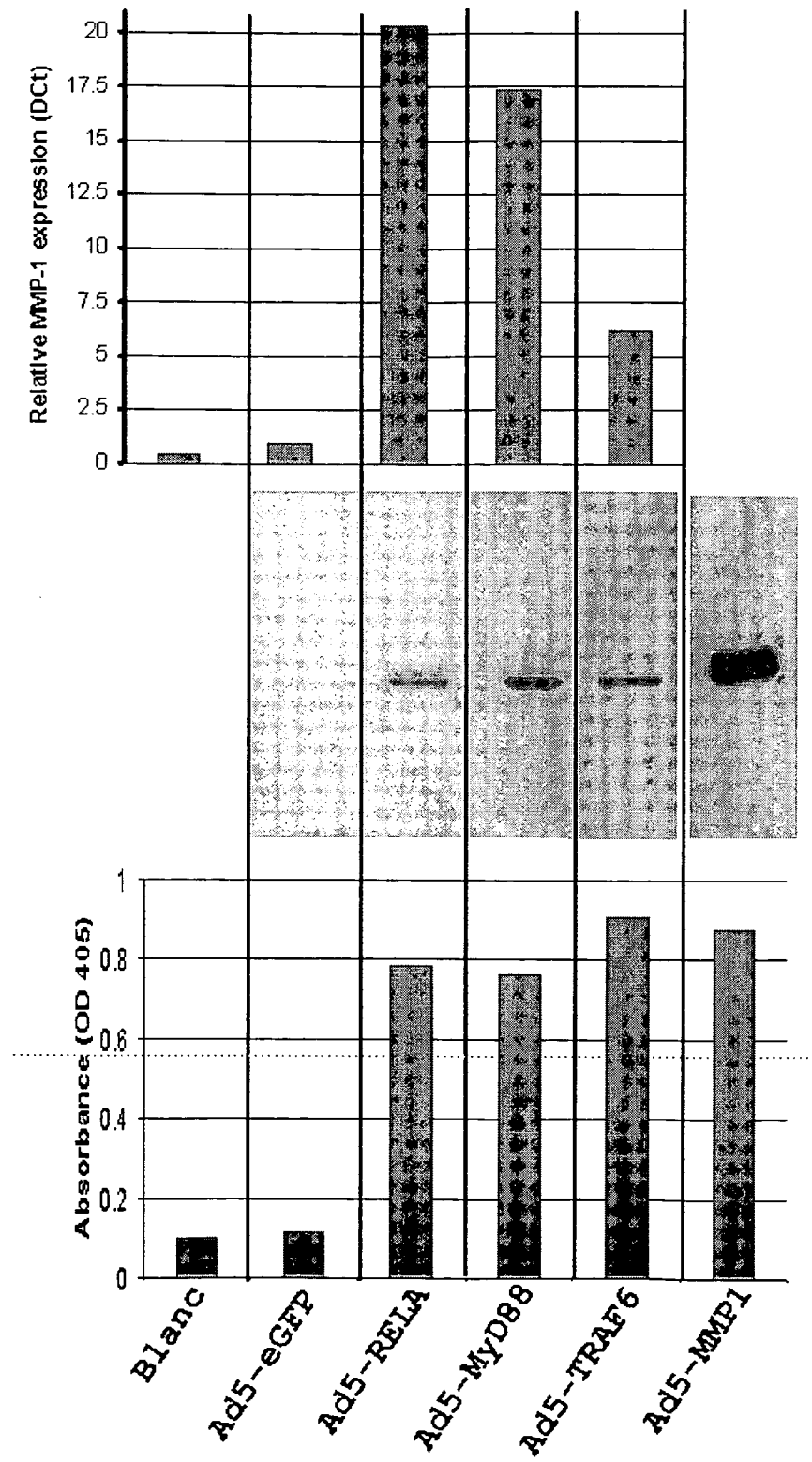
FIG. 2. Characterization of the expression of MMP1 by synovial fibroblasts. In panel A, the MMP1 mRNA levels present in the SF lysate are determined by real-time PCR. These MMP1 levels are normalized to the 18S levels that are also determined by real-time PCR for the same samples. Panel B shows the MMP1 signal detected from the supernatant that is subjected to Western blotting for detection of MMP1 protein levels using an MMP1-specific polyclonal antibody. Panel C shows the results of subjecting the supernatant to a commercially available MMP1 "activity ELISA" (Amersham Biosciences). The signal represented is proportional to the MMP1 activity present in the samples tested.

The level of MMP1 expressed by SFs is also determined at the protein level by Western Blotting. Two days after infection, supernatant of cells, infected with various recombinant adenoviruses as indicated for the Real-time PCR experiment, is collected and concentrated 15 times by classical TCA precipitation. 15 µl of the supernatant are resolved by SDS-PAGE using a 10% polyacrylamide gel. For these experiments, the medium used is M199 medium+1% FBS. For the MMP1 control sample, non-concentrated supernatant of cells infected with Ad5-MMP1 is loaded onto the gel. The resolved proteins are transferred onto a nitrocellulose membrane. The quality of the transfer and equal loading of the samples are verified by Ponceau-S staining of the membrane. Immunodetection is performed using a goat anti-MMP1 polyclonal antibody as primary antibody (R&D Systems, 1/500 dilution) and an HRP-linked rabbit anti-goat antibody (DAKO, 1/10000 dilution) as secondary antibody and ECL plus HRP substrate (Amersham Biosciences). The Western Blotting revealed a strongly increased level of MMP1 protein in the supernatant of the SFs infected with the adenoviruses mediating expression of Ad5-p65/RelA, Ad5-TRAF6 or Ad5-MYD88 as compared to the Ad5-eGFP infected cells. A very strong signal is detected for the supernatant of cells infected with Ad5-MMP1 (FIG. 2, panels B and C).

The high levels of MMP1 protein present in the supernatant of the Ad5-p65/RelA, Ad5-TRAF6 or Ad5-MYD88 infected SFs are confirmed using a commercially available MMP1 activity ELISA (RPN2629, Amersham Biosciences). In this ELISA, MMP1 is captured by an antibody immobilized in a well and the amount is subsequently quantified based on the conversion of a MMP1 substrate. 50 µl of non-concentrated supernatant of SFs (prepared as indicated for the western blotting experiment) are processed in this ELISA as recommended by the manufacturer.

These experiments confirm the capacity of SFs, in general, and of the cell batch used for screening and validation experiments, to produce MMP1 protein upon triggering of inflammatory pathways.

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 µg/ml anti-MMP1 antibody MAB1346 (Chemicon). The antibody is diluted in buffer 40 (1.21 g Tris base (Sigma), 0.58 g NaCl (Calbiochem) and 5 ml 10% NaN3 (Sigma) in 1 L milliQ water and adjusted to pH 8.5). After overnight incubation at 4° C., plates are washed with PBS (80 g NaCl, 2 g KCl (Sigma), 11.5 g Na2HPO4.7H$_2$O and 2 g KH2PO4 in 10 L milliQ; pH 7.4) and blocked with 100 µl/well Casein buffer (2% Casein (VWR International) in PBS). Next day, casein buffer is removed from ELISA plates and replaced by 50 µl/well EC buffer (4 g casein, 2.13 g Na2HPO4 (Sigma), 2 g bovine albumin (Sigma), 0.69 g NaH2PO4.H2O (Sigma), 0.5 g CHAPS (Roche), 23.3 g NaCl, 4 ml 0,5 M EDTA pH 8 (Invitrogen), 5 ml 10% NaN3 in 1 L milliQ and adjusted to pH 7.0). 0.25 mM DTT (Sigma) is added to the thawed samples plates. After removal of the EC buffer, 20 µl of sample is transferred to the ELISA plates. After overnight incubation at 4° C. plates are washed twice with PBS and once with PBST (PBS with 0.05% Tween-20 (Sigma)) and incubated with 35 µl/well biotinylated anti-MMP1 antibody solution (R&D). This secondary antibody is diluted in buffer C (0.82 g NaH2PO4.H2O, 4.82 g Na2HPO4, 46.6 g NaCl, 20 g bovine albumin and 4 ml 0.5M EDTA pH 8 in 2 L milliQ and adjusted to pH 7.0) at a concentration of 5 µg/ml. After 2 h of incubation at RT, plates are washed as described above and incubated with 50 µl/well streptavidin-HRP conjugate (Biosource). Streptavidin-HRP conjugate is diluted in buffer C at a concentration of 0.25 µg/ml. After 45 min, plates are washed as decribed above and incubated for 5 min with 50 µl/well BM Chem ELISA Substrate (Roche). Readout is performed on the Luminoscan Ascent Luminometer (Labsystems) with an integration time of 200 msec or with an Envision reader (Perkin Elmer).

Figure 3:
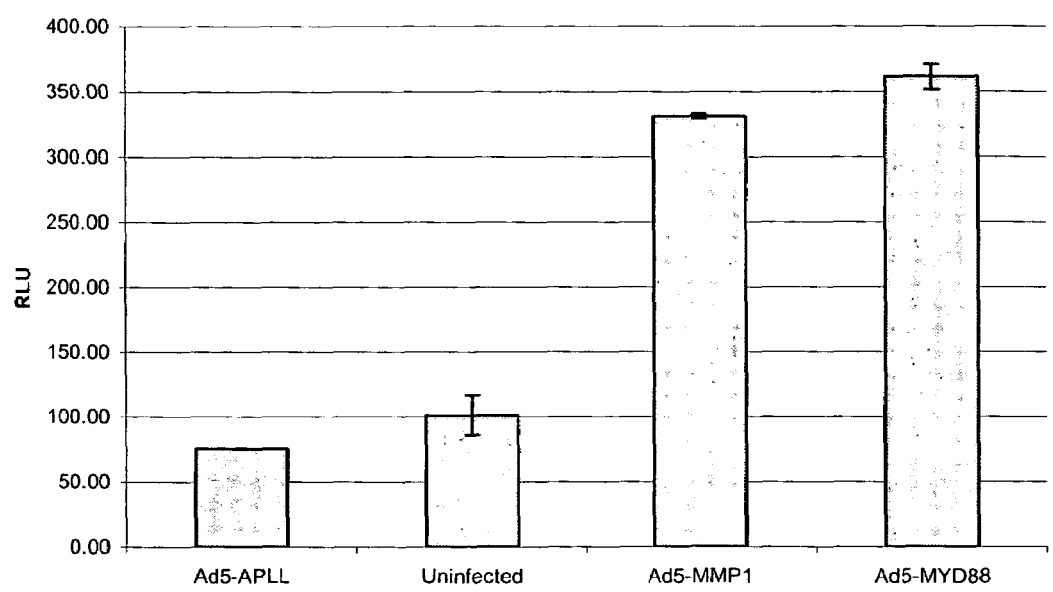
FIG. 3. Increased expression of MMP1 by SFs triggered with various model adenoviruses. The SF supernatant uninfected SFs and SFs infected with the indicated model recombinant adenoviruses is subjected to the MMP1 ELISA and the MMP1 level measured by using a luminescence generating substrate is shown.

Typical results obtained with the MMP1 ELISA developed are shown in FIG. 3. For this experiment, 3000 SFs are seeded in a 96 well plate in DMEM+10% FBS. 24 h later, SFs are either infected at an MOI of 10000 with adenoviruses mediating the expression of ALPP, MYD88, MMP1; or left uninfected. One day after the infection, the medium of the cells is replaced by M199 medium (Invitrogen) supplemented with 1% FBS. After an incubation time of 48 hrs, the supernatant is harvested, transferred to a 384 well plate and subjected to the MMP1 ELISA procedure described above. A robust, more than 3.5-fold up-regulation of the signal is observed. This experiment demonstrated the robustness and specificity of the MMP1 ELISA.

Figure 10:
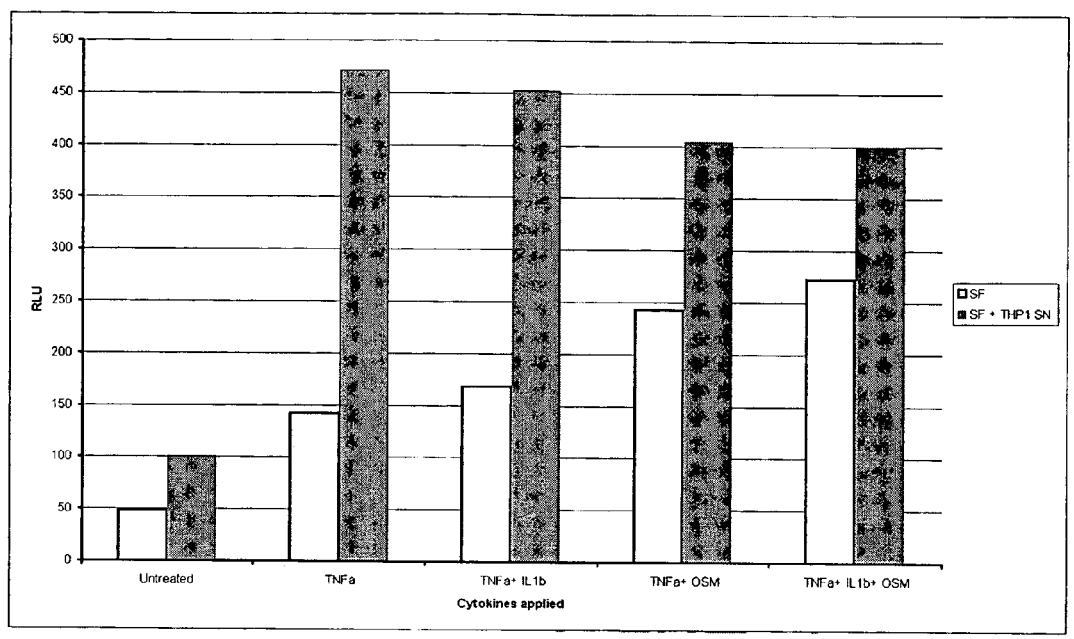
FIG. 10. Activation of SFs by various complex cytokine mixtures. Shown are the raw luminescence signals from MMP1 ELISA measurements of the supernatant of SFs collected 72 hours after being triggered with the indicated recombinant cytokines or with the supernatant of THP1 cells activated with the indicated cytokines. These measurements are proportional to MMP1 levels.

The increase of MMP1 expression by SFs upon treatment with cytokines relevant in the field of RA (TNFα, IL1β and OSM) or a combination thereof is monitored. Results is shown in FIG. 10 as white bars. For this experiment, SFs are seeded in 96 well plates at 3000 cells/well. 24 h later, the medium is changed to M199 medium supplemented with 1%

FBS. One day after the medium change, cytokines or combinations thereof are added to the cultures, each cytokine being added to a final concentration of 25 ng/ml. 72 h after cytokine addition, the supernatant is collected and processed in the ELISA, as described for FIG. 3. As shown in FIG. 10, white bars, TNFα alone induces an almost 3-fold increase in MMP1 expression. Triggering of SFs with a combination of TNFα and OSM and/or IL1β leads to even higher MMP1 expression levels. This experiment demonstrates that the sensitivity of the MMP1 ELISA developed is sufficient to measure increases in MMP1 expression by SFs driven by cytokines involved in RA pathogenesis.

Example 2

Screening of 4224 Recombinant Adenoviruses in an MMP1 Assay

A 384 well control plate is generated to assess the quality of the assay during the different screening runs. The composition of this plate is shown in FIG. 4A. Wells are filled with control viruses that are produced under the same conditions as the FlexSelect adenoviral cDNA library. This control plate contains three sets of 48 positive control viruses ($P_1$ (Ad5-MMP1), $P_2$ (Ad5-TRAF6), $P_3$ (Ad5-MYD88)), arranged in diagonal, interspaced with three sets of 48 negative control viruses ($N_1$ (Ad5-eGFP), $N_2$ (Ad5-LacZ), $N_3$ (Ad5-ALPP), B1: blanco, uninfected). Every well contains 50 µl of virus crude lysate. The viruses contained in the control plate are generated according to the protocol applied for the construction of the FlexSelect collection. Multiple aliquots of this control plate are produced and stored at −80° C.

Optimal screening protocol: RASFs are cultured in DMEM medium (Invitrogen) supplemented with 10% fetal calf serum (ICN), 100 units/ml penicillin (Invitrogen) and 100 µg/ml streptomycin (Invitrogen) and incubated at 37° C. and 10% $CO_2$. The cells are passed once a week by a ⅓ split. The maximal passage number for RASFs used in the screening is 11. For screening, SFs are seeded in transparent 384 well plates (Greiner) coated with 0.1% gelatin (Merck) at a density of 1500 cells/well in 25 µl Synovial Cell growth medium (Cell Applications, Inc.). After overnight incubation, cells are infected with 3 µl Ad-cDNA from the Galapagos FlexSelect adenoviral cDNA library. As the average titer of the adenoviral library is $3 \times 10^9$ virus particles/ml, this represents an MOI of 6000. 24 h after infection, the medium is changed to 50 µl of M199 medium supplemented with 1% FCS. 40 µl supernatant is collected 72 h later into new transparent 384 well plates (Greiner) and stored at −80° C. until further processing in the MMP1 ELISA. The infection, medium change and medium collection steps are performed with a TECAN Freedom pipettor. The ELISA step is performed as indicated in Example 1.

A representative example of the performance of the control plate tested with the protocol described above is shown in FIG. 4B. Synovial fibroblasts are infected with 3 µl of the viruses contained in the control plate in an arrayed fashion using a TECAN 384 channel pipettor. The medium is refreshed the day after infection and the supernatant is harvested after 72 h production time and subjected to the 384 well format MMP1 ELISA described in previous example. The raw luminescence signal obtained is shown.

A stringent cutoff is applied, that is the average of all 144 negative control viruses plus 4.5 times the standard deviation over these samples. As expected, the Ad5-MMP1 control virus scored very well in the assay, with all 48 Ad5-MMP1 viruses being picked up as a hit above this cutoff. The Ad5-MYD88 control virus also scored robustly, with 84% of the Ad5-MYD88 control viruses being picked up above the applied cutoff. The weaker Ad5-TRAF6 control, which gave rise to weaker increases in MMP1 mRNA levels (see Example 1) did not perform strongly, indicating that this cutoff will likely identify strong MMP1 inducers.

The MMP1 assay on RASFs described above is screened against the adenoviral cDNA libraries (FlexSelect™ collection) developed at Galapagos Genomics. The main part of this adenoviral collection contains cDNAs of genes from "drugable" classes like GPCRs, kinases, proteases, phosphodiesterases and nuclear hormone receptors. The majority of these cDNAs are obtained by a PCR-based approach briefly described below. Based on the sequences of the selected genes, which are obtained from the RefSeq database, PCR primers are designed for amplification of the complete open reading frame from ATG start codon to the stop codon. Primers are received in an arrayed format with forward and reverse primers mixed at a PCR ready concentration in 96 well plates. From this point on, the arrayed format is maintained throughout all the handlings (from PCR till virus production) resulting in an arrayed adenoviral cDNA library. As a template for the PCR reactions, placental, fetal liver, fetal brain and spinal cord cDNA libraries are used (from Invitrogen or Edge Biosystems). For the genes encoded by a single exon, PCR reactions are performed on human genomic DNA. After the amplification reactions, the size of the PCR products is estimated and compared to the predicted size based on sequence information. The PCR products obtained are purified with a 96-well PCR clean-up system (Wizard magnesil, Promega, Madison, Wis., USA), digested with the appropriate restriction enzymes (AscI, NotI or SalI restriction sites are included in the primers) and directly cloned into the adenoviral adapter plasmid pIspAd-Adapt-10-Zeo (described in U.S. Pat. No. 6,340,595) using DNA ligation kit version 2 (TaKaRa, Berkeley, Calif., USA). After a transformation and selection step, multiple clones per gene, one of which is sequence verified, are used for the preparation of plasmid DNA and subsequent generation of adenovirus according to the procedure described in WO99/64582.

The total FlexSelect adenoviral cDNA library consisted of 11×384 well plates at the time it is screened. 4224 samples represents 1705 genes.

Figure 5:
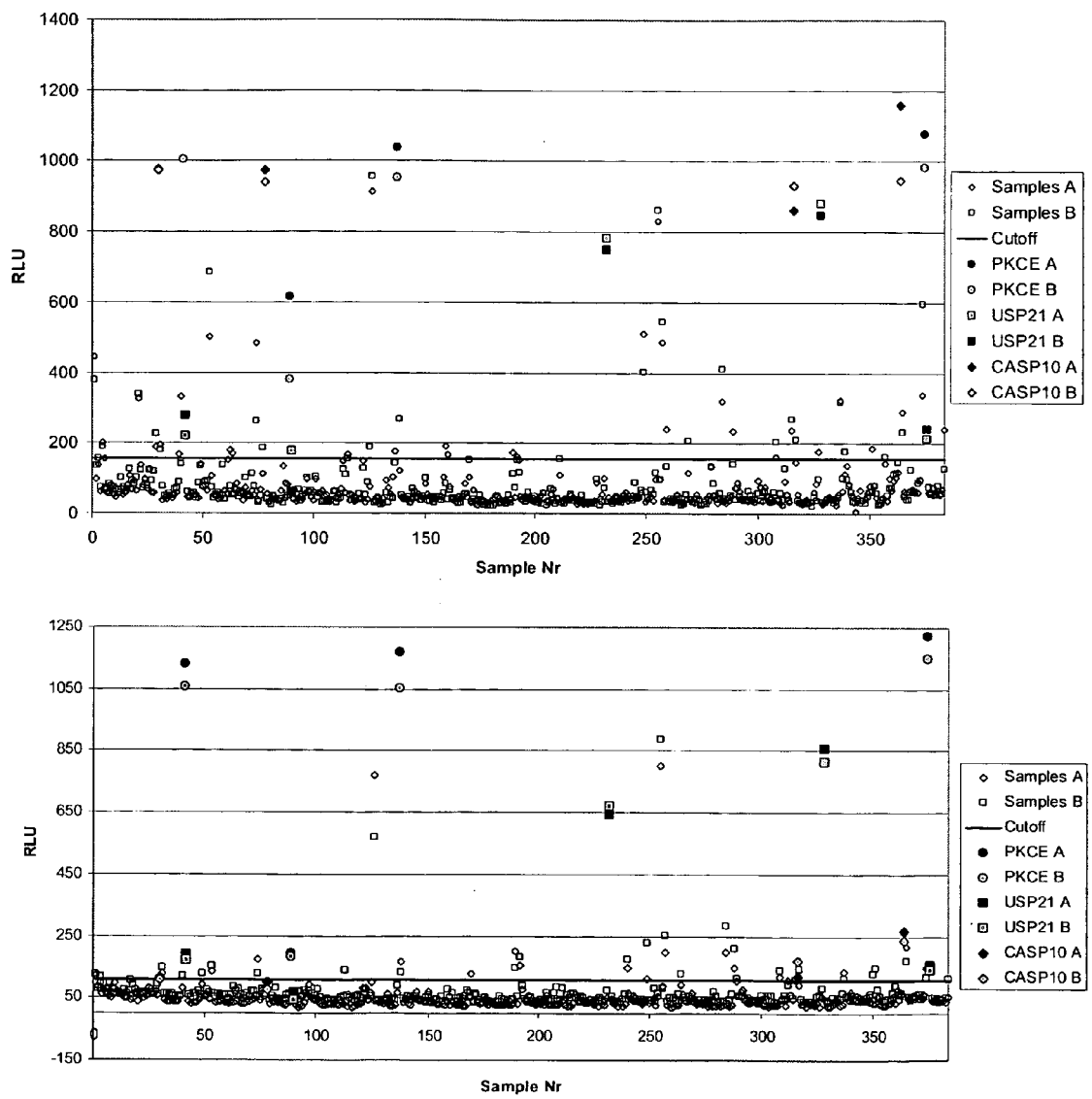
FIG. 5. Representative example of the performance of the MMP1 ELISA run on a subset of 384 Ad-cDNAs of the FlexSelect collection that are tested in duplicate in a primary screen (A) and a rescreen (B).

The MMP1 assay is screened against the FlexSelect adenoviral cDNA library using the optimized protocol described above. Every cDNA library plate is screened in duplicate in a primary screen and in a rescreen. As such, four data points are obtained for each cDNA clone. A representative example of screening results and of the analysis performed to identify hits is shown in FIG. 5.

SFs are seeded in 384 well plates and infected with 3 µl of 384 different recombinant adenoviruses of the FlexSelect collection contained in an arrayed fashion (using a TECAN pipetor), in a 384 well plate. The medium is refreshed the day after infection; the supernatant is harvested after 72 h production time and subjected to the MMP1 ELISA using a luminescent substrate. The raw luminescence signal obtained is shown. For every individual virus, the viruses mediating he expression of PRKCE, CASP10 and USP21 in particular, the 2 datapoints (FIGS. 5A and B) obtained in the primary screen (FIG. 5A) and in the rescreen (FIG. 5B) are shown.

To determine the cutoff value for hit calling, the average as well as standard deviation are calculated on all data points obtained per screening batch after removal of the 10% highest and 10% lowest values. The cutoff value is then defined as 3 times the standard deviation added to the average. This cutoff is indicated as a horizontal line in the graph in FIG. 5. Screening and rescreening results are presented in FIG. 6 for 4 cDNA encoding PRKCE, 5 cDNAs encoding USP21 and 4 cDNAs encoding CASP10. All 4 PRKCE cDNA clones scored above cutoff in duplicate in both the primary screen and rescreen, 4 out of 5 USP21 clones scored above cutoff in primary screening and rescreening, and 3 out of 4 CASP10 cDNA clones scored in duplicate in primary screening and rescreening. These data are indicative of the quality of the screening and of the FlexSelect cDNA collection.

As mentioned, every screening plate is screened and rescreened in duplicate. Only samples that scored above the cutoff value (the average plus 3 times standard deviation) for 3 out of the 4 datapoints are selected as hits. In addition, if multiple clones scored positive, maximally 2 clones per gene are further processed through the collagen degradation assay. As such, 253 hit Ad-cDNAs, representing 229 genes, are finally picked, propagated and tested in the collagen degradation assay.

Figure 13:
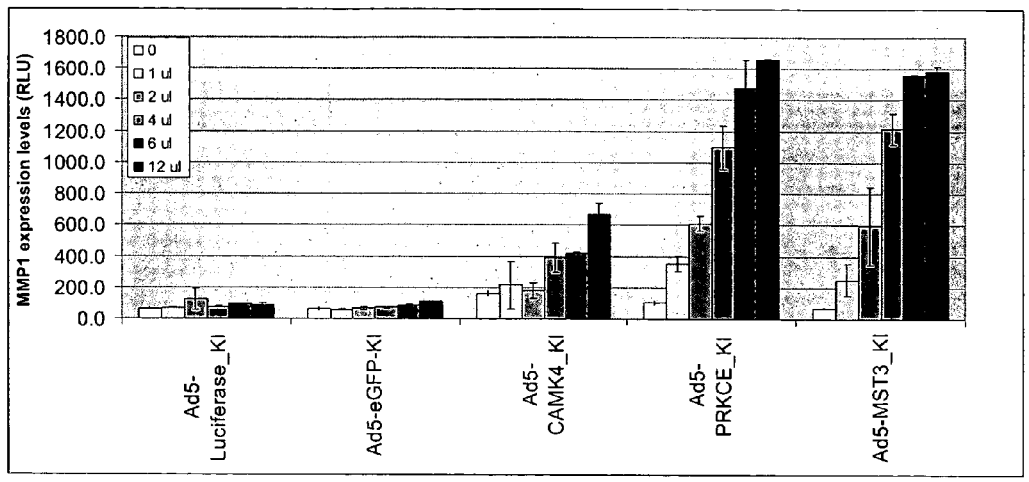
FIG. 13. Effect of adenovirus-mediated overexpression of target genes in SFs on the MMP1 expression by these cells. A) Result of infection of SFs with recombinant adenoviruses driving the expression of SEPT1, TPST1, USP21, MKNK1 and RIPK2; B) result of infection of SFs with recombinant adenoviruses driving the expression of PGPEP1 and RIT1; C) result of infection of SFs with recombinant adenoviruses driving the expression of CAMK4, MST3 and PRKCE; and D) result of infection of SFs with recombinant adenoviruses driving the expression of CD72, TM7SF1 and GPR21.
Figure 13:
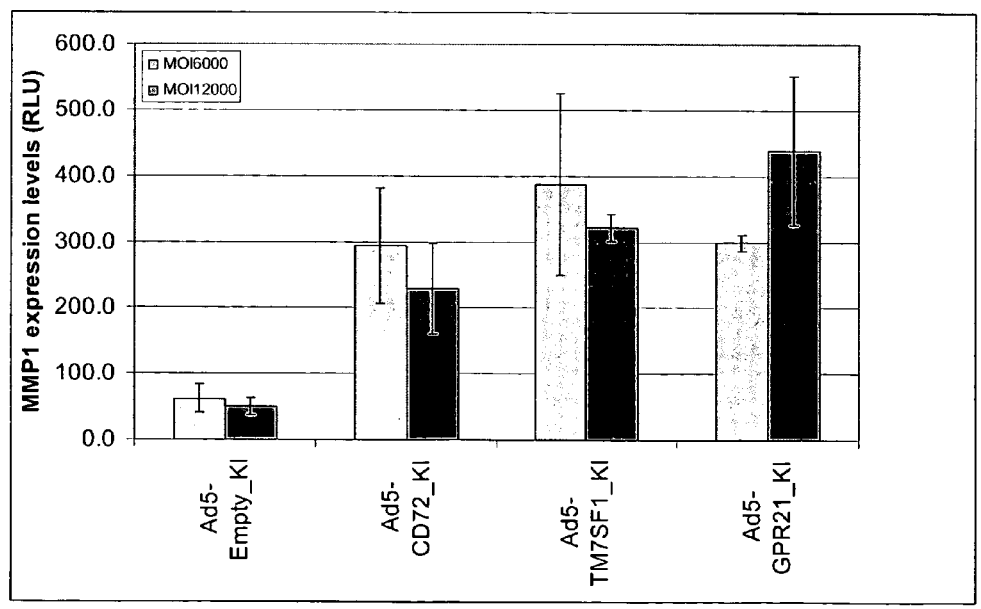

'Knock-in viruses' mediating the expression of various target genes listed in Table 1 are tested as follows. On day 1, SFs are seeded, in Synovial growth medium, in gelatin coated 96 well plates at a density of 3000 cells per well or in 384 well plates at a density of 1500 cells per well. 1 day after seeding, the cells are infected at the volumes or MOIs indicated on the figures. On day 3, the medium is refreshed to M199 medium supplemented with 1% FBS. On day 6, the supernatant is collected and subjected to the MMP1 ELISA according to the protocol described above. The Ad5-Luciferase, Ad5-eGFP or Ad5-Empty viruses are used as negative control viruses. Infection of SFs with recombinant adenoviruses driving the expression of SEPT1, TPST1, USP21, MKNK1, RIPK2 (FIG. 13 A), PGPEP1, RIT1 (FIG. 13 B), CAMK4, MST3, PRKCE (FIG. 13 C) and CD72, TM7SF1, GPR21 (FIG. 13 D) clearly mediated an increased expression of MMP1 by the infected SFs. The results shown in FIG. 13 are the averages of duplicate datapoints.

Example 3

Development of a Screening Method for the Measurement of the Collagenolytic Activity of Primary Synovial Fibroblasts (SFs): Collagen Degradation Assay The MMP1 assay is used as a first filter to select bits that mediated an increase in the MMP1 expression in SFs. The amount of MMP1 present in the supernatant of SFs might not, however, be sufficient to mediate the degradation of native collagen. In addition, besides MMP1, additional proteases might be expressed by SFs that, alone or in synergy with MMP1, mediate collagen breakdown. In order to rank our hits according to their potential to increase the collagenolytic activity of SFs, the present inventors developed a functional assay that determines the extent of degradation of native collagen in the supernatant of SFs. The various reagents and buffers used to perform the assay described below are from Chondrex (Redmond, USA), unless mentioned otherwise.

Figure 6:
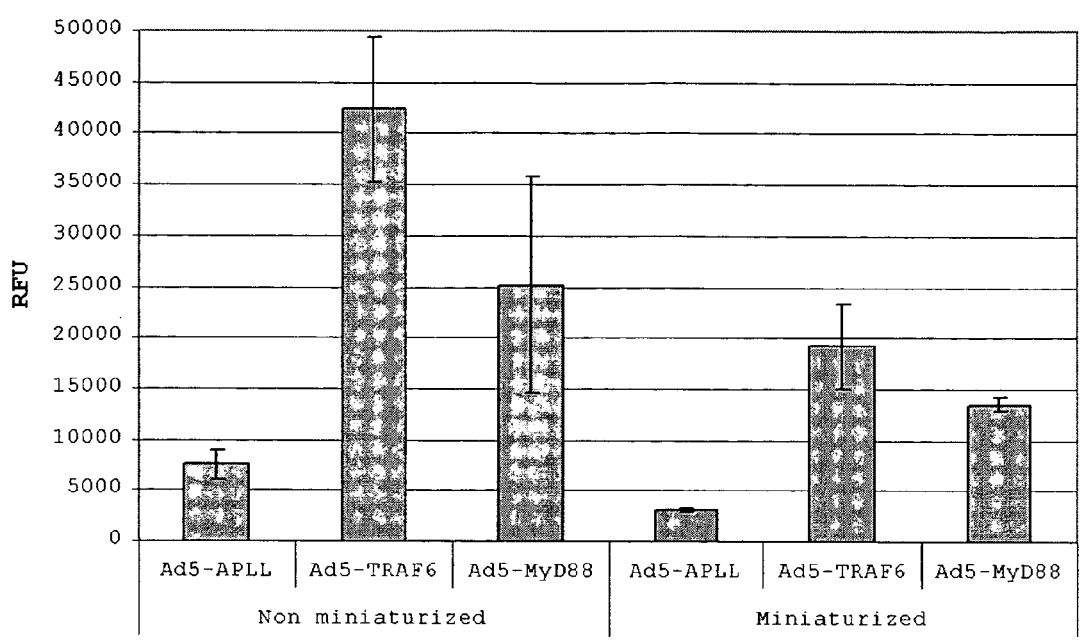
FIG. 6. Downscaling of the collagen degradation assay.

In first instance, the assay is developed to be compatible with a cDNA library screening on primary human cells. As a second development step, the assay is miniaturized to be compatible with an arrayed, medium throughput assay. Experiments confirmed that the sensitivity of the collagen assay performed on primary cells in miniaturized configuration is conserved as compared to the assay in non-miniaturized configuration. The results of a typical experiment illustrating this finding are shown in FIG. 6. For this experiment, SFs (seeded at a density of 3000 cells/well in a 96 well plate in M199 medium supplemented with 1% FBS) are infected (MOI 10,000) with Ad5-ALPP, AD5-TRAF6 or Ad5-MYD88. After an incubation time of 48 hrs (post infection), the supernatant is harvested and tested in both the miniaturized and non-miniaturized collagen degradation assays. Fluorescence signal, which is proportional to the level of collagen degradation, is indicated.

"Non-miniaturized" collagen degradation assay protocol: 100 µl of the SF supernatant or 100 µl of M199 medium+1% FBS supplemented with the indicated amount of rMMP1 (R&D systems) or chymotrypsin (Sigma) are mixed with 90 µl of buffer B. These mixes are added to either 10 µl of trypsin activating solution, or 10 µl of APMA (4-aminophenyl mercuric acetate, 2 mM final, Sigma) activating solution. These activating solutions mediate the removal of the prodomain of MMPs that keep these proteases in an inactive state. In the case of trypsin activation, the mixture is incubated for 60 min at 35° C., followed by the addition of SBTI (soybean trypsin inhibitor) to inactivate all non-collagenolytic proteases, whereas in the case of APMA activation, the mixture is incubated for 10 min at 35° C. 100 µl of Buffer A and 100 µl of native FITC-labeled bovine collagen type I (1 mg/ml, in 0.01N acetic acid) are mixed and added to the activated samples followed by an incubation step of 2 h at 35° C. during which collagenases cleave the FITC-labeled collagen in the typical ¼ and ¾ fragments. The reaction is stopped by addition of 10 µl of the stop solution (1,10 phenantroline, 10 mM final, Sigma). The large collagenase pieces are further digested by the addition of 10 µl of elastase (the "enhancer" solution) and incubation for 30 min at 35° C. After cooling down the samples, 400 µl of extraction buffer is added to precipitate the non-cleaved collagen fragments. These fragments are separated from the digested collagen pieces by a centrifugation step (10,000 rpm, 10 min). 200 µl sample is transferred to a black 96 well plate for a fluorescence measurement (520 nm, 480 nm as emission and excitation wavelengths, respectively) performed on a Fluostar reader (BMG).

Figure 8:
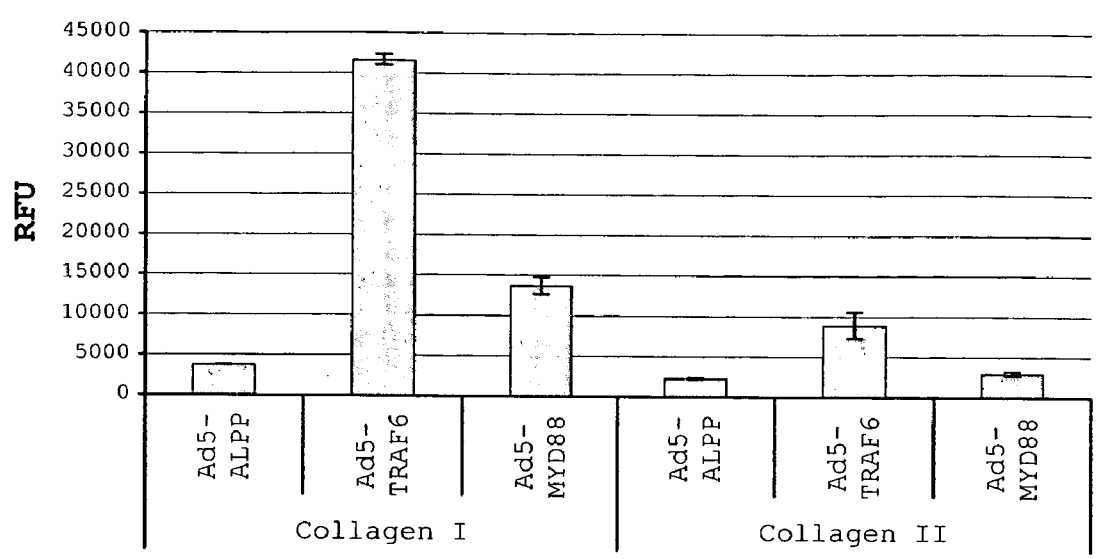
FIG. 8. Comparison of the degradation of FITC-labeled collagen type II and FITC-labeled Collagen type I in the collagen degradation assay.

"Miniaturized collagen degradation assay" protocol: A 96 well plate (V-bottom, Greiner) is filled with 9 µl of solution B and 1 µl of trypsin solution per well. 10 µl of sample is added per well, followed by incubation for 15 min at 34° C. After incubation, 1 µl SBTI is added. 20 µl of FITC-Collagen mix (10 µl FITC-labeled collagen type I+10 µl solution A) are added to the activated sample followed by incubation for 24 h at 34° C. One µl of 1.10 Phenantroline (Sigma) is added to the reaction mixture. One µl of enhancer solution (elastase) is added, followed by incubation for 30 min at 34° C. When the reaction mixture is at room temperature, 40 µl extraction buffer are added and the plate is sealed (Nunc seals) and vortexed. After centrifugation for 25 min at 4000 rpm (Beckman centrifuge), 50 µl of the supernatant are transferred into a black F-bottom plate (Greiner) and fluorescence is measured on a Fluostar reader (BMG), 480 nm excitation wavelength, 520 nm emission wavelength). The results of the experiment are shown in FIG. 8, and shows increased collagen type I degradation in the supernatant of Ad5-TRAF6 as well as Ad5-MYD88 infected cells. As such, the 2 positive controls identified for the "MMP1 assay" on SFs also mediate increased collagenolytic capacity of SFs. This suggests that the potency of a cDNA in the "MMP1 assay" is predictive for its capacity to increase the global collagenolytic activity of SFs. Although the levels of the fluorescent signal in the miniaturized assay are lower as compared to the non-miniaturized assay, the relative increase in fluorescence in the positive samples as compared to the Ad5-ALPP control is maintained. Thus, a miniaturized collagen degradation assay on SFs has been developed that has a sensitivity level comparable to the non-miniaturized assay. This result establishes that the method used for the collagen degradation assay described above is compatible with the screening of cDNA libraries (in adenoviral format in this example) on primary cells (human SFs in this example). Various experiments established that following aspects of the protocol are important:

- the use of trypsin for the activation of the latent MMPs in the supernatant of the cells is useful for the detection of collagenase activity using the assay.
- the supernatant of non-infected cells does not contain any detectable background collagenase activity. It is held that the use of medium without phenol red (M199 medium, no phenol red, Invitrogen) with low serum content (1% FBS) is preferred to obtain this low background signal.
- the collagen used for this assay is mostly in native, triple helix conformation, as no collagen degradation is mediated by chymotrypsin, an enzyme that has the capacity to degrade denatured collagen (gelatin). The native character of the collagen used is also preferred for this assay.

Figure 7:
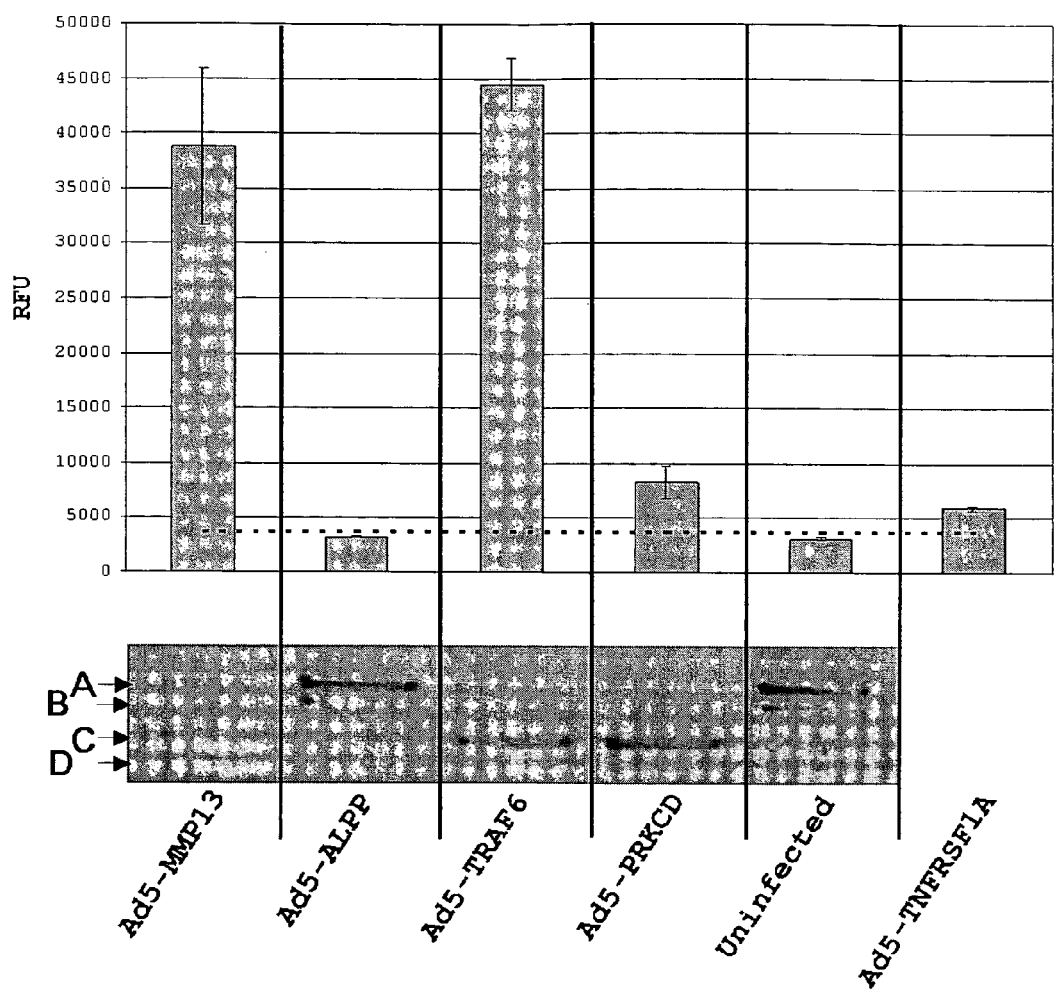
FIG. 7. Matching of the collagen degradation assay readout to the visual assessment of collagen degradation.

The above miniaturized assay is compared to another low-throughput detection method for collagen degradation, in which the following samples are tested: supernatant of SFs (cultured in 96 well plates in M199 medium supplemented with 1% FBS) uninfected or infected with Ad5-ALPP, Ad5-TRAF6, Ad5-PRKCD, Ad5-MMP13 (MMP13 is a potent collagenase), or Ad5-TNFR1A, all at an MOI of 10,000. The results of the miniaturized collagen degradation assay run on these samples (following the protocol described in former example) is shown in FIG. 7: Supernatant obtained after infection of SFs with the indicated recombinant adenoviruses and a 48 hrs production time, is subjected to both the miniaturized (fluorescence-based) collagen degradation assay and the lower throughput visual assessment of collagen degradation. For the latter test, the various supernatants are incubated with native collagen. The reaction mixtures are resolved on a polyacrylamide gel and degradation of the heterotrimeric collagen type I fibrils from the native (bands A and B) to the ¾ N-terminal $TC^A$ fragments (bands C and D) is assessed after Coomassie staining.

A cutoff value for hits versus non-hits in this experiment is defined as the average over the data points for the uninfected control samples plus 3 times the standard deviation over these data points and is indicated as a dotted line on the bar graph in FIG. 7. These data indicate that, in addition to the Ad5-TRAF6 and Ad5-MMP13 positive controls, the collagenolytic potential of SFs increased upon overexpression of PRKCD and TNFR1A. As TNFalpha is a well-known trigger involved in RA pathogenesis, it can be expected that the overexpression of TNFR1A, the TNFα receptor, will lead to an increase in collagen degradation. This result further validates our approach to identify relevant cDNAs involved in RA pathogenesis. In this experiment, PRKCD is identified as another relevant mediator of collagen degradation by SFs.

The same samples are then tested in the following setup: a 10 μl sample is mixed with 10 μl EDANS buffer (50 mM Tris-HCl, pH 7.5; 150 mM NaCl; 10 mM $CaCL_2$; 0.05% Brij-35, 50 μM $ZnCl_2$), 10 μl of a solution of collagen type I (IBFB, Germany, 1 mg/ml dissolved in 0.01N acetic acid). APMA is added to this reaction mixture to a final concentration of 2 mM. The reaction mixture is incubated for 48 h at 35° C. 25 μl of the reaction mixture is then boiled and resolved on a 8% SDS poly acryl amide gel (Novex) which is then subjected to a coomassie blue staining. Native collagen type I is a triple helix composed of 2 α1 and 1 α2 chains. These chains are visible on the gel in the control samples and are indicated by arrows A and B in the lower part of FIG. 7. In the positive control samples, Ad5-MMP13, Ad5-TRAF6 and Ad5-PRKCD, these 2 bands are cleaved into the ¾N-terminal "$TC^A$" fragments, indicated by arrows C and D. This typical restriction pattern is indicative for the action of MMP-type collagenases, which cleaves the collagen triple helix at a single position, thereby generating characteristic ¼ C-terminal "$TC^B$" and ¾ N-terminal "$TCA^A$" fragments. These results confirm in a visual way the direct relationship that exists between the signal obtained in the collagen degradation assay and the collagen degrading activity present in the tested samples. These data also confirm that the signal obtained in the collagen degradation assay is the result of the activity of MMP-type collagenases.

As the main component of cartilage is collagen type II, we compared the collagen degradation assay readout performed with FITC-labeled collagen type I and with FITC-labeled collagen type II. Results of a representative experiment are shown in FIG. 8. For this experiment, supernatant is used of SFs (cultured in 96 wells plates, 3000 cells/well in M199+ 1% FBS) that are infected with Ad5-TRAF6, Ad5-ALPP or Ad5-MYD88 at an MOI of 10,000. Supernatant of these cells is harvested 48 h post-infection and subjected to the non-miniaturized collagen degradation assay procedure described for FIG. 8 with either FITC-labeled native collagen type I or FITC-labeled collagen type II (same amounts as FITC-labeled collagen type I). Results shown in FIG. 8 indicate that the degradation of collagen type II gave rise to lower fluorescent signals, suggesting a higher resistance of collagen type II to proteolytic degradation as compared to collagen type I. Notwithstanding the lower signal levels obtained when using collagen type II, cDNAs mediating increased collagen type II degradation are identified, as exemplified here with Ad5-TRAF6. The order of potency of the hits towards induction of collagen degradation is maintained in the collagen degradation assay run with collagen type II as compared to the assay run with collagen type I. These results indicate that the capacity of a hit to induce the degradation of collagen type I in this assay is predictive for its capacity to induce the degradation of collagen type II.

Example 4

Testing of 253 Hits of the "MMP1 Assay" and Screening of 1679 Recombinant Adenoviruses in the Collagen Degradation Assay The adenoviruses identified as hits in the MMP1 assay on primary synovial fibroblasts (SFs) are picked from the FlexSelect adenoviral cDNA library and are re-propagated in 96 well plate format by infection of PER.E2A producer cells (see WO99/64582). These plates are further referred to as the "MMP1 hit propagation plates". On these plates, 4 Ad5-ALPP and 4 Ad5-Luciferase control viruses are also included. The border wells of these plates are not used to avoid eventual "border effects" in the experiments. The MMP1 hit propagation plates contain 50 hit viruses and 10 negative control viruses. This virus material is then tested at 3 MOI's in duplicate in the collagen type I degradation assay on SFs as follows. SFs are trypsinized and seeded in 96 well plates (Nunc, transparant plates, tissue culture treated). Trypsinized SFs are resuspended in Synoviocyte Growth medium (Cell Applications) at a density of 30,000 cells/ml and 100 µl of this suspension is dispensed in each well using a multidrop dispenser (Labsystems). Approximately 24 h after seeding of the cells, a duplicate infection of the cells is performed with 6, 12 or 18 µl of the virus material present in 96 well MMP1 hit propagation plates using a Tecan Freedom 200 pipettor (Tecan). As such, the content of the MMP1 hit propagation plates is transferred to 6 96 well plates containing the seeded SFs. 6 data points in the collagen degradation assay are generated per hit virus. Approximately 24 h after infection, virus and medium are removed from the cells using an 8 channel Vacusafe device (Integra) and 60 µl M199 medium supplemented with +0.5% FBS is added to every well.

72 h after medium refreshment, supernatant is transferred to a 96 well plate (V-bottom, Greiner) with the Tecan Freedom 200 pipettor. The supernatant is stored at −80° C. until use. To perform the assay, the supernatant is thawed and the assay is performed according to the protocol of the miniaturized collagen type I degradation assay described above in Example 3.

Hit selection is performed as follows: For each plate, the average and standard deviation are calculated for the fluorescence measurements obtained for the 8 wells infected with control viruses. The cutoff for hits versus no-hit is defined as the average plus 2 times the standard deviation for these control samples. A virus is considered a hit if it induced a signal above the cutoff value for at least 3 out of 6 data points. 253 hits identified in the MMP1 assay have been retested according to this procedure. Out of these, 61 Ad-cDNAs significantly increased the collagenolytic activity of SFs, representing 55 individual genes when redundancy is taken into account. Besides these 55 hits, two Ad-cDNAs picked up in the screening delivered a proof of principle for the screening. One of these hits encoded MMP1. Another hit encodes IKKβ (IKBKB). This kinase has a central role in the response of cells to inflammatory triggers as e.g. TNFα. Small drug inhibitors, with RA as therapeutic indication, are currently being designed against IKKβ (Andreakos et al., 2003). The fact that hits, relevant in the field of RA, are picked up confirms the quality of our screening concept and the quality if the materials (assays and libraries) used.

As final quality control on these hit Ad-cDNAs, their identity is checked by sequence analysis. The procedure for sequence analysis is as follows. The hit viruses are propagated using PER.E2A producer cells in a 96 well plate. PER.E2A cells are seeded in 96 well plates at a density of 40,000 cells/well in 180 µl medium. Cells are incubated overnight at 390° C. in a 10% $CO_2$ humidified incubator. One day later, cells are infected with 1 µl of crude cell lysate from FlexSelect stocks containing the hit Ad-cDNA. Cells are incubated further at 34° C., 10% $CO_2$ until appearance of cytopathic effect (as revealed by the swelling and rounding up of the cells, typically 7 days post infection). The supernatant is collected and the virus crude lysate is treated with proteinase K: 12 µl crude lysate is added to 4 µl Lysis buffer (1× Expand High Fidelity buffer with $MgCl_2$ (Roche Molecular Biochemicals, Cat. No 1332465) supplemented with 1 mg/ml proteinase K (Roche Molecular Biochemicals, Cat No 745 723) and 0.45% Tween-20 (Roche Molecular Biochemicals, Cat No 1335465) in sterile PCR tubes. These are incubated at 550° C. for 2 h followed by a 15 mm inactivation step at 95° C. For the PCR reaction, 1 µl lysate is added to a PCR master mix composed of 5 µl 10× Expand High Fidelity buffer with $MgCl_2$, 0.5 µl of dNTP mix (10 mM for each dNTP), 1 µl of 'Forward primer' (10 mM stock, sequence: 5' GGT GGG AGG TCT ATA TAA GC; SEQ ID NO: 230), 1 µl of 'Reverse Primer' (10 mM stock, sequence: 5' GGA CAA ACC ACA ACT AGA ATG C; SEQ ID NO: 231), 0.2 µl of Expand High Fidelity DNA polymerase (3.5 U/µl, Roche Molecular Biochemicals) and 41.3 µl of $H_2O$.

PCR is performed in a PE Biosystems GeneAmp PCR system 9700 as follows: the PCR mixture (50 µl in total) is incubated at 95° C. for 5 min; each cycle runs at 95° C. for 15 sec, 55° C. for 30 sec, 68° C. for 4 min, and is repeated for 35 cycles. A final incubation at 68° C. is performed for 7 min. 5 µl of the PCR mixture is mixed with 2 µl of 6× gel loading buffer, loaded on a 0.8% agarose gel containing 0.5 µg/µl ethidium bromide to resolve the amplification products. The size of the amplified fragments is estimated from a standard DNA ladder loaded on the same gel. For sequencing analysis, the cDNAs expressed by the target adenoviruses are amplified by PCR using primers complementary to vector sequences flanking the SapI site of the pIPspAdapt6 plasmid. The sequence of the PCR fragments is determined and compared with the expected sequence.

Screening of the FlexSelect Collection Subset in the Collagen Degradation Assay

The possibility exists that certain factors mediate an increased collagenolytic activity of SFs through collagenases other than MMP1. In order to identify such factors, a subset of the FlexSelect collection is screened in the collagen degradation assay on SFs. 384 well plates from the FlexSelect collection containing mainly Ad-cDNAs mediating the expression of kinases and GPCRs are screened. The following screening protocol is applied. SFs are trypsinized and resuspended in Synoviocyte Growth medium (Cell Applications) at a density of 30,000 cells/ml. 100 µl of this cell suspension is dispensed in each well of 96 well plates (Nunc, tissue culture treated) using a 'multidrop' dispenser (Labsystems). Approximately 24 h after seeding of the cells, they are infected with the library Ad-cDNAs as follows. The FlexSelect library aliquot plates (384 well format, stored at −80° C.) to be processed are thawed at RT in a laminar air flow cabinet for 1 h. Plates are then stored at 4° C. until further processing.

For every well of a quadrant of a 384-well adenoviral cDNA library aliquot plate, 10 µl of virus crude lysate is transferred to a well of a 96 well plate containing the SFs. This action is performed with the 96 needle head of a TECAN Freedom 200 pipettor. Each virus is assayed in duplicate. As such, for every 384-well virus library aliquot plates, 8 96-well plates containing SF are infected. In between every pipeting step, needles of the pipettor are emptied in a bleach wash station and rinsed two times with 175 µl of bleach (5%) and two times with 200 µl of water and finally with 200 µl of ethanol (20%). Approximately 24 h after infection, the medium of the cells is refreshed. Virus and medium are removed with the Vacusafe (Integra) and 60 µl of fresh M199 medium+0.5% FBS is added. 72 h after refreshment of the medium, the cell supernatant is transferred from the 96 well plates containing the infected SFs to a 96 well plate (V-bottom, Greiner) with the TECAN Freedom 200 pipettor. The samples are then subjected to the miniaturized collagen type I degradation assay. In total, 1679 samples are screened in duplicate in this assay, representing 449 genes.

Figure 9:
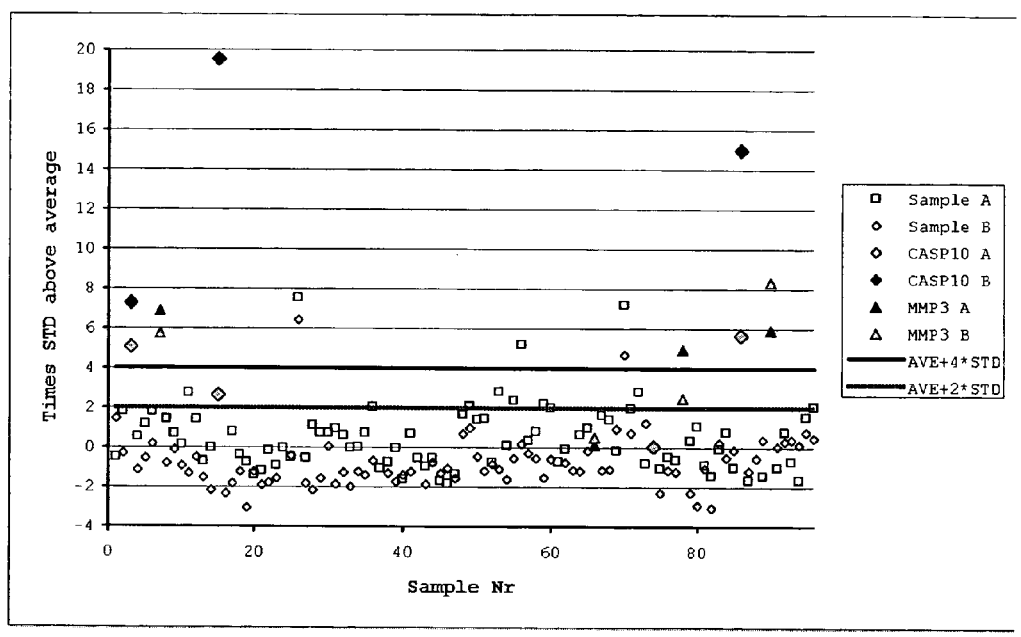
FIG. 9. Performance of the collagen degradation assay.

The following analysis is performed for hit selection: Per screening batch, the average and standard deviation is calculated on all samples after removal of the 10% highest and 10% lowest values. As mentioned above, 2 data points are obtained for every Ad-cDNA sample screened. The Ad-cDNA samples for which one of the 2 data points scored above the average plus 4 times the standard deviation as well as the samples for which both data points scored above the average plus 2 times standard deviation are selected as hits. A representative example of the results obtained during screening for 96 viruses (1 assay plate) screened in duplicate is shown in FIG. 9. For every individual virus, the 2 datapoints (A and B) obtained in the primary screen are shown. Viruses mediating the expression of CASP10 and MMP3 are indicated. The signal obtained for the samples is expressed relative to the standard deviation and average using following formula: [Times standard deviation difference from average=(Value Sample-Value Average)/Standard deviation]. The cutoff for hit calling (average plus 2 or 4 times standard deviation) is indicated as a full or dotted line, respectively. Among the 96 Ad-cDNAs for which screening results are shown, 4, out of which 3 scored according to the selection criterion, mediated the expression of MMP3 and 4, out of which 3 scored according to the selection criterion, mediated the expression of CASP10. 108 Ad-cDNAs, representing 79 genes when taking redundancy into account, are selected as hits according to this procedure.

These hits are re-propagated and rescreened using the procedure described for the screening of the hits of the MMP1 assay in the collagen degradation assay. 31 hits, representing 20 individual genes, out of the 108 primary hits mediated a significant level of collagen type I degradation in the rescreen procedure. As 4 genes out of the 55 identified as hits through the "MMP1 assay" and validated in the collagen degradation assay are also present among the 20 genes identified as hits in the screening of a subset of the FlexSelect collection in the collagen degradation assay, a total of 71 genes are identified that increased the collagenolytic potential when expressed or activated in primary human SFs. The preferred hit genes identified in this assay are listed in Table 1. The performance of these in the collagen degradation assay in summarized in Table 4.

TABLE 4

Summary of the Features of the TARGET Genes

Experiment Description

| Gene Symbol | Knock-in MMP1 induction | Knock-in Induction of collagen degradation | Expression in primary RASFs | Knock down Inhibition of cytokine induced MMP1 | Knock down Inhibition of cytokine induced collagen degradation |
|---|---|---|---|---|---|
| RIPK2 | SP | SP | SP | SP | NT |
| PRKCE | SP | SP | P | SP | SP |
| MST3 | SP | SP | P | P | NT |
| MAPKAPK5 | N | N | P | SP | SP |
| MKNK1 | SP | SP | P | N | NT |
| CAMK4 | P | P | P | SP | SP |
| SEPT1 | P | P | P | SP | NT |
| PGPEP1 | P | P | P | SP | NT |
| CD72 | P | P | P | SP | NT |
| TPST1 | P | P | SP | SP | P |
| GPR21 | P | P | P | SP | NT |
| USP21 | SP | SP | P | P | NT |
| FZD4 | N | N | P | SP | NT |
| TM7SF1 | P | P | P | SP | NT |
| FXYD5 | N | N | SP | SP | NT |
| RIT1 | P | P | P | SP | SP |
| CASP10 | SP | SP | P | N | NT |

P: positive response in the assay
SP: Strong positive response in the assay
NT: not tested
N: negative response in the assay Example 5

Expression Analysis of the TARGETS Identified in Human Primary Synovial Fibroblasts Derived from Synovium of RA Patients Expression levels for all the TARGETS identified are determined in at least three different isolates of primary human synovial fibroblasts.

One isolate of RASF's is obtained as cryopreserved passage 2 cells from Cell Applications Inc. (Cat. No. 404-05). These cells are cultured and propagated in DMEM (Invitrogen) supplemented with 10% (v/v) heat-inactivated FBS (ICN) and 1× Pen/Strep (Invitrogen).

Two other isolates are established starting from synovial membrane biopsy specimens obtained during knee arthroscopy of patients who are diagnosed as suffering from RA. Upon removal, the tissue samples are frozen in DMEM (Invitrogen) containing 15% (v/v) heat-inactivated FBS, 1× sodium pyruvate (Invitrogen), IX antibiotics (Invitrogen) and 10% (v/v) DMSO (Sigma) and stored in liquid nitrogen. Cell culture is initiated from these synovial tissue specimens as follows: the tissues are washed thoroughly with Hanks balanced salt solution (Invitrogen) supplemented with 2× antibiotics and are digested overnight at 37° C. with 0.2% (w/v) Type IV Collagenase (Invitrogen) in DMEM containing 10% (v/v) heat-inactivated FBS, 1× sodium pyruvate, 2× antibiotics. Cells are collected, washed, resuspended in growth medium (DMEM supplemented with 10% heat-inactivated FBS, 1× sodium pyruvate, 1× antibiotics) and finally plated in 3 different wells of a 6-wells tissue culture plate. Non-adherent cells are removed after 3 days by changing growth medium. When cells reached 90-95% confluency, they are harvested by trypsinization (0.25% trypsin/1 mM EDTA) and passaged to a 25-cm2 tissue culture flask. Further passaging is done by ⅓ splitting and growth medium is changed twice a week. For expression analysis, cells are used at passages 6 to 10.

For RNA preparation, the primary human synovial fibroblasts are seeded in 10-cm Petri dishes (500,000 cells/dish). After overnight incubation, medium is refreshed to 6 ml of M199 medium supplemented with 1% (v/v) heat-inactivated FBS containing 1× Pen/Strep. 24 h later, total RNA is extracted using the 'SV Total RNA Isolation kit' (Promega). Certain samples are stimulated before harvesting. In this case, the following medium is added to the dishes for 24 h before harvesting: supernatant of THP1 cells (a human monocytic cell line) triggered with recombinant human TNFα (25 ng/ml) for 72 h in M199 medium+1% FBS diluted 2 fold in fresh M199+1% FBS.

The concentration of RNA in each sample is fluorimetrically quantified using the 'Ribogreen RNA quantitation kit' (Molecular Probes). A similar amount of RNA from each preparation is reverse transcribed into first strand cDNA with the 'Taqman reverse transcription kit' from Applied Biosystems. Briefly, 40 ng RNA is included per 20 µl reaction mix containing 50 pmol of random hexamers, 10 U Rnase inhibitor, 25 U Multiscribe reverse transcriptase, 5 mM $MgCl_2$ and 0.5 mM of each dNTP. The reaction mixture is incubated at 25° C. for 10 min, followed by 30 min incubation at 48° C. and heat inactivation (5 min 95° the reverse transcriptase in a thermocycler (Dyad, MJ Research). Reactions are immediately chilled to 4° C. at the end of the program. To avoid multiple freeze/thaw cycles of the obtained cDNA, the different samples are pooled in 96-well plates, aliquoted and stored at −20° C.

Real-time PCR reactions are performed and monitored using the 'ABI PRISM 7000 Sequence Detection System Instrument' (Applied Biosystems). Primers are designed with 'Primer Express software version 2.0' (Applied Biosystems) and purchased from Sigma-Genosys. The specificity of the primers is confirmed by BLASTN searches. The PCR mixture consisted of 1× Sybr Green PCR Master mix (Aplied Biosystems), 7.5 pmol of forward and reverse primers and 2 µl of the retrotranscription reaction product in a total volume of 25 µl. After an initial denaturation step at 95° C. for 10 min, the cDNA products are amplified with 40 cycles consisting of 95° C. for 15 s and 60° C. for 1 min, followed by a dissociation protocol, which is defined as a slow ramp from 60 to 95° C. Using the dissociation protocol single peaks are confirmed in each of the PCR reactions for the various genes to exclude non-specific amplification. In order to normalize for variability in the initial quantities of cDNA between different samples, amplification reactions with the same cDNA are performed for the housekeeping genes β-actin/18S rRNA using either home made β-actin primers and SYBR Green PCR Master Mix or the 'predeveloped primer and Taqman probe mix' for human 18S rRNA and 'Taqman Universal PCR Mastermix no AmpErase UNG' (all Applied Biosystems) according to the manufacturer's instruction. To identify any contamination resulting from residual genomic DNA, real-time PCR reactions with product from a control (−RT) reverse transcription reaction that is performed under the same conditions but without the addition of the reverse transcriptase are included for each sample. Threshold cycle values (Ct), i.e. the cycle number at which the amount of amplified gene of interest reached a fixed threshold are determined for each sample.

For each sample, the ΔCt value is determined by substracting the Ct value of the endogenous control (β-actin) from the Ct value obtained for the target gene. A gene is considered as expressed in primary human SFs if the ΔCt value obtained for this hit is lower as 13.3 in at least one of the 3 synovial isolates, activated or not, that are available. The results of the expression profiling experiments are summarized in Table 5. The DCt value relative to β-actin obtained for all target genes (listed in Table 1) in untriggered SFs or SFs triggered with 25% 'complex cytokine mixture' are given in this Table 5. The primers used in this study are listed in Table 2.

TABLE 5

Expression of target genes in primary synovial fibroblasts

| Gene symbol | Untriggered RASFs | Triggered RASFs |
|---|---|---|
| RIPK2 | 6.7 | 3.7 |
| PRKCE | 8.8 | 7.8 |
| MST3 | 6.4 | 5.2 |
| MAPKAPK5 | 7.5 | 6.0 |
| MKNK1 | 5.9 | 5.6 |
| CAMK4 | 14.2 | 11.6 |
| SEPT1 | 7.0 | 7.1 |
| PGPEP1 | 8.7 | 8.1 |
| CD72 | 9.0 | 9.1 |
| TPST1 | 5.1 | 3.1 |
| GPR21 | 11.5 | 9.8 |
| USP21 | 8.1 | 6.9 |
| FZD4 | 7.4 | 7.3 |
| TM7SF1 | 7.6 | 7.1 |
| FXYD5 | 2.8 | 2.1 |
| RIT1 | 6.5 | 4.4 |
| CASP10 | 14.5 | 11.9 |

Example 6A

Testing of the TARGETS Identified Using siRNA Technology

When the adenoviral expression or the activation of a factor in SFs increases the collagen degrading potency of these cells, activation of this factor is sufficient to increase collagen degradation by these cells. This indicates that the factor controls or is acting on signaling pathways that are important for the regulation of MMP1 and/or other proteases involved in collagen degradation. However, to confirm that a factor is indispensable for the expression of MMP1 or degradation of collagen, the following "reverse MMP1 assay" experiments are performed. These experiments are key in determining whether the inhibition of a TARGET protein will reduce the cytokine-induced MMP1 expression, collagen degradation and thus has therapeutic potential for diseases involving ECM degradation.

This assay used multiple "knock down" viruses corresponding to the TARGET genes that, when overexpressed or activated in SFs, increase the potency of these cells to express MMP1 or to degrade collagen. Certain "knock down" viruses are also designed against 3 other target genes (MAPKAPK5, FXYD5 and FZD4) that are not identified through the screening of the FlexSelect collection in the "MMP assay". A "knock down" virus is defined as an adenovirus that drives the expression of a self-complementing single-stranded siRNA molecule polynucleotide, resulting in the reduction of the corresponding mRNAs levels that encode the target polypeptides. The siRNA polynucleotides are designed based on the sequence of the gene encoding the TARGET polypeptide and selected according to siRNA designing rules that give an improved reduction of the target sequence expression compared to nucleotide sequences that do not comply with these siRNA designing rules (See PCT/EP03/04362). Multiple viruses are generated and tested for each TARGET gene as not every siRNA is as efficient in reducing the mRNA levels for a given TARGET gene.

SFs are seeded in 384 or 96 well plates and infected at various MOI's with the knockdown viruses generated against the targets identified as players modulating SF MMP1 expression in, or SF collagen degradation. Five days after infection, at the time the levels of the target mRNA in the SFs are efficiently reduced by the knock down virus, the SFs are "activated" with a trigger or a mixture of triggers relevant in the field of arthritis. In uninfected SFs, or SFs infected with control knock down viruses, this trigger or mix of triggers lead to an increase in the expression of MMP1 and the potency of the cells to degrade collagen.

Two days after application of the trigger, the levels of MMP1 in the supernatant of the SFs are measured in an MMP1 ELISA, or the degradation of collagen by the supernatant of the SFs is measured in the collagen degradation assay. If the reduction in the expression level for a certain target gene leads to a reduced response of the cells to RA-relevant trigger applied, this indicates that this target gene is indispensable for the SFs to respond to this trigger. The inhibition of the activity of the polypeptide product of this gene, or the reduction in expression of this gene, might thus represent a suitable approach for treatment of RA.

In order to work in an unbiased way, a complex mixture of factors relevant in the field of RA is generated as follows: THP-1 cells, a representative human monocyte cell line, is cultured in the presence of human recombinant TNFalpha (Sigma, 25 ng/ml) for 48 h. Supernatant of this cell line is then collected and stored at −80° C. until further use. The monocytes respond to the TNF-alpha trigger by the production of a variety of other cytokines and factors, most of which will be pro-inflammatory. As monocytes (macrophages) as well as high levels of TNF-alpha are present in the affected joints of RA patients, the trigger mixture produced in this way is relevant in the field of RA and will be representative for the mixture of factors present in the joints of RA patients. The unbiased character of this method represents an important advantage, as the mixture produced is very complex and might contain factors unknown to be involved in RA or even factors unknown to date.

The white bars in FIG. 10 show the increase of SF MMP1 expression upon treatment with cytokines relevant in the field of RA (TNFα, IL1β and OSM) or a combination thereof. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/ml. 72 h after cytokine addition, the supernatant is collected and processed in the MMP1 ELISA. In parallel with this experiment, SFs are triggered, using the same protocol, with the supernatant of THP1 cells (2-fold diluted in M199+1% FBS) that are left untreated or are treated with the same cytokines or combinations of cytokines for 48 h in M199 medium+1% FBS. MMP1 levels for these samples are shown in FIG. 10 as grey bars. The induction of the MMP1 expression levels by the supernatants of TNFα-treated THP1 cells is stronger (>4.5 fold induction) as compared to the induction by recombinant TNFα alone (3-fold induction) and almost equals the 5-fold induction obtained by a mixture of 3 purified cytokines (TNFalpha, IL1b, OSM). This result indicates that the supernatant of TNFα-induced THP1 cells contains additional pro-inflammatory factors that trigger the SFs towards MMP1 production.

Figure 11:
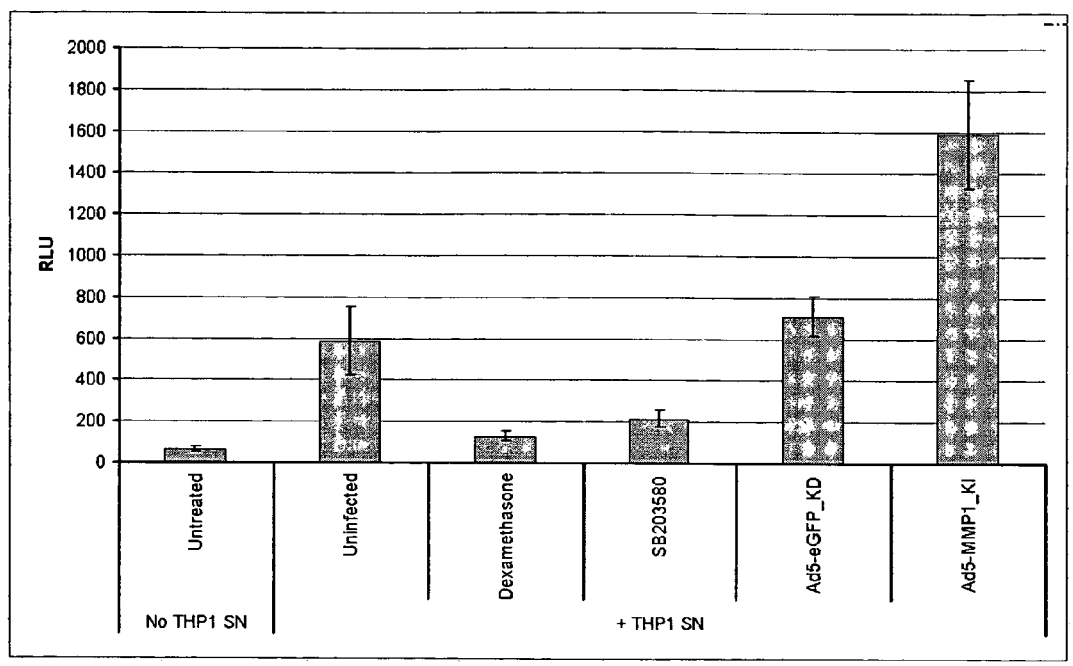
FIG. 11. Inhibition of the response of SFs to a complex cytokine mixture by two inhibitors.

In another experiment, inhibition of the response of SFs to the SN (supernatant) of TNFα-triggered THP1 cells is investigated. SFs are seeded in 384 well plates at 1500 cells/well and left uninfected or infected with the control knock-down virus Ad5-eGFP_KD or the control knock-in virus Ad5-MMP1. One day after infection, dexamethasone, a classical anti-inflammatory agent and SB203580 (an inhibitor of p38alpha and p38beta (kinases involved in the response of cells to TNFα and other cytokines), purchased at Calbiochem, dissolved in 100% DMSO), are added to the SF cultures at a final concentration of 100 nM and 5 μM respectively, 1 h before triggering of the cells with 2-fold diluted SN of TNFα-activated THP1 cells. 72 h after treatment, the SN is collected and subjected to the MMP1 ELISA. Results are depicted in FIG. 11: SFs are left uninfected or are infected with a control knock-in virus (Ad5-MMP1_KI) or a control knock-down virus (Ad5-eGFP_KD). Raw luminescence signals, which are proportional to the MMP1 levels, are shown.

Triggering of the cells led to a 6-fold increase of MMP1 expression. Even higher MMP1 levels are measured in the samples infected with Ad5-MMP1, indicating that the THP1 SN-induced MMP1 levels are not saturating for the MMP1 ELISA. The MMP1 levels obtained in the dexamethasone and SB203580 treated samples are 4 and 3 fold lower as the control levels, respectively, indicating that the assay as set up is suitable for the identification of inhibitors of the inflammatory response of SFs. Efficient reduction of gene expression in SFs can be obtained by RNAi (RNA interference) using knockdown viruses or transfection of siRNA duplexes.

Example 6B

Analysis of the Reduction in mRNA Expression of TARGET Genes by Ad-siRNA

Primary human synovial fibroblasts are seeded in gelatin coated 6-well plates (75,000 cells/well) in 2 ml synovial growth medium (Cell Applications Inc.) supplemented with 1× Pen/Strep (Invitrogen). After overnight incubation, cells are infected with the Ad5-siRNA targeting the gene of interest at an MOI of 3000. As a negative control, other wells are infected at the same MOI with Ad5-siRNA targeting the firefly luciferase gene. Five days post infection, medium is refreshed with 2 ml M199 medium supplemented with 1% (v/v) heat-inactivated FBS. At the same time, parallel samples are stimulated by refreshing the medium with 2 ml of a 2-fold dilution of the 'complex cytokine mixture' in M199+1% FBS. 48 h later, total RNA is extracted using the 'SV Total RNA Isolation kit' (Promega). RNA is quantitated and cDNA is prepared as described in Example 5. For each sample, real-time PCR reactions are performed for the TARGET and the 18S rRNA genes and ΔCt values are calculated as previously described in Example 5. To calculate the % knock-down of the endogenous TARGET mRNA after infection with the Ad5-siRNA, values are first expressed relative to the control samples that are infected with Ad5-luciferase-v13_KD virus using the equation: relative expression=$2^{\Delta\Delta Ct}$ with $\Delta\Delta Ct=\Delta Ct_{(sample\ infected\ with\ Ad5\text{-}luciferase\text{-}v13\_KD)} - \Delta Ct_{(sample\ infected\ with\ TARGET specific\ Ad5\text{-}siRNA)}$. The DCt values indicate the expression relative to β-actin as indicated in Example 5. Table 6 shows that after infection with most of the selected Ad5-siRNAs, more than 60% reduction of the TARGET mRNA, irrespective of whether the cells are stimulated with the 'complex cytokine mixture'. The abbreviation "Rel Expr" means relative expression.

NP001). 10 µl of Seablue Plus Prestained standard (Invitrogen LC5925) is used to estimate protein size on the gel. The proteins on the gel are then transferred onto a PVDF membrane (Invitrogen LC2002) by a wet blotting procedure

TABLE 6

| TARGET | Ad5-siRNA | no trigger | | | | triggered | | | |
|---|---|---|---|---|---|---|---|---|---|
| | | DCt | DDCt | Rel. Expr. | % KD | DCt | DDCt | Rel. Expr. | % KD |
| CAMKIV | Ad5-CamK4-v1_KD | 16.7 | −2.9 | 0.13 | 86.6 | 18.3 | −3.8 | 0.07 | 92.8 |
| | Ad5-Luciferase-v13_KD | 13.8 | 0 | 1.00 | 0.0 | 14.5 | 0 | 1.00 | 0.0 |
| PRKCE | Ad5-PRKCE-v11_KD | 10 | −1.1 | 0.47 | 53.3 | 8.7 | −0.9 | 0.54 | 46.4 |
| | Ad5-Luciferase-v13_KD | 8.9 | 0 | 1.00 | 0.0 | 7.8 | 0 | 1.00 | 0.0 |
| MMP1 | Ad5-MMP1-v10_KD | 13.4 | −4.9 | 0.03 | 96.7 | 5 | −3.2 | 0.11 | 89.1 |
| | Ad5-Luciferase-v13_KD | 8.5 | 0 | 1.00 | 0.0 | 1.8 | 0 | 1.00 | 0.0 |
| MAPKAPK5 | Ad5-MAPKAPK5-v2_KD | 9.3 | −2.3 | 0.20 | 79.7 | 7.4 | −3 | 0.13 | 87.5 |
| | Ad5-MAPKAPK5-v8_KD | 9.2 | −2.2 | 0.22 | 78.2 | 7.3 | −2.9 | 0.13 | 86.6 |
| | Ad5-Luciferase-v13_KD | 7 | 0 | 1.00 | 0.0 | 4.4 | 0 | 1.00 | 0.0 |
| RIT | Ad5-RIT-v5_KD | 7.1 | −1.2 | 0.44 | 56.5 | 6.5 | −1.9 | 0.27 | 73.2 |
| | Ad5-Luciferase-v13_KD | 5.9 | 0 | 1.00 | 0.0 | 4.6 | 0 | 1.00 | 0.0 |
| TPST1 | Ad5-TPST1-v1_KD | 7.3 | −0.9 | 0.54 | 46.4 | 8.2 | −2.3 | 0.20 | 79.7 |
| | Ad5-Luciferase-v13_KD | 6.4 | 0 | 1.00 | 0.0 | 5.9 | 0 | 1.00 | 0.0 |
| USP21 | Ad5-USP21-v3_KD | 9.5 | −1.2 | 0.44 | 56.5 | 8.9 | −1.3 | 0.41 | 59.4 |
| | Ad5-Luciferase-v13_KD | 8.3 | 0 | 1.00 | 0.0 | 7.6 | 0 | 1.00 | 0.0 |
| MST3 | Ad5-MST3-v4_KD | 6.9 | −2 | 0.25 | 75.0 | 7.1 | −2.1 | 0.23 | 76.7 |
| | Ad5-STK24-v1_KD | 7.8 | −2.9 | 0.13 | 86.6 | 6.4 | −1.4 | 0.38 | 62.1 |
| | Ad5-Luciferase-v13_KD | 4.9 | 0 | 1.00 | 0.0 | 5 | 0 | 1.00 | 0.0 |

Example 6C

Figure 14:
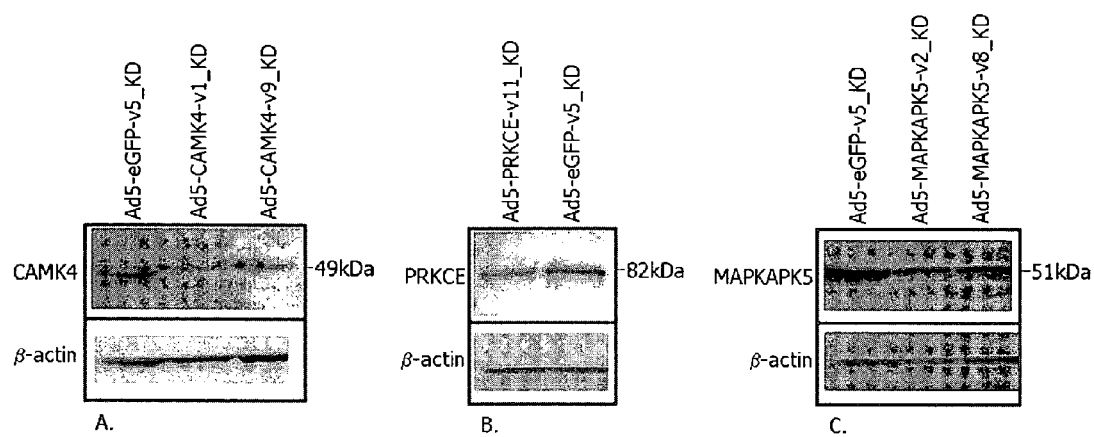
FIG. 14. Reduction, at the protein level, of the expression of MAPKAPK5, PRKCE and CAMK4 by infection of the cells with various Ad-siRNA viruses targeting these genes FIG. 15. Inhibition of the collagen degradation by SFs as a response to a complex cytokine mixture by infection of the cells with various "knock down" viruses.

Ad-siRNA Viruses Function to Knock Down Expression of MAPKAPK5, PRKCE and CAMK4 at the Protein Level FIG. 14 illustrates the functionality of Ad-siRNAs for reducing expression of TARGET genes (PRKCE, MAPKAPK5 and CAMK4) at the protein level in human cells.

Recombinant adenoviruses mediating the expression of siRNA's targeting MAPKAPK5, PRKCE and CAMK4 are generated according to the procedure described in WO03/020931. The target sequences in these genes based on which the siRNAs were designed and that were used to generate the recombinant adenoviruses are listed in Table 3.

The functionality of MAPKAPK5 targeting adenoviruses is tested as follows: On day 1, 500.000 primary human SFs are seeded per petri dish. One day later, the cells are infected with Ad5-MAPKAPK5-v2_KD, Ad5-MAPKAPK5-v8_KD or Ad5-eGFP-v5_KD at an MOI of 4000 (based on the titers (number of virus particles per ml) defined for the viruses by Q-rt-PCR). On day 7, cells are detached from the petri dish according to standard procedure using a trypsin EDTA solution. The trypsin is then neutralized by addition of DMEM growth medium supplemented with 10% FBS. The cells are then collected by a centrifugation step (1000 rpm, 5 min). The pellet is lysed in 100 µl of fresh RIPA buffer (50 mM Tris pH7.5, 150 mM NaCl, 1% deoxycholate, 1% Triton X100, 0.1% SDS). The samples are then sonicated for 10 sec. The protein concentration of the samples is then determined using the BCA kit (Pierce, Cat No 23227) as described by the provider, using BSA as a standard. To 30 µg of cell lysate diluted to 19.51 µl in RIPA buffer, 3.5 µl of reducing agent (NuPage reducing agent No 10, Invitrogen NP0004) and 7.5 µl of sample buffer (NuPage LDS sample buffer, Invitrogen NP0007) are added. The 30 µl sample is then boiled for 5 min and loaded on a 10% polyacrylamide gel (Invitrogen NP0301). The gel is then run for 2 hours at 100V in 1× MOPS/SDS NuPage running buffer (Invitrogen using a transfer buffer prepared by mixing 100 ml Nupage Transfer buffer 20* (NP0006-1), 400 ml methanol and 1500 ml Milli Q water. Before the transfer, the membrane is first soaked in methanol and in transfer buffer. The transfer is performed at 100V for 90 minutes. The membrane is then blocked by 30 min soaking in blocking buffer (2% blocking blocking powder (Amersham, RPN 2109) prepared in PBST (PBS supplemented with 0.1% Tween 20 (Sigma, P1379)). After blocking, the immunodetection is performed using a mouse monoclonal antibody against MAPKAPK5 (BD Biosciences, Cat No 612080) diluted 250 fold in blocking buffer. After overnight incubation with this primary antibody, the membrane is washed 3 times with PBST and incubated 1 hr with the secondary antibody ((Polyclonal goat anti-mouse Ig, HRP conjugated (DAKO P0447) diluted 50000 fold in blocking buffer. The blot is then washed 3 times in PBST and the detection is performed with ECL advance (RPN2109, Amersham) on a Kodakimager according to the manufacturers instructions. The Western Blotting revealed a lower expression level of MAPKAPK5 in the Ad5-MAPKAPK5-v2_KD and Ad5-MAPKAPK5-v8_KD infected cells compared to the cells infected with the Ad5-eGFP-v5_KD negative control virus. Equal loading of the 30 µg samples is demonstrated by immunodetection of β-actin after removal of the MAPKAPK5 antibody by a 'stripping procedure' (5 minutes boiling of the membrane in PBST). Immunodetection of β-actin is performed according to the method described for MAPKAPK5 detection, but using a goat polyclonal antibody against β-actin (Santa Cruz, Cat No SC-1615) at a 1000 fold dilution as primary antibody and a rabbit anti goat antibody at a 50000 fold dilution as a secondary antibody. Results of this experiment are shown in FIG. 14 C.

The functionality of the PRKCE targeting adenovirus (Ad5-PRKCE-v11_KD) is tested according to the same protocol as the one described above for MAPKAPK5, with the difference that an MOI of 2000 is used for infection of the cells. The western blotting procedure is the same as the one described for MAPKAPK5 detection, with the difference that a PRKCE specific antibody is used (BD Biosciences, Cat No 610085) at a dilution of 250-fold. The same secondary antibody is used as for the detection of MAPKAPK5. Results are shown in FIG. 14 B.

The functionality of the CAMK4 targeting adenovirus is tested as follows: These adenoviruses are used to infect Hek293T cells cultured in 6-well plates as follows. On day 1, 400000 Hek293T cells are seeded per 6-well plate in DMEM+10% FBS. One day later, the cells are infected with Ad5-CAMK4-v1_KD, CAMK4-CAMK4-v9_KD or Ad5-eGFP-v5_at an MOI (multiplicity of infection) of 500 (based on the titers (number of virus particles per ml) defined for the viruses by Q-rt-PCR). One day after the infection, the medium is refreshed. On day 7, cells are detached from the petri dish according to standard procedure using a trypsin EDTA solution. The handling of the cell pellet, the running/blotting of the gel and the immunodetection procedure is identical to what is described for MAPKAPK5, with the difference that 40 µg protein is loaded on the gel and that a mouse monoclonal antibody against CAMK4 (Santa Cruz, Sc-17762, diluted 100-fold in blocking buffer) is used. The Western Blotting reveals a lower expression level of CAMK4 in the Ad5-CAMK4-v1_KD and the Ad5-CAMK4-v9_KD infected cells compared to the cells infected with the Ad5-eGFP-v5_KD negative control virus. Equal loading of the 30 µg samples is demonstrated by immunodetection of β-actin after removal of the CAMK4 antibody by a 'stripping procedure'. Results of this experiment are given in FIG. 14 A.

These experiments demonstrate that the Ad-siRNA virus function to reduce the expression levels of the corresponding MAPKAPK5, CAMK4 and PRKCE polpeptides in human cells.

Example 6D

Figure 12:
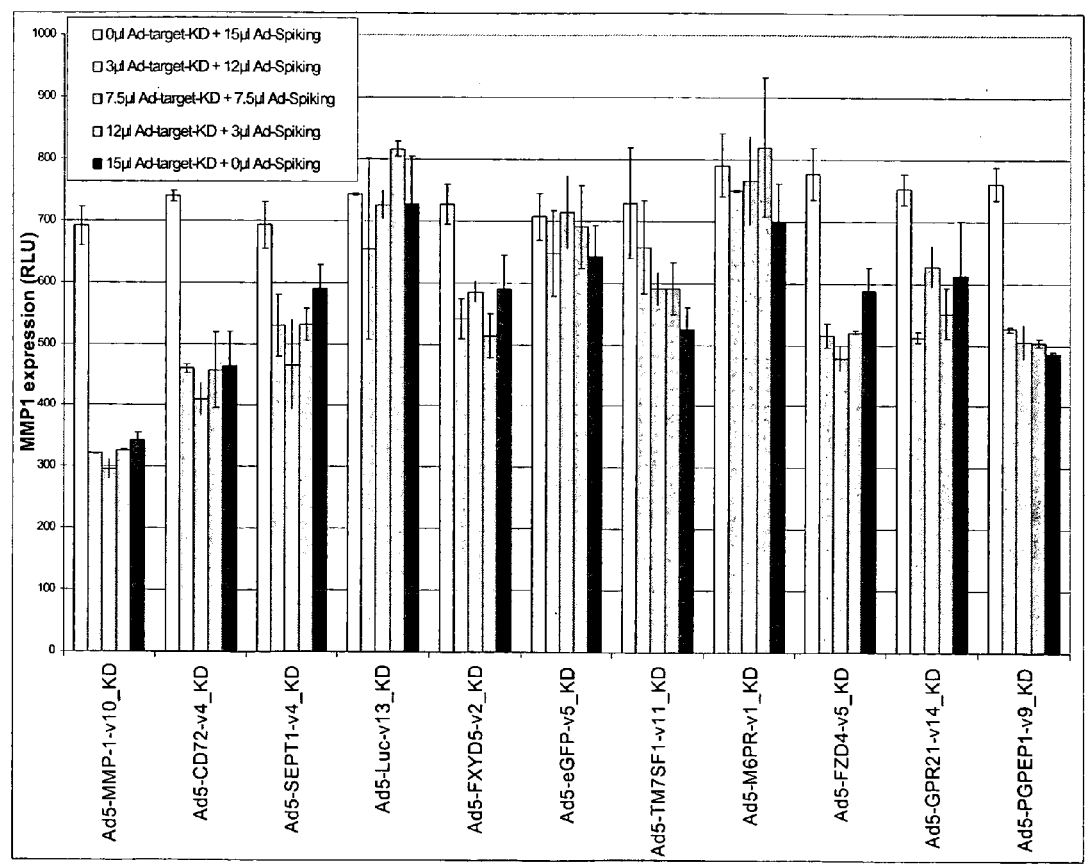
FIG. 12. Ad-siRNA mediated reduction in the expression of various target genes in SF's reduces the capacity of these cells to express MMP1 as a response to cytokines. A) Results of cells infected with 3, 7.5, 12 or 15 µL of Ad-siRNAs designed against GPR21, FZD4, TM7SF1, PGPEP1, SEPT1, CD72 and FXYD5; B) results of cells infected with 3, 6, 9, 12 and 15 µL of Ad-siRNAs designed against PRKCE, CAMK4 and MAPKAPK5; C) results of cells infected with 3, 6, 9, and 12 µL of Ad-siRNAs designed against RIPK2 and RIT1; and D) results of cells infected with 3, 6, 9, and 12 µL of Ad-siRNAs designed against PPST1. USP21 and STK24.
Figure 12:
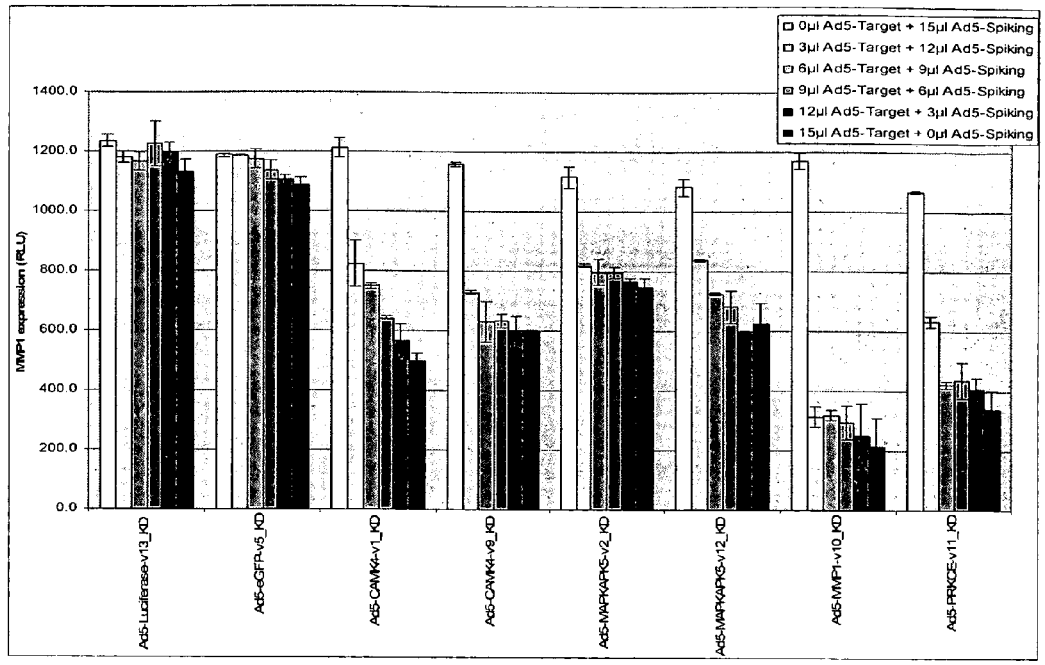
Figure 12:
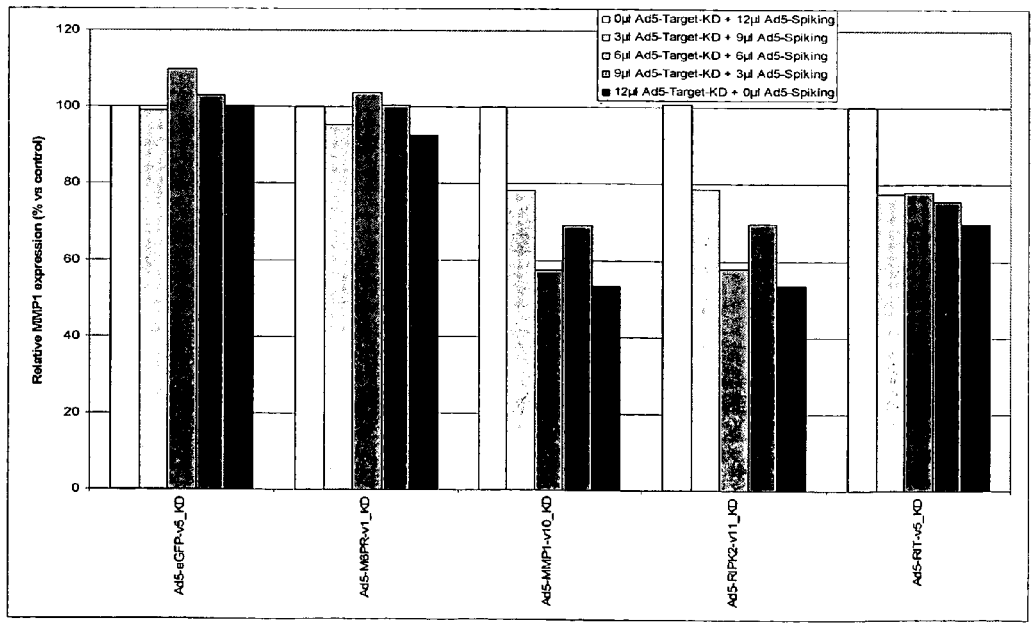
Figure 12:
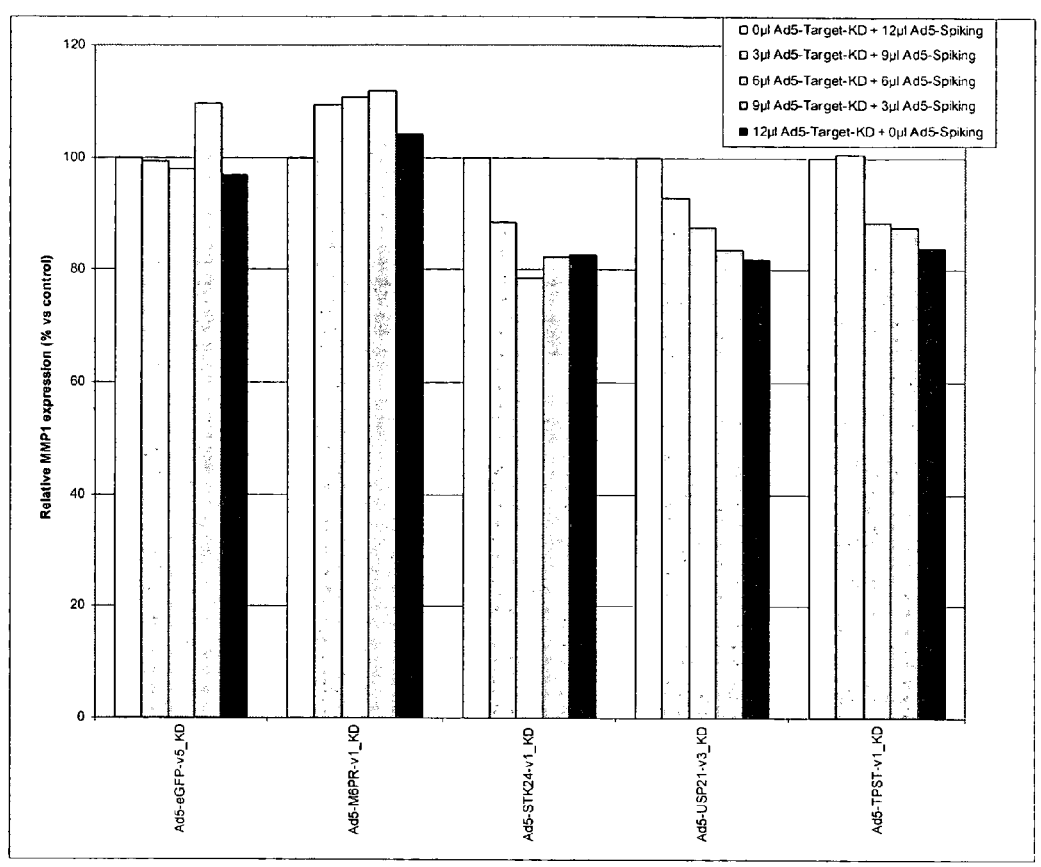

Reduction of the Expression in Primary SFs of Various TARGET Genes by Ad-siRNAs Inhibit SF-induced MMP1 Expression FIG. 12 illustrates the reduction of cytokine-induced SF MMP1 expression by Ad-siRNAs reducing the expression of TARGET genes. These Ad-siRNAs are generated according to the procedure described in WO03/020931. The target sequences (KD SEQ) in these genes, based on which the siRNAs were designed and that were used to generate the recombinant adenoviruses, are listed in Table 3.

The efficacy of Ad5-siRNAs in the 'MMP assay' is tested as follows. Day 1, SFs (passage 9 to 10) are seeded in 96 well plates at a density of 3000 cells per well in complete synovial growth medium (Cell Applications). One day later, the cells are infected with increasing amounts (3, 7.5, 12 or 15 µl in experiment shown in FIG. 12 A; 3, 6, 9, 12 and 15 µl in experiment shown in FIG. 12 B; and 3, 6, 9, and 12 µl in the experiments represented on FIGS. 12 C and 12 D) of the Ad-siRNA's. The following viruses are used as negative control: Ad5-eGFP-v5_KD, Ad5-Luciferase-v13_KD and Ad-M6PR-v1_KD. Ad5-MMP1-v10_KD is used as a positive control virus. The virus load is corrected by addition of the neutral virus Ad5-Luciferase-v13_KD to bring the final virus volume on the cells to 15 µl in every well. This correction guarantees that the effects observed do not result from differences in the virus load applied to the cells. The cells are then incubated for 5 days before the activation step. This step involves the replacement, in every well, of the growth medium by 75 µl of M199 medium supplemented with 25 µl of 'complex trigger'. 48 hrs after the activation step, the supernatant is collected and subjected to the MMP1 ELISA as described above.

The results of the experiment are shown in FIG. 12A, B, C and D. The average of duplicate data points is shown in these Figures. The quality of the experiment is demonstrated by the efficacy of the Ad-siRNA virus targeting MMP1 itself. This positive control virus strongly reduces the MMP1 expression by SFs, whereas the negative control viruses, designed to target the expression of luciferase, M6PR and eGFP do not influence the levels of MMP1 expression, as expected. The Ad-siRNAs designed against TARGET genes (GPR21, FZD4, TM7SF1, PGPEP1, SEPT1, CD72, FXYD5 (FIG. 12 A.); PRKCE, CAMK4, MAPKAPK5 (FIG. 12 B.), RIPK2, RIT1 (FIG. 12 C.) and PPST1, USP21 and STK24 (FIG. 12 D.), also lead to a clear reduction of the complex trigger induced MMP1 expression by primary human SFs. For certain TARGET genes (e.g. CAMK4, MAPKAPK5), 2 independent Ad-siRNAs showed efficacy in reducing cytokine induced MMP1 expression by SFs. In FIG. 12 A and B, the MMP1 expression levels are shown in terms of raw data (RLU) whereas in FIGS. 12 C and 12 D, the MMP1 expression levels are expressed relative to the samples infected with Ad5-luciferase-v13_KD only set to 100%.

For most TARGET genes, at least 1 of the 5 Ad-siRNAs designed per TARGET gene mediated a reduction of the cytokine-induced MMP1 expression by SFs. This was not the case for MKNK1 and CASP10. The effects observed were weaker for USP21 and MST3.

It can be concluded, from this experiment, that these genes represent valuable drug targets that are shown to modulate MMP1 expression in SFs. Similarly, the inhibition of the activity of the protein product of these genes by a small molecule compound is expected to reduce the 'complex cytokine' induced MMP1 expression in the 'MMP assay'. The inhibition of the activity of the protein products of these genes by small molecule compounds is also predicted to reduce the degradation of the joint associated with RA.

Example 6E

Reduction of the Expression in Primary SFs of MAPKAPK5 and CAMK4 by Ad-siRNAs Inhibit Cytokine-induced Collagen Degradation This experiment measures the ability of Ad-siRNAs to reduce cytokine-induced degradation of collagen type I, which is even more stringent than the MMP1 ELISA, as the degradation of native collagen might be due to the action of proteases different from MMP1. The Ad-siRNAs used in this experiment are generated according to the procedure described in WO03/020931. The recombinant Ad-siRNAs used in this experiment were generated based on target sequences in the target genes that are listed in Table 3.

Figure 15:
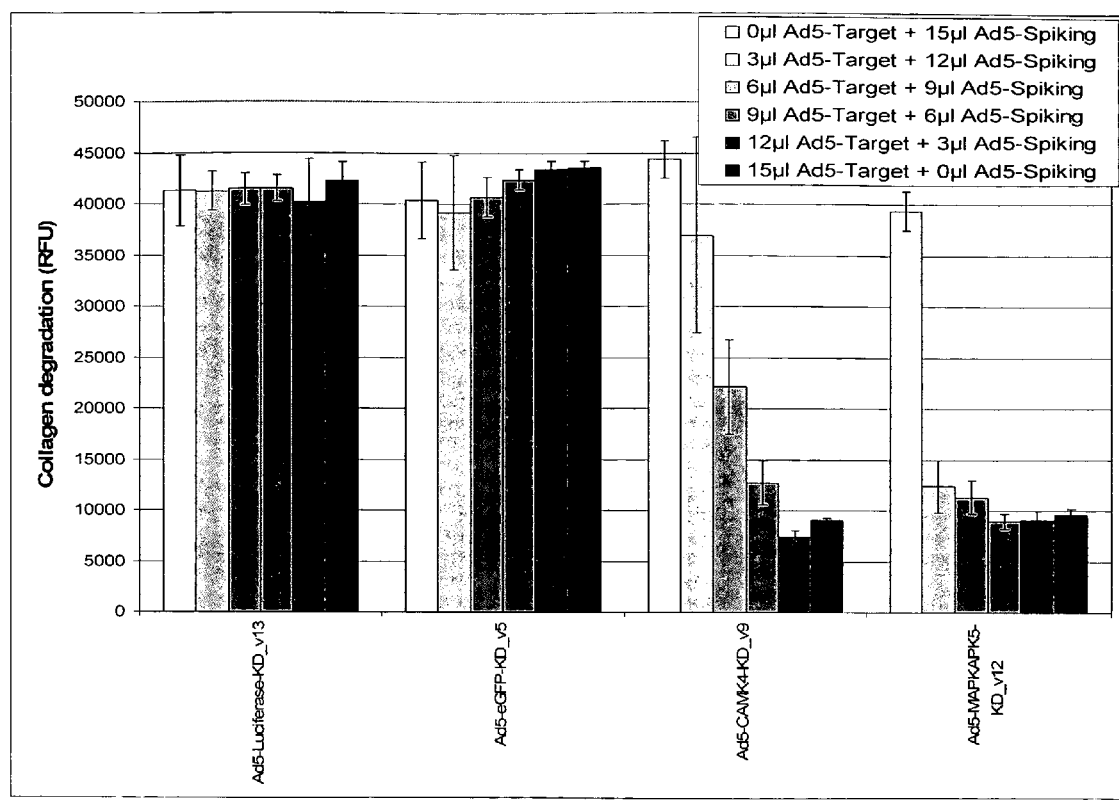

The efficacy of Ad5-siRNAs in the 'miniaturized native collagen type I degradation assay' described above is tested as follows: Day 1, SFs (passage 9 to 10) are seeded in 96 well plates at a density of 3000 cells per well in complete synovial growth medium (Cell Applications). One day later, the cells are infected with increasing amounts (3, 6, 9, 12 and 15 µl) of the Ad-siRNA's indicated on the figure. The following viruses are used as negative control: Ad5-eGFP-v5_KD, and Ad5-Luciferase-v13_KD. The virus load is corrected by addition of the neutral virus Ad5-Luciferase-v13_KD to bring the final virus volume added to each well to 15 µl. This correction guarantees that the effects observed do not result from differences in the virus load applied to the cells. The cells are then incubated for 5 days before the activation step. This step involves the replacement, in every well, of the growth medium by 45 µl of M199 medium supplemented with 15 µl of 'complex trigger'. 4 days later, the supernatant is collected and subjected to the miniaturized collagen type I degradation assay according to the protocol as described above. The results of the experiment are shown in FIG. 15.

The negative control viruses, designed to target the expression of luciferase and eGFP, do not influence the levels of collagen degradation, as expected. The Ad-siRNAs targeting MAPKAPK5 and CAMK4 do mediate a clear reduction of the complex trigger-induced collagen degradation by primary human SFs. It can be concluded, from this experiment, that these genes represent valuable drug targets that are shown to modulate collagen degradation by SFs. Similarly, the inhibition of the activity of the protein product of these genes by a small molecule compound is expected to reduce the 'complex cytokine' induced collagen degradation by SFs. The inhibition of the activity of the protein products of these genes by small molecule compounds is also predicted to reduce the degradation of the joint associated with RA. In similar experiments, the Ad5-MMP1-v10_KD virus is shown to strongly reduce the cytokine induced collagen degradation by SFs, which implies the fact that MMP1 itself is the main collagenase responsible for the cytokine induced collagen degradation by SFs. As such, this means that modulation of MMP1 expression by SFs is sufficient to reduce cartilage degradation associated with RA.

Example 7

Identification of Small Molecules that Inhibit TARGET Kinase Activity

Compounds are screened for inhibition of the activity of the TARGETS that are kinase polypeptides. The affinity of the compounds to the polypeptides is determined in an experiment detecting changed reaction conditions after phosphorylation. The TARGET kinase polypeptides are incubated with its substrate and ATP in an appropriate buffer. The combination of these components results in the in vitro phosphorylation of the substrate. Sources of compounds include commercially available screening library, peptides in a phage display library or an antibody fragment library, and compounds that have been demonstrated to have binding affinity for a TARGET kinase.

The TARGET kinase polypeptides can be prepared in a number of ways depending on whether the assay will be run using cells, cell fractions or biochemically, on purified proteins. The polypeptides can be applied as complete polypeptides or as polypeptide fragments, which still comprise TARGET kinase catalytic activity.

Identification of small molecules inhibiting the activity of the TARGET kinase polypeptides is performed by measuring changes in levels of phosphorylated substrate or ATP. Since ATP is consumed during the phosphorylation of the substrate, its levels correlate with the kinase activity. Measuring ATP levels via chemiluminescent reactions therefore represents a method to measure kinase activity in vitro (Perkin Elmer). In a second type of assay, changes in the levels of phosphorylated substrate are detected with phosphospecific agents and are correlated to kinase activity. These levels are detected in solution or after immobilization of the substrate on a microtiter plate or other carrier. In solution, the phosphorylated substrate is detected via fluorescence resonance energy transfer (FRET) between the Eu labeled substrate and an APC labeled phosphospecific antibody (Perkin Elmer), via fluorescence polarization (FP) after binding of a phosphospecific antibody to the fluorescently labeled phosphorylated substrate (Panvera), via an Amplified Luminescent Proximity Homogeneous Assay (ALPHA) using the phosphorylated substrate and phosphospecific antibody, both coupled to ALPHA beads (Perkin Elmer) or using the IMAP binding reagent that specifically detects phosphate groups and thus alleviates the use of the phosphospecific antibody (Molecular Devices). Alternatively, the substrate is immobilized directly or by using biotin-streptavidin on a microtiter plate. After immobilization, the level of phosphorylated substrate is detected using a classical ELISA where binding of the phosphospecific antibody is either monitored via an enzyme such as horseradish peroxidase (HRP) or alkaline phospahtase (AP) which are either directly coupled to the phosphospecific antibody or are coupled to a secondary antibody. Enzymatic activity correlates to phosphorylated substrate levels. Alternatively, binding of the Eu-labeled phosphospecific antibody to the immobilized phosphorylated substrate is determined via time resolved fluorescence energy (TRF) (Perkin Elmer). In addition, the substrate can be coated on FLASH plates (Perkin Elmer) and phosphorylation of the substrate is detected using $^{33}P$ labeled ATP or $^{125}I$ labeled phosphospecific antibody.

Small molecules are randomly screened or are preselected based upon drug class, (i.e. known kinase inhibitors), or upon virtual ligand screening (VLS) results. VLS uses virtual docking technology to test large numbers of small molecules in silico for their binding to the polypeptide of the invention. Small molecules are added to the kinase reaction and their effect on levels of phosphorylated substrate is measured with one or more of the above-described technologies.

Small molecules that inhibit the kinase activity are identified and are subsequently tested at different concentrations. $IC_{50}$ values are calculated from these dose response curves. Strong binders have an $IC_{50}$ in the nanomolar and even picomolar range. Compounds that have an $IC_{50}$ of at least 10 micromol or better (nmol to pmol) are applied in alkaline phosphatase assay or bone mineralization assay to check for their effect on the induction of osteogenesis.

Example 8

Ligand Screens for TARGET GPCRs. Reporter Gene Screen

Mammalian cells such as Hek293 or CHO-K1 cells are either stably transfected with a plasmid harboring the luciferase gene under the control of a cAMP dependent promoter (CRE elements) or transduced with an adenovirus harboring a luciferase gene under the control of a cAMP dependent promoter. In addition reporter constructs can be used with the luciferase gene under the control of a $Ca^{2+}$ dependent promoter (NF-AT elements) or a promoter that is controlled by activated NF-κB. These cells, expressing the reporter construct, are then transduced with an adenovirus harboring the cDNA of a TARGET GPCR. Forty (40) hours after transduction the cells are treated with the following:
  a) an agonist for the receptor and screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of the SEQ ID NOs of the TARGET GPCRs; or b) a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs.

Compounds, which decrease the agonist induced increase in luciferase activity or the constitutive activity, are considered to be antagonists or inverse agonists for a TARGET GPCR. These compounds are screened again for verification and screened against their effect on osteoblast differentiation. The compounds are also screened to verify binding to the GPCR. The binding, osteogenesis and reporter activity assays can be performed in essentially any order to screen compounds.

In addition, cells expressing the NF-AT reporter gene can be transduced with an adenovirus harboring the cDNA encoding the α-subunit of G15 or chimerical Gα subunits. G15 is a promiscuous G protein of the Gq class that couples to many different GPCRs and as such re-directs their signaling towards the release of intracellular Ca2+ stores. The chimerical G alpha subunits are members of the Gs and Gi/o family by which the last 5 C-terminal residues are replaced by those of Gαq, these chimerical G-proteins also redirect cAMP signaling to Ca2+ signaling.

FLIPR Screen.

Mammalian cells such as Hek293 or CHO-K1 cells are stably transfected with an expression plasmid construct harboring the cDNA of a TARGET GPCR. Cells are seeded, grown, and selected until sufficient stable cells can be obtained. Cells are loaded with a $Ca^{2+}$ dependent fluorophore such as Fura3 or Fura4. After washing away the excess of fluorophore the cells are screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs, by simultaneously adding an agonist (alternatively no agonist need be added if the constitutive activity of the receptor is used) and a compound to the cells. Activation of the receptor is measured as an almost instantaneously increase in fluorescence due to the interaction of the fluorophore and the $Ca^{2+}$ that is released. Compounds that reduce or inhibit the agonist induced increase in fluorescence (or constitutive fluorescence) are considered to be antagonists or inverse agonists for the receptor they are screened against. These compounds are screened again to measure the amount of osteoblast differentiation as well as binding to a TARGET GPCR.

AequoScreen.

CHO cells, stably expressing Apoaequorin are stably transfected with a plasmid construct harboring the cDNA of a TARGET GPCR. Cells are seeded, grown, and selected until sufficient stable cells can be obtained. The cells are loaded with coelenterazine, a cofactor for apoaequorin. Upon receptor activation intracellular $Ca^{2+}$ stores are emptied and the aequorin will react with the coelenterazine in a light emitting process. The emitted light is a measure for receptor activation. The CHO, stable expressing both the apoaequorin and the receptor are screened against a large collection of reference compounds comprising peptides (LOPAP, Sigma Aldrich), lipids (Biomol, TimTech), carbohydrates (Specs), natural compounds (Specs, TimTech), small chemical compounds (Tocris), commercially available screening libraries, and compounds that have been demonstrated to have binding affinity for a polypeptide comprising an amino acid sequence selected from the group consisting of SEQ ID NOs of the TARGET GPCRs, by simultaneously adding an agonist (alternatively no agonist need be added if the constitutive activity of the receptor is used) and a compound to the cells. Activation of the receptor is measured as an almost instantaneously light flash due to the interaction of the apoaequorin, coelenterazine, and the $Ca^{2+}$ that is released. Compounds that reduce or inhibit the agonist induced increase in light or the constitutive activity are considered to be antagonists or inverse agonists for the receptor they are screened against. These compounds are screened again to measure the amount of osteoblast differentiation as well as binding to a TARGET GPCR.

In addition, CHO cells stable expressing the apoaequorin gene are stably transfected with a plasmid construct harboring the cDNA encoding the α-subunit of $G_{15}$ or chimerical $G_\alpha$ subunits. $G_{15}$ is a promiscuous G protein of the $G_q$ class that couples to many different GPCRs and as such redirects their signaling towards the release of intracellular $Ca^{2+}$ stores. The chimerical G alpha subunits are members of the $G_s$ and $G_{i/o}$ family by which the last 5 C-terminal residues are replaced by those of $G_{\alpha q}$, these chimerical G-proteins also redirect cAMP signaling to $Ca^{2+}$ signaling.

Screening for Compounds that Bind to the GPCR Polypeptides (Displacement Experiment)

Compounds are screened for binding to the TARGET GPCR polypeptides. The affinity of the compounds to the polypeptides is determined in a displacement experiment. In brief, the GPCR polypeptides are incubated with a labeled (radiolabeled, fluorescent labeled) ligand that is known to bind to the polypeptide and with an unlabeled compound. The displacement of the labeled ligand from the polypeptide is determined by measuring the amount of labeled ligand that is still associated with the polypeptide. The amount associated with the polypeptide is plotted against the concentration of the compound to calculate $IC_{50}$ values. This value reflects the binding affinity of the compound to its TARGET, i.e. the TARGET GPCR polypeptides. Strong binders have an $IC_{50}$ in the nanomolar and even picomolar range. Compounds that have an $IC_{50}$ of at least 10 micromol or better (nmol to pmol) are applied an osteoblast differentiation assay to check for their effect on osteogenesis. The TARGET GPCR polypeptides can be prepared in a number of ways depending on whether the assay are run on cells, cell fractions or biochemically, on purified proteins.

Screening for Compounds that Bind to a TARGET GPCR (Generic GPCR Screening Assay)

When a G protein receptor becomes constitutively active, it binds to a G protein ($G_q$, $G_s$, $G_i$, $G_o$) and stimulates the binding of GTP to the G protein. The G protein then acts as a GTPase and slowly hydrolyses the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. Moreover, a preferred approach is the use of a GPCR-G protein fusion protein. The strategy to generate a TARGET GPCR-G protein fusion protein is well known for those known in the art. Membranes expressing TARGET GPCR-G protein fusion protein are prepared for use in the direct identification of candidate compounds such as inverse agonist. Homogenized membranes with TARGET GPCR-G protein fusion protein are transferred in a 96-well plate. A pin-tool is used to transfer a candidate compound in each well plus [$^{35}$S]GTPγS, followed by incubation on a shaker for 60 minutes at room temperature. The assay is stopped by spinning of the plates at 4000 RPM for 15 minutes at 22° C. The plates are then aspirated and radioactivity is then read.

Receptor Ligand Binding Study on Cell Surface

The receptor is expressed in mammalian cells (Hek293, CHO, COS7) by adenoviral transducing the cells (see U.S. Pat. No. 6,340,595). The cells are incubated with both labeled ligand (iodinated, tritiated, or fluorescent) and the unlabeled compound at various concentrations, ranging from 10 µM to 10 µM (3 hours at 4° C.: 25 mM HEPES, 140 mM NaCl, 1 mM CaCl$_2$ 5 mM MgCl$_2$ and 0.2% BSA, adjusted to pH 7.4). Reactions mixtures are aspirated onto PEI-treated GF/B glass filters using a cell harvester (Packard). The filters are washed twice with ice cold wash buffer (25 mM HEPES, 500 mM NaCl, 1 mM CaCl$_2$, 5 mM MgCl$_2$, adjusted to pH 7.4). Scintillant (MicroScint-10; 35 µl) is added to dried filters and the filters counted in a (Packard Topcount) scintillation counter. Data are analyzed and plotted using Prism software (GraphPad Software, San Diego, Calif.). Competition curves are analyzed and IC$_{50}$ values calculated. If one or more data points do not fall within the sigmoidal range of the competition curve or close to the sigmoidal range the assay is repeated and concentrations of labeled ligand and unlabeled compound adapted to have more data points close to or in the sigmoidal range of the curve.

Receptor Ligand Binding Studies on Membrane Preparations

Membranes preparations are isolated from mammalian cells (Hek293, CHO, COS7) cells over expressing the receptor is done as follows: Medium is aspirated from the transduced cells and cells are harvested in 1× PBS by gentle scraping. Cells are pelleted (2500 rpm 5 min) and resuspended in 50 mM Tris pH 7.4 (10×10$^6$ cells/ml). The cell pellet is homogenized by sonicating 3×5 sec (UP50H; sonotrode MS1; max amplitude: 140 µm; max Sonic Power Density: 125 W/cm$^2$). Membrane fractions are prepared by centrifuging 20 min at maximal speed (13,000 rpm~15,000 to 20,000 g or rcf). The resulting pellet is resuspended in 500 µl 50 mM Tris pH 7.4 and sonicated again for 3×5 sec. The membrane fraction is isolated by centrifugation and finally resuspended in PBS. Binding competition and derivation of IC$_{50}$ values are determined as described above.

Internalization Screen (1)

Activation of a GPCR-associated signal transduction pathway commonly leads to translocation of specific signal transduction molecules from the cytoplasm to the plasma membrane or from the cytoplasm to the nucleus. Norak has developed their transfluor assay based on agonist-induced translocation of receptor-β-arrestin-GFP complex from the cytosol to the plasma membrane and subsequent internalization of this complex, which occurs during receptor desensitization. A similar assay uses GFP tagged receptor instead of β-arrestin. Hek293 cells are transduced with a TARGET GPCR vector that translates for a TARGET GPCR-eGFP fusion protein. 48 hours after transduction, the cells are set to fresh serum-free medium for 60 minutes and treated with a ligand for 15, 30, 60 or 120 minutes at 37° C. and 5% CO$_2$. After indicated exposure times, cells are washed with PBS and fixed with 5% paraformaldehyde for 20 minutes at RT. GFP fluorescence is visualized with a Zeiss microscope with a digital camera. This method aims for the identification of compounds that inhibit a ligand-mediated (constitutive activity-mediated) translocation of the fusion protein to intracellular compartments.

Internalization Screen (2)

Various variations on translocation assays exists using β-arrestin and β-galactosidase enzyme complementation and BRET based assays with receptor as energy donor and β-arrestin as energy acceptor. Also the use of specific receptor antibodies labeled with pH sensitive dyes are used to detect agonist induced receptor translocation to acidic lysosomes. All of the translocation assays are used for screening for both agonistic and antagonistic acting ligands.

Melanophore Assay (Arena Pharmaceutical)

The melanophore assay is based on the ability of GPCRs to alter the distribution of melanin containing melanosomes in *Xenopus* melanophores. The distribution of the melanosomes depends on the exogenous receptor that is either Gi/o or Gs/q coupled. The distribution of the melanosomes (dispersed or aggregated) is easily detected by measuring light absorption. This type of assay is used for both agonist as well as antagonist compound screens.

REFERENCES

Andreakos E, et al. (2003). Arthritis Rheum. 48: 1901-12.
Choy E H, Panayi G S. (2001). N Engl J. Med. 344: 907-16.
Cortez-Retamozo V, et al. (2004). Cancer Res. 64(8): 2853-7
Coussens L M, et al. (2002). Science 295: 2387-92.
Creemers E E, et al. (2001). Circ Res. 2001 89:201-10
Cunnane G, et al. (2001). Arthritis Rheum 44: 2263-74.
Firestein G S. (2003). Nature. 423:356-61.
Gapski R, et al. (2004). J Periodontol. 75:441-52.
Gomez-Reino J J, et al. (2003). Arthritis Rheum. 48: 2122-7.
Lee D M, Weinblatt M E (2001). Lancet. 358: 903-11.
Lipinski C A, et al. (2001). Advanced Drug Delivery Reviews. 46(1-3): 3-26.
Maini R N, et al. (2004). Arthritis Rheum. 50: 1051-65.
Rosenberg G A. (2002). Glia. 39:279-91.
Schanstra J P, et al. (2002). J Clin Invest. 110:371-9.
Smolen J S, Steiner G. (2003). Nat Rev Drug Discov. 2: 473-88.
Suzuki R, et al. (2004). Treat Respir Med. 3:17-27.
Vincenti M P, Brinckerhoff C E. (2002). Arthritis Res 4:157-64

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the inventi on. Thus, the invention is intended to be defined not by the above description, but by the following claims and their equivalents.

We claim:

1. A method for identifying a compound that inhibits extra-cellular matrix (ECM) degradation, comprising
   contacting a compound with a polypeptide comprising the amino acid sequence of SEQ ID NO: 31; and
   measuring a compound-polypeptide property related to extra-cellular matrix (ECM) degradation.

2. The method according to claim 1, wherein said polypeptide is in an in vitro cell-free preparation.

3. The method according to claim 1, wherein said polypeptide is present in a mammalian cell.

4. The method of claim 1, wherein said property is a binding affinity of said compound to said polypeptide.

5. The method of claim 3, wherein said property is activation of a biological pathway producing a biochemical marker indicative of extra-cellular matrix (ECM) degradation.

6. The method of claim 5 wherein said indicator is MMP1.

7. The method according to claim 1, wherein said compound is selected from the group consisting of compounds of a commercially available screening library and compounds having binding affinity for a polypeptide comprising the amino acid sequence of SEQ ID NO: 31.

8. The method according to claim 1, wherein said compound is a peptide in a phage display library or an antibody fragment library.

9. The method of claim 4, further comprising the steps of
   selecting a compound that exhibits moderate or high binding affinity to said polypeptide;
   contacting a population of mammalian cells with said compound; and
   measuring a second compound-polypeptide property related to extra-cellular matrix degradation.

10. The method of claim 9, wherein said second compound-polypeptide property is MMP1 activity.

11. The method of claim 9, wherein said second compound-polypeptide property is MMP1 expression.

* * * * *